US012642787B2

(12) United States Patent
Witowski et al.

(10) Patent No.: US 12,642,787 B2
(45) Date of Patent: Jun. 2, 2026

(54) COMPOSITIONS OF MATTER AND PHARMACEUTICAL COMPOSITIONS

(71) Applicant: Atai Therapeutics, Inc., New York, NY (US)

(72) Inventors: Christopher G. Witowski, Tampa, FL (US); Jacqueline L. Salm, Tampa, FL (US)

(73) Assignee: Atai Therapeutics, Inc., New York, NY (US)

( * ) Notice: Subject to any disclaimer, the term of this patent is extended or adjusted under 35 U.S.C. 154(b) by 0 days.

(21) Appl. No.: 19/431,424

(22) Filed: Dec. 23, 2025

(65) Prior Publication Data

US 2026/0124174 A1 May 7, 2026

Related U.S. Application Data

(63) Continuation of application No. 19/358,021, filed on Oct. 14, 2025, which is a continuation of application No. 19/173,537, filed on Apr. 8, 2025, now Pat. No. 12,472,163, which is a continuation of application No. 18/744,484, filed on Jun. 14, 2024, now Pat. No. 12,396,982, which is a continuation of application No. 18/229,286, filed on Aug. 2, 2023, now Pat. No. 12,053,453, which is a continuation of application No. 17/314,107, filed on May 7, 2021, now Pat. No. 11,759,452.

(60) Provisional application No. 63/134,805, filed on Jan. 7, 2021, provisional application No. 63/106,516, filed on Oct. 28, 2020, provisional application No. 63/021,866, filed on May 8, 2020.

(51) Int. Cl.

| | |
|---|---|
| ***A61K 31/4045*** | (2006.01) |
| ***A61K 9/00*** | (2006.01) |
| ***A61K 9/06*** | (2006.01) |
| ***A61K 9/20*** | (2006.01) |
| ***A61K 9/70*** | (2006.01) |
| ***A61K 31/405*** | (2006.01) |
| ***A61K 31/48*** | (2006.01) |
| ***A61K 31/55*** | (2006.01) |
| ***A61K 31/675*** | (2006.01) |
| ***C07D 209/16*** | (2006.01) |

(52) U.S. Cl.

CPC ........ *A61K 31/4045* (2013.01); *A61K 9/0043* (2013.01); *A61K 9/06* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/7061* (2013.01); *A61K 9/7069* (2013.01); *A61K 31/405* (2013.01); *A61K 31/48* (2013.01); *A61K 31/55* (2013.01); *A61K 31/675* (2013.01); *C07D 209/16* (2013.01)

(58) Field of Classification Search

CPC .... A61K 31/4045; A61K 9/0043; A61K 9/06; A61K 9/2009; A61K 9/2013; A61K 9/2018; A61K 9/2027; A61K 9/2054; A61K 9/7061; A61K 9/7069; A61K 31/405; A61K 31/48; A61K 31/55; A61K 31/675; C07D 209/16

USPC .......................................................... 514/415

See application file for complete search history.

(56) References Cited

U.S. PATENT DOCUMENTS

| | | | |
|---|---|---|---|
| 2,774,763 | A | 12/1956 | Garbrect |
| 2,997,470 | A | 8/1961 | Pioch |
| 3,078,214 | A | 2/1963 | Albert et al. |
| 3,224,945 | A | 12/1965 | Tyler, Jr. |
| 3,499,003 | A | 3/1970 | Welstead, Jr. |
| 3,594,391 | A | 7/1971 | Wolf et al. |
| 3,781,300 | A | 12/1973 | Wolf et al. |
| 4,101,552 | A | 7/1978 | Mago nee Karacsony et al. |
| 4,176,182 | A | 11/1979 | Ferrari et al. |
| 4,180,581 | A | 12/1979 | Stadler |
| 4,230,854 | A | 10/1980 | Beacco et al. |
| 4,252,803 | A | 2/1981 | Webb |
| 4,252,941 | A | 2/1981 | Mantegani et al. |
| 4,348,391 | A | 9/1982 | Stutz et al. |
| 5,340,838 | A | 8/1994 | Gidda et al. |
| 5,347,029 | A | 9/1994 | Johnson |
| 5,637,593 | A | 6/1997 | Porter et al. |
| 5,705,527 | A | 1/1998 | Ishihara et al. |
| 5,811,436 | A | 9/1998 | Leonard et al. |
| 6,201,025 | B1 | 3/2001 | Dax et al. |
| 6,403,808 | B1 | 6/2002 | Glennon et al. |
| 6,436,950 | B1 | 8/2002 | Achari et al. |
| 6,500,456 | B1 | 12/2002 | Capella |
| 7,458,374 | B2 | 12/2008 | Hale et al. |
| 7,482,273 | B1 | 1/2009 | Klein et al. |
| 8,268,856 | B2 | 9/2012 | Hamann et al. |

(Continued)

FOREIGN PATENT DOCUMENTS

| | | | |
|---|---|---|---|
| CA | 3103707 | C | 9/2023 |
| CH | 578565 | A5 | 8/1976 |

(Continued)

OTHER PUBLICATIONS

Abiero et al., "Four Novel Synthetic Tryptamine Analogs Induce Head-Twitch Responses and Increase 5-HTR2a in the Prefrontal Cortex in Mice." Biomol Ther (Seoul). Jan. 1, 2020; 28(1): 83-91.

(Continued)

*Primary Examiner* — Kristin A Vajda

(74) *Attorney, Agent, or Firm* — COOLEY LLP

(57) ABSTRACT

Pharmaceutical formulations of novel indole compounds and psilocybin analogs are manufactured, provided in novel oral, transdermal, and nasal pharmaceutical compositions for use to treat neurological, mood or abuse diseases and disorders.

29 Claims, 2 Drawing Sheets

(56) References Cited

U.S. PATENT DOCUMENTS

| | | | |
|---|---|---|---|
| 9,370,629 | B2 | 6/2016 | Damani et al. |
| 9,388,395 | B2 | 7/2016 | Nazor et al. |
| 9,549,942 | B2 | 1/2017 | Jo et al. |
| 9,687,487 | B2 | 6/2017 | Hodges et al. |
| 10,064,856 | B2 | 9/2018 | Bosse et al. |
| 10,519,175 | B2 | 12/2019 | Londesbrough et al. |
| 10,550,140 | B2 | 2/2020 | Wiles et al. |
| 10,947,257 | B2 | 3/2021 | Londesbrough et al. |
| 10,954,259 | B1 | 3/2021 | Londesbrough et al. |
| 11,149,044 | B2 | 10/2021 | Londesbrough et al. |
| 11,180,517 | B2 | 11/2021 | Londesbrough et al. |
| 11,242,318 | B2 | 2/2022 | Nivorozhkin et al. |
| 11,292,765 | B2 | 4/2022 | Bryson |
| 11,332,441 | B2 | 5/2022 | Chadeayne |
| 11,406,619 | B2 | 8/2022 | Layzell et al. |
| 11,447,510 | B2 | 9/2022 | Londesbrough et al. |
| 11,478,449 | B1 | 10/2022 | Witowski et al. |
| 11,518,742 | B2 | 12/2022 | Feilding-Mellen et al. |
| 11,518,743 | B2 | 12/2022 | Feilding-Mellen et al. |
| 11,591,353 | B2 | 2/2023 | Slassi et al. |
| 11,602,521 | B2 | 3/2023 | Rao et al. |
| 11,603,353 | B2 | 3/2023 | Feilding-Mellen et al. |
| 11,643,391 | B2 | 5/2023 | Perni et al. |
| 11,680,044 | B2 | 6/2023 | Feilding-Mellen et al. |
| 11,759,452 | B2 | 9/2023 | Witowski et al. |
| 11,773,063 | B1 | 10/2023 | Gray et al. |
| 11,980,605 | B1 | 5/2024 | Gray |
| 12,012,381 | B2 | 6/2024 | Perni et al. |
| 12,053,453 | B2 | 8/2024 | Witowski et al. |
| 12,065,405 | B2 | 8/2024 | Perni |
| 12,128,027 | B2 | 10/2024 | Rao et al. |
| 12,246,005 | B2 | 3/2025 | Gray |
| 12,264,131 | B2 | 4/2025 | Gray et al. |
| 12,378,194 | B2 | 8/2025 | Short et al. |
| 12,396,982 | B2 | 8/2025 | Witowski et al. |
| 12,472,163 | B2 | 11/2025 | Witowski et al. |
| 12,534,441 | B2 | 1/2026 | Muratore et al. |
| 2002/0037887 | A1 | 3/2002 | Pintor et al. |
| 2002/0052370 | A1 | 5/2002 | Barber et al. |
| 2002/0115715 | A1 | 8/2002 | Dax et al. |
| 2003/0079301 | A1 | 5/2003 | Sauter et al. |
| 2004/0235899 | A1 | 11/2004 | Maria Assunta et al. |
| 2005/0019411 | A1 | 1/2005 | Colombo et al. |
| 2005/0068062 | A1 | 3/2005 | Yamasaki et al. |
| 2005/0088924 | A1 | 4/2005 | Hatanaka et al. |
| 2005/0152858 | A1 | 7/2005 | Bertz et al. |
| 2005/0227384 | A1 | 10/2005 | Nagano et al. |
| 2005/0245594 | A1 | 11/2005 | Sutter et al. |
| 2005/0250839 | A1 | 11/2005 | Marnett et al. |
| 2006/0016440 | A1 | 1/2006 | Labbe |
| 2006/0204159 | A1 | 9/2006 | Yoon |
| 2007/0082267 | A1 | 4/2007 | Goodenough et al. |
| 2007/0099909 | A1 | 5/2007 | Chen et al. |
| 2007/0140977 | A1 | 6/2007 | Yoneto et al. |
| 2008/0015181 | A1 | 1/2008 | Roberts et al. |
| 2008/0069235 | A1 | 3/2008 | Abe et al. |
| 2008/0093385 | A1 | 4/2008 | Yui |
| 2008/0248511 | A1 | 10/2008 | Daily et al. |
| 2008/0293695 | A1 | 11/2008 | Bristol et al. |
| 2008/0306025 | A1 | 12/2008 | Yu et al. |
| 2008/0318957 | A1 | 12/2008 | Glinka et al. |
| 2009/0221549 | A1 | 9/2009 | Gerber et al. |
| 2009/0258053 | A1 | 10/2009 | Horvers |
| 2010/0113539 | A1 | 5/2010 | Scott et al. |
| 2010/0114194 | A1 | 5/2010 | Bharmi et al. |
| 2010/0152108 | A1 | 6/2010 | Hung et al. |
| 2010/0166889 | A1 | 7/2010 | Sanfilippo |
| 2011/0245215 | A1 | 10/2011 | Carrara et al. |
| 2012/0028995 | A1 | 2/2012 | Ansorge et al. |
| 2012/0108510 | A1 | 5/2012 | Young et al. |
| 2012/0122948 | A1 | 5/2012 | Soubhye et al. |
| 2013/0129812 | A1 | 5/2013 | Ozpolat et al. |
| 2015/0071994 | A1 | 3/2015 | Schentag et al. |
| 2015/0284365 | A1 | 10/2015 | Elder et al. |
| 2015/0346226 | A1 | 12/2015 | McConnell et al. |
| 2016/0002195 | A1 | 1/2016 | Makriyannis et al. |
| 2016/0074411 | A1 | 3/2016 | Krumpl |
| 2016/0106694 | A1 | 4/2016 | Roberts et al. |
| 2016/0296957 | A1 | 10/2016 | Baillet et al. |
| 2016/0303079 | A1 | 10/2016 | Hung |
| 2017/0348303 | A1 | 12/2017 | Bosse et al. |
| 2017/0360772 | A1 | 12/2017 | Bosse et al. |
| 2018/0021326 | A1 | 1/2018 | Stamets |
| 2018/0147142 | A1 | 5/2018 | Knight |
| 2018/0221396 | A1 | 8/2018 | Chadeayne |
| 2019/0119310 | A1 | 4/2019 | Londesbrough et al. |
| 2019/0315689 | A1 | 10/2019 | Chen et al. |
| 2019/0345103 | A1 | 11/2019 | Batchelor et al. |
| 2020/0179349 | A1 | 6/2020 | Yun et al. |
| 2020/0187777 | A1 | 6/2020 | Luderer et al. |
| 2020/0199119 | A1 | 6/2020 | Thompson et al. |
| 2020/0325124 | A1 | 10/2020 | LaVoie et al. |
| 2020/0331939 | A1 | 10/2020 | Londesbrough et al. |
| 2020/0390746 | A1 | 12/2020 | Rands et al. |
| 2020/0397752 | A1 | 12/2020 | Perez Castillo et al. |
| 2021/0015738 | A1 | 1/2021 | LaRosa et al. |
| 2021/0058956 | A1 | 2/2021 | Chatterjee et al. |
| 2021/0069170 | A1 | 3/2021 | Stamets |
| 2021/0085671 | A1 | 3/2021 | Chadeayne |
| 2021/0087212 | A1 | 3/2021 | Londesbrough et al. |
| 2021/0108238 | A1 | 4/2021 | Protzko |
| 2021/0145851 | A1 | 5/2021 | Stamets |
| 2021/0155642 | A1 | 5/2021 | Londesbrough et al. |
| 2021/0236523 | A1 | 8/2021 | Schindler et al. |
| 2021/0246152 | A1 | 8/2021 | Londesbrough et al. |
| 2021/0277433 | A1 | 9/2021 | Protzko |
| 2021/0292278 | A1 | 9/2021 | Chadeayne |
| 2021/0322306 | A1 | 10/2021 | Espinoza et al. |
| 2021/0322447 | A1 | 10/2021 | Plakogiannis et al. |
| 2021/0322743 | A1 | 10/2021 | Rinti et al. |
| 2021/0346347 | A1 | 11/2021 | Witowski et al. |
| 2021/0353615 | A1 | 11/2021 | Chadeayne |
| 2021/0363104 | A1 | 11/2021 | Nivorozhkin et al. |
| 2021/0378969 | A1 | 12/2021 | Rands et al. |
| 2021/0395201 | A1 | 12/2021 | Rands et al. |
| 2021/0403425 | A1 | 12/2021 | Bryson |
| 2022/0015749 | A1 | 1/2022 | Sanders et al. |
| 2022/0024956 | A1 | 1/2022 | Slassi et al. |
| 2022/0031662 | A1 | 2/2022 | Terwey |
| 2022/0062238 | A1 | 3/2022 | Layzell et al. |
| 2022/0071958 | A1 | 3/2022 | Terwey |
| 2022/0073548 | A1 | 3/2022 | Londesbrough et al. |
| 2022/0079881 | A1 | 3/2022 | Modi |
| 2022/0096504 | A1 | 3/2022 | Blumstock et al. |
| 2022/0152088 | A1 | 5/2022 | Becker et al. |
| 2022/0259147 | A1 | 8/2022 | Feilding-Mellen |
| 2022/0267267 | A1 | 8/2022 | Feilding-Mellen |
| 2022/0273628 | A1 | 9/2022 | Liechti et al. |
| 2022/0273644 | A1 | 9/2022 | Ribeiro et al. |
| 2022/0304980 | A1 | 9/2022 | Arnold et al. |
| 2022/0339139 | A1 | 10/2022 | Rao et al. |
| 2022/0354824 | A1 | 11/2022 | Witowski et al. |
| 2022/0362237 | A1 | 11/2022 | Barrow et al. |
| 2022/0362491 | A1 | 11/2022 | Petit et al. |
| 2022/0388956 | A1 | 12/2022 | Short et al. |
| 2022/0396552 | A1 | 12/2022 | Feilding-Mellen et al. |
| 2023/0031944 | A1 | 2/2023 | Feilding-Mellen et al. |
| 2023/0041584 | A1 | 2/2023 | Perni et al. |
| 2023/0066720 | A1 | 3/2023 | Perni et al. |
| 2023/0075124 | A1 | 3/2023 | Terwey |
| 2023/0094051 | A1 | 3/2023 | Antalich Raibar |
| 2023/0099972 | A1 | 3/2023 | Rao et al. |
| 2023/0126298 | A1 | 4/2023 | Nivorozhkin et al. |
| 2023/0136824 | A1 | 5/2023 | Rao et al. |
| 2023/0227407 | A1 | 7/2023 | Perni et al. |
| 2023/0227421 | A1 | 7/2023 | Perni et al. |
| 2023/0233537 | A1 | 7/2023 | Dornbierer et al. |
| 2023/0310374 | A1 | 10/2023 | Rao et al. |
| 2023/0321039 | A1 | 10/2023 | Rao et al. |
| 2023/0322735 | A1 | 10/2023 | Kruegel |
| 2023/0348381 | A1 | 11/2023 | Feilding-Mellen et al. |
| 2023/0357146 | A1 | 11/2023 | Perni et al. |
| 2023/0372295 | A1 | 11/2023 | Witowski et al. |
| 2023/0382858 | A1 | 11/2023 | Feilding-Mellen et al. |

(56) References Cited

U.S. PATENT DOCUMENTS

| | | | |
|---|---|---|---|
| 2024/0101514 | A1 | 3/2024 | Gray et al. |
| 2024/0116896 | A1 | 4/2024 | Khan et al. |
| 2024/0199544 | A1 | 6/2024 | Fawaz et al. |
| 2024/0285578 | A1 | 8/2024 | Spector et al. |
| 2024/0287107 | A1 | 8/2024 | Khan |
| 2024/0307350 | A1 | 9/2024 | Terwey |
| 2024/0400511 | A1 | 12/2024 | Perni et al. |
| 2024/0415811 | A1 | 12/2024 | Gray |
| 2025/0002457 | A1 | 1/2025 | Yacoub et al. |
| 2025/0041273 | A1 | 2/2025 | Witowski et al. |
| 2025/0064783 | A1 | 2/2025 | Witowski et al. |
| 2025/0100975 | A1 | 3/2025 | Muratore et al. |
| 2025/0163044 | A1 | 5/2025 | Banister et al. |
| 2025/0193970 | A1 | 6/2025 | Gray |
| 2025/0235428 | A1 | 7/2025 | Witowski et al. |
| 2025/0388538 | A1 | 12/2025 | Fawaz et al. |
| 2026/0027082 | A1 | 1/2026 | Craig et al. |
| 2026/0035334 | A1 | 2/2026 | Gray |
| 2026/0041667 | A1 | 2/2026 | Rudd Gretton |

FOREIGN PATENT DOCUMENTS

| | | | |
|---|---|---|---|
| CN | 102816103 | A | 12/2012 |
| CN | 103249407 | A | 8/2013 |
| CN | 103816150 | A | 5/2014 |
| CN | 113288883 | A | 8/2021 |
| DE | 2617738 | A1 | 11/1976 |
| EP | 0008802 | A1 | 3/1980 |
| EP | 0026899 | A1 | 4/1981 |
| EP | 0131301 | A2 | 1/1985 |
| EP | 0821957 | A2 | 2/1998 |
| EP | 1336602 | A1 | 8/2003 |
| EP | 0933093 | B1 | 9/2003 |
| EP | 2067780 | A1 | 6/2009 |
| EP | 1884254 | B1 | 12/2010 |
| EP | 3868364 | A1 | 8/2021 |
| EP | 3941583 | A1 | 1/2022 |
| EP | 4159192 | A1 | 4/2023 |
| EP | 4159201 | A1 | 4/2023 |
| EP | 3927337 | B1 | 2/2024 |
| GB | 912715 | A | 12/1962 |
| GB | 981192 | A | 1/1965 |
| GB | 1410349 | A | 10/1975 |
| GB | 1584464 | A | 2/1981 |
| GB | 2588505 | A | 4/2021 |
| GB | 2596884 | A | 1/2022 |
| KR | 20020056818 | A | 7/2002 |
| KR | 20180103379 | A | 9/2018 |
| WO | WO-8100961 | A1 | 4/1981 |
| WO | WO-1981000961 | A1 | 4/1981 |
| WO | WO-9506638 | A1 | 3/1995 |
| WO | WO-1995024200 | A1 | 9/1995 |
| WO | WO-9617842 | A1 | 6/1996 |
| WO | WO-1997043281 | A1 | 11/1997 |
| WO | WO-0041755 | A1 | 7/2000 |
| WO | WO-0051672 | A1 | 9/2000 |
| WO | WO-2001015677 | A2 | 3/2001 |
| WO | WO-0211800 | A2 | 2/2002 |
| WO | WO-0115677 | A3 | 3/2002 |
| WO | WO-2002038142 | A2 | 5/2002 |
| WO | WO-02068029 | A2 | 9/2002 |
| WO | WO-02068030 | A2 | 9/2002 |
| WO | WO-02068031 | A2 | 9/2002 |
| WO | WO-02068032 | A2 | 9/2002 |
| WO | WO-2002083144 | A1 | 10/2002 |
| WO | WO-03000310 | A2 | 1/2003 |
| WO | WO-03009240 | A1 | 1/2003 |
| WO | WO-2003009240 | A1 | 1/2003 |
| WO | WO-03020350 | A1 | 3/2003 |
| WO | WO-03026559 | A2 | 4/2003 |
| WO | WO-03082393 | A1 | 10/2003 |
| WO | WO-03084591 | A1 | 10/2003 |
| WO | WO-03090812 | A2 | 11/2003 |
| WO | WO-2004000849 | A2 | 12/2003 |
| WO | WO-2004043462 | A1 | 5/2004 |
| WO | WO-2004085392 | A1 | 10/2004 |
| WO | WO-2004089915 | A1 | 10/2004 |
| WO | WO-2006099416 | A1 | 9/2006 |
| WO | WO-2006105615 | A1 | 10/2006 |
| WO | WO-2008003028 | A2 | 1/2008 |
| WO | WO-2009071607 | A2 | 6/2009 |
| WO | WO-2010054202 | A2 | 5/2010 |
| WO | WO-2010151258 | A1 | 12/2010 |
| WO | WO-2011041870 | A1 | 4/2011 |
| WO | WO-2012045118 | A1 | 4/2012 |
| WO | WO-2012173701 | A1 | 12/2012 |
| WO | WO-2013063492 | A1 | 5/2013 |
| WO | WO-2013191704 | A1 | 12/2013 |
| WO | WO-2015106025 | A1 | 7/2015 |
| WO | WO-2016118541 | A1 | 7/2016 |
| WO | WO-2016145193 | A1 | 9/2016 |
| WO | WO-2017172957 | A1 | 10/2017 |
| WO | WO-2018064465 | A1 | 4/2018 |
| WO | WO-2018081456 | A1 | 5/2018 |
| WO | WO-2018094106 | A2 | 5/2018 |
| WO | WO-2018148605 | A1 | 8/2018 |
| WO | WO-2018195455 | A1 | 10/2018 |
| WO | WO-2019016071 | A1 | 1/2019 |
| WO | WO-2019064031 | A1 | 4/2019 |
| WO | WO-2019073379 | A1 | 4/2019 |
| WO | WO-2019081764 | A1 | 5/2019 |
| WO | WO-2019173797 | A1 | 9/2019 |
| WO | WO-2019213551 | A1 | 11/2019 |
| WO | WO-2019246532 | A1 | 12/2019 |
| WO | WO-2020023084 | A1 | 1/2020 |
| WO | WO-2020037372 | A1 | 2/2020 |
| WO | WO-2020157569 | A1 | 8/2020 |
| WO | WO-2020169850 | A1 | 8/2020 |
| WO | WO-2020169851 | A1 | 8/2020 |
| WO | WO-2020176597 | A1 | 9/2020 |
| WO | WO-2020181194 | A1 | 9/2020 |
| WO | WO-2020212948 | A1 | 10/2020 |
| WO | WO-2020212951 | A1 | 10/2020 |
| WO | WO-2021003467 | A1 | 1/2021 |
| WO | WO-2021005308 | A2 | 1/2021 |
| WO | WO-2021030571 | A1 | 2/2021 |
| WO | WO-2021041407 | A1 | 3/2021 |
| WO | WO-2021076572 | A1 | 4/2021 |
| WO | WO-2021089872 | A1 | 5/2021 |
| WO | WO-2021111098 | A1 | 6/2021 |
| WO | WO-2021155468 | A1 | 8/2021 |
| WO | WO-2021155470 | A1 | 8/2021 |
| WO | WO-2021168082 | A1 | 8/2021 |
| WO | WO-2021170614 | A1 | 9/2021 |
| WO | WO-2021175816 | A1 | 9/2021 |
| WO | WO-2021179091 | A1 | 9/2021 |
| WO | WO-2021188782 | A1 | 9/2021 |
| WO | WO-2021209815 | A1 | 10/2021 |
| WO | WO-2021222885 | A1 | 11/2021 |
| WO | WO-2021225796 | A1 | 11/2021 |
| WO | WO-2021226041 | A1 | 11/2021 |
| WO | WO-2021226416 | A1 | 11/2021 |
| WO | WO-2021244831 | A1 | 12/2021 |
| WO | WO-2021250434 | A1 | 12/2021 |
| WO | WO-2021250435 | A1 | 12/2021 |
| WO | WO-2021253116 | A1 | 12/2021 |
| WO | WO-2021259962 | A1 | 12/2021 |
| WO | WO-2022000091 | A1 | 1/2022 |
| WO | WO-2022008627 | A2 | 1/2022 |
| WO | WO-2022016289 | A1 | 1/2022 |
| WO | WO-2022038299 | A1 | 2/2022 |
| WO | WO-2022051670 | A1 | 3/2022 |
| WO | WO-2022061242 | A1 | 3/2022 |
| WO | WO-2022082058 | A1 | 4/2022 |
| WO | WO-2022094719 | A1 | 5/2022 |
| WO | WO-2022104475 | A1 | 5/2022 |
| WO | WO-2022109050 | A1 | 5/2022 |
| WO | WO-2022117359 | A1 | 6/2022 |
| WO | WO-2022123128 | A1 | 6/2022 |
| WO | WO-2022123232 | A1 | 6/2022 |
| WO | WO-2022125616 | A1 | 6/2022 |
| WO | WO-2022133314 | A1 | 6/2022 |
| WO | WO-2022150675 | A1 | 7/2022 |
| WO | WO-2022153266 | A1 | 7/2022 |

(56) References Cited

FOREIGN PATENT DOCUMENTS

| | | | |
|---|---|---|---|
| WO | WO-2022153268 | A1 | 7/2022 |
| WO | WO-2022160056 | A1 | 8/2022 |
| WO | WO-2022170438 | A1 | 8/2022 |
| WO | WO-2022170442 | A1 | 8/2022 |
| WO | WO-2022171969 | A1 | 8/2022 |
| WO | WO-2022175821 | A1 | 8/2022 |
| WO | WO-2022189662 | A1 | 9/2022 |
| WO | WO-2022195011 | A1 | 9/2022 |
| WO | WO-2022195489 | A2 | 9/2022 |
| WO | WO-2022207746 | A1 | 10/2022 |
| WO | WO-2022208014 | A1 | 10/2022 |
| WO | WO-2022232179 | A1 | 11/2022 |
| WO | WO-2022235514 | A1 | 11/2022 |
| WO | WO-2022235529 | A1 | 11/2022 |
| WO | WO-2022243285 | A1 | 11/2022 |
| WO | WO-2022246572 | A1 | 12/2022 |
| WO | WO-2022251351 | A1 | 12/2022 |
| WO | WO-2022261383 | A1 | 12/2022 |
| WO | WO-2022271969 | A2 | 12/2022 |
| WO | WO-2023002005 | A1 | 1/2023 |
| WO | WO-2023283386 | A2 | 1/2023 |
| WO | WO-2023021112 | A1 | 2/2023 |
| WO | WO-2023028086 | A1 | 3/2023 |
| WO | WO-2023036473 | A1 | 3/2023 |
| WO | WO-2023050010 | A1 | 4/2023 |
| WO | WO-2023055992 | A1 | 4/2023 |
| WO | WO-2023076135 | A1 | 5/2023 |
| WO | WO-2023076150 | A1 | 5/2023 |
| WO | WO-2023078604 | A1 | 5/2023 |
| WO | WO-2023111544 | A2 | 6/2023 |
| WO | WO-2023114557 | A2 | 6/2023 |
| WO | WO-2023115166 | A1 | 6/2023 |
| WO | WO-2023129956 | | 7/2023 |
| WO | WO-2023186797 | A1 | 10/2023 |
| WO | WO-2023186798 | A1 | 10/2023 |
| WO | WO-2023186806 | A1 | 10/2023 |
| WO | WO-2023186808 | A1 | 10/2023 |
| WO | WO-2023186816 | A1 | 10/2023 |
| WO | WO-2023186820 | A1 | 10/2023 |
| WO | WO-2023186821 | A1 | 10/2023 |
| WO | WO-2023186823 | A1 | 10/2023 |
| WO | WO-2023186824 | A1 | 10/2023 |
| WO | WO-2023186826 | A1 | 10/2023 |
| WO | WO-2023186827 | A1 | 10/2023 |
| WO | WO-2023186828 | A1 | 10/2023 |
| WO | WO-2023186829 | A1 | 10/2023 |
| WO | WO-2023186830 | A1 | 10/2023 |
| WO | WO-2023186831 | A1 | 10/2023 |
| WO | WO-2023186832 | A1 | 10/2023 |
| WO | WO-2023186834 | A1 | 10/2023 |
| WO | WO-2023186835 | A1 | 10/2023 |
| WO | WO-2023186837 | A1 | 10/2023 |
| WO | WO-2024010537 | A1 | 1/2024 |
| WO | WO-2024020361 | A2 | 1/2024 |
| WO | WO-2024054866 | A2 | 3/2024 |
| WO | WO-2024092106 | A2 | 5/2024 |
| WO | WO-2024105379 | A1 | 5/2024 |
| WO | WO-2024108195 | A1 | 5/2024 |
| WO | WO-2024118767 | A2 | 6/2024 |
| WO | WO-2024119075 | A1 | 6/2024 |
| WO | WO-2024130140 | A2 | 6/2024 |
| WO | WO-2024130140 | A3 | 7/2024 |
| WO | WO-2024146917 | A1 | 7/2024 |
| WO | WO-2024160389 | A1 | 8/2024 |
| WO | WO-2024160390 | A1 | 8/2024 |
| WO | WO-2024160391 | A1 | 8/2024 |
| WO | WO-2024160392 | A1 | 8/2024 |
| WO | WO-2024173954 | A2 | 8/2024 |
| WO | WO-2024224115 | A1 | 10/2024 |
| WO | WO-2024227149 | A2 | 10/2024 |
| WO | WO-2024243488 | A2 | 11/2024 |
| WO | WO-2024256821 | A1 | 12/2024 |
| WO | WO-2025019800 | A1 | 1/2025 |
| WO | WO-2025024637 | A1 | 1/2025 |
| WO | WO-2025054397 | A1 | 3/2025 |
| WO | WO-2025068714 | A1 | 4/2025 |
| WO | WO-2025076151 | A1 | 4/2025 |
| WO | WO-2025083212 | A1 | 4/2025 |
| WO | WO-2025137581 | A1 | 6/2025 |
| WO | WO-2025170990 | A1 | 8/2025 |

OTHER PUBLICATIONS

Acasta Gneiss, “information on IV/IM HCl doses needed.” 5 Hive forums.5meodmt.org, [Online] (Sep. 11, 2017); Retrieved from Internet Archive Wayback Machine at: [https://web.archive.org/web/20240108165249/https://forums.5meodmt.org/index.php/topic,50525.msg54571.html#msg54571] on [Oct. 27, 2025]; 5 pages.

Acosta-Urquidi, “EEG studies of the acute effects of 5-MeO-DMT.” World Bufo Alvarius Conference, Mexico, Jul. 27-29, 2018, presentation, 31 pages.

Aghajanian, G K, “LSD and 2-bromo-LSD: comparison on effects on serotonergic neurones and on neurones in two serotonergic projection areas, the ventral lateral geniculate and amygdala.” Neuropharmacology. Sep. 1976;15(9):521-8. doi: 10.1016/0028-3908(76)90102-7.

Agurell et al., “Alkaloid Content of Banisteriopsis Rusbyana.” American Journal of Pharmacy and the Sciences Supporting Public Health. Sep.-Oct. 1968;140(5):148-51.

Alexander et al., “Preclinical models for evaluating psychedelics in the treatment of major depressive disorder.” Br J Pharmacol. Oct. 28, 2024. doi: 10.1111/bph.17370, 22 pages.

American Journal of Managed Care, “Dr. Michael Thase on the Prevalence of Stigma Surrounding Major Depressive Disorder,” [Video] American Journal of Managed Care (AJMC) Psych Congress Conference, (Nov. 19, 2018) [retrieved on unknown date from https://www.ajmc.com/view/dr-michael-thase-on-the-prevalence-of-stigma-surrounding-major-depressive-disorder]; 6 pages.

Andersson, M. et al., “Psychoactive substances as a last resort—a qualitative study of self-treatment of migraine and cluster headaches,” Harm Reduction Journal, 14:60 (Sep. 5, 2017), DOI:10.1186/s12954-017-0186-6, 11 pages.

Anonymous, “Self served Bufo and set my soul free,” Reveddit.com, comment in forum post, [Online] (Sep. 2019); [Retrieved from the internet on Oct. 27, 2025 from URL: https://www.reveddit.com/v/5MeODMT/comments/daiff3/self_served_bufo_and_set_my_soul_free/f1pwdof/?utm_source=share&utm_medium=web2x&context=3]; 2 pages.

Anonymous, “The God Molecule.” Reddit, forum post comment, [Online] (Nov. 17, 2019) [retrieved from the internet on Nov. 24, 2025 at URL: https://www.reveddit.com/v/5MeODMT/comments/dxtdcx/the_god_molecule/f7w0yi7/?utm_source=share&utm_medium=web2x&context=3]; 1 page.

Anonymous, “The Sonoran Desert Toad, Bufo alvarius.” EROWID.org, [Online] (Oct. 18, 2017); retrieved from Internet Archive Wayback Machine at URL: [https://web.archive.org/web/20171018062456/http://www.erowid.org:80/archive/sonoran_desert_toad/5meo.htm] on [Oct. 1, 2025]; 5 pages.

APA, Archived version of the American Psychiatric Association website page “What Is Depression” [Online] (2018), Retrieved from Internet Archive Wayback Machine at: [https://web.archive.org/web/20190117034902/https://www.psychiatry.org/patients-families/depression/what-is-depression] on [Jan. 17, 2019]; 4 pages.

APA, “Diagnostic and Statistical Manual of Mental Disorders, Fifth Edition, DSM-5.” American Psychiatric Association, Jun. 2013, p. 5-15, 19-25, 155-188, 271-281, 36 pages.

Araujo et al., “The hallucinogenic world of tryptamines: an updated review.” Arch Toxicol. Aug. 2015; 89(8): 1151-73.

Archer et al., “5-Methoxy-N, N-dimethyltryptamine-induced analgesia is blocked by alpha-adrenoceptor antagonists in rats.” Br J Pharmacol. Oct. 1986;89(2):293-8. doi: 10.1111/j.1476-5381.1986.tb10259.x.

Australian and New Zealand Clinical Trials Registry, Identifier ACTRN12622000851763. “A phase 1,First-in-Human, open-label, Safety, Tolerability and Pharmacokinetic Study of Single-Ascending Doses of VLS-01 in Healthy Adult Volunteers.” [Internet]: Sydney (NSW): NHMRC Clinical Trials Centre, University of

(56) References Cited

OTHER PUBLICATIONS

Sydney Australia; (Jun. 16, 2022); last updated Nov. 14, 2022. [Retrieved from the Internet Oct. 24, 2025, from https://www.anzctr.org.au/Trial/Registration/TrialReview.aspx?id=383956&isReview=true]; 6 pages.
Australian and New Zealand Clinical Trials Registry, Identifier ACTRN12624000025538. "A Phase 1b, Single-Centre, Open-Label Dose Ranging Study of an Optimized Formulation of VLS-01 in Healthy Adult Volunteers." [Internet]: Sydney (NSW): NHMRC Clinical Trials Centre, University of Sydney Australia; (Jan. 12, 2024); last updated Oct. 6, 2025. [Retrieved from the Internet Oct. 24, 2025, from https://www.anzctr.org.au/Trial/Registration/TrialReview.aspx?id=386607&isReview=true]; 6 pages.
Australian and New Zealand Clinical Trials Registry, Identifier NCT06524830. "A Phase 2, Multicenter, Double-blind, Randomized, Placebo-controlled Trial to Assess the Efficacy, Safety, and Tolerability of Repeated Doses of VLS-01 Buccal Film in Participants With Treatment Resistant Depression." [Internet]: Sydney (NSW): NHMRC Clinical Trials Centre, University of Sydney Australia; (Jul. 29, 2024); last updated Oct. 2, 2025. [Retrieved from the Internet Oct. 24, 2025, from https://www.anzctr.org.au/Trial/Registration/TrialReview.aspx?id=24321&isClinicalTrial=True]; 6 pages.
Baker et al., "Neurochemical and neuropharmacological investigation of N-cyanoethyltryptamine, a potential prodrug of tryptamine." Proceedings of the Western Pharmacology Society, Jan. 1, 1987, 30:307-311.
Baker et al., "Neuropharmacological and Neurochemical Properties of N-(2-Cyanoethyl)-2-Phenylethylamine, a Prodrug of 2-Phenylethylamine." Br J Pharmacol. Oct. 1987; 92(2): 243-55.
Banker, G. S., et al, "Modern Pharmaceutics," Third Edition, Revised, and Expanded, Marcel Dekker, Inc. (Jun. 1996); pp. 451 and 596; 3 pages.
Barker, "Administration of N,N-dimethyltryptamine (DMT) in psychedelic therapeutics and research and the study of endogenous DMT." Psychopharmacology (Berl). Jun. 2022; 239(6): 1749-1763. Epub Jan. 22, 2022, with erratum, 16 pages.
Barker, "N, N-Dimethyltryptamine (DMT), an Endogenous Hallucinogen: Past, Present, and Future Research to Determine Its Role and Function." Front Neurosci. Aug. 6, 2018:12:536. doi: 10.3389/fnins.2018.00536. eCollection 2018. 17 pages.
Barrett (2017) "The Challenging Experience Questionnaire: Characterization of challenging experiences with psilocybin mushrooms." J Psychopharmacol. Dec. 2016;30(12):1279-1295. doi: 10.1177/0269881116678781. Epub Nov. 17, 2016.
Barrett et al., "Qualitative and Quantitative Features of Music Reported to Support Peak Mystical Experiences during Psychedelic Therapy Sessions." Front Psychol. Jul. 25, 2017:8:1238. doi: 10.3389/fpsyg.2017.01238. eCollection 2017, 12 pages.
Barrett et al. "Validation of the revised Mystical Experience Questionnaire in experimental sessions with psilocybin." Journal of Psychopharmacology. Nov. 2015; 29(11): 1182-1190. doi: 10.1177/0269881115609019.
Barsuglia et al., "Intensity of mystical experiences occasioned by 5-MeO-DMT and comparison with a prior psilocybin study." Front Psychol. Dec. 6, 2018: 9: 2459. doi: 10.3389/fpsyg.2018.02459. eCollection 2018. 6 pages.
Baumeister et al. "Classical hallucinogens as antidepressants? A review of pharmacodynamics and putative clinical roles." Therapeutic Advances in Psychopharmacology. Aug. 2014;4(4):156-169. doi: 10.1177/2045125314527985.
Beliveau, et al., "A High-Resolution In Vivo Atlas of the Human Brain's Serotonin System," J Neurosci. Jan. 4, 2017; 37(1):120-128.
Belser, et al., "Patient Experiences of Psilocybin-Assisted Psychotherapy: An Interpretative Phenomenological Analysis," Journal of Humanistic Psychology Apr. 2017; vol. 57(4):354-388.
Benneyworth, et al., Complex discriminative stimulus properties of (+) lysergic acid diethylamide (LSD) in C57BI/6J mice, Psychopharmacology, Jun. 2005, pp. 854-862.
Berge et al. "Pharmaceutical salts." J Pharm Sci. Jan. 1977; 66(1):1-19.
Bergin, "Preliminary X-ray crystallographic study of some psychoactive indole bases." Acta Cryst. (Jun. 1968). B24, 882, https://doi.org/10.1107/S0567740868003353, 1 page.
Bergin, "The structure of the catecholamines. II. The crystal structure of dopamine hydrochloride." Acta Crystallogr B Struct Crystallogr Cryst Chem. Nov. 15, 1968;24(11):1506-10. doi: 10.1107/s0567740868004553.
Bibi et al., "Use of Permeapad® for prediction of buccal absorption: A comparison to in vitro, ex vivo and in vivo method." Eur J Pharm Sci. Oct. 10, 2016:93:399-404. doi:10.1016/j.ejps.2016.08.041. Epub Aug. 24, 2016.
Biffhenderson, forum post in thread titled: "The Big & Dandy 5-MeO-DMT Thread—Second Launch." [Online] bluelight.org (May 2012) available at: [https://bluelight.org/xf/threads/the-big-dandy-5-meo-dmt-thread-second-launch.599032/post-10587079]; retrieved from Internet Archive Wayback Machine at URL: [https://web.archive.org/web/20240120193627/https://bluelight.org/xf/threads/the-big-dandy-5-meo-dmt-thread-second-launch.599032/page-2#post-10587079] on [Sep. 30, 2025]; 2 pages.
Birnbaum et al., "Employer burden of mild, moderate, and severe major depressive disorder: mental health services utilization and costs, and work performance." Depress Anxiety. 2010;27(1):78-89. doi: 10.1002/da.20580, Epub Jun. 30, 2009.
Blinny, "Cranial Chomping 5-MeO-DMT," [Online] Erowid Experience Vaults, (Aug. 29, 2003); Retrieved from Internet Archive Wayback Machine at URL: [https://web.archive.org/web/20070607053411/https://erowid.org/experiences/exp.php?ID=26469 on [Oct. 1, 2025]; 2 pages.
Blough, B. E., et al., "Alpha-ethyltryptamines as dual dopamine-serotonin releasers." Bioorganic & Medicinal Chemistry Letters (2014); 24(19): 4754-4758. doi: 10.1016/j.bmcl.2014.07.062. Epub Jul. 29, 2014.
Brandt et al., "Analytical methods for psychoactive N,N-dialkylated tryptamines." Trends in Analytical Chemistry, vol. 29, No. 8, Sep. 2010, pp. 858-869.
Brandt et al., "Characterization of the synthesis of N,N-dimethyltryptamine by reductive amination using gas chromatography ion trap mass spectrometry." Drug Test Anal. Jul. 2010; 2(7): 330-8. doi: 10.1002/dta.142.
Breaking Convention, "Rafael Lancelotta—5-MeO-DMT Use in the Global Population." [Video] Youtube.com, posted (Sep. 2019); available at: https://www.youtube.com/watch?v=7GSsqoKj0Vs] (accessed Sep. 30, 2025); 1 page.
Brito-Da-Costa, et al., "Toxicokinetics and toxicodynamics of ayahuasca alkaloids N, N-dimethyltryptamine (DMT), harmine, harmaline and tetrahydroharmine: clinical and forensic impact." Pharmaceuticals (Basel). Oct. 23, 2020; 13(11): 334. doi: 10.3390/ph13110334. 36 pages.
Buchwald, Peter, "Soft drugs: design principles, success stories, and future perspectives." Expert Opin Drug Metab Toxicol. Aug. 2020; 16(8): 645-650. Epub Jun. 20, 2020.
Bugaenko et al., "Synthesis of indoles: recent advances." Russ. Chem. Rev., Feb. 2019, 88 (2)99-159, 62 pages.
Cameron et al., "A non-hallucinogenic psychedelic analogue with therapeutic potential." Nature. Jan. 2021;589(7842):474-479. doi: 10.1038/s41586-020-3008-z. Epub Dec. 9, 2020, and Reporting Summary, 24 pages.
Cameron et al., "Chronic, Intermittent Microdoses of the Psychedelic N , N-Dimethyltryptamine (DMT) Produce Positive Effects on Mood and Anxiety in Rodents." ACS Chemical Neuroscience, vol. 10, No. 7, Jul. 17, 2019 (Jul. 17, 2019), pp. 3261-3270.
Cameron et al., "Effects of N, N-Dimethyltryptamine on Rat Behaviors Relevant to Anxiety and Depression." ACS Chem Neurosci, Jul. 18, 2018; 9(7): 1582-1590. Epub Apr. 24, 2018.
Canal CE. "Serotonergic psychedelics: experimental approaches for assessing mechanisms of action." In New Psychoactive Substances: Pharmacology, Clinical, Forensic and Analytical Toxicology, Springer International Publishing. Mar. 13, 2018; 227-260.
Canal et al. "Head-twitch response in rodents induced by the hallucinogen 2, 5dimethoxy4iodoamphetamine: a comprehensive

(56) References Cited

OTHER PUBLICATIONS history, a reevaluation of mechanisms, and its utility as a model." Drug Test Anal. Apr. 19, 2012;4(0):556-576. doi: 10.1002/dta.1333.
Carhart-Harris, et al., "LSD enhances suggestibility in healthy volunteers." Psychopharmacology (Berl). Feb. 2015;232(4):785-94. Epub Sep. 23, 2014, 10 pages.
Carhart-Harris et al., "Psilocybin for treatment-resistant depression: fMRI-measured brain mechanisms," Scientific Reports; 7(1):13187, (Oct. 2017), 11 pages.
Carhart-Harris, et al., "Psilocybin with psychological support for treatment-resistant depression: an open-label feasibility study," Lancet Psychiatry. Jul. 2016;3(7):619-27. Epub May 17, 2016.
Carhart-Harris et al. "Psilocybin with psychological support for treatment-resistant depression: six-month follow-up." Psychopharmacology. 235(2):399-408 (Feb. 2018). doi: 10.1007/s00213-017-4771-x.
Carhart-Harris et al. "The therapeutic potential of psychedelic drugs: past, present, and future." Neuropsychopharmacology. Oct. 2017;42(11):2105-2113. doi: 10.1038/npp.2017.84.
Carpenter, David E., "5-MeO-DMT: The 20-Minute Psychoactive Toad Experience That's Transforming Lives," Forbes.com [Online] (Feb. 2, 2020) updated Dec. 10, 2021, [retrieved on Sep. 30, 2025 from the Internet at: https://www.forbes.com/sites/davidcarpenter/2020/02/02/5-meo-dmt-the-20-minute-psychoactive-toad-experience-thats-transforming-lives/?sh=3b79337838a1]; 11 pages.
Carter et al., "Modulating the rate and rhythmicity of perceptual rivalry alternations with the mixed 5-HT2A and 5-HT1A agonist psilocybin." Neuropsychopharmacology. Jun. 2005; 30(6): 1154-62. doi: 10.1038/sj.npp.1300621.
Carvalho et al., "Mucoadhesive drug delivery systems," BJPS, vol. 46, n. 1, Jan./Mar. 2010. 18 pages.
CAS Registry No. 1152718-19-8, "Benzenemethanamine, N-[4-(1,1-dimethylethyl)cyclohexyl]-2,4-difluoro-alpha-methyl-", [Online Database] CAS Registry®, Chemical Abstracts Service, Columbus, OH. (Jun. 5, 2009), [Retrieved from Internet on unknown date at https://www.cas.org]; 1 page.
CAS Registry No. 1152826-22-6, "Benzenemethanamine, 5-bromo-N-[4-(1,1-dimethylpropyl)cyclohexyl]-2-fluoro-", [Online Database] Cas Registry®, Chemical Abstracts Service, Columbus, OH. (Jun. 7, 2009), [Retrieved from Internet on unknown date at https://www.cas.org]; 1 page.
CAS Registry No. 1154138-59-6, "Benzenemethanamine, N-[4-(1,1-dimethylpropyl)cyclohexyl]-2,5-difluoro-", [Online Database] Cas Registry®, Chemical Abstracts Service, Columbus, OH. (Jun. 9, 2009), [Retrieved from Internet on unknown date, at https://www.cas.org]; 1 page.
CAS Registry No. 127456-43-3, "Phenol, 2-[[[4-(1,1-dimethylethyl)cyclohexyl]amino]methyl]-4-(1,1-dimethylpropyl)-, trans-(9CI)", [Online Database] Cas Registry®, Chemical Abstracts Service, Columbus, OH. (Jun. 1, 1990), [Retrieved from Internet on unknown date, at https://www.cas.org]; 1 page.
CAS Registry No. 127456-44-4, "1H-Inden-5-ol, 6-[[[4-(1,1-dimethylethyl)cyclohexyl]amino]methyl]-2,3-dihydro-, trans-(9CI)", [Online Database] CAS Registry®, Chemical Abstracts Service, Columbus, OH. (Jun. 1, 1990), [Retrieved from Internet on unknown date, at https://www.cas.org]; 1 page.
CAS Registry No. 127456-45-5, "Phenol, 4-(1,1-dimethylethyl)-2-[[[4-(1,1-dimethylethyl)cyclohexyl]amino]methyl]-, trans-(9CI)", [Online Database] CAS Registry®, Chemical Abstracts Service, Columbus, OH. (Jun. 1, 1990), [Retrieved from Internet on unknown date, at https://www.cas.org]; 1 page.
CAS Registry No. 127456-46-6, "Phenol, 4-(1,1-dimethylethyl)-2-[[[4-(1,1-dimethylethyl) cyclohexyl]amino]methyl]-6-methyl-, hydrochloride, trans-(9CI)", [Online Database] CAS Registry®, Chemical Abstracts Service, Columbus, OH. (Jun. 1, 1990), [Retrieved from Internet on unknown date, at https://www.cas.org]; 1 page.
CAS Registry No. 127456-52-4, "Phenol, 2-[[[4-(1,1-dimethylethyl)cyclohexyl]amino]methyl]-4-(1-methylethyl)-, cis-(9CI)", [Online Database] CAS Registry®, Chemical Abstracts Service, Columbus, OH. (Jun. 1, 1990), [Retrieved from Internet on unknown date, at https://www.cas.org]; 1 page.
CAS Registry No. 127456-56-8, "Phenol, 4-chloro-2-[[[4-(1,1-dimethylethyl)cyclohexyl]amino]methyl]-, trans-(9CI)", [Online Database] CAS Registry®, Chemical Abstracts Service, Columbus, OH. (Jun. 1, 1990), [Retrieved from Internet on unknown date, at https://www.cas.org]; 1 page.
CAS Registry No. 127456-57-9, "Phenol, 2-[[[4-(1,1-dimethylethyl)cyclohexyl]amino]methyl]-4-fluoro-, trans-(9CI)", [Online Database] CAS Registry®, Chemical Abstracts Service, Columbus, OH. (Jun. 1, 1990), [Retrieved from Internet on Oct. 31, 2022, at https://www.cas.org]; 2 pages.
CAS Registry No. 1308467-14-2, "1,2-Benzenediol, 3-[[[4-(1,1-dimethylpropyl) cyclohexyl]amino]methyl]-", [Online Database] CAS Registry®, Chemical Abstracts Service, Columbus, OH. (Jun. 10, 2011), [Retrieved from Internet on unknown date, at https://www.cas.org]; 1 page.
CAS Registry No. 1405571-87-0, "Benzenemethanamine, 2-bromo-N-[4-(1,1-dimethylpropyl)cyclohexyl]-5-fluoro-", [Online Database] CAS Registry®, Chemical Abstracts Service, Columbus, OH. (Nov. 23, 2012), [Retrieved from Internet on unknown date, at https://www.cas.org]; 1 page.
CAS Registry No. 1406541-63-6, "Phenol, 2-chloro-4-[[[4-(1,1-dimethylpropyl)cyclohexyl]amino]methyl]-", [Online Database] CAS Registry®, Chemical Abstracts Service, Columbus, OH. (Nov. 25, 2012), [Retrieved from Internet on unknown date, at https://www.cas.org]; 1 page.
CAS Registry No. 1411655-23-6, "Benzenemethanamine, N-[4-(1,1-dimethylpropyl)cyclohexyl]-2,3-difluoro-", [Online Database] CAS Registry®, Chemical Abstracts Service, Columbus, OH. (Dec. 5, 2012), [Retrieved from Internet on unknown date, at https://www.cas.org]; 1 page.
CAS Registry No. 1456349-79-3, "Benzenemethanamine, 2,3-dichloro-N-[4-(1,1-dimethylpropyl)cyclohexyl]-", [Online Database] CAS Registry®, Chemical Abstracts Service, Columbus, OH. (Oct. 6, 2013), [Retrieved from Internet on unknown date, at https://www.cas.org]; 1 page.
CAS Registry No. 1458497-71-6, "Benzenemethanamine, 2,4-dichloro-N-[4-(1,1-dimethylethyl)cyclohexyl]-a-methyl-", [Online Database] CAS Registry®, Chemical Abstracts Service, Columbus, OH. (Oct. 15, 2013), [Retrieved from Internet on unknown date, at https://www.cas.org]; 1 page.
CAS Registry No. 1459328-13-2, "Phenol, 2-bromo-4-[[[4-(1,1-dimethylpropyl) cyclohexyl]amino]methyl]-", [Online Database] CAS Registry®, Chemical Abstracts Service, Columbus, OH. (Oct. 16, 2013), [Retrieved from Internet on unknown date, at https://www.cas.org]; 1 page.
CAS Registry No. 1490220-45-5, "Benzenemethanamine, 2-bromo-5-chloro-N-[4-(1,1-dimethylpropyl)cyclohexyl]-", [Online Database] CAS Registry®, Chemical Abstracts Service, Columbus, OH. (Dec. 8, 2013), [Retrieved from Internet on unknown date, at https://www.cas.org]; 1 page.
CAS Registry No. 1515984-46-9, "Benzamide, N-(4-aminocyclohexyl)-3-chloro-N,5-dimethyl-", [Online Database] CAS Registry®, Chemical Abstracts Service, Columbus, OH. (Jan. 10, 2014), [Retrieved from Internet on unknown date, at https://www.cas.org]; 1 page.
CAS Registry No. 1542027-51-9, "Phenol, 3-chloro-2-[[[4-(1,1-dimethylpropyl) cyclohexyl]amino]methyl]-", [Online Database] CAS Registry®, Chemical Abstracts Service, Columbus, OH. (Feb. 11, 2014), [Retrieved from Internet on unknown date, at https://www.cas.org]; 1 page.
CAS Registry No. 1624268-56-9, "Benzamide, 4-[[[4-(1,1-dimethylethyl)cyclohexyl]amino]methyl]-N-methyl-", [Online Database] CAS Registry®, Chemical Abstracts Service, Columbus, OH. (Sep. 22, 2014), [Retrieved from Internet on unknown date, at https://www.cas.org]; 1 page.
CAS Registry No. 1712122-27-4, Benzenemethanamine, 5-chloro-N-[4-(1,1-dimethylpropyl)cyclohexyl]-2-fluoro-, [Online Database] CAS Registry®, Chemical Abstracts Service, Columbus, OH. (May 25, 2015), [Retrieved from Internet on unknown date, at https://www.cas.org]; 1 page.
CAS Registry No. 1772618-27-5, "Phenol, 3-[[[4-(1,1-dimethylpropyl) cyclohexyl]amino]methyl]-5-fluoro-", [Online Data-

(56) References Cited

OTHER PUBLICATIONS base] CAS Registry®, Chemical Abstracts Service, Columbus, OH. (Jun. 3, 2015), [Retrieved from Internet on unknown date, at https://www.cas.org]; 1 page.
CAS Registry No. 1775706-37-0, "Phenol, 2-chloro-6-[[[4-(1,1-dimethylpropyl)cyclohexyl]amino]methyl]-", [Online Database] CAS Registry®, Chemical Abstracts Service, Columbus, OH. (Jun. 8, 2015), [Retrieved from Internet on unknown date, at https://www.cas.org]; 1 page.
CAS Registry No. 1858436-76-6, "Bicyclo[3.1.0]hexan-2-amine, N-[(3-chloro-5-methylphenyl)methyl]-", [Online Database] CAS Registry®, Chemical Abstracts Service, Columbus, OH. (Feb. 3, 2016), [Retrieved from Internet on unknown date, at https://www.cas.org]; 1 page.
CAS Registry No. 1931388-10-1, "Benzenemethanamine, 2,5-dichloro-N-[4-(1,1-dimethylpropyl)cyclohexyl]-", [Online Database] CAS Registry®, Chemical Abstracts Service, Columbus, OH. (Jun. 14, 2016), [Retrieved from Internet on unknown date, at https://www.cas.org]; 1 page.
CAS Registry No. 1939264-55-7, "Phenol, 4-[[[4-(1,1-dimethylpropyl)cyclohexyl]amino]methyl]-2-fluoro-", [Online Database] CAS Registry®, Chemical Abstracts Service, Columbus, OH. (Jun. 26, 2016), [Retrieved from Internet on unknown date, at https://www.cas.org]; 1 page.
CAS Registry No. 1939792-99-0, "Benzenemethanamine, 5-Bromo-2-Chloro-N-[4-(1,1-Dimethylpropyl)Cyclohexyl]-", [Online Database] CAS Registry®, Chemical Abstracts Service, Columbus, OH. (Jun. 27, 2016), [Retrieved from Internet on unknown date, at https://www.cas.org]; 1 page.
CAS Registry No. 1962333-15-8, "Benzenemethanamine, N-[4-(1,1-dimethylpropyl)cyclohexyl]-5-fluoro-2-methyl-", [Online Database] CAS Registry®, Chemical Abstracts Service, Columbus, OH. (Jul. 29, 2016), [Retrieved from Internet on unknown date, at https://www.cas.org]; 1 page.
CAS Registry No. 2032268-58-7, Cyclohexanecarboxylic acid, 4-[[(3-chloro-5-methylphenyl)methyl]amino]-, [Online Database] CAS Registry®, Chemical Abstracts Service, Columbus, OH. (Nov. 15, 2016), [Retrieved from Internet on unknown date, at https://www.cas.org]; 1 page.
CAS Registry No. 2107153-36-4, "1H-Indole-3-ethanamine, 2-chloro-4-methoxy-N-methyl-", [Online Database] Cas Registry®, Chemical Abstracts Service, Columbus, OH. (Aug. 2, 2017), [Retrieved from Internet on unknown date, at https://www.cas.org]; 1 page.
CAS Registry No. 2199998-08-6, "Cyclohexanecarboxylic acid, 2-[[(3-chloro-5-methylphenyl)methyl]amino]-1-methyl-", [Online Database] CAS Registry®, Chemical Abstracts Service, Columbus, OH. (Mar. 27, 2018), [Retrieved from Internet on unknown date, at https://www.cas.org]; 1 page.
CAS Registry No. 2202151-69-5, "Cyclohexanecarboxylic acid, 3-[[(3-chloro-5-methylphenyl)methyl]amino]-", [Online Database] CAS Registry®, Chemical Abstracts Service, Columbus, OH. (Mar. 30, 2018), [Retrieved from Internet on unknown date, at https://www.cas.org]; 1 page.
CAS Registry No. 2322790-81-6, "Benzenemethanamine, N-[4-(1,1-dimethylethyl)cyclohexyl]-3-(trifluoromethyl)-", [Online Database] CAS Registry®, Chemical Abstracts Service, Columbus, OH. (Jun. 2, 2019), [Retrieved from Internet on unknown date, at https://www.cas.org]; 1 page.
CAS Registry No. 2419600-39-6, "Benzenemethanamine, 3-chloro-N-[4-(1,1-dimethylpropyl)cyclohexyl]-5-methyl-", [Online Database] CAS Registry®, Chemical Abstracts Service, Columbus, OH. (Jun. 5, 2020), [Retrieved from Internet on unknown date, at https://www.cas.org]; 1 page.
CAS Registry No. 415970-94-4, "Benzenemethanamine, N-[4-(1,1-dimethylethyl)cyclohexyl]-3,5-dimethoxy-", [Online Database] CAS Registry®, Chemical Abstracts Service, Columbus, OH. (May 15, 2002), [Retrieved from Internet on unknown date, at https://www.cas.org]; 1 page.
CAS Registry No. 744981-83-7, "Phenol, 2,6-dibromo-4-[[[4-(1,1-dimethylethyl)cyclohexyl]amino]methyl]-", [Online Database] CAS Registry® Chemical Abstracts Service, Columbus, OH. (Sep. 15, 2004), [Retrieved from Internet on unknown date, at https://www.cas.org]; 1 page.
CAS Registry No. 793633-39-3, "Phenol, 4-(1,1-dimethylethyl)-2-[[[trans-4-(1,1-dimethylethyl)cyclohexyl]amino]methyl]-6-methyl-", [Online Database] CAS Registry®, Chemical Abstracts Service, Columbus, OH. (Dec. 6, 2004), [Retrieved from Internet on unknown date, at https://www.cas.org]; 1 page.
Cayman Chemical "Safety Data Sheet Acc. to OSHA HCS", N,N-DMT (Succinate), CAS No. 2853570-32-6, Cayman Chemical: pp. 1-7, Revised Feb. 15, 2024.
Cayman Chemical, "Safety Data Sheet", Cayman Chemical, Apr. 21, 2021, 6 printed pages.
Cayman Chemical, product information for Item No. 33586, "N,N-DMT (succinate)." Cayman Chemical, Apr. 26, 2021, 1 page.
Chadeayne, Andrew R. et al., "The Crystal Structure of 4-AcO-DMT Fumarate." Psychedelic Science Review, Science Review Team, Mar. 25, 2019, 11 pages.
Chaosbydesign, "A Blissful Peace of Mind, Buprenorphine & 5-MeO-DMT." Erowid.org, [Online] (Sep. 29, 2017), Retrieved from Internet Archive Wayback Machine at URL: [URL: https://web.archive.org/web/20170929165328/https://erowid.org/experiences/exp.php?ID=83974] on [Sep. 29, 2025]; 3 pages.
Chegaev, et al., "No-donor melatonin derivatives: synthesis and in vitro pharmacological characterization", J Pineal Res. Apr. 2007; 42(4): 371-85.
Chen, et al., "Structure-activity relationships in a series of 5-[(2,5-dihydroxybenzyl) amino] salicylate inhibitors of EGF-receptor-associated tyrosine kinase: importance of additional hydrophobic aromatic interactions." J Med Chem. Mar. 18, 1994;37(6):845-59. doi: 10.1021/jm00032a020.
Clinical trial application form for clinical trial GH001-MDD-102, pp. 1 and 19, dated Oct. 20, 2020, 2 pages.
Clinical trial application form for clinical trial GH001-MDD-102, pp. 1 and 19, dated Jun. 3, 2019, 2 pages.
ClinicalTrials.gov Identifier NCT04353024, "Effects of Dimethyltryptamine in Healthy Subjects (DMT)", [Online] (Apr. 20, 2020), [Retrieved on Jun. 24, 2022 from the Internet at: https://clinicaltrials.gov/ct2/show/NCT04353024]; 9 pages.
Cocchi et al., "Novel Psychoactive Phenethylamines: Impact on Genetic Material." Int J Mol Sci. Dec. 17, 2020; 21(24): 9616. doi: 10.3390/ijms21249616. 17 pages.
Corne et al. "A possible correlation between drug-induced hallucinations in man and a behavioural response in mice." Psychopharmacologia. Jan. 1967;11(1):65-78. doi: 10.1007/BF00401509.
Cowen, "Altered states: psilocybin for treatment-resistant depression." Lancet Psychiatry. Jul. 2016;3(7):592-3. doi: 10.1016/S2215-0366(16)30087-6. Epub May 17, 2016.
Cozzi, Nicholas V. et al., "Synthesis and characterization of high-purity N,N-dimethyltryptamine hemifumarate for human clinical trials." Drug Test Anal. Oct. 2020;12(10): 1483-1493. doi: 10.1002/dta.2889. Epub Jul. 14, 2020.
Daiber et al., "Organic Nitrate Therapy, Nitrate Tolerance, and Nitrate-Induced Endothelial Dysfunction: Emphasis on Redox Biology and Oxidative Stress." Antioxid Redox Signal. Oct. 10, 2015;23(11):899-942.
Dakic et al., "Short term changes in the proteome of human cerebral organoids induced by 5-MeO-DMT." Sci Rep. Oct. 9, 2017;7(1):12863. doi: 10.1038/s41598-017-12779-5. 13 pages.
Dalgleish, T., et al., "Transdiagnostic Approaches to Mental Health Problems: Current Status and Future Directions." J Consult Clin Psychol. Mar. 2020;88(3):179-195. doi: 10.1037/ccp0000482.
Dameron, Emerson, "Mr. Toad's Wild Ride: 4 Seasons in 30 Minutes on 5-MeO-DMT." Medium, [Online] (May 25, 2017) Retrieved from Internet Archive at: [https://archive.ph/LHIDV] on [Jan. 28, 2024]; 5 pages.
Davis, AK, "The healing potential of 5-MeO-DMT: Results from two survey studies." Abstract of a presentation given in Apr. 2018 at the Midwest Psychedelic Therapy Symposium, Madison Wisconsin, 2 pages.
Davis et al., "5-methoxy-N, N-dimethyltryptamine (5-MeO-DMT) used in a naturalistic group setting is associated with unintended

(56) References Cited

OTHER PUBLICATIONS improvements in depression and anxiety." Am J Drug Alcohol Abuse. 2019; 45(2): 161-169. doi: 10.1080/00952990.2018.1545024. Epub Mar. 1, 2019. 10 pages.
Davis, et al., "5-Methoxy-N,N-Dimethyltryptamine (5-MeO-DMT): Patterns of use, motives for consumption, and acute subjective effects." Poster given at the 12th Annual Bayview Research Symposium, Johns Hopkins University School of Medicine, Baltimore, MD. Dec. 2017, 10.13140/RG.2.2.32653.84960, 2 pages.
Davis, et al., "The epidemiology of 5-methoxy-N, N-dimethyltryptamine (5-MeO-DMT) use: Benefits, consequences, patterns of use, subjective effects, and reasons for consumption." Psychopharmacol. Jul. 2018;32(7):779-792. doi: 10.1177/0269881118769063. Epub Apr. 30, 2018.
De Barros et al., "Synthesis of 25X-BOMes and 25X-NBOHs (X=H, I, Br) for pharmacological studies and as reference standards for forensic purposes." (Jan. 2021) Tetrahedron Letters 66:152804, DOI:10.1016/j.tetlet.2020.152804, 4 pages.
Dean, et. al, "Indolethylamine-N-methyltransferase Polymorphisms: Genetic and Biochemical Approaches for Study of Endogenous N,N,-dimethyltryptamine." Front Neurosci. Apr. 23, 2018:12:232. doi: 10.3389/fnins.2018.00232. eCollection 2018, 16 pages.
Declaration and CV of Dr. Michael Thase, dated May 22, 2025, submitted in Opposition proceedings of EP Patent No. 3927337; Applicant GH Res Limited; 121 pages.
Declaration of Dr. Mark Seelig dated Jul. 7, 2025, filed in European Opposition proceedings against EP Patent No. 3927337; Applicant GH Res Limited; 3 pages.
Declaration of Dr. Mark Seelig dated Nov. 13, 2024, filed in European Opposition proceedings against EP Patent No. 3927337; Applicant GH Res Limited; 3 pages.
Declaration of Majed Fawaz under 37 C.F.R. § 1.130, dated Jun. 14, 2024; submitted Jan. 24, 2025 in U.S. Appl. No. 17/824,861; Applicant ATAI Therapeutics, Inc.; 2 pages.
Demyttenaere, et al., "The Impact of (the Concept of) Treatment-Resistant Depression: An Opinion Review," Int J Neuropsychopharmacol. Feb. 1, 2019; 22(2):85-92.
Dimoitou, "Nasal spray" Post #3, Jun. 27, 2014 6:58:57 pm, DMT-Nexus [Online] (Jun. 27, 2014) [retrieved from the internet on Apr. 3, 2025, from URL: https://forum.dmt-nexus.me/threads/nasal-spray.343226/]; 5 pages.
Dos Santos et al., "Long-term effects of ayahuasca in patients with recurrent depression: a 5-year qualitative follow-up." Archives of Clinical Psychiatry. 45(1):22-24. Jan.-Feb. 2018. https://doi.org/10.1590/0101-60830000000149.
Du, M., "An Overview on Transmucosal Permeability and Formulation." J Develop Drugs. 13:227, (Jan. 29, 2024), 2 pages.
Dunlap et al., "Identification of psychoplastogenic N, N-dimethylaminoisotryptamine (isoDMT) analogues through structure-activity relationship studies." J Med Chem Feb. 13, 2020; 63(3): 1142-1155. Epub Jan. 24, 2020. 14 pages.
Dunlap, Lee, E. et al., "Reaction of N,N-Dimethyltryptamine with Dichloromethane Under Common Experimental Conditions." ACS Omega, May 2018, 3, 4968-4973.
Durham et al., "Regulation of calcitonin gene-related peptide secretion by a serotonergic antimigraine drug." J Neurosci. May 1, 1999; 19(9): 3423-9. doi: 10.1523/JNEUROSCI.19-09-03423.1999.
Emo Earache, "Friday Night Alone in the Universe." [Online] Erowid.org, (Oct. 21, 2006); [Retrieved Sep. 29, 2025 from the internet at URL: https://www.erowid.org/experiences/exp.php?ID=56696]; 6 pages.
Entheohealing, "Interplay between psychotherapy and psychedelics." Reddit, [Online] (Jun. 30, 2018); [retrieved from the internet on Sep. 30, 2025 from URL: https://www.reddit.com/r/TripTherapy/comments/8v5c4f/interplay_between_psychotherapy_and_psychedelics/]; 6 pages.
Entheohealing, "The Nuclear Option: A Personal Story of Treating Social Anxiety with 5-MeO-DMT Psychedelic Therapy." Reddit [Online] (Jun. 2018), [retrieved Sep. 30, 2025 from the internet at URL: https://www.reddit.com/r/TripTherapy/comments/8zdhxg/the_nuclear_option_a_personal_story_of_treating/]; 5 pages.
EP Application No. 19158774.0, filed Feb. 22, 2019; inventor Terwey; Theis.
EP Application No. 20710059.5, communication in Opposition proceedings dated Dec. 3, 2024; Applicant GH Research Ireland Limited; 35 pages.
EP Application No. 20710059.5, communication in Opposition proceedings dated Jul. 15, 2025; Applicant GH Research Ireland Limited; 10 pages.
EP Application No. 20710059.5, communication in Opposition proceedings dated Jun. 10, 2025; Applicant GH Research Ireland Limited; 127 pages.
EP Application No. 20710059.5, communication in Opposition proceedings dated Sep. 9, 2025; Applicant GH Research Ireland Limited; 23 pages.
EP Application No. 20710059.5, Third Party Observation dated Oct. 26, 2023, Applicant/proprietor GH Research Ireland Limited; 31 pages.
EP Application No. 20710059.5, Third Party Observation submitted Jan. 19, 2024; Applicant/Proprietor GH Research Ireland Limited; 3 pages.
EP Application No. 20710060.3, Communication under Article 94(3) dated Dec. 16, 2022; Applicant GH Research Ireland Limited 14 pages.
EP Application No. 21800237.6, Extended European Search Report Apr. 15, 2024; Applicant Psilera Inc.; 8 pages.
EP Application No. 22796577.9, Extended European Search Report dated Mar. 10, 2025; Applicant ATAI Therapeutics, Inc.; 10 pages.
EP Application No. 22812068.9, Extended European Search Report dated Mar. 28, 2025; Applicant ATAI Therapeutics, Inc.; 13 pages.
EP Application No. 22821070.4, Extended European Search Report dated May 26, 2025; Applicant ATAI Therapeutics, Inc.; 11 pages.
EP Application No. 22877368.5, Extended European Search Report dated Jun. 16, 2025, Applicant atai Life Sciences AG; 9 pages.
EP Application No. 22917527.8, Extended European Search Report mailed Oct. 31, 2025; Applicant ATAI Therapeutics, Inc.; 8 pages.
EP Patent No. 3927337, Notice of opposition dated May 22, 2024, Applicant GH Research Ireland Limited; 21 pages.
EP Patent No. 3927337, Notice of opposition dated Nov. 19, 2024; Applicant GH Research Ireland Limited; 58 pages.
EP Patent No. 3927337, Reply from Opponent in opposition proceedings, filed Jul. 9, 2025; Applicant GH Research Ireland Limited; 9 pages.
EP Patent No. 3927337, Reply of the patent proprietor in Opposition proceedings, dated Jun. 3, 2025; Applicant GH Research Ireland Limited; 126 pages.
Erowid, "5-MeO-DMT Dosage." EROWID.org [Online] (Feb. 14, 1999); Modified Jan. 1, 2000, Retrieved from Internet Archive Wayback Machine at URL: [https://web.archive.org/web/20000407105145/https://erowid.org/chemicals/5meo_dmt/5meo_dmt_dose.shtml] on [Oct. 1, 2025]; 1 page.
Erowid Crew Blog, "Intractable Byproduct in 5-MeO-DMT Samples." [Online] Erowid.org (Aug. 3, 2021); [retrieved Oct. 1, 2025 from https://www.erowid.org/columns/crew/2021/08/5-meo-dmt_synthesis_byproduct/]; 4 pages.
Euda, "The drug situation in Europe up to 2023—an overview and assessment of emerging threats and new developments." European Union Drugs Agency, European Drug Report 2023, last updated Jun. 16, 2023, 16 pages.
EudraCT 2018-004208-20, GH Research Limited, "A phase ½ study of GH001 in patients with treatment-resistant depression." [Online Database] EU Clinical Trials Register, (Jul. 1, 2019); [retrieved from the internet on Sep. 10, 2024, from https://www.clinicaltrialsregister.eu/ctr-search/trial/2018-004208-20/NL]; 5 pages.
European Medicines Agency, EudraCT & EU CTR Frequently Asked Questions, V. 2.5, (Jan. 31, 2025), 30 pages.
European Medicines Agency, EudraCT & EU CTR Question and Answer table, Frequently Asked Questions & Answers (FAQs)—V1.3 (Mar. 2019), 32 pages.
Ewing, Christopher G., "Ground to Source—Experiencing the Divine Within." Thepracticaltripper.wordpress.com, [Online] (Apr. 15, 2017) [retrieved on Sep. 30, 2025 from the Internet at: https://

(56) References Cited

OTHER PUBLICATIONS thepracticaltripper.wordpress.com/2017/04/15/ground-to-source-experiencing-the-divine-within-2/]; 10 pages.
Fabbri et al., "The Genetics of Treatment-Resistant Depression: A Critical Review and Future Perspectives." Int J Neuropsychopharmacol. Feb. 1, 2019;22(2):93-104. doi: 10.1093/ijnp/pyy024.
Falkenberg et al., "The crystal and molecular structure of (N,N)-dimethyltryptamine." Acta Crystallogr., Sect B28, 3075-3083, Mar. 9, 1972, 9 pages.
Filip.Zaruba, "introduction of me andy my 5-MeO movie." 5 Hive forums.5meodmt.org, [Online] (May 31, 2018); Retrieved from Internet Archive Wayback Machine at: [https://web.archive.org/web/20231122183352/https://forums.5meodmt.org/index.php/topic,50738.msg55435.html#msg55435] on [Oct. 27, 2025]; 2 pages.
Form F-1 (Registration Statement Under Securities Act 1933) filed by GH Research PLC (of which GH Research is a subsidiary) with the Securities and Exchange Commission on Jun. 21, 2021, 248 pages.
Garcia, Isra, "Bufo Alvarius Toad / 5MeO-DMT—the awakening." [Online] (Jan. 28, 2019), [retrieved on Sep. 30, 2025 from the Internet at: https://isragarcia.com/bufo-alvarius-toad-5meo-dmt-awakening]; 9 pages.
Garcia-Romeu et al. "Psilocybin-occasioned mystical experiences in the treatment of tobacco addiction." Current Drug Abuse. Reviews. 7(3):157-164 (Dec. 2014). doi: 10.2174/1874473708666150107121331.
Gaujac et al. "Determination of N,N-dimethyltryptamine in beverages consumed in religious practices by headspace solid-phase microextraction followed by gas chromatography ion trap mass spectrometry," Talanta. Mar. 15, 2013: 106:394-8. doi: 10.1016/j.talanta.2013.01.017. Epub Feb. 1, 2013.
Gaujac et al., "Investigations into the polymorphic properties of N, N-dimethyltryptamine by X-ray diffraction and differential scanning calorimetry," Microchemical Journal 110, Mar. 2, 2013, 12 pages.
GH Reasearch, "GH Research Announces Closing of $125 Million Oversubscribed Series B Financing." Press-release, Apr. 12, 2021, 1 page.
GH Research Announces Appointment of Dr. Velichka "Villy" Valcheva of Chief Executive Officer, Press-release dated Sep. 3, 2024, 1 page.
GH Research, Corporate Presentation, Mar. 2022, 15 pages.
GH Research, Corporate Presentation, Mar. 2023, 30 pages.
GH Research, Corporate Presentation, May 2022, 28 pages.
GH Research, Corporate Presentation, May 2023, 30 pages.
GH Research, Corporate Presentation, Nov. 2022, 28 pages.
GH Research (year: 2025, month: unknown), data for Spravato (esketamine), 3 pages.
Glatfelter G, et al., "Synthesis, Structural Characterization, and Pharmacological Activity of Novel Quaternary Salts of 4-Substituted Tryptamines", ACS Omega, Jul. 2022, vol. 7(28), pp. 24888-24894.
Glennon et al., "Hallucinogens as discriminative stimuli: A comparison of 4-OMe and 5-OMe DMT with their methylthio counterparts", Life Science, Pergamon Press, Oxford, GB, vol. 30, No. 5, Feb. 1, 1982 (Feb. 1, 1982), pp. 465-467, XP023723306, ISSN: 0024-3205, DOI: 10.1016/0024-3205(82)90463-5 [retrieved on Feb. 1, 1982].
Glennon et al., "Influence of amine substituents on 5-HT2A versus 5-HT2C binding of phenylalkyl-and indolylalkylamines." J Med Chem. Jun. 24, 1994; 37(13): 1929-35. doi: 10.1021/jm00039a004.
Glennon et al., "Synthesis and evaluation of a novel series of N,N-dimethylisotryptamines", J Med Chem. Jan. 1984; 27(1): 41-5.
Gonzalez-Maeso et al., "Hallucinogens Recruit Specific Cortical 5-HT2A Receptor-Mediated Signaling Pathways to Affect Behavior," Neuron, Feb. 2007, 53, 439-452.
Goodwin et al., "Single-Dose Psilocybin for a Treatment-Resistant Episode of Major Depression." N Engl J Med. Nov. 3, 2022;387(18):1637-1648. doi: 10.1056/NEJMoa2206443.
Goodwin et al., "Supplementary Appendix to Single-Dose Psilocybin for a Treatment-Resistant Episode of Major Depression." Supplementary Appendix; N Engl J Med. Nov. 3, 2022;387(18):1637-1648, 249 pages.
Graeff F.G., et al., "Role of 5-HT in stress, anxiety and depression", Pharmacology Biochemistry and Behavior, Elsevier, US, vol. 54, No. 1, Jan. 1, 1996 (Jan. 1, 1996), pp. 129-141.
Greatmoosey, "Update: 30 days after my 5meoDMT experience," Reddit, [Online] (Oct. 27, 2019); [retrieved from the Internet on Sep. 30, 2025 at: https://www.reddit.com/r/Psychonaut/comments/dnup28/update_30_days_after_my_5meodmt_experience/]; 5 pages.
Gribble, "Recent developments in indole ring synthesis-methodology and applications", Journal of the Chemical Society, Perkin Transactions, Mar. 23, 2000, pp. 1045-1075.
Griffiths et al. "Psilocybin produces substantial and sustained decreases in depression and anxiety in patients with life-threatening cancer: A randomized double-blind trial," Journal of Psychopharmacology. 30(12):1181-1197 (Dec. 2016).
Grundke et al., "Photochemical α-Aminonitrile Synthesis Using Zn-Phthalocyanines as Near-Infrared Photocatalysts", J Org Chem. May 6, 2022; 87(9): 5630-5642, with supporting info. Epub Apr. 14, 2022. 60 pages.
Gumpper, Ryan, H. et al., "The structural diversity of psychedelic drug actions revealed," Nat Commun. Mar. 19, 2025;16(1):2734. doi: 10.1038/s41467-025-57956-7, 13 pages.
Gurevich and Gurevich, "GPCR Signaling Regulation: The Role of GRKs and Arrestins", Front Pharmacol. Feb. 19, 2019: 10: 125. eCollection 2019, 11 pages.
Gyermek L., "A New Class of 5-Hydroxytryptamine Antagonists", Journal of Medicinal Chemistry, vol. 7, Jan. 1, 1964 (Jan. 1, 1964), pp. 280-282.
Halberstadt, A. L., "Recent Advances in the Neuropsychopharmacology of Serotonergic Hallucinogens." Behav Brain Res. Jan. 15, 2015: 277: 99-120. doi: 10.1016/j.bbr.2014.07.016. Epub Jul. 15, 2014.
Halberstadt et al., "Behavioral effects of „,-tetradeutero-5-MeO-DMT in rats: comparison with 5-MeO-DMT administered in combination with a monoamine oxidase inhibitor," Psychopharmacology (Berl). Jun. 2012;221(4):709-18. doi: 10.1007/s00213-011-2616-6. Epub Jan. 6, 2012.
Halberstadt et al., "Differential contributions of serotonin receptors to the behavioral effects of indoleamine hallucinogens in mice", J Psychopharmacol. Nov. 2011; 25(11): 1548-61. Epub Dec. 8, 2010.
Halberstadt et al., "Modification of the effects of 5-methoxy-N,N-dimethyltryptamine on exploratory behavior in rats by monoamine oxidase inhibitors." Psychopharmacology (Berl). Nov. 2008;201(1):55-66. doi: 10.1007/s00213-008-1247-z. Epub Jul. 8, 2008.
Hamada et al., "Water-soluble prodrugs of dipeptide HIV protease inhibitors based on O → N intramolecular acyl migration: Design, synthesis and kinetic study" Bioorg Med Chem. Jan. 2, 2004;12(1):159-70. doi: 10.1016/j.bmc.2003.10.026.
Handshake, "Toads Poison Use Is Not an Ancient Indigneous Tradition." 5 Hive forums.5meodmt.org, [Online] (Nov. 30, 2017); Retrieved from Internet Archive Wayback Machine at: [https://web.archive.org/web/20231122182449/https://forums.5meodmt.org/index.php /topic,50611.msg54941.html#msg54941] on [Oct. 27, 2025]; 6 pages.
Hansen et al., "Synthesis and pharmacological evaluation of N-benzyl substituted 4-bromo-2,5-dimethoxyphenethylamines as 5-HT2A/2C partial agonists." Bioorganic & Medicinal Chemistry, vol. 23, Issue 14, Jul. 15, 2015, pp. 3933-3937.
Hansen et al., "Synthesis and Structure-Activity Relationships of N-Benzyl Phenethylamines as 5-HT2A/2C Agonists." ACS Chem Neurosci. Mar. 19, 2014;5(3):243-9. doi: 10.1021/cn400216u. Epub Jan. 15, 2014.
Harbonic_Older, "Journey to the Center of the Onion, 5-MeO-DMT." Erowid.org, [Online] (Nov. 1, 2004); Retrieved from Internet Archive Wayback Machine at URL: [https://web.archive.org/web/20130209080256/https://www.erowid.org/experiences/exp.php?ID=34918] on [Sep. 29, 2025]; 2 pages.
Harriott et al., "Animal models of migraine and experimental techniques used to examine trigeminal sensory processing", J Headache Pain. Aug. 29, 2019; 20(1): 91. 15 pages.

(56) References Cited

OTHER PUBLICATIONS

Hart, "Melting Point Determination, Melting Range", Adapted from Organic Chemistry: A Short course. Hart et al., 13th ed. Houghton-Mifflin, Boston, 4 pages.
Hasegawa et al., "A Novel Methodology for Preparing 5-chloro- and 5-bromo-tryptamines and tryptophans, and its Application to the Synthesis of (+/−)-bromochelonin BI." (Dec. 1999), Heterocycles, vol. 51, No. 12, pp. 2815-2821.
Hassan et al., "A Review on the Pharmacological and Traditional Properties of Mimosa Pudica." International Journal of Pharmacy and Pharmaceutical Sciences, (Mar. 2019) 11(3), 12-16.
Hermann (Aug. 2, 2005) "Psychiatric Comorbidity in Chronic Epilepsy: Identification, Consequences, and Treatment of Major Depression" Epilepsia. 2000:41 Suppl 2:S31-41. doi: 10.1111/j.1528-1157.2000.tb01522.x.
Herrmann, "The Sunnybrook Stroke Study: A Prospective Study of Depressive Symptoms and Functional Outcome." Stroke. Mar. 1998;29(3):618-24.
Hesselink, et. al., "Transformative Psychopharmacology: the Case of 5-Methoxy-N,N-Dimethyltryptamine." International Journal of Psychotherapy Practice and Research, (Jan. 2019), 1(3), 9-15.
Holtzheimer, et al., "Deep Brain Stimulation for Treatment-Resistant Depression," Clinical Case Conference from the Emory University School of Medicine, Am J Psychiatry, Dec. 2010; 167:12, pp. 1437-1444.
Holze et al. "Distinct acute effects of LSD, MDMA, and D-amphetamine in healthy subjects." Neuropsychopharmacology. Feb. 2020;45(3):462-471. doi: 10.1038/s41386-019-0569-3.
Huang et al., "Nose-to-brain delivery of drug nanocrystals by using Ca2+ responsive deacetylated gellan gum based in situ-nanogel." Int J Pharm. Feb. 1, 2021:594:120182. doi: 10.1016/j.ijpharm.2020.120182. Epub Dec. 17, 2020. 41 pages.
Humphrey et al., "Practical methodologies for the synthesis of indoles", Chem Rev. Jul. 2006; 106(7): 2875-911, 37 pages.
Huttunen, et al., "Prodrugs-from Serendipity to Rational Design", Pharmacological Reviews, vol. 63, No. 3, Sep. 2011, pp. 750-771.
Innerexplorer, "Defining Intramuscular Dosage Range, 5-MeO-DMT." Erowid.org, [Online] (Jan. 2, 2017); [retrieved Sep. 29, 2025 from the internet at URL: https://www.erowid.org/experiences/exp.php?ID=109250]; 3 pages.
Jabberwocky, forum post in thread titled "Euphorigenic, entactogenic, non-toxic, non-hallucinogenic tryptamine(s)?" bluelight.org [Online] (Mar. 10, 2009) Available at: [https://bluelight.org/xf/threads/euphorigenic-entactogenic-non-toxic-non-hallucinogenic-tryptamine-s.423423/post-6922410]; Retrieved from Internet Archive Wayback Machine at URL: [https://web.archive.org/web/20240121145750/https://bluelight.org/xf/threads/euphorigenic-entactogenic-non-toxic-non-hallucinogenic-tryptamine-s.423423/#post-6922410] on [Oct. 27, 2025]; 10 pages.
Jacob, et al. "Structure-activity relationships of classic hallucinogens and their analogs." NIDA Research Monograph, (Year: 1994, month: unknown), 19 pages.
Jaffe et al., "The humanistic and economic burden of treatment-resistant depression in Europe: a cross-sectional study." BMC Psychiatry. Aug. 7, 2019;19(1):247. doi: 10.1186/s12888-019-2222-4.
Japanese Patent Office, Official Action, for JP 2022-567840, dated Nov. 28, 2024, with English translation, 5 pages.
Johns Hopkins Medicine, "Fast-Acting Psychedelic Associated With Improvements in Depression/Anxiety," Johns Hopkins Medicine News & Publications Newsroom, [Online] (Mar. 18, 2019); [retrieved on Sep. 30, 2025 from the Internet at: https://www.hopkinsmedicine.org/news/newsroom/news-releases/2019/03/fast-acting-psychedelic-associated-with-improvements-in-depressionanxiety]; 3 pages.
Johnson&Johnson, "Janssen Announces U.S. FDA Approval of Spravato (esketamine) CIII Nasal Spray for Adults with Treatment-Resistant Depression (TRD) Who Have Cycled Through Multiple Treatments Without Relief," Johnson & Johnson press release, Mar. 5, 2019, 11 pages.
Johnson&Johnson, "Janssen Announces U.S. FDA Approval of Spravato (esketamine) CIII Nasal Spray to Treat Depressive Symptoms in Adults with Major Depressive Disorder with Acute Suicidal Ideation or Behavior," Johnson & Johnson press release, Aug. 3, 2020, 13 pages.
Johnson&Johnson, "Spravato (esketamine) approved in the U.S. as the first and only monotherapy for adults with treatment-resistant depression," Johnson & Johnson press release, Jan. 21, 2025,10 pages.
Kaelen et al., "The hidden therapist: evidence for a central role of music in psychedelic therapy." Psychopharmacology (Berl). Feb. 2018;235(2):505-519. doi: 10.1007/s00213-017-4820-5. Epub Feb. 2, 2018.
Kaminska et al., "25C-NBOMe short characterization." Forensic Toxicology (2020) 38:490495 https://doi.org/10.1007/s11419-020-00530-1, Epub Mar. 30, 2020.
Karst, Matthias et al., "The non-hallucinogen 2-bromo-lysergic acid diethylamide as preventative treatment for cluster headache: an open, non-randomized case series." Cephalalgia. Sep. 2010;30(9):1140-4. doi: 10.1177/0333102410363490. Epub Mar. 26, 2010.
Kaufman, et. al, "The 5-HT1A receptor in Major Depressive Disorder." Eur Neuropsychopharmacol. Mar. 2016; 26(3):397-410. doi:10.1016/j.euroneuro.2015.12.039. Epub Jan. 11, 2016.
Kennett, et al., "Single administration of 5-HT1A agonists decreases 5-HT1A presynaptic, but not postsynaptic receptor-mediated responses: relationship to antidepressant-like action." Eur J Pharmacol. Jun. 12, 1987;138(1):53-60.
Klein et al., "Toward selective drug development for the human 5-hydroxytryptamine 1E receptor: a comparison of 5-hydroxytryptamine 1E and 1F receptor structure-affinity relationships", J Pharmacol Exp Ther. Jun. 2011; 337(3): 860-7. Epub Mar. 21, 2011.
Kline et al, "Structure-activity relationships in potentially hallucinogenic N, N-dialkyltryptamines substituted in the benzene moiety." J Med Chem. Aug. 1982; 25(8): 908-13. doi: 10.1021/jm00350a005.
Kraehenmann et al. "Dreamlike effects of LSD on waking imagery in humans depend on serotonin 2A receptor activation." Psychopharmacology. Jul. 2017;234(13):2031-2046. doi: 10.1007/s00213-017-4610-0.
Kraehenmann et al. "LSD Increases Primary Process Thinking via Serotonin 2A Receptor Activation." Frontiers in Pharmacology. Nov. 2017;8(814):1-9. doi: 10.3389/fphar.2017.00814.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Kucklander, et al., "Synthesis and Oxidation of 2-(2, 5-Dihydroxyphenyl)-ethylamine Derivatives, II", Zeitschrift fr Naturforschung B, (Dec. 1, 1987), pp. 1567-1577 (with English abstract). 12 pages.
Lambert, Geoffrey, A., "Looking in the wrong place? The search for an ideal migraine preventative", Drug Development Research, New York, NY, US, vol. 68, No. 6, Dec. 18, 2007 (Dec. 18, 2007), pp. 376-388, DOI: 10.1002/DDR.20204.
Lawlor, Sean, "5-MeO-DMT: Light and Shadow in the Psychedelic Toad." [Online] Psychedelic Times, (Nov. 20, 2019), [retrieved from the Internet Sep. 30, 2025, at: https://psychedelictimes.com/5-meo-dmt-psychedelic-toad/]; 16 pages.
Lawrence et al., "Sports Medicine, Mental Health & Well-Being, and Psychedelics." [Online] British Journal of Sports Medicine (Nov. 28, 2019) [retrieved from internet Sep. 29, 2025, from https://blogs.bmj.com /bjsm/2019/11/28/sports-medicine-mental-health-well-being-and-psychedelics/], 14 pages.
Lewis et al., "Two dose investigation of the 5-HT-agonist psilocybin on relative and global cerebral blood flow." Neuroimage. Oct. 1, 2017:159:70-78. doi: 10.1016/j.neuroimage.2017.07.020. Epub Jul. 12, 2017.
Lewis, V., et al., "A non-hallucinogenic LSD analog with therapeutic potential for mood disorders." Cell Rep. Mar. 28, 2023;42(3):112203. doi: 10.1016/j.celrep.2023.112203. Epub Mar. 6, 2023. 27 pages.
Li et al., "Treatment of breast and lung cancer cells with a N-7 benzyl guanosine monophosphate tryptamine phosphoramidate

(56) References Cited

OTHER PUBLICATIONS pronucleotide (4Ei-1) results in chemosensitization to gemcitabine and induced elF4E proteasomal degradation." Mol Pharm., Feb. 2013, pp. 523-531.
Liechti, "Modern Clinical Research on LSD." Neuropsychopharmacology. Oct. 2017;42(11):2114-2127. doi: 10.1038/npp.2017.86. Epub Apr. 27, 2017.
Lima da Cruz et al., "Corrigendum: A Single Dose of 5-MeO-DMT Stimulates Cell Proliferation, Neuronal Survivability, Morphological and Functional Changes in Adult Mice Ventral Dentate Gyrus." Front Mol Neurosci. Sep. 4, 2018:11:312. doi: 10.3389/fnmol.2018.00312. eCollection 2018. 11 pages.
Llado-Pelfort, et al., "Effects of Hallucinogens on Neuronal Activity." Curr Top Behav Neurosci. 2018: 36:75-105. doi: 10.1007/7854_2017_473. Epub Feb. 26, 2017, 31 pages.
Lyon et al. "3, 4-Methylenedioxymethamphetamine (MDMA): stereoselective interactions at brain 5-HT1 and 5-HT2 receptors." Psychopharmacology. Apr. 1986;88(4):525-526. doi: 10.1007/BF00178519.
Lyon et al., "Indolealkylamine analogs share 5-HT2 binding characteristics with phenylalkylamine hallucinogens." Eur J Pharmacol. Jan. 19, 1988;145(3):291-7. doi: 10.1016/0014-2999(88)90432-3.
Madhav, et al., "Orotransmucosal drug delivery systems: A review", Journal of Controlled Release (Nov. 16, 2009); 140(1): 2-11. doi:10.1016/j.jconrel.2009.07.016. Epub Aug. 6, 2009.
Madsen et al., "Psilocybin-induced reduction in chronic cluster headache attack frequency correlates with changes in hypothalamic functional connectivity", medRxiv. Jul. 10, 2022: Jul. 2022, 17 pages.
Madsen et al., "Psychedelic effects of psilocybin correlate with serotonin 2A receptor occupancy and plasma psilocin levels." Neuropsychopharmacology. Jun. 2019;44(7):1328-1334. doi: 10.1038/s41386-019-0324-9. Epub Jan. 26, 2019.
Mahalingam, "Semisolid Dosages: Ointments, Creams, and Gels." in Pharmaceutical Manufacturing Handbook: Production and Processes. (Chapter 9, 267-312), Shayne C. Gad ed., John Wiley & Sons, Inc. 2008.
Majic, "Peak experiences and the afterglow phenomenon: When and how do therapeutic effects of hallucinogens depend on psychedelic experiences?" Journal of Psychopharmacology. 29(3):241-253 (Feb. 9, 2015).
Malaca, S., et al., "Toxicology and Analysis of Psychoactive Tryptamines." Int J Mol Sci. Dec. 4, 2020; 21(23): 9279. doi: 10.3390/ijms21239279. 30 pages.
Malhi et al., "Treatment-resistant depression: problematic illness or a problem in our approach?" Br J Psychiatry. Jan. 2019;214(1): 1-3. doi: 10.1192/bjp.2018.246.
Marek et. al., "Evidence for involvement of 5-hydroxytryptamine1 receptors in antidepressant-like drug effects on differential-reinforcement-of-low-rate 72-second behavior." J Pharmacol Exp Ther. Jul. 1989;250(1):60-71.
Mcbride, "Bufotenine: Toward an Understanding of Possible Psychoactive Mechanisms", Journal of Psychoactive Drugs, Jul.-Sep. 2000, pp. 321-331.
Mcclure-Begley and Roth, "The promises and perils of psychedelic pharmacology for psychiatry", Nat Rev Drug Discov. Jun. 2022; 21(6): 463-473. Epub Mar. 17, 2022.
Mcilhenny, et al., "Ayahuasca characterization, metabolism in humans, and relevance to endogenous N,N-dimethyltryptamines." Doctoral dissertation, (Aug. 2012), Louisiana State University and Agricultural and Mechanical College. Available from LSU Digital Commons. (No. 2049), 215 pages.
Mckenna, et al., "Monoamine oxidase inhibitors in South American hallucinogenic plants: tryptamine and beta-carboline constituents of ayahuasca." Journal of Ethnopharmacology. Apr. 1984;10(2):195-223. doi: 10.1016/0378-8741(84)90003-5.
Meccia et al., "Treatment of major depressive disorder and treatment resistant depression with 5-MeO-DMT: impact of 25 years of non-traditional public scientific communication and education on clinical development and commercialization." Porta Sophia, Madison, WI USA (Nov. 12, 2024), 15 pages.
Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.
Milliere et al., "Psychedelics, Meditation, and Self-Consciousness." Front Psychol. Sep. 4, 2018:9:1475. doi: 10.3389/fpsyg.2018.01475. eCollection 2018, 29 pages.
Millipore Sigma, "Succinic acid, Butanedioic acid." CAS No. 110-15-6, Merck KGaA, (Year: 2023, month: unknown), 4 pages.
Milne et al., "Metabolic engineering of *Saccharomyces cerevisiae* for the de novo production of psilocybin and related tryptamine derivatives." Metab Eng. Jul. 2020:60:25-36. doi: 10.1016/j.ymben.2019.12.007. Epub Mar. 26, 2020.
Mithoefer et al. "The safety and efficacy of3, 4-methylenedioxymethamphetamine-assisted psychotherapy in subjects with chronic, treatment-resistant posttraumatic stress disorder: the first randomized controlled pilot study." Journal of Psychopharmacology. Apr. 2011;25(4):439-452.
Mohebbi (2018) "Patient centric measures for a patient centric era: Agreement and convergent between ratings on the Patient Global Impression of Improvement (PGI-I) scale and the Clinical Global Impressions Improvement (CGI-S) scale in bipolar and major depressive disorder" Eur Psychiatry. Sep. 2018:53:17-22. doi: 10.1016/j.eurpsy.2018.05.006. Epub May 30, 2018.
Mokler D J et al.,"The 5HT"2 antagonist pirenperone reverses disruption of FR-40 by hallucinogenic drugs." Pharmacol Biochem Behav. May 1985;22(5):677-82. doi: 10.1016/0091-3057(85)90512-x.
Mukherjee, Pranoy, "How can I overcome (existential) depression?" Quora forum response, [Online] (Jan. 27, 2018) Retrieved from Internet Archive at URL: [https://archive.ph/7PThx] on [Oct. 27, 2025]; 2 pages.
Muller (2003) "Differentiating moderate and severe depression using the Montgomery-Asberg depression rating scale (MADRS)" J Affect Disord. Dec. 2003;77(3):255-60. doi: 10.1016/s0165-0327(02)00120-9.
National Center for Biotechnology Information (2023). PubChem Substance Record for SID 309311543, SID 309311543, Source: Aurora Fine Chemicals LLC. [Online Database] (Jan. 30, 2016), [retrieved Nov. 7, 2023 from https://pubchem.ncbi.nlm.nih.gov/substance/309311543], 5 pages.
National Center for Biotechnology Information. PubChem Compound Summary for CID 10624, Psilocybin. [Online database] ( Mar. 3, 2005), [Accessed May 5, 2025 from https://pubchem.ncbi.nlm.nih.gov/compound/Psilocybin]; 62 pages.
National Center for Biotechnology Information. PubChem Compound Summary for CID 123606, Almotriptan. [Online database] (Aug. 8, 2005), modified Mar. 29, 2025, [retrieved on Apr. 4, 2025, from https://pubchem.ncbi.nlm.nih.gov/compound/Almotriptan]; 53 pages.
National Center for Biotechnology Information. PubChem Compound Summary for CID 149771082, 1-[3-[2-(dimethylamino)ethyl]-1H-indol-4-yl]-N-methylmethanesulfonamide. [Online database] (Aug. 12, 2020), Modified Mar. 29, 2025, [retrieved on Apr. 4, 2025, from https://pubchem.ncbi.nlm.nih.gov/compound/149771082]; pp. 1-8.
National Center for Biotechnology Information. PubChem Compound Summary for CID 15274381, 2-(7-Bromo-1H-indol-3-yl)ethan-1-amine. [Online database] (Feb. 9, 2007), Modified Jan. 25, 2025, [retrieved on unknown date at https://pubchem.ncbi.nlm.nih.gov/compound/2-_7-Bromo-1H-indol-3-yl_ethan-1-amine]; 14 pages.
National Center for Biotechnology Information. PubChem Compound Summary for CID 156821129, [3-[2-(Dimethylamino)ethyl]-4-hydroxyindol-1-yl]methylphosphonic acid. [Online Database] (Nov. 10, 2021), Modified Aug. 23, 2024, [retrieved on unknown date from https://pubchem.ncbi.nlm.nih.gov/compound/156821129]; 10 pages.
National Center for Biotechnology Information. PubChem Compound Summary for CID 157042555, [2-bromo-3-[2-(dimethylamino)ethyl]-1H-indol-4-yl] acetate. [Online Database]

(56) References Cited

OTHER PUBLICATIONS (Nov. 30, 2021), Modified Apr. 12, 2025, [retrieved Apr. 16, 2025, from https://pubchem.ncbi.nlm.nih.gov/compound/157042555.]; pp. 1-9.
National Center for Biotechnology Information. PubChem Compound Summary for CID 162478135, 3-[2-(dimethylamino)ethyl]-2-fluoro-1H-indol-4-ol. [Online Database] (Feb. 6, 2022), modified Apr. 12, 2025, [retrieved Apr. 16, 2025, from https://pubchem.ncbi.nlm.nih.gov/compound/3-_2-_dimethylamino_ethyl_-2-fluoro-1H-indol-4-ol.]; pp. 1-9.
National Center for Biotechnology Information. PubChem Compound Summary for CID 162478146, [3-[2-(dimethylamino)ethyl]-2-fluoro-1H-indol-4-yl] acetate. [Online Database] (Feb. 6, 2022), modified Mar. 29, 2025, [retrieved Apr. 4, 2025 from https://pubchem.ncbi.nlm.nih.gov/compound/162478146]; pp. 1-8.
National Center for Biotechnology Information. PubChem Compound Summary for CID 166138444, [3-[2-[di(propan-2-yl)amino]ethyl]-1H-indol-4-yl] dihydrogen phosphate.[Online database] (Dec. 20, 2022), retrieved Apr. 4, 2025 from https://pubchem.ncbi.nlm.nih.gov/compound/166138444]; pp. 1-7.
National Center for Biotechnology Information. PubChem Compound Summary for CID 24801868, 4-Acetoxy-N,N-diisopropyltryptamine. https://pubchem.ncbi.nlm.nih.gov/compound/4-Acetoxy-N_N-diisopropyltryptamine. Create date: Jun. 6, 2008, Modify date Mar. 29, 2025, accessed Apr. 4, 2025, 21 pages.
National Center for Biotechnology Information. PubChem Compound Summary for CID 24802108, N-Isopropyl-N-(2-(4-methoxy-1H-indol-3-yl)ethyl)propan-2-amine. [Online database] (Jun. 6, 2008), Modified Mar. 29, 2025, [retrieved Apr. 5, 2025, from https://pubchem.ncbi.nlm.nih.gov/compound/24802108];13 pages.
National Center for Biotechnology Information. PubChem Compound Summary for CID 6089, Dimethyltryptamine. https://pubchem.ncbi.nlm.nih.gov/compound/Dimethyltryptamine. Create date: Mar. 26, 2005 (Mar. 26, 2005), 6 pages.
National Center for Biotechnology Information. PubChem Compound Summary for CID 84056101, 2-(2-chloro-4-methoxy-1H-indol-3-yl)ethanamine. https://pubchem.ncbi.nlm.nih.gov/compound/2-_2-chloro-4-methoxy-1H-indol-3-yl_ethanamine, Create date Oct. 20, 2014, 7 pages.
National Center for Biotechnology Information. PubChem Compound Summary for CID 84058691, 1-(2-chloro-4-methoxy-1H-indol-3-yl)propan-2-amine. https://pubchem.ncbi.nlm.nih.gov/compound/1-_2-chloro-4-methoxy-1H-indol-3-yl_propan-2-amine, Create date Oct. 20, 2014, Modify date Mar. 29, 2025, pp. 1-7.
National Center for Biotechnology Information. PubChem Compound Summary for CID 88309097, [1-[[2-(1H-indol-3-yl)-1-(2-methylphenyl)ethyl]amino]-2-oxoethyl] carbamate. https://pubchem.ncbi.nlm.nih.gov/compound/88309097, Created date Feb. 12, 2015, Modified date Nov. 9, 2024, 8 pages.
National Center for Biotechnology Information. PubChem Substance Record for SID 310331158, SID 310331158, Source: Aurora Fine Chemicals LLC. https://pubchem.ncbi.nlm.nih.gov/substance/310331158, Modify Date: Feb. 15, 2015, retrieved Sep. 20, 2022, 4 pages.
National Center for Biotechnology Information. PubChem Substance Record for SID 313512691, 1H-Indole-4-methanol, 3-(2-aminoethyl)-, Source: Chemhere. https://pubchem.ncbi.nlm.nih.gov/substance/313512691, Available date Jun. 11, 2016, 5 pages.
National Center for Biotechnology Information. PubChem Substance Record for SID 369863280, SID 369863280, Source: Ambinter. https://pubchem.ncbi.nlm.nih.gov/substance/369863280. Deposit date May 25, 2018, Modify Date: May 25, 2018, 5 pages.
National Center for Biotechnology Information. PubChem Substance Record for SID 433987242, N,N-dimethyltryptamine, Source: BioCyc. https://pubchem.ncbi.nlm.nih.gov/substance/433987242, Available Date: Sep. 28, 2020 [retrieved on Mar. 2, 2023], 7 pages.
National Center for Biotechnology Information. PubChem Substance Record for SID 471368824, SID 471368824, Source: Patentscope (WIPO). https://pubchem.ncbi.nlm.nih.gov/substance/471368824. Available Date Sep. 27, 2002, 5 pages.
National Center for Biotechnology Information. PubChem Substance Record for SID 474211406, 3-(2-aminoethyl)-1H-indole-4-carboxylic acid, Source: Enamine. https://pubchem.ncbi.nlm.nih.gov/substance/474211406. Available Date Dec. 15, 2002 [retrieved on Feb. 1, 2023], 7 pages.
National Center for Biotechnology Information. PubChem Substance Record for SID 627609, 2-(1H-indol-3-yl)ethanamine, Source: NIAID ChemDB. https://pubchem.ncbi.nlm.nih.gov/substance/627609, Modify Date: Jan. 21, 2015 [retrieved on Mar. 2, 2023]. 8 pages.
National Institutes of Health, "Depression Screening," (NIH)/National Library of Medicine, U.S. Dept. of Health & Human Services,(Dec. 15, 2022); [retrieved from the Internet on unknown date from: https://medlineplus.gov/lab-tests/depression-screening/]; 7 pages.
Nichols, D. E., "Psychedelics." Pharmacol Rev. Apr. 2016;68(2):264-355.
Nichols, "Hallucinogens." Pharmacol Ther. Feb. 2004; 101(2):131-81.
Nichols, "Structure-Activity Relationships of Phenethylamine Hallucinogens." J Pharm Sci. Aug. 1981; 70(8): 839-49.
Null24, "N,N-DMT and it's connection to spiritual consciousness (or something like that)," dmt.nexus.me [Online] (Feb. 7, 2014); Retrieved from Internet Archive Wayback Machine at URL: [https://web.archive.org/web/20240108174403/https://www.dmt-nexus.me/forum/default.aspx?g=posts&m=520577#post520577] on [Oct. 1, 2025]; 4 pages.
Olin et al., "Mortality and Suicide Risk in Treatment-Resistant Depression: An Observational Study of the Long-Term Impact of Intervention." PLoS One. Oct. 2012; 7(10):e48002. doi: 10.1371/journal.pone.0048002. Epub Oct. 25, 2012, 11 pages.
Oliver et al., "Beta-blockers: Historical Perspective and Mechanisms of Action." Rev Esp Cardiol (Engl Ed). Oct. 2019; 72(10): 853-862.
Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.
Osorio et al., "Antidepressant effects of a single dose of ayahuasca in patients with recurrent depression: a preliminary report." Braz J Psychiatry. Jan.-Mar. 2015;37(1):13-20. doi: 10.1590/1516-4446-2014-1496.
Ott, J., "Pharmañopo—Psychonautics: Human intranasal, sublingual, intrarectal, pulmonary and oral pharmacology of bufotenine." J Psychoactive Drugs. Jul.-Sep. 2001; 33(3): 273-81.
Ott, J., "Pharmepena-psychonautics: human intranasal, sublingual and oral pharmacology of 5-methoxy-N, N-dimethyl-tryptamine." J Psychoactive Drugs. Oct.-Dec. 2001;33(4):403-7.
Palhano-Fontes et al., "A randomized placebo-controlled trial on the antidepressant effects of the psychedelic ayahuasca in treatment-resistant depression." bioRxiv preprint doi: https://doi.org/10.1101/103531, Aug. 15, 2017, 10 pages.
Palhano-Fontes et al., "Rapid antidepressant effects of the psychedelic ayahuasca in treatment-resistant depression: a randomized placebo-controlled trial." Psychol Med. Mar. 2019;49(4):655-663. doi: 10.1017/S0033291718001356. Epub Jun. 15, 2018.
Pandy-Szekeres et al., "GPCRdb in 2023: state-specific structure models using AlphaFold2 and new ligand resources", Nucleic Acids Res. Jan. 6, 2023; 51(D1): D395-D402. 8 pages.
Pandy-Szekeres et al., "The G Protein Database, GproteinDb." Nucleic Acids Res. Jan. 7, 2022; 50(D1): D518-D525.
PCT Application No. PCT/US2021/031215, International Search Report and Written Opinion mailed Oct. 1, 2021, Applicant Psilera Inc; 10 pages.
PCT Application No. PCT/US2022/026396, International Preliminary Report on Patentability mailed Nov. 9, 2023, Applicant Atai Life Sciences AG; 8 pages.
PCT Application No. PCT/US2022/026396, International Search Report and Written Opinion mailed Jul. 28, 2022, Applicant Atai Life Sciences AG; 10 pages.
PCT Application No. PCT/US2022/030912, International Preliminary Report on Patentability mailed Dec. 7, 2023, Applicant Atai Life Sciences AG; 10 pages.

(56) References Cited

OTHER PUBLICATIONS

PCT Application No. PCT/US2022/030912, International Search Report and Written Opinion mailed Oct. 5, 2022, Applicant Atai Life Sciences AG; 20 pages.
PCT Application No. PCT/US2022/030912, Invitation to Pay Additional Fees mailed Jul. 28, 2022, Applicant Atai Life Sciences AG; 8 pages.
PCT Application No. PCT/US2022/032918, International Preliminary Report on Patentability mailed Dec. 21, 2023, Applicant Atai Life Sciences AG; 7 pages.
PCT Application No. PCT/US2022/032918, International Search Report and Written Opinion mailed Oct. 12, 2022, Applicant Atai Life Sciences AG; 10 pages.
PCT Application No. PCT/US2022/032918, Invitation to Pay Additional Fees mailed Aug. 12, 2022, Applicant Atai Life Sciences AG; 2 pages.
PCT Application No. PCT/US2022/045336, International Preliminary Report on Patentability mailed Apr. 11, 2024, Applicant Atai Life Sciences AG; 7 pages.
PCT Application No. PCT/US2022/045336, International Search Report and Written Opinion mailed Jan. 13, 2023, Applicant Atai Life Sciences AG; 14 pages.
PCT Application No. PCT/US2022/047520, International Preliminary Report on Patentability mailed May 10, 2024, Applicant Psilera Inc; 8 pages.
PCT Application No. PCT/US2022/047520, International Search Report and Written Opinion mailed Mar. 1, 2023, Applicant Psilera Inc; 11 pages.
PCT Application No. PCT/US2022/047520, Invitation to Pay Additional Fees mailed Jan. 3, 2023, Applicant Psilera Inc; 2 pages.
PCT Application No. PCT/US2022/082465, International Search Report and Written Opinion mailed Jun. 6, 2023, Applicant Atai Life Sciences AG; 11 pages.
PCT Application No. PCT/US2022/082465, Invitation to Pay Additional Fees mailed Mar. 16, 2023, Applicant Atai Life Sciences AG; 3 pages.
PCT Application No. PCT/US2023/073574, International Preliminary Report on Patentability mailed Mar. 20, 2025, Applicant Atai Life Sciences AG; 9 pages.
PCT Application No. PCT/US2023/073574, International Search Report and Written Opinion mailed Feb. 16, 2024, Applicant Atai Life Sciences AG; 13 pages.
PCT Application No. PCT/US2023/073574, Invitation to Pay Additional Fees mailed Nov. 6, 2023, Applicant Atai Life Sciences AG; 2 pages.
PCT Application No. PCT/US2023/077879, International Preliminary Report on Patentability mailed May 8, 2025, Applicant Atai Therapeutics Inc; 9 pages.
PCT Application No. PCT/US2023/077879, International Search Report and Written Opinion mailed Apr. 4, 2024, Applicant Atai Therapeutics Inc; 11 pages.
PCT Application No. PCT/US2023/082080, International Preliminary Report on Patentability mailed Jun. 12, 2025, Applicant Atai Life Sciences AG; 7 pages.
PCT Application No. PCT/US2023/082080, International Search Report and Written Opinion mailed Apr. 4, 2024, Applicant Atai Life Sciences AG; 8 pages.
PCT Application No. PCT/US2023/084319, International Preliminary Report on Patentability mailed Jun. 26, 2025, Applicant Atai Therapeutics Inc; 9 pages.
PCT Application No. PCT/US2023/084319, International Search Report and Written Opinion mailed May 20, 2024, Applicant Atai Therapeutics Inc; 13 pages.
PCT Application No. PCT/US2024/026797, International Search Report and Written Opinion mailed Sep. 6, 2024, Applicant Atai Therapeutics Inc; 10 pages.
PCT Application No. PCT/US2024/026797, Invitation to Pay Additional Fees mailed Jun. 25, 2024, Applicant Atai Therapeutics Inc; 2 pages.
PCT Application No. PCT/US2024/038804, International Search Report and Written Opinion mailed Dec. 17, 2024, Applicant Atai Therapeutics Inc; 14 pages.
PCT Application No. PCT/US2024/038804, Invitation to Pay Additional Fees mailed Sep. 23, 2024, Applicant Atai Therapeutics Inc; 3 pages.
PCT Application No. PCT/US2024/039503, International Search Report and Written Opinion mailed Nov. 5, 2024, Applicant Atai Therapeutics Inc; 17 pages.
PCT Application No. PCT/US2024/039503, Invitation to Pay Additional Fees mailed Sep. 10, 2024, Applicant Atai Therapeutics Inc; 2 pages.
PCT Application No. PCT/US2024/045494, International Search Report and Written Opinion mailed Nov. 15, 2024, Applicant Atai Therapeutics Inc; 11 pages.
PCT Application No. PCT/US2024/049678, International Search Report and Written Opinion mailed Jan. 21, 2025, Applicant Atai Therapeutics Inc; 9 pages.
PCT Application No. PCT/US2024/061478, International Search Report and Written Opinion mailed Apr. 23, 2025, Applicant Atai Therapeutics Inc; 10 pages.
PCT Application No. PCT/US2024/061478, Invitation to Pay Additional Fees mailed Feb. 25, 2025, Applicant Atai Therapeutics Inc; 2 pages.
PCT Application No. PCT/US2025/014571, International Search Report and Written Opinion mailed Mar. 21, 2025, Applicant Atai Therapeutics Inc; 15 pages.
PCT Application No. PCT/US2025/039639, International Search Report and Written Opinion mailed Dec. 31, 2025, Applicant Atai Therapeutics, Inc. et al.; 17 pages.
PCT Application No. PCT/US2025/039639, Invitation to Pay Additional Fees mailed Oct. 27, 2025, Applicant Atai Therapeutics, Inc.; 2 pages.
Perez Custodio et al., "25B-NBOMe, a novel N-2-methoxybenzyl-phenethylamine (NBOMe) derivative, may induce rewarding and reinforcing effects via a dopaminergic mechanism: evidence of abuse potential." Addict Biol. Nov. 2020; 25(6):e12850. doi: 10.1111/adb.12850. Epub Nov. 20, 2019, 12 pages.
Pokorny et al., "Modulatory effect of the 5-HT1A agonist buspirone and the mixed non-hallucinogenic 5-HT1A/2A agonist ergotamine on psilocybin-induced psychedelic experience." Eur Neuropsychopharmacol. Apr. 2016; 26(4):756-66. doi: 10.1016/j.euroneuro.2016.01.005. Epub Jan. 22, 2016.
Polanco, Martin, "Psychedelic therapy with 5MeO-DMT." Martinpolancomd.com, [Online] (Jan. 3, 2020); retrieved from Internet Archive Wayback Machine at URL: [https://web.archive.org/web/20240216113910/https://www.martinpolancomd.com/post/psychedelic-therapy-with-5meo-dmt] on [Oct. 27, 2025]; 2 pages.
Porta Sophia, "Porta Sophia Publishes Narrative Review Manuscript Summarizing Historical Evidence of 5-MeO-DMT as a Compound Used in Therapeutic Practice." Press release, Nov. 12, 2024, 2 pages.
Porter, MD, et al., "The Merck Manual of Diagnosis and Therapy," Twentieth Edition, Merck Sharp & Dohme Corp., (Apr. 2018), pp. 1757-1761.
Pottie et al., "Identification of psychedelic new psychoactive substances (NPS) showing biased agonism at the 5-HT2AR through simultaneous use of β-arrestin 2 and miniGαq bioassays", Biochem Pharmacol. Dec. 2020: 182: 114251. Epub Sep. 28, 2020. 37 pages.
Preller et al., "Effects of serotonin 2A/1A receptor stimulation on social exclusion processing," PNAS, May 3, 2016, vol. 113, No. 18, 5119-5124.
Preller et al. "Role of the 5-HT2A Receptor in Self- and Other-Initiated Social Interaction in Lysergic Acid Diethylamide-Induced States: A Pharmacological fMRI Study." Journal of Neuroscience. Apr. 2018;38(14):3603-3611. doi: 10.1523/JNEUROSCI.1939-17.2018.
Preller et al. "The fabric of meaning and subjective effects in LSD-induced states depend on serotonin 2A receptor activation." Current Biology. Feb. 2017;27(3):451-457. doi: 10.1016/j.cub.2016.12.030.

(56) References Cited

OTHER PUBLICATIONS

Prescribing information for Brevibloc (Esmolol Hydrochloride): www.baxterpi.com/pi-pdf/Brevibloc_PI.pdf), Initial U.S. approval: 1986, revised Apr. 2018, 19 pages.
Psychedelics Today, "Rafael Lancelotta—Exploring 5-MeO-DMT." [Video] YouTube.com, posted (May 10, 2018). Available at: https://www.youtube.com/watch?v=kEp-Az9ibLM], (accessed Sep. 30, 2025), 1 page.
Puledda et al., "An update on migraine: current understanding and future directions." J Neurol. Sep. 2017;264(9):2031-2039. doi: 10.1007/s00415-017-8434-y. Epub Mar. 20, 2017.
Puri et al., "Thiolation of Biopolymers for Developing Drug Delivery Systems with Enhanced Mechanical and Mucoadhesive Properties: A Review." Polymers (Basel). Aug. 11, 2020;12(8): 1803. doi: 10.3390/polym12081803. 27 pages.
Qi et al., "The Development of Toad Toxins as Potential Therapeutic Agents." Toxins (Basel). Aug. 20, 2018;10(8):336. doi: 10.3390/toxins10080336, 14 pages.
Queensland Brain Institute, "Deep brain stimulation for depression hits a(nother) roadblock," The University of Queensland, [Online] (Aug. 20, 2015); last updated May 18, 2017, [retrieved from the internet on unknown date from: https://qbi.uq.edu.au/blog/2017/02/deep-brain-stimulation-depression-hits-another-roadblock]; 4 pages.
Quilty et al., "The structure of the Montgomery-sberg depression rating scale over the course of treatment for depression." Int J Methods Psychiatr Res. Sep. 2013;22(3):175-84. doi: 10.1002/mpr.1388. Epub Aug. 19, 2013.
Rakofsky, et al., "The prevalence and severity of depressive symptoms along the spectrum of unipolar depressive disorders: a post hoc analysis," J Clin Psychiatry. Nov. 2013; 74(11):1084-91.
Ramaekers, et al., "Regarding the clinical study with ref GH001-MDD-102 / NL70411.068.19 / METC 19-036." Letter to the CCMO, concerning clinical trial GH001-MDD-102, Oct. 13, 2020, 3 pages.
Raskin, Jonathan D., "Are There Viable Alternatives to DSM-5? Can ICD, PDM, HiTOP, RDoC, or PTMF win a kind of diagnostic game of thrones?," Psychology Today, [Online] (May 22, 2019) [retrieved from the Internet on Oct. 1, 2025 at: https://www.psychologytoday.com/us/blog/making-meaning/201905/are-there-viable-alternatives-to-the-dsm-5]; 15 pages.
Ray, T., "Psychedelics and the Human Receptorome." PLoS One. Feb. 2, 2010;5(2):e9019. doi: 10.1371/journal.pone.0009019.17 pages.
Reckweg, et al., "A Phase 1, Dose-Ranging Study to Assess Safety and Psychoactive Effects of a Vaporized 5-Methoxy-N, N-Dimethyltryptamine Formulation (GH001) in Health Volunteers," Frontiers in Pharmacology, Nov. 2021; vol. 12, Article 760671, pp. 1-12.
Reckweg et al. "A phase 1/2 trial to assess safety and efficacy of a vaporized 5-methoxy-N, N-dimethyltryptamine formulation (GH001) in patients with treatment-resistant depression." Front Psychiatry. Jun. 20, 2023:14:1133414. doi: 10.3389/fpsyt.2023.1133414. eCollection 2023, 8 pages.
Response to Office Action, European Patent Office, EP Application Serial No. 21800237.6, Oct. 30, 2024. 13 pages.
Retreat.Guru, "Dr. Gerardo Sandoval Isaac, About the teacher," Retreat.Guru, [Online] (publication date unknown); [retrieved Mar. 4, 2025 from https://retreat.guru/teachers/756-59/dr-g]; 3 pages.
Riba, et al., "Metabolism and urinary disposition of N,N-dimethyltryptamine after oral and smoked administration: a comparative study", Drug Test Anal. May 2015;7(5):401-6. Epub Jul. 28, 2014.
Riga, et al., "The natural hallucinogen 5-MeO-DMT, component of Ayahuasca, disrupts cortical function in rats: reversal by antipsychotic drugs." Int J Neuropsychopharmacol. Aug. 2014;17(8):1269-82. doi: 10.1017/S1461145714000261. Epub Mar. 20, 2014.
Riga, et al., "The serotonin hallucinogen 5-MeO-DMT alters cortico-thalamic activity in freely moving mice: Regionally-selective involvement of 5-HT1A and 5-HT2A receptors." Neuropharmacology. Nov. 2018;142:219-230.
Rivier L., et al., "Ayahuasca," the South American hallucinogenic drink: An ethnobotanical and chemical investigation. Economic Botany 26, (Apr. 1972). https://doi.org/10.1007/BF02860772, 101-129.
Roger R., (Feb. 26, 2016) "What is the difference between 5-MeO DMT and DMT? Choosing a DMT Therapy", Psychedelic Times online, Feb. 26, 2016, 5 pages.
Roseman et al. "Quality of acute psychedelic experience predicts therapeutic efficacy of psilocybin for treatment-resistant depression." Frontiers in Pharmacology. Jan. 2018.8:974, 10 pages. doi: 10.3389/fphar.2017.00974.
Roth et al., "High-affinity Agonist Binding Is Not Sufficient for Agonist Efficacy at 5-Hydroxytryptamine2A Receptors: Evidence in Favor of a Modified Ternary Complex Model", The Journal of Pharmacology and Experimental Therapeutics, 1997, vol. 280, No. 2, pp. 576-583.
Ruiz et al , "Routes of Drug Administration: Dosage, Design, and Pharmacotherapy Success", In book: ADME Processes in Pharmaceutical Sciences, Chapter 6, Jan. 2018, DOI:10.1007/978-3-319-99593-9_6, 44 pages.
Santos-Longhurst, A, "How Long Does DMT Last?" Healthline.com, [Online] (Nov. 24, 2019); [retrieved from the internet on Jun. 24, 2022 from https://www.healthline.com/health/how-long-does-dmt-last]; 12 pages.
Sargent et al., "Radiohalogen-Labeled Imaging Agents. 3. Compounds for Measurement of Brain Blood Flow by Emission Tomography," Journal of Medicinal Chemistry (Aug. 1984), 27(8), 1071-1077.
Schenberg (2017) "Translation and cultural adaptation of the States of Consciousness Questionnaire (SOCQ) and statistical validation of the Mystical Experience Questionnaire (MEQ30) in Brazilian Portuguese" Archives of Clinical Psychiatry. Jan. 26, 2017, 44(1):1-5.
Schifano et al., "New psychoactive substances (NPS) and serotonin syndrome onset: A systematic review", Exp Neurol. May 2021: 339: 113638. Epub Feb. 8, 2021. 29 pages.
Schifano et al., "New Psychoactive Substances (NPS), Psychedelic Experiences and Dissociation: Clinical and Clinical Pharmacological Issues." Current Addiction Reports. Jun. 2019, 6:140-152.
Schindler et al., "Exploratory Controlled Study of the Migraine-Suppressing Effects of Psilocybin", Neurotherapeutics, Jan. 2021; 18(1): 534-543. Epub Nov. 12, 2020. 10 pages.
Schlag et al., "Adverse effects of psychedelics: From anecdotes and misinformation to systematic science." J Psychopharmacol. Mar. 2022; 36(3): 258-272.
Schmid et al., "Serotonin, but not N-Methyltryptamines, activates the serotonin 2A receptor via a β-Arrestin2/Src/Akt signaling complex in vivo." The Journal of Neuroscience, Oct. 6, 2010, 30(40), 13513-13524.
Shaikh et al., "Medicinal Value of Mimosa Pudica as an Anxiolytic and Antidepressant: a Comprehensive Review." World Journal of Pharmacy and Pharmaceutical Sciences. Mar. 2016 5(3), 420-432, 14 pages.
Shen et al., "Nonlinear pharmacokinetics of 5-methoxy-N,Ndimethyltryptamine in mice." Drug Metab Dispos. Jul. 2011; 39(7): 1227-34. doi: 10.1124/dmd.111.039107. Epub Apr. 4, 2011.
Shen et al., "Psychedelic 5-Methoxy-N,N-dimethyltryptamine: Metabolism, Pharmacokinetics, Drug Interactions, and Pharmacological Actions", Curr Drug Metab., Oct. 2010; 11(8): 659-666.
Shen L, et al., "Bufotenines-loaded liposome exerts anti-inflammatory, analgesic effects and reduce gastrointestinal toxicity through altering lipid and bufotenines metabolism", Biomed Pharmacother, Sep. 2022, vol. 153, pp. 1-12.
Sherwood et al. "Synthesis and characterization of 5-MeO-DMT succinate for clinical use." ACS Omega. Dec. 2020;5(49):32067-32075. doi: 10.1021/acsomega.0c05099.
Sizemore et al., "Serotonergic Modulation Across Sensory Modalities." J Neurophysiol. Jun. 1, 2020;123(6):2406-2425. doi: 10.1152/jn.00034.2020. Epub May 13, 2020.
Sizemore, T.R, and Dacks, A.M., "Circadian Clocks: Mosquitoes Master the Dark Side of the Room", Curr Biol. Aug. 17, 2020; 30(16): R932-R934. 3 pages.

(56) References Cited

OTHER PUBLICATIONS

Stafford, Peter. "Psychedelics Encyclopedia." Ronin, Third Edition, Jan. 12, 1993, 257 pages.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Strassman, "Dose-response study of N,N-dimethyltryptamine in humans: II. Subjective effects and preliminary results of a new rating scale", Arch Gen Psychiatry. Feb. 1994; 51(2): 98-108.
Studerus, E. et al., "Psychometric evaluation of the altered states of consciousness rating scale (OAV)," PloS One, 5:e12412, 19 pages (Aug. 31, 2010).
Sullenchoirboy, "Molecular Death for the Warrior, 5-MeO-DMT." [Online] Erowid.org, (Feb. 15, 2003); Retrieved from Internet Archive Wayback Machine at URL: [https://web.archive.org/web/20130110114001/https://erowid.org/experiences/exp.php?ID=21268] on [Oct. 27, 2025]; 2 pages.
Szabo et al., "Psychedelics and immunomodulation: novel approaches and therapeutic opportunities." Front Immunol. Jul. 14, 2015:6:358. doi: 10.3389/fimmu.2015.00358. eCollection 2015, 11 pages.
Terry, Alvin V., "Drugs that target serotonergic receptors." Cognitive Enhancing Drugs, pp. 79-80, Ed. J. Buccafusco, Birkhauser, (Year: 2004, month: unknown), 2 pages.
Thase et al., "Safety and Efficacy of GH001 in TRD: Results from a Phase 2b, Double-blind, Randomized Controlled Trial," Poster presented at the American Society of Clinical Psychopharmacology Annual Meeting, May 27-30, 2025, 1 page.
Thase et al., "Safety and Efficacy of GH001 in TRD: Results from a Phase 2b, Double-blind, Randomized Controlled Trial." Presentation at the American Society of Clinical Psychopharmacology Annual Meeting, May 27-30, 2025, 16 pages.
Thase, Michael E., "How Should Efficacy Be Evaluated in Randomized Clinical Trials of Treatments for Depression?," J Clin Psychiatry, Apr. 1, 1999; 60 (suppl 4), pp. 23-31.
Thase, Michael E., "Psychiatric and medical comorbidity as contributing factors in treatment-resistant depression," 31st International Symposium on Controversies in Psychiatry—Innovation in Mental Health—Barcelona, Spain, Apr. 10-11, 2025, 6 pages.
Thase, Michael E., "The multifactorial presentation of depression in acute care." J Clin Psychiatry. Oct. 15, 2013; 74 Suppl 2:3-8, 6 pages.
Thase, Michael E., "Using biomarkers to predict treatment response in major depressive disorder: evidence from past and present studies," Dialogues Clin Neurosci. Dec. 2014; 16(4):539-44.
Third Wave, "The Essential Guide to 5-MEO-DMT, (5-MEO, Five-methoxy, the Power, Toad venom)." [Online] Thethirdwave.co (publication date unknown); retrieved from Internet Archive Wayback Machine at URL: [https://web.archive.org/web/20181109024846/https://thethirdwave.co/psychedelics/5-meo-dmt/] on [Sep. 29, 2025]; 22 pages.
Thoai, et al., "Design and Synthesis of Sustain-Acting Melatonin Prodrugs", Sep. 12, 2013 (Sep. 12, 2013), Journal of Chemistry, vol. 2013, Issue 1, pp. 1-6.
Timmermann, Christopher et al. "Neural correlates of the DMT experience assessed with multivariate EEG." Sci Rep. Nov. 19, 2019;9(1):16324. 13 pages.
Tirapegui et al., "Synthesis of N-(halogenated) benzyl analogs of superpotent serotonin ligands." Journal of the Chilean Chemical Society (Sep. 2014) 59(3):2625-2627.
Titeler et al. "Radioligand binding evidence implicates the brain 5 HT2 receptor as a site of action for LSD and phenylisopropylamine hallucinogens." Psychopharmacology. Feb. 1988;94(2):213-216. doi: 10.1007/BF00176847.
Tomaszewski et al., "Benzofuran Bioisosteres of Hallucinogenic Tryptamines," J. Med. Chem., May 1992, 35, pp. 2061-2064.
University of Zurich. Compositions and kits comprising N,N-dimethyltryptamine and harmine and their use in therapy. European Patent Application Serial No. EP20181489, filing date Jun. 24, 2020, receipt by WIPO Jul. 6, 2021. 56 pages.
U.S. Appl. No. 18/675,614, Third Party Pre-Issuance Submission filed Oct. 16, 2024; Inventor Terwey, Theis, 12 pages.
U.S. Appl. No. 19/284,159, filed Jul. 29, 2025; Inventor Craig, Kevin et al.
U.S. Appl. No. 19/358,021, filed Oct. 14, 2025; Inventor Witowski, Christopher G. et al.
U.S. Appl. No. 19/431,440, filed Dec. 23, 2025; Inventor Witowski, Christopher G et al.
U.S. Appl. No. 19/431,453, filed Dec. 23, 2025; Inventor Witowski, Christopher G et al.
U.S. Appl. No. 19/478,315, filed Oct. 24, 2025; inventor Gibbs, Alan et al.
Uthaug et al., "A single inhalation of vapor from dried toad secretion containing 5-methoxy-N,N-dimethyltryptamine (5-MeO-DMT) in a naturalistic setting is related to sustained enhancement of satisfaction with life, mindfulness-related capacities, and a decrement of psychopathological symptoms." Psychopharmacology (Berl). Sep. 2019;236(9):2653-2666. doi: 10.1007/s00213-019-05236-w. Epub Apr. 13, 2019.
Uthaug, et al., "Prospective examination of synthetic 5-methoxy-N, N-dimethyltryptamine inhalation: effects on salivary IL-6, cortisol levels, affect, and non-judgment," Psychopharmacology Mar. 2020; 237: 773-785. Epub Dec. 10, 2019.
Uthaug, et. al, "The Ethical and Ecological Considerations of Inhaling Bufotoxins from Incilius Alvarius." Psychedelics Today, [Online] (Oct. 3, 2018); [retrieved from the internet on Sep. 29, 2025 from URL: https://psychedelicstoday.com/2018/10/03/ethics-ecology-bufotoxins/]; 20 pages.
Valle et al. "Inhibition of alpha oscillations through serotonin-2A receptor activation underlies the visual effects of ayahuasca in humans." European Neuropsychopharmacology. Jul. 2016;26(7):1161-1175. doi: 10.1016/j.euroneuro.2016.03.012.
Viracocha, "The DMT Handbook." [Online] (Dec. 2008); [retrieved from the internet on unknown date from URL:https://catbull.com/alamut/Bibliothek/DMT_Handbook.pdf]; 31 pages.
Vollenweider et al. "Psilocybin induces schizophrenia-like psychosis in humans via a serotonin-2 agonist action." Neuroreport. Dec. 1998;9(17):3897-3902. doi: 10.1097/00001756-199812010-00024.
Vollenweider et al. "Psychedelic drugs: neurobiology and potential for treatment of psychiatric disorders." Nature Reviews Neuroscience. Nov. 2020;21(11):611-624. doi: 10.1038/s41583-020-0367-2.
Wang et al., "Anti-inflammatory and analgesic actions of bufotenine through inhibiting lipid metabolism pathway." Biomed Pharmacother. Aug. 2021:140:111749. doi: 10.1016/j.biopha.2021.111749. Epub May 28, 2021, 11 pages.
Wey et al., "Structure-based design, synthesis, and biological evaluation of indomethacin derivatives as cyclooxygenase-2 inhibiting nitric oxide donors." J Med Chem. Dec. 13, 2007;50(25):6367-82. doi: 10.1021/jm0611861. Epub Nov. 10, 2007.
Wikipedia, "Perfusion", Wikipedia.org, [Online] (Dec. 29, 2020); [retrieved from the internet on Jun. 24, 2022 from https://en.wikipedia.org/w/index.php?title=Perfusion&oldid=996968059]; 5 pages.
Winter et al., "The Paradox of 5-Methoxy-N,N-Dimethyltryptamine: An Indoleamine Hallucinogen That Induces Stimulus Control via 5-HT1A Receptors." Pharmacol Biochem Behav. Jan. 1, 2000;65(1):75-82. doi: 10.1016/s0091-3057(99)00178-1.
Winter, J.C. et al., "Psilocybin-induced stimulus control in the rat," Pharmacology Biochemistry and Behavior, 87(4):472480 (Oct. 2007) Epub Jun. 22, 2007.
Wolff, M., "Burger's Medicinal Chemistry and Drug Discovery." (Fifth Edition), John Wiley & Sons, New York, (1995); 1: 975-977.
Wood et al., "Prevalence of use and acute toxicity associated with the use of NBOMe drugs", Clin Toxicol (Phila). Feb. 2015; 53(2): 85-92. doi:10.3109/15563650.2015.1004179.
Wordsworth, Richard, "LSD doesn't just treat mental illness, 'it could actually heal the brain.'" [Online] Wired.uk (Mar. 9, 2017) article, Retrieved from Internet Archive Wayback Machine at URL: [https://web.archive.org/web/20230510125630/https://www.wired.co.uk/article/khaliya-mental-health] on [Sep. 30, 2025]; 9 pages.
Yaesutom, forum post in thread titled: "The Big & Dandy 5-MeO-DMT Thread—First Launch." [Online] bluelight.org(Jan. 28, 2004); available at: [https://bluelight.org/xf/threads/the-big-dandy-5-meo-dmt-thread-first-launch.72085/post-1589648]; retrieved from Inter-

(56) References Cited

OTHER PUBLICATIONS net Archive Wayback Machine at URL: [https://web.archive.org/web/20240119092733/https://bluelight.org/xf/threads/the-big-dandy-5-meo-dmt-thread-first-launch.72085/page-5#post-1589648] on [Oct. 27, 2025]; 10 pages.
Yann, "Yann with Ayahuasca, My experience healing with Ayahuasca and other entheogens." [Online] Yannwithayahuasca.com (Sep. 19, 2017); Retrieved from Internet Archive Wayback Machine at URL: [https://web.archive.org/web/20211026092140/https://yannwithayahuasca.com/about/] on [Oct. 27, 2025]; 7 pages.
Yannwithayahuasca, "Can you Bad Trip on Bufo Alvarius / Sapito? Against depression : Ayahuasca or Bufo Alvarius?" [Video] Youtube.com, posted (May 25, 2017). Available at: [https://www.youtube.com/watch?v=4GcU2outMFs], (accessed Sep. 30, 2025), 3 pages.
Yu, A.M., "Indolealkylamines: Biotransformations and Potential Drug-Drug Interactions," The AAPS Journal, Jun. 2008, vol. 10, No. 2, pp. 242-253.
Zagorski, Nick, "Experts Debate What's Next for DBS for Depression," Psychiatry Online, Clinical & Research, Psychiatric News, Mar. 2020; vol. 55, Issue 6, 4 pages.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018. 22 pages.
Zomakmk7, "5-meo-dmt cured my depression," dmt.nexus.me, [Online] (Nov. 14, 2018); Retrieved from Internet Archive Wayback Machine at URL: [https://web.archive.org/web/20240120142828/https://www.dmt-nexus.me/forum/default.aspx?g=posts&m=926667] on [Oct. 27, 2025]; 1 page.
Agin-Liebes et al., "Long-term follow-up of psilocybin-assisted psychotherapy for psychiatric and existential distress in patients with life-threatening cancer," J Psychopharmacol. 34(2):155-166 (Feb. 2020).
Agurell et al., "Metabolism of 5-methoxy-N,-N dimethyltryptamine-14C in the rat," Biochemical Pharmacology. 18:2771-2781 (1969).
Akai et al., "Anxiolytic effects of lisuride and its agonistic action to central 5-HT1A receptors," Nihon Yakurigaku Zasshi. 97(4):209-20 (English Abstract Included) (Apr. 1991).
Akerman et al. "Animal models for trigeminal autonomic cephalalgias," In 'Cluster Headache and other Trigeminal Autonomic Cephalalgias', Chapter 9, eds. Leone M, May A. Springer Nature Switzerland AG (2020).
Akerman et al., "Oxygen inhibits neuronal activation in the trigeminocervical complex after stimulation of trigeminal autonomic reflex, but not during direct dural activation of trigeminal afferents," Headache. 49(8):1131-43 (Sep. 2009).
Al-Harbi, K. S., "Treatment-resistant depression: therapeutic trends, challenges, and future directions," Patient Preference and Adherence. 6:369-88 (Apr. 2012) (20 pages).
Ali et al., "Revisiting the general solubility equation: in silico prediction of aqueous solubility incorporating the effect of topographical polar surface area," Journal of chemical information and modeling, Feb. 27, 2012;52(2):420-8.
Alnefeesi et al., "Real-world effectiveness of ketamine in treatment-resistant depression: A systematic review & Meta-analysis," Journal of Psychiatric Research, (Jul. 2022), vol. 151: pp. 693-709.
Anderson et al., "Microdosing psychedelics: personality, mental health, and creativity differences in microdosers," Psychopharmacology (Berl). 236(2):731-740 (Feb. 2019).
Arias-de la Torre et al., "Prevalence and variability of current depressive disorder in 27 European countries: a population-based study," Lancet Public Health. 6(10):e729-e738 (Oct. 2021).
Atai Life Sciences, "atai Life Sciences and Beckley Psytech Announce Positive Topline Results from the Phase 2b Study of BPL-003 in Patients with Treatment-Resistant Depression," [press release], Jul. 1, 2025, Globe Newswire, [available at URL: https://ir.atai.life/news-releases/news-release-details/atai-life-sciences-and-beckley-psytech- announce-positive-topline], 4 pages.
Atai Life Sciences, "atai Life Sciences and Beckley Psytech to Combine Creating a Global Leader in Psychedelic Mental Health Therapies," [press release] Jun. 2, 2025, Globe Newsier, [available online at: https://ir.atai.life/news-releases/news-release-details/atai-life-sciences-and-beckley-psytech-combine-creating-global], 4 pages.
Atai Life Sciences, "atai Life Sciences Announces $50 Million Private Placement Financing," [press release], Jul. 1, 2025 [available online at: https://ir.atai.life/news-releases/news-release-details/atai-life-sciences-announces-50-million-private-placement], 2 pages.
Atai Life Sciences, "atai Life Sciences Announces Closing of Public Offering and Full Exercise of Option to Purchase Additional Common Shares," [press release], Feb. 20, 2025, Global Newswire, [Available online at URL: https://ir.atai.life/news-releases/news-release-details/atai-life-sciences-announces-closing-public-offering-and-full], 2 pages.
Atai Life Sciences, "atai Life Sciences Announces Completion of Enrollment in Phase 2b Clinical Trial Evaluating BPL-003 for Treatment-Resistant Depression," Mar. 5, 2025, Globe Newswire, [Available online at URL: https://ir.atai.life/news-releases/news-release-details/atai-life-sciences-announces-completion-enrollment-phase-2b], 2 pages.
Atai Life Sciences, "atai Life Sciences Announces Dosing of First Patient in Part 2 of Beckley Psytech's Phase 2a Study Exploring BPL-003 Adjunctive to SSRIs in Patients with Treatment Resistant Depression," [press release], Apr. 24, 2024, Globe Newswire, [available online at URL: https://ir.atai.life/news-releases/news-release-details/atai-life-sciences- announces-dosing-first-patient-part-2-beckley], 2 pages.
Atai Life Sciences, "atai Life Sciences Announces First Participant Dosed in Phase 1 b Trial of VLS-01," [press release], Mar. 4, 2024, Globe Newswire, [Available online at URL: https://ir.atai.life/news-releases/news-release-details/atai-life-sciences- announces-first-participant-dosed-phase-1b], 2 pages.
Atai Life Sciences, "atai Life Sciences Announces First Patient Dosed in Elumina, the Phase 2 Clinical Trial of VLS-01 for Treatment-Resistant Depression," [press release], Mar. 11, 2025, [Available online at URL: https://ir.atai.life/news-releases/news-release-details/atai-life-sciences-announces-first-patient-dosed-elumina-phase-2], 2 pages.
Atai Life Sciences, "atai Life Sciences Announces First Patient Dosed in Phase 2 Study of EMP-01 for the Treatment of Social Anxiety Disorder," [press release] May 13, 2025, Globe Newswire, [available online at URL: https://ir.atai.life/news-releases/news-release-details/atai-life- sciences-announces-first-patient-dosed-phase-2-study], 2 pages.
Atai Life Sciences, "atai Life Sciences Announces Key Leadership Appointments as it Advances its Pipeline of Novel Psychedelic Therapeutics for Mental Health," [press release] Jan. 10, 2025, Globe Newswire, [Available online at URL: https://ir.atai.life/news-releases/news-release-details/atai-life-sciences-announces-key-leadership-appointments-it], 2 pages.
Atai Life Sciences, "atai Life Sciences Announces Positive Initial Results from Beckley Psytechs Phase 2a Open Label Study of BPL-003 (Intranasal 5-MeO-DMT) in Treatment Resistant Depression," Mar. 27, 2024. [Available https://ir.atai.life/news-releases/news-release-details/atai-life-sciences-announces-positive- initial-results-beckley] (2 pages).
Atai Life Sciences, "atai Life Sciences Announces Positive Preliminary Results from Phase 1b Trial of VLS-01 (Buccal Film DMT)," press-release], Aug. 13, 2024, Globe Newswire, [Available online at URL: https://ir.atai.life/news-releases/news-release- details/atai-life-sciences-announces-positive-preliminary-results-phase], 2 pages.
Atai Life Sciences, "atai Life Sciences Announces Positive Topline Data from Part 2 of Beckley Psytechs Phase 2a Study of BPL-003 in Combination with SSRIs for Treatment-Resistant Depression," [press release], May 20, 2025, Globe Newswire, [Available online at URL: https://ir.atai.life/news-releases/news-release-details/atai-life-sciences-announces-positive-topline- data-part-2], 2 pages.
Atai Life Sciences, "atai Life Sciences Announces Positive Topline Results from Beckley Psytech's BPL-003 (intranasal 5-MeO-DMT benzoate) Phase 2a Open-Label Study for Alcohol Use Disorder," [press release], Jan. 28, 2025, [Available online at URL: https://ir.ataibeckley.com/node/8791/pdf], 2 pages.

(56) References Cited

OTHER PUBLICATIONS

Atai Life Sciences, "atai Life Sciences Announces Positive Topline Results from Single Ascending Dose Phase 1 Studywith EMP-01 (R-MDMA)," [press release] Jan. 2, 2024, [Available online at URL: https://ir.atai.life/news-releases/news-release-details/atai-life-sciences-announces-positive-topline-results-single], 2 pages.
Atai Life Sciences, "atai Life Sciences Announces Pricing of Public Offering of Common Shares," [press release], Feb. 12, 2025, Global Newswire, [Available online at URL: https://ir.atai.life/news-releases/news-release-details/atai-life-sciences-announces-pricing-public-offering-common], 1 page.
Atai Life Sciences, "atai Life Sciences Announces Proposed Public Offering of Common Shares," [press release], Feb. 12, 2025, Globe Newswire, [Available online at URL: https://ir.atai.life/news-releases/news-release-details/atai-life-sciences-announces-proposed-public-offering-common], 1 page.
Atai Life Sciences, "atai Life Sciences Announces Strategic Investment in Beckley Psytech to Accelerate the Clinical Development of Short-Duration Psychedelics," Press-release, Jan. 4, 2024. [Available https://ir.atai.life/news-releases/news-release-details/atai-life-sciences-announces-strategic-investment-beckley], (2 pages).
Atai Life Sciences, "atai Life Sciences Announces the Publication of Beckley Psytech's Phase 1 Study of BPL-003 in the Journal of Psychopharmacology," [press release], Apr. 17, 2024, Globe Newswire, [Available online at URL: https://ir.atai.life/news- releases/news-release-details/atai-life-sciences-announces-publication-beckley-psytechs-phase], 2 pages.
Atai Life Sciences, "atai Life Sciences Announces Update on Beckley Psytech's Phase 1/2a Trial of ELE-101 (IV Psilocin) for Major Depressive Disorder, with Initial Results from Phase 1 and First Patients Dosed in Phase 2a," [press release], Jun. 20, 2024, Globe Newswire, [Available online at URL: https://ir.atai.life/news-releases/news-release-details/atai-life-sciences-announces-update-beckley-psytechs-phase-2a], 2 pages.
Atai Life Sciences, "atai Life Sciences Appoints Anne Johnson as Chief Financial Officer," [press release], Feb. 6, 2024, Globe Newswire, [Available online at URL: https://ir.atai.life/news-releases/news-release-details/atai-life-sciences-appoints-anne-johnson-chief-financial-officer], 1 page.
Atai Life Sciences, "atai Life Sciences Reports First Quarter 2024 Financial Results and Corporate Updates," [press release], May 15, 2024, Globe Newswire, [Available online at URL: https://ir.atai.life/news-releases/news-release-details/atai-life-sciences-reports-first-quarter-2024-financial-results], 4pages.
Atai Life Sciences, "atai Life Sciences Reports First Quarter 2025 Financial Results and Recent Corporate Updates," [press release] May 14, 2025, Globe Newswire, [Available online at URL: https://ir.atai.life/news-releases/news-release-details/atai-life-sciences-reports-first- quarter-2025-financial-results], 4 pages.
Atai Life Sciences, "atai Life Sciences Reports Fourth Quarter and Full Year 2023 Financial Results and Provides Corporate and Clinical Highlights," Mar. 28, 2024, Globe Newswire, [Available online at URL: https://ir.atai.life/news-releases/news-release-details/atai-life-sciences-reports-fourth-quarter-and-full-year-2023], 4 pages.
Atai Life Sciences, "atai Life Sciences Reports Fourth Quarter and Full Year 2024 Financial Results and Recent Corporate Highlights," Mar. 17, 2025, Globe Newswire, [Available online at URL: https://ir.atai.life/news-releases/news-release-details/atai-life-sciences-reports-fourth-quarter-and-full-year-2024], 4 pages.
Atai Life Sciences, "atai Life Sciences Reports Second Quarter 2024 Financial Results and Provides Corporate Updates," [press release], Aug. 13, 2024, Globe Newswire, [Available online at URL: https://ir.atai.life/news-releases/news-release-details/atai-life-sciences-reports-second-quarter-2024-financial-results], 4 pages.
Atai Life Sciences, "atai Life Sciences Reports Third Quarter 2024 Financial Results and Provides Corporate Updates," [press release], Nov. 13, 2024, Globe Newswire, [Available online at URL: https://ir.atai.life/news-releases/news-release-details/atai-life-sciences-reports-third-quarter-2024-financial-results], 4 pages.
Atai Life Sciences, "atai Life Sciences Strengthens Board with Appointment of Two New Independent Directors," [press release], May 23, 2024, Globe Newswire, [Available online at URL: https://ir.atailife/news-releases/news-release-details/atai-life-sciences-strengthens-board-appointment-two-new], 1 page.
Atai Life Sciences, "atai Life Sciences to Participate in the 2024 Maxim Healthcare Virtual Summit," [press release], Oct. 15, 2024, Globe Newswire, [Available online at URL: https://ir.atai.life/news-releases/news-release-details/atai-life-sciences-participate-2024-maxim-healthcare-virtual], 1 page.
Atai Life Sciences, "atai Life Sciences to Participate in the Canaccord Genuity 44th Annual Growth Conference," [press release], Aug. 7, 2024, Globe Newswire, [Available online at URL: https://ir.atai.life/news-releases/news-release-details/atai-life-sciences-participate-canaccord-genuity-44th-annual], 1 page.
Atai Life Sciences, "atai Life Sciences to Participate in the H.C. Wainwright 26th Annual Global Investment Conference," Sep. 4, 2024. [Available https://ir.atai.life/news-releases/news-release-details/atai-life-sciences-participate-hc-wainwright-26th-annual-global] (1 page).
Atai Life Sciences, "atai Life Sciences to Participate in the H.C. Wainwright 5th Annual Neuro Perspectives Conference," [press release], Jun. 26, 2024, Globe Newswire, [Available online at URL: https://ir.atai.life/news-releases/news-release-details/atai-life-sciences-participate-hc-wainwright-5th-annual-neuro], 1 page.
Atai Life Sciences, "atai Life Sciences to Participate in the Jefferies 2024 Global Healthcare Conference," [press release], May 31, 2024, Globe Newswire, [Available online at URL: https://ir.atai.life/news-releases/news-release-details/atai-life-sciences-participate-jefferies-2024-global-healthcare], 1 page.
Atai Life Sciences, "atai Life Sciences to Participate in the TD Cowen 45th Annual Health Care Conference," [press release], Feb. 24, 2025, Globe Newswire, [Available online at URL: https://ir.atai.life/news-releases/news-release-details/atai-life-sciences-participate-td-cowen-45th-annual-health-care], 1 page.
Atai Life Sciences, "atai Life Sciences to Participate in the Upcoming TD Cowen 44th Annual Health Care Conference," [press release], Feb. 28, 2024, Globe Newswire, [Available online at URL: https://ir.atai.life/news-releases/news-release-details/atai-life-sciences-participate-upcoming-td-cowen-44th-annual], 1 page.
Atai Life Sciences, "Pioneering the development of highly effective mental health treatments to transform patient outcomes," atai Life Sciences Corporate Presentation, Mar. 2025, [Available online at URL: https://ir.atai.com/static-files/93ac20a9-2c59-4ce6-b69d-3add22e34fc3], (36 pages).
Atai Life Sciences, "Pioneering the development of highly effective mental health treatments to transform patient outcomes." Corporate Presentation, Oct. 2025; 17 pages.
Bacque-Cazenave et al., "Serotonin in Animal Cognition and Behavior," Int J Mol Sci. 21(5):1649 (Feb. 2020) (23 pages).
Baell J.B., et al., New substructure filters for removal of pan assay interference compounds (PAINS) from screening libraries and for their exclusion in bioassays. Journal of medicinal chemistry. Apr. 8, 2010;53(7):2719-40.
Baggott et al., "Abnormal visual experiences in individuals with histories of hallucinogen use: a Web-based questionnaire," Drug Alcohol Depend. 114(1):61-7 (Mar. 2011).
Bannister et al., "What the brain tells the spinal cord," Pain. 157(10):2148-2151 (Oct. 2016).
Barbut Siva et al., "Interactions between classic psychedelics and serotonergic antidepressants: Effects on the acute psychedelic subjective experience, well-being and depressive symptoms from a prospective survey study," Journal of Psychopharmacology. 38(2): 145-155 (Jan. 2024).
Barker et al., "A critical review of reports of endogenous psychedelic N, N-dimethyltryptamines in humans: 1955-2010," Drug Test Analysis. (Feb. 2012) (19 pages).
Barker et al., "Distribution of the hallucinogens N, N-dimethyltryptamine and 5-methoxy-N,N-dimethyltryptamine in rat brain following intraperitoneal injection: application of a new solid-phase extraction LC-APci-MS-MS-isotope dilution method," J Chromatogr B. 751:37-47 (2001).

(56) References Cited

OTHER PUBLICATIONS

Barrett et al., "Emotions and brain function are altered up to one month after a single high dose of psilocybin," Sci Rep. 10(1 ):2214 (Feb. 2020) (14 pages).
Barry et al., "GC/MS comparison of the West Indian aphrodisiac 'Love Stone' to the Chinese medication 'chan su': bufotenine and related bufadienolides," J Forensic Sci. 41 (6):1068-1073 (1996).
Barsuglia et al., "A case report SPECT study and theoretical rationale for the sequential administration of ibogaine and 5-MeO-DMT in the treatment of alcohol use disorder," Prog Brain Res. 242:121-158 (2018).
Bartsch et al., "Deep brain stimulation of the posterior hypothalamic area in intractable shortlasting unilateral neuralgiform headache with conjunctival injection and tearing (SUNCT)," Cephalalgia. 31 (13):1405-8 (Oct. 2011).
Bastin et al., "Salt Selection and Optimisation Procedures for Pharmaceutical New Chemical Entities," Organic Process Research & Development, (Sep. 15, 2000), 4(5):427-35.
Becker et al., "Acute effects of psilocybin after escitalopram or placebo pretreatment in a randomized, double-blind, placebo-controlled, crossover study in healthy subjects," Clinical Pharmacology & Therapeutics. 111 (4):886-895 (Apr. 2022).
"Beckley Psytech announces 14m raise to conduct clinical trials on psychedelic medicine pipeline," Beckley Psytech Press Release Dec. 22, 2020 (5 pages).
Beckley Psytech, "Beckley Psytech and PsyPAN launch Participant Impact Report and Peer Support Pilot Program," [press Release], Jun. 14, 2024, [retrieved Oct. 2, 2024 from URL: https://www.beckleypsytech.com/posts/beckley-psytech-and-psypan-launch-participant-Impact-report-and-peer-support-pilot-program], 7 pages.
Beckley Psytech, "Beckley Psytech Announces Dosing of First Healthy Volunteers in Phase 1 Clinical Trial Assessing Safety and Pharmacokinetics of Second Innovative Formulation of 5-MeO-DMT," [press release], Apr. 5, 2022, [available online at URL: https://www.businesswire.com/news/home/20220404005960/en/Beckley-Psytech-Announces-Dosingof-First-Healthy-Volunteers-in-Ph ase-1-Clinical-Trial-Assessing-Safety-and-Pharmacokinetics-of-Second-Innovative-Formulation-of-5-MeO-DMT], 2 pages.
Beckley Psytech, "Beckley Psytech Announces First Cohort Dosed in Phase 1 Clinical Trial Assessing Safety and Tolerability of Intranasal 5-MeO-DMT," [press release], Oct. 25, 2021, [available online at URL: https://www.businesswire.com/news/home/20211024005026/en/Beckley-Psytech-Announces-First- Cohort-Dosed-in-Phase-1-Clinical-Trial-Assessing-Safety-and-Tolerability-of-Intranasal-5-MeO-DMT], 2 pages.
Beckley Psytech, "Beckley Psytech Announces First Cohort of Psychotherapists Have Begun Training for Treatment Resistant Depression Phase 2 Trials," [press release], Jan. 24, 2022, [Available online at URL: https://www.businesswire.com/news/home/20220123005101/en/Beckley-Psytech-Announces-First-Cohort-of-Psychotherapists-Have-Begun-Training-for-Treatment-Resistant-Depression-Phase-2-Trials], 3 pages.
Beckley Psytech, "Beckley Psytech Announces First Participant Dosed in Phase I Trial of ELE-101, A Novel Intravenous Formulation of Psilocin," Nov. 9, 2022, [Available online at URL: https://www.businesswire.com/news/home/20221108005986/en/Beckley-Psytech-Announces-First-Participant-Dosed-in-Phase-I-Trial-of-ELE-101-A-Novel-Intravenous-Formulation-of-Psilocin], 2 pages.
Beckley Psytech, "Beckley Psytech announces first patient has received low-dose psilocybin in world-first clinical trial for rare headache disorder," [press release], Sep. 14, 2021, 5 pages.
Beckley Psytech, "Beckley Psytech announces initial results from Phase I study and first patients dosed in Phase IIa study of ELE-101 (IV psilocin benzoate) for Major Depressive Disorder," [press release], Jun. 20, 2024, 7 pages.
Beckley Psytech, "Beckley Psytech Announces Partnership With Empatica in Latest Step of Digital Strategy, Designed to Deliver Personalised Patient Care," [press release], May 19, 2022, [Available online at URL: https://www.businesswire.com/news/home/20220518006041/en/Beckley-Psytech-Announces-Partnership-With-Empatica-in-Latest-Step-of-Digital-Strategy-Designed-to-Deliver-Personalised-Patient-Care], 4 pages.
Beckley Psytech, "Beckley Psytech Announces Partnership With Ksana Health, Building on Digital Strategy to Deliver Optimised Patient Outcomes," Jun. 14, 2022, [Available online at URL: https://www.businesswire.com/news/home/20220613005701/en/Beckley-Psytech-Announces-Partnership-With-Ksana-Health-Building-on-Digital-Strategy-to-Deliver-Optimised-Patient-Outcomes], 3 pages.
Beckley Psytech, "Beckley Psytech announces positive initial data from Phase IIa study of novel 5-MeO-DMT formulation BPL-003 for Treatment Resistant Depression," Mar. 27, 2024, [Available online at URL: https://www.businesswire.com/news/home/20240326357401/en/Beckley-Psytech-announces-positive-initial-data-from-Phase-IIa-study-of-novel-5-MeO-DMT-formulation-BPL-003-for-Treatment-Resistant-Depression], 3 pages.
Beckley Psytech, "Beckley Psytech announces positive topline data from Part 2 of its Phase IIa study of BPL-003 (intranasal 5-MeO-DMT benzoate) in combination with SSRIs for treatment resistant depression," [press release], May 20, 2025, available online at URL: https://www.beckleypsytech.com/posts/positive-data-from-phase-2a-study-of-bpl-003-with-ssris-for-treatment-resistant-depression], 8 pages.
Beckley Psytech, "Beckley Psytech announces positive topline data from Phase IIa study of BPL-003 (intranasal 5-MeO-DMT benzoate) for Alcohol Use Disorder," [press release], Jan. 28, 2025, [Available online at URL: https://www.beckleypsytech.com/posts/beckley-psytech-announces-positive-topline-data-from-phase-iia-study-of-bpl-003-for-alcohol-use-disorder], 7 pages.
Beckley Psytech, "Beckley Psytech announces positive topline results from Phase IIa study of ELE-101 (IV psilocin benzoate) for Major Depressive Disorder," [press release], Dec. 16, 2024, [Available online at URL: https://www.beckleypsytech.com/posts/beckley-psytech-announces-positive-topline-results-from-phase-iia-study-of-ele-101-for-major-depressive-disorder], 7 pages.
Beckley Psytech, "Beckley Psytech announces strategic investment from atai Life Sciences to accelerate the clinical development of short-duration psychedelics," [Press Release], Jan. 4, 2024, 10 pages.
Beckley Psytech, "Beckley Psytech applies for B Corporation status as part of its commitment to have a positive impact on society," [press release], Dec. 21, 2021, 5 pages.
Beckley Psytech, "Beckley Psytech appoints Dr Rob Hershberg to its Board of Directors," [press release], Jun. 24, 2024, 6 pages.
Beckley Psytech, "Beckley Psytech Completes Enrolment in Phase IIb study of BPL-003 for Treatment Resistant Depression," [press release], Mar. 5, 2025, [Available online at URL: https://www.beckleypsytech.com/posts/beckley-psytech-completes-enrolment-in-phase-iib-study-of-bpl-003-for-treatment-resistant-depression], 6 pages.
Beckley Psytech, "Beckley Psytech completes oversubscribed \$80m (£58m) fundraise to develop portfolio of psychedelic medicine breakthroughs," [press release], Aug. 15, 2021, 3 pages.
Beckley Psytech, "Beckley Psytech grows team with new Clinical Operations and Communications hires," [press release], Oct. 18, 2022, 4 pages.
Beckley Psytech, "Beckley Psytech initiates Phase IIa study of 5-MeO-DMT candidate BPL-003 for Alcohol Use Disorder," [press release], Apr. 5, 2023, [available online at URL: https://www.businesswire.com/news/home/20230405005132/en/Beckley-Psytech-initiates-Phase-IIa-study-of-5-MeO-DMT-candidate-BP-003-for-Alcohol-Use-Disorder], 2 pages.
Beckley Psytech, "Beckley Psytech Launches Phase IIa Study of Lead Candidate BPL-003, a Novel Benzoate Formulation of 5-MeO-DMT, for Treatment Resistant Depression," [press release], Dec. 21, 2022, [available online at URL: https://www.businesswire.com/news/home/20221221005221/en/Beckley-Psytech-Launches-Phase-IIa-Study-of-Lead-Candidate-BPL-003-a-Novel-Benzoate-Formulation-of-5-MeO-DMT-for-Treatment-Resistant-Depression], 2 pages.
Beckley Psytech, "Beckley Psytech's Phase I study results of novel 5-MeO-DMT formulation BPL-003 published in The Journal of Psychopharmacology," [Press Release], Apr. 17, 2024, (6 pages).
Beckley Psytech, "Beckley Psytech publishes peer-reviewed paper on 5-MeO-DMT in Journal of Psychopharmacology," [press release], Feb. 22, 2022, 4 pages.

(56) References Cited

OTHER PUBLICATIONS

Beckley Psytech, "Beckley Psytech receives approval for clinical trial using psychedelic agent to treat severe headache condition," [press release], Jan. 27, 2021, 4 pages.
Beckley Psytech, "Beckley Psytech receives FDA Investigational New Drug (IND) approval for Phase IIb study of BPL-003, a novel synthetic formulation of 5-MeO-DMT (Mebufotenin)," [press release], Feb. 21, 2023, [available online at URL: https://www.businesswire.com/news/home/20230221005523/en/Beckley-Psytech-receives-FDA-Investigational-New-Drug-IND-approval-for-Phase-IIb-study-of-BPL-003-a-novel-synthetic-formulation-of-5-MeO-DMT-Mebufotenin], 2 pages.
Beckley Psytech, "Beckley Psytech Strengthens Pipeline and Development Team With Acquisition of Eleusis Therapeutics Limited," [press release] Businesswire, Oct. 24, 2022, [available online at URL: https://www.businesswire.com/news/home/20221023005029/en/Beckley-Psytech-Strengthens-Pipeline-and-Development-Team-With-Acquisition-of-Eleusis-Therapeutics-Limited], 3 pages.
Beckley Psytech, "Beckley Psytech Strengthens Senior Leadership Team With Appointment of Dr. Laura Trespidi as Chief Development Officer," [press release], Businesswire, May 24, 2022, [available online at URL: https://www.businesswire.com/news/home/20220523005870/en/Beckley-Psytech-Strengthens-Senior-Leadership-Team-With-Appointment-of-Dr.-Laura-Trespidi-as-Chief-Development-Officer], 4 pages.
Beckley Psytech, "Beckley Psytech Successfully Completes Phase I Clinical Study of Lead Candidate BPL-003, a Novel Benzoate Formulation of 5-MeO-DMT," [press release], Business Wire, Nov. 15, 2022, [available online at URL: https://www.businesswire.com/news/home/20221114005907/en/Beckley-Psytech-Successfully-Completes-Phase-I-Clinical-Study-of-Lead-Candidate-BPL-003-a-Novel-Benzoate-Formulation-Of-5-MeO-DMT], 2 pages.
Beckley Psytech, "Beckley Psytech to attend 11th Annual LifeSci Partners Virtual Corporate Access Event," [press release], Dec. 8, 2021, Business Wire, [available online at URL: https://www.businesswire.com/news/home/20211207006217/en/Beckley-Psytech-to-attend-11th-Annual-LifeSci-Partners-Virtual-Corporate-Access-Event], 2 pages.
Beckley Psytech, "Beckley Psytech to Attend and Present at 8th Annual LSX World Congress 2022," [press release], Business Wire, Apr. 13, 2022, [available online at URL: https://www.businesswire.eom/news/home/20220412005773/en/Beckley-Psytech-to-Attend-and-Present-at-8th-Annual-LSX-World-Congress-2022], 2 pages.
Beckley Psytech, "Beckley Psytech to Attend and Present at the Jefferies London Healthcare Conference—Nov. 15-17, 2022," [press release], Business Wire, Nov. 4, 2022, [available online at URL: https://www.businesswire.com/news/home/20221104005095/en/Beckley-Psytech-to-Attend-and-Present-at-the-Jefferies-London-Healthcare-Conference-7oE27o80%93-November-15-17-2022], 2 pages.
Beckley Psytech, "Beckley Psytech to participate in Canaccord Genuity's Symposium on New Paradigms and Treatment Approaches in Mental Health—Dec. 13, 2022," [press release], Dec. 7, 2022, 4 pages.
Beckley Psytech, "Beckley Psytech to Present at 32nd Annual Oppenheimer Healthcare Conference," [press release], Business Wire, Mar. 10, 2022, [available online at URL: https://www.businesswire.com/news/home/20220309005837/en/Beckley-Psytech-to-Present-at-32nd-Annual-Oppenheimer-Healthcare-Conference], 2 pages.
Beckley Psytech, "Beckley Psytech to present at H.C. Wainwright 2nd Annual Psychedelics Conference and Stifel 2nd Annual Conference 'The Future of Healthcare'", [press release], Business Wire, Dec. 2, 2021, [available online at URL: https://www.businesswire.com/news/home/20211201006018/en/Beckley-Psytech-to-present-at-H.C.-Wainwright-2nd-Annual-Psychedelics-Conference-and-Stifel-2nd-Annual-Conference- %E2%8O%9CThe-Future-of-Healthcare%E2%8O%9D], 2 pages.
Beckley Psytech, "Beckley Psytech to present at Jefferies 2021 London Healthcare Conference," [press release], Nov. 2, 2021, [available online at URL: https://www.businesswire.com/news/home/20211102005131/en/Beckley-Psytech-topresent- at-Jefferies-2021-London-Healthcare-Conference], 2 pages.
Beckley Psytech, "Beckley Psytech to present data from Phase I study of BPL-003, a novel synthetic formulation of 5-MeO-DMT (Mebufotenin), at upcoming scientific conference," [press release], Apr. 24, 2023, 5 pages.
Beckley Psytech, "Beckley Psytech to present data on BPL-003, a novel synthetic intranasal formulation of 5-MeO-DMT benzoate, at ECNP 2024," [press release], Sep. 16, 2024, [Available online at URL: https://www.beckleypsytech.com/posts/beckley-psytech-to-present-data-on-bpl-003-at-ecnp- 2024], 5 pages.
"Beckley Psytech Bolsters Pipeline of Next-Generation Psychedelic Medicines With Research Collaboration and Strengthening of Relationship With Lophora ApS," May 11, 2022.https://www.beckleypsytech.com/posts/beckley-psytech-bolsters-pipeline-of-next-generation- psychedelic-medicines-with-research-collaboration-and-strengthening-of-relationship-with-lophora- aps (6 pages).
Beckley Psytech, "Brunch with Sifted: Amanda Feilding and Cosmo Feilding-Mellen on the psychedelic renaissance,"[Press Release], Nov. 24, 2021, (13 pages).
Beckley Psytech, "Dr Frank Wiegand, Experienced Neuroscience Leader Joins Beckley Psytech as Chief Medical Officer," [press release], Business Wire, Nov. 3, 2021, [available online at URL: https://www.businesswire.com/news/home/20211103005056/en/Dr-Frank-Wiegand-Experienced-Neuroscience-Leader-Joins-Beckley-Psytech-as-Chief-Medical-Officer], (2 pages).
Beckley Psytech, "European companies set to dominate psychedelics market," Beckley Psytech Press Release Mar. 1, 2021, (12 pages).
Beckley Psytech, "Meet our new Scientific Advisory Board!" Beckley Psytech Press Release Sep. 10, 2020, (6 pages).
Beckley Psytech, "Prescribe Software for Mental Health Treatment," [press release], Jun. 16, 2021, (6 pages).
Beckley Psytech, "Psychedelics breakthroughs—why now?," [press release], Sep. 10, 2020, 6 pages.
Beckley Psytech, "Researchers in Europe, U.S. Team up to Produce First Ever 5-MeO-DMT Psychedelic Training Program," [Press Release] Apr. 19, 2021, 8 pages.
"Beckley Psytech to present data from Phase IIa study of BPL-003 (intranasal 5-MeO-DMT benzoate) at Society of Biological Psychiatry's Annual Meeting," Apr. 24, 2025, [https://www.beckleypsytech.com/posts/beckley-psytech-to-present-data-from-phase-IIa-study-of-bpl-003-at-sobp-2025].
Beckley Psytech, "Understanding 5-MeO-DMT: Historical use," Beckley Psytech Press Release Mar. 11, 2021 (5 pages).
Beemster et al., "Test-Retest Reliability, Agreement and Responsiveness of Productivity Loss (iPCQ-VR) and Healthcare Utilization (TiCP-VR) Questionnaires for Sick Workers with Chronic Musculoskeletal Pain," J Occup Rehabil. 29(1 ):91-103 (Mar. 2018).
Belouin et al., "Psychedelics: Where we are now, why we got here, what we must do," Neuropharmacology. 142:7-19 (Nov. 2018).
Benington et al., "5-methoxy-N, N-dimethyltryptamine, a possible endogenous psychotoxin," The Alabama Journal of Medical Sciences. 2(4):397-403 (1965) (8 pages).
Benington F., et al., "Synthesis of O- and N-Methylated Derivatives of 5-Hydroxytryptamine," The Journal of Organic Chemistry, 1958, vol. 23, No. 12, pp. 1977-1979.
Bennabi et al., "Clinical guidelines for the management of treatment-resistant depression: French recommendations from experts, the French Association for Biological Psychiatry and Neuropsychopharmacology and the fondation FondaMental," BMC Psychiatry. 19(1 ):262 (Aug. 2019) (12 pages).
Berendsen et al., "Selective activation of 5HT1A receptors induces lower lip retraction in the rat," Pharmacology Biochemistry & Behavior. 33(4):821-7 (1989).
Berger et al, "Carbon 11 labeling of the psychoactive drug o-methyl-bufotenine and its distribution in the animal organism," Eur J Nucl Med. 3:101-4 (1978).
Bergman et al., "Synthesis and Reactions of some 3-(2-Haloacyl)indoles," Pergamon Press. 29:971-976 (1973).

(56) References Cited

OTHER PUBLICATIONS

Blair et al. "Effect of ring fluorination on the pharmacology of hallucinogenic tryptamines," J Med Chern. 43(24):4701-10 (Nov. 2000).
Bogenschutz et al., "Classic hallucinogens in the treatment of addictions," Prog Neuropsychopharmacol Biol Psychiatry. 64:250-8 (Jan. 2016).
Bogenschutz et al., "Psilocybin-assisted treatment for alcohol dependence: a proof-of-concept study," Journal of Psycopharmacology. 29(3):289-99 (2015).
Bonson et al., "Alterations in responses to LSD in humans associated with chronic administration of tricyclic antidepressants, monoamine oxidase inhibitors or lithium," Behavioural Brain Research. 73:229-233 (1996).
Bonson et al., "Chronic administration of serotonergic antidepressants attenuates the subjective effects of LSD in humans," Neuropsychopharmacology. 14(6):425-36 (1996).
Borissova et al., "The development of psilocybin therapy for treatment-resistant depression: an update," BJPsych Bulletin. 48:38-44 (Feb. 2024).
Borowiak et al., "Psilocin multiple intake resulted and in cardiotoxic effects," Acta Toxicologica. 14(1-2):23-30 (Jan. 2006) (9 pages).
Borowiak et al., "Psilocybin mushroom (*Psilocybe semilanceata*) intoxication with myocardial infarction," J Toxicol Clin Toxicol. 36(1-2):47-9 (1998).
Breeksema et al., "Patient perspectives and experiences with psilocybin treatment for treatmentresistant depression: a qualitative study," Scientific Reports. 14(2929) (Feb. 2024) (12 pages).
Brenk et al., "Lessons learnt from assembling screening libraries for drug discovery for neglected diseases," ChemMedChem. Mar. 2008;3(3):435-44.
Brouwer et al., "Pivotal mental states," J Psychopharmacol. 35(4):319-352 (Apr. 2021).
Brown et al., "Pharmacokinetics of Escalating Doses of Oral Psilocybin in Healthy Adults," Clin Pharmacokinet. 56(12):1543-1554 (Dec. 2017).
Brummett et al., "Cortisol responses to emotional stress in men: association with a functional polymorphism in the 5HTR2C gene," Biol Psychol. 89(1):94-8 (Jan. 2012) (11 pages).
Brush et al., "Monoamine oxidase inhibitor poisoning resulting from Internet misinformation on illicit substances," J Toxicol Clin Toxicol. 42(2):191-5 (2004) (6 pages).
Buckholtz et al., "Lysergic acid diethylamide (LSD) administration selectively downregulates serotonin(2) receptors in rat brain," Neuropsychopharmacology. 3(2):137-148 (1990).
Buckley, "Serotonin syndrome," BMJ. 348:g1626. (Feb. 2014) (4 pages).
Busner, J. and S.D. Targum (Jul. 2007) The clinical global impressions scale: applying a research tool in clinical practice. Psychiatry, 4:28-37.
Callaway et al., "Pharmacokinetics of Hoasca alkaloids in healthy humans," J Ethnopharmacol. 65(3):243-56 (Jun. 1999).
"Cancer," MedLine Plus, [available online at URL: http://www.nlm.nih.gov/medlineplus/cancer.html, retrieved Jul. 6, 2007], (10 pages).
Cao et al., "Secondary Short-Lasting Unilateral Neuralgiform Headache with Conjunctival Injection and Tearing: A New Case and a Literature Review," J Clin Neurol. 14(4):433-443 (Oct. 2018).
CAplus. Chemical Abstracts Service: Columbus. CAplus Accession No. 2017:1595854. Title: Preparation of tetrahydropyridoindolylcycloalkylacrylic acid derivatives and analogs for use as estrogen receptor modulators. Inventor: Huang, P.Q. et al. (4 pages).
Carbonaro et al., "Survey study of challenging experiences after ingesting psilocybin mushrooms: Acute and enduring positive and negative consequences," Journal of Psychopharmacology. 30(12) (Aug. 2016) (11 pages).
Carbonaro et al., "Neuropharmacology of N,N-dimethyltryptamine," Brain Res Bull. 126(Pt 1):74-88 (Sep. 2016).
Carhart-Harris et al., "Serotonin and brain function: a tale of two receptors," Journal of Psychopharmacology. 31 (9): 1091-1120 (Aug. 2017).
Carhart-Harris et al., "Implications for psychedelic-assisted psychotherapy: functional magnetic resonance imaging study with psilocybin," Br J Psychiatry. 200(3):238-44 (Mar. 2012).
Carhart-Harris et al., "Neural correlates of the psychedelic state as determined by fMRI studies with psilocybin," Proc Natl Acad Sci USA. Feb. 7, 2012; 109(6): 2138-43. doi: 10.1073/pnas.1119598109. Epub Jan. 23, 2012.
Carhart-Harris et al., "Psilocybin with psychological support for treatment-resistant depression: sixmonth follow-up," Psychopharmacology (Berl). 235(2):399-408 (Feb. 2018).
Carhart-Harris et al., "Psychedelics and connectedness," Psychopharmacology (Berl). 235(2):547-550 (Feb. 2018).
Carhart-Harris et al., "Psychedelics and the essential importance of context," J Psychopharmacol. 32(7)725-731 (Jul. 2018).
Carhart-Harris et al., "Rebus and the Anarchic Brain: Toward a Unified Model of the Brain Action of Psychedelics," Pharmacol Rev. Jul. 2019;71(3):316-344.
Carhart-Harris et al., "The administration of psilocybin to healthy, hallucinogen-experienced volunteers in a mock-functional magnetic resonance imaging environment: a preliminary investigation of tolerability," J Psychopharmacol. Nov. 2011;25(11): 1562-7. doi: 10.1177/0269881110367445. Epub Apr. 15, 2010.
Carhart-Harris et al., "The Effects of Acutely Administered 3,4-Methylenedioxymethamphetamine on Spontaneous Brain Function in Healthy Volunteers Measured with Arterial Spin Labeling and Blood Oxygen Level-Dependent Resting State Functional Connectivity," Biol Psychiatry. Oct. 15, 2015; 78(8): 554-62. doi: 10.1016/j.biopsych.2013.12.015. Epub Jan. 10, 2014.
Carhart-Harris et al., "The entropic brain: a theory of conscious states informed by neuroimaging research with psychedelic drugs," Front Hum Neurosci. 8: 20(Feb. 2014) (22 pages).
Carhart-Harris et al., "The Therapeutic Potential of Psychedelic Drugs: Past, Present, and Future," Neuropsychopharmacology. 42(11 ):2105-2113 (Oct. 2017).
Carhart-Harris et al. "Trial of psilocybin versus escitalopram for depression." New England Journal of Medicine. Apr. 15, 2021;384(15):1402-1411. doi: 10.1056/NEJMoa2032994.
Carhart-Harris et al., "User perceptions of the benefits and harms of hallucinogenic drug use: A web-based questionnaire study," Journal of Substance Use. 15(4):283-300 (Jul. 2010).
Carter et al., "Using psilocybin to investigate the relationship between attention, working memory, and the serotonin 1A and 2A receptors," J Cogn Neurosci. 17(10):1497-508 (Oct. 2005) (13 pages).
Cartwright et al., "Long-term antidepressant use: patient perspectives of benefits and adverse effects," Patient Prefer Adherence. 10:1401-7 (Jul. 2016).
Castellanos et al., "Chronic pain and psychedelics: a review and proposed mechanism of action," Reg Anesth Pain Med. 45(7):486-494 (Jul. 2020) (9 pages).
Catlow et al., "Effects of psilocybin on hippocampal neurogenesis and extinction of trace fear conditioning," Exp Brain Res. 228(4):481-91 (Jun. 2013).
Chadeayne et al., "Active Metabolite of Aeruginascin (4-Hydroxy-N,N,N-trimethyltryptamine): Synthesis, Structure, and Serotonergic Binding Affinity," ACS Omega. 5(27):16940-16943 (Jul. 2020).
Chagraoui et al., "5-HT2C receptors in psychiatric disorders: A review," Prog Neuropsychopharmacol Biol Psychiatry. 66:120-135 (Apr. 2016).
Chemazone Product No. 171.355.434, "N-[2-(1-methyl-1H-indol-3-yl)ethyl]oxan-4-amine," [publicly available online at URL: https://chemazone.com/info?ID=171.355.434, retrieved Oct. 24, 2024], (4 pages).
Chemcats. Chemical Abstracts Service: Columbus, OH. Chemical Name: 1 H-Pyrrolo[2,3-b]pyridin-4(7H)-one. Chemcats Accession No. 1621739382. Catalog Name: Ambeed, Inc. Product List. Order Number Catalog: A763560. CAS Registry No. 1076197-59-5 (May 2021) (1 page).
Chemcats. Chemical Abstracts Service: Columbus, OH. Chemical Name: 1 H-Pyrrolo[2,3-B]Pyridin-4(7H)-One. Chemcats Accession

(56) References Cited

OTHER PUBLICATIONS

No. 2022337458. Catalog Name: Chemieliva Pharmaceutical Product List. Order Number Catalog: CE0957308. CAS Registry No. 1076197-59-5 (Jan. 2021) (1 page).
Chemcats. Chemical Abstracts Service: Columbus, OH. Chemical Name: 1 H-pyrrolo [2,3-b]pyridin-4-ol hydrate. Chemcats Accession No. 0968477988. Catalog Name: ASW MedChem Product List.Order Number Catalog: TH-45275. CAS Registry No. 2031269-35-7 (Jun. 2020) (1 page).
Chemcats. Chemical Abstracts Service: Columbus, OH. Chemical Name: 1 H-Pyrrolo[2,3-b]pyridin-4-ol hydrate. Chemcats Accession No. 1773869211. Catalog Name: Aurora Building Blocks 3. Order Number Catalog: 129.194.895. CAS Registry No. 2031269-35-7 (Apr. 2021) (1 page).
Chemcats. Chemical Abstracts Service: Columbus, OH. Chemical Name: 1-methyl-1 H-pyrrolo[2,3-b]pyridin-4-ol. Chemcats Accession No. 1545199867. Catalog Name: Azepine Product List. Order Number Catalog: AZ04819515. CAS Registry No. 1781876-60-5 (Mar. 2019) (1 page).
Chemcats. Chemical Abstracts Service: Columbus, OH. Chemical Name: 1-methylpyrrolo[2,3-b]pyridin-4-ol. Chemcats Accession No. 1442516433. Catalog Name: Aurora Building Blocks 2. Order Number Catalog: 115.267.167. CAS Registry No. 1781876-60-5 (Apr. 2021) (1 page).
Chemcats. Chemical Abstracts Service: Columbus, OH. Chemical Name: 1-methyl-1H-pyrrolo[2,3-b]pyridin-4-ol. Chemcats Accession No. 0002254898. Catalog Name: FCH Group Reagents for Synthesis. Order Number Catalog: FCH1635008. Cas Registry No. 1781876-60-5 (May 2021) (1 page).
Chemcats. Chemical Abstracts Service: Columbus, OH. Chemical Name: 4H-Pyrrolo[2,3-b]pyridine-4-one, 1,7-dihydro-. Chemcats Accession No. 1756550559. Catalog Name: Sagechem Limited Product List. Order Number Catalog: S243355. CAS Registry No. 1076197-59-5 (May 2020) (1 page).
Chen et al. "Determining the pharmacokinetics of psilocin in rat plasma using ultra-performance liquid chromatography coupled with a photodiode array detector after orally administering an extract of Gymnopilus spectabilis," J Chromatogr B Analyt Technol Biomed Life Sci. 879(25):2669-2672 (Sep. 2011).
Cheng T., et al., Computation of octanol-water partition coefficients by guiding an additive model with knowledge. Journal of chemical information and modeling. Nov.-Dec. 2007;47(6):2140-2148.
Cingolani et al., "In vitro investigation on the impact of airway mucus on drug dissolution and absorption at the air-epithelium interface in the lungs," Eur J. Pharm Biopharm. 141: 210-220 (Aug. 2019).
Cleare et al. "Neuroendocrine and hypothermic effects of 5-HT1A receptor stimulation with ipsapirone in healthy men: a placebo-controlled study," Int Clin Psychopharmacol. 13(1):23-32 (Jan. 1998).
"Clinical Practice Guideline: Intranasal Medication Administration," Emergency Nurses Association. (36 pages) (2016).
"Clomipramine," https://www.drugs.com/monograph/clomipramine.html, medically reviewed on May 22, 2024 (16 pages).
Cohen, A.S. "Short-lasting unilateral neuralgiform headache attacks with conjunctival injection and tearing," Cephalalgia. 27(7):824-832 (Jul. 2007).
Cohen, Sidney, "LSD and the Anguish of Dying," Harper's Magazine. 231 (1384):69-78 (Sep. 1965).
Conway et al. "Toward an Evidence-Based, Operational Definition of Treatment-Resistant Depression: When Enough Is Enough," JAMA Psychiatry. 74(1 ):9-10 (Jan. 2017).
Cornelisse et al., "Reduced 5-HT1A- and GABAB Receptor Function in Dorsal Raphe Neurons Upon Chronic Fluoxetine Treatment of Socially Stressed Rats," J Neurophysiol. 98:196-204 (Jul. 2007).
Cortes-Altamirano et al. "Review: 5-HT1,5-HT2, 5-HT3 and 5-HT7 Receptors and their Role in the Modulation of Pain Response in the Central Nervous System," Curr Neuropharmacol. 16(2):210-221 (Jan. 2018).
"Cosmo Feilding Mellen on Beckley Psytech's plans for 2021," Beckley Psytech Press Release Apr. 12, 2021 (6 pages).
Costa et al. "The Neuropharmacology of Cluster Headache and other Trigeminal Autonomic Cephalalgias," Curr Neuropharmacol. 13(3):304-323 (2015).
Cowen et al., "What has serotonin to do with depression?," World Psychiatry. 14(2):158-60 (Jun. 2015).
Critchley et al. "Effects in the X-maze anxiety model of agents acting at 5-HT1 and 5-HT2 receptors," Psychopharmacology (Berl). 93(4):502-506 (1987).
Cumming et al. "Molecular and Functional Imaging Studies of Psychedelic Drug Action in Animals and Humans," Molecules. 26(9):2451 (Apr. 2021) (26 pages).
Dabire et al. "Comparison of effects of some 5-HT1 agonists on blood pressure and heart rate of normotensive anaesthetized rats," Eur J Pharmacol. 140(3):259-266 (Aug. 1987).
Dabire et al. "Vascular postsynaptic effects of some 5-HT 1-like receptor agonists in the pithed rat," Eur J Pharmacol. 150(1-2):143-148 (May 1988).
Dabire, Hubert, "Central 5-hydroxytryptamine (5-HT) receptors in blood pressure regulation," Therapie. 46:421-9 (Nov. 1991) (10 pages).
Dahmane et al. "Exposure-Response Analysis to Assess the Concentration-QTc Relationship of Psilocybin/Psilocin," Clin Pharmacol Drug Dev. 10(1 ):78-85 (Jan. 2021—ePub Apr. 6, 2020).
Daly et al. "Efficacy and safety of intranasal esketamine adjunctive to oral antidepressant therapy in treatment-resistant depression: a randomized clinical trial." JAMA Psychiatry. Feb. 2018;75(2):139-148. doi: 10.1001/jamapsychiatry.2017.3739.
Database Registry. Chemical Abstracts Service: Columbus, OH. Chemical Name: 1H-Indole-3-ethanamine, 5-methoxy-N,N dimethyl-, benzoate (1:1); RN 282103-25-7; ED Aug. 1, 2000 (1 page).
Davies et al., "Binding affinity and biological activity of oxygen and sulfur isosteres at melatonin receptors as a function of their hydrogen bonding capability," Bioorganic Chemistry. 32(1):1-12 (Feb. 2004) (6 pages).
Davis et al., "Effects of psilocybin-assisted therapy on major depressive disorder: a randomized clinical trial," JAMA Psychiatry. 78(5):481-489 (May 2021—ePub Nov. 4, 2020).
Davis et al. "Psychedelic Treatment for Trauma-Related Psychological and Cognitive Impairment Among US Special Operations Forces Veterans," Chronic Stress. vol. 4 (Jul. 2020) (11 pages).
Davis et al. "The epidemiology of 5-methoxy- N, N-dimethyltryptamine (5-MeO-DMT) use: Benefits, consequences, patterns of use, subjective effects, and reasons for consumption," J Psychopharmacol. 32(7)779-792 (Jul. 2018) (29 pages).
Daws et al., "Increased global integration in the brain after psilocybin therapy for depression," Nat Med. (Apr. 2022); 28(4): 844-851. doi: 10.1038/s41591-022-01744-z. Epub Apr. 11, 2022.
De Coo et al. "Increased use of illicit drugs in a Dutch cluster headache population," Cephalalgia. 39(5):626-634 (Apr. 2019).
Deakin et al., "5-HT and mechanisms of defence," Journal of Psychopharmacology. 5(4):305-15 (Jul. 1991).
Declaration from Professor Carhart-Harris, dated Jan. 9, 2026; submitted in Notice of Opposition in EP Patent EP4349407; Applicant GH Res Limited, 61 pages.
Declaration from Professor Robert Gibbons, dated Jan. 6, 2026; submitted in Notice of Opposition in EP Patent EP4349407, Applicant GH Res Limited, 49 pages.
Delaney J.S., ESOL: Estimating aqueous solubility directly from molecular structure. Journal of chemical information and computer sciences May-Jun. 2004;44(3):1000-5.
Delay et al. "[The psychophysiological effects of psilocybine]," C R Hebd Seances Acad Sci. 247(16):1235-1238 (Oct. 1958).
Delva et al. "Effects of short-term administration of valproate on serotonin-1 A and dopamine receptor function in healthy human subjects," J Psychiatry Neurosci. 27(6):429-437 (Nov. 2002).
Deodhar et al., "Assessing the Mechanism of Fluoxetine-Mediated CYP2D6 Inhibition," Pharmaceutics. 13(148) (Jan. 2021) (10 pages).
Devlin, "Psychoactive Effects of GH001 in Patients With Treatment-Resistant Depression: Results From a Phase 2b, Double-Blind, Randomised Controlled Trial," Presented at the European College

(56) References Cited

OTHER PUBLICATIONS of Neuropsychopharmacology 38th ECNP Congress, Amsterdam, The Netherlands, Oct. 11-14, 2025; 1 page.
Di Lorenzo et al. "The use of illicit drugs as self-medication in the treatment of cluster headache: Results from an Italian online survey," Cephalalgia. 36(2): 194-198 (Feb. 2016).
Di Sciullo et al., Changes in anterior pituitary hormone levels after serotonin 1A receptor stimulation. Endocrinology. 127(2):567-72 (Aug. 1990).
Dinis-Oliveira, Ricardo Jorge, "Metabolism of psilocybin and psilocin: clinical and forensic toxicological relevance," Drug Metabolism Reviews. 49(1 ):84-91 (Jan. 2017) (22 pages).
Donovan et al., Effects of a single dose of psilocybin on behaviour, brain 5-HT2A receptor occupancy and gene expression in the pig. European Neuropsychopharmacology. 42: 1-11 (Jan. 2021).
Dourron et al., "5-MeO-DMT: An atypical psychedelic with unique pharmacology, phenomenology & risk?" Psychopharmacology Berl. (Jul. 2025); 242(7): 1457-1479.
D'Souza et al., "Exploratory study of the dose-related safety, tolerability, and efficacy of dimethyltryptamine (DMT) in healthy volunteers and major depressive disorder," Neuropsychopharmacology. 47:1854-62 (Jun. 2022).
Drug Enforcement Administration (DEA), Department of Justice, "Schedules of controlled substances: placement of 5-methoxy-N,N-dimethyltryptamine into Schedule I of the Controlled Substances Act. Final rule," Fed Regist. 75(243):79296-300 (Dec. 2010).
Dunkley et al., The Hunter Serotonin Toxicity Criteria: simple and accurate diagnostic decision rules for serotonin toxicity. Q J Med. 96(9): 635-42 (Sep. 2003).
Dupuis et al. Actions of novel agonists, antagonists and antipsychotic agents at recombinant rat 5-HT6 receptors: a comparative study of coupling to G alpha s, Eur J Pharmacol. 588(2-3):170-177 (Jul. 2008).
Duvvuri et al. "5-HT1A receptor activation is necessary for 5-MeODMT-dependent potentiation of feeding inhibition," Pharmacol Biochem Behav. 93(3): 349-353 (Sep. 2009).
Egashira et al., "Involvement of 5-hydroxytryptamine neuronal system in Delta(9)-tetrahydrocannabinol-induced impairment of spatial memory," Eur J Pharmacol. 445(3):221-9 (Jun. 2002) (1 page).
Eide et al. "Subsensitivity of serotonin and substance P receptors involved in nociception after repeated administration of a serotonin receptor agonist," J Neural Transm. 77(1 ):1-10 (1989).
Eison et al., "5-HT1A and 5-HT2 receptors mediate discrete behaviors in the Mongolian Gerbil," Pharmacology Biochemistry and Behavior. 43(1 ):131-137 (Sep. 1992).
El Mansari et al., "Responsiveness of 5-HT 1A and 5-HT2 receptors in the rat orbitofrontal cortex after long-term serotonin reuptake inhibition," Rev Psychiatr Neurosci. 30(4):268-74 (Jul. 2005).
Ellahi, R., "Serotonin syndrome: A spectrum of toxicity," BJPsych Advances. 21:324-332 (2015).
Emami et al. "Toxicology Evaluation of Drugs Administered via Uncommon Routes: Intranasal, Intraocular, Intrathecal/Intraspinal, and Intra-Articular," Int J Toxicol. 37(1):4-27 (Jan.-Feb. 2018) (49 pages).
"Enhancing the accessibility of psychedelic healthcare," Beckley Psytech Press Release Nov. 23, 2021 (7 pages).
EP Application No. 24213283.5, Extended European Search Report mailed Feb. 3, 2025; Applicant Beckley Psytech Limited.; 9 pages.
EP Patent No. 3927337, Brief Communication mailed Oct. 23, 2025; Letter from the proprietor of the patent Oct. 17, 2025; Applicant GH Research Ireland Limited; 55 pages.
EP Patent No. 4349407, Communication of a Notice of Opposition mailed Jan. 16, 2026; Applicant GH Research Ireland Limited; 90 pages.
Ermakova et al. "A narrative synthesis of research with 5-MeO-DMT," J Psychopharmacol. 36(3):273-294 (Mar. 2022).
Ertl P., et al., "Estimation of synthetic accessibility score of drug-like molecules based on molecular complexity and fragment contributions." Journal of cheminformatics. Jun. 10, 2009;1(1):8.
EudraCT No. 2022-003743-10, "A Quadruple Masked, Dose-Finding Study to Evaluate the Efficacy and Safety of Intranasal BPL-003, with Open Label Extension, in Patients with Treatment Resistant Depression," [EU Clinical Trials Register], May 16, 2023, Sponsor: Beckley Psytech Ltd., [publicly available at https://www.clinicaltrialsregister.eu/ctr-search/trial/2022-003743-10/PL], 8 pages.
Fabing et al. "Intravenous bufotenine injection in the human being," Science. 123(3203):886-887 (May 1956).
Falkenberg, G. et al., "The Crystal and Molecular Structure of 5-Methoxy-(N,N)-dimethyltryptamine Hydrochloride," Acta Crystallographica Section B, 1971, vol. 27, pp. 411-418.
Family et al., "Safety, tolerability, pharmacokinetics, and pharmacodynamics of low dose lysergic acid diethylamide (LSD) in healthy older volunteers," Psychopharmacology. 237(3):841-853 (13 pages) (Dec. 2019).
Fanciullacci et al. "Hypersensitivity to lysergic acid diethylamide (LSD-25) and psilocybin in essential headache," Experientia. 30(12):1441-1442 (Dec. 1974).
Fanelli et al., "Meta-assessment of bias in science," Proc Natl Acad Sci USA, (Apr. 4, 2017); 114(14): 3714-3719.
Fantegrossi et al. "Hallucinogen-like actions of 2,5-dimethoxy-4-(n)-propylthiophenethylamine (2C-T-7) in mice and rats," Psychopharmacology (Berl). 181 (3):496-503 (Jun. 2005).
Fantegrossi et al. "Transient reinforcing effects of phenylisopropylamine and indolealkylamine hallucinogens in rhesus monkeys," Behav Pharmacol. 15(2):149-157 (Mar. 2004).
Fedgchin et al. "Efficacy and Safety of Fixed-Dose Esketamine Nasal Spray Combined With a New Oral Antidepressant in Treatment-Resistant Depression: Results of a Randomized, DoubleBlind, Active-Controlled Study (Transform-1)," Int J Neuropsychopharmacol. 22(10):616-630 (Oct. 2019).
Fiorella et al. "Potentiation of LSD-induced stimulus control by fluoxetine in the rat," Life Sci. 59(18):PL283-287 (1996).
"First participant dosed in research study investigating the effects of BPL-003, a novel formulation of 5-MeO-DMT, on the human brain," Beckley Psytech Press Release Jun. 3, 2024 (6 pages).
"First patient dosed in Beckley Psytech's international Phase lib study of BPL-003, a novel synthetic intranasal formulation of 5-MeO-DMT, for Treatment Resistant Depression (TRD)," Beckley Psytech Press Release Oct. 24, 2023 (6 pages).
"First Patient Dosed in Beckley Psytech's Phase IIa Study of BPL-003 for Treatment Resistant Depression," May 4, 2023. https://www.businesswire.com/news/home/20230504005020/en/First- Patient-Dosed-in-Beckley-Psytech%E2%800/o99s-Phase-IIa-Study-of-BPL-003-for-Treatment-Resistant-Depression. (2 pages).
"First patient dosed in Beckley Psytech's Phase IIa study of BPL-003 in combination with SSRIs for Treatment Resistant Depression," Beckley Psytech Press Release Apr. 24, 2024 (6 pages).
Fitzgerald et al. "Selective serotonin reuptake inhibitor exposure," Top Companion Anim Med. 28(1 ):13-17 (Feb. 2013).
Flinn Scientific Inc, "Quiet! Seed Crystals Growing," Flinn Scientific Inc, 2017, [Available online at URL: https://www.flinnsci.com/api/library/Download/fcd83e5a579b470f9cOacc678ac6564c], 6 pages.
Florence, "Polymorph screening in pharmaceutical development," European PharmaceuticalReview, Issue 4, dated Aug. 19, 2010, retrieved Nov. 30, 2023, at[https://www.europeanpharmaceuticalreview.com/article/3659/polymorph-screening-in-pharmaceutical-development (19 pages).
Fontanilla et al., "The hallucinogen N, N-dimethyltryptamine (DMT) is an endogenous sigma-1 receptor regulator," Science. 323(5916):934-937 (Feb. 2009) (9 pages).
"Former GW Pharmaceuticals CFO joins Beckley Psytech's Board," Beckley Psytech Press Release Apr. 13, 2021 (4 pages).
Franzini et al. "Deep brain stimulation of the posteromedial hypothalamus: indications, long-term results, and neurophysiological considerations," Neurosurg Focus. 29(2):E13 (Aug. 2010) (13 pages).
Fuentes et al. "Therapeutic Use of LSD in Psychiatry: A Systematic Review of Randomized-Controlled Clinical Trials," Front Psychiatry. 10:943 (Jan. 2020) (14 pages).
Fukunishi Y., et al., Prediction of synthetic accessibility based on commercially available compound databases. Journal of chemical information and modeling. Dec. 22, 2014;54(12):3259-67.

(56) References Cited

OTHER PUBLICATIONS

Fuller, R.W. "Serotonergic stimulation of pituitary-adrenocortical function in rats," Neuroendocrinology. 32(2): 118-127 (Feb. 1981).
Fuller, R.W. "Tissue distribution, metabolism and effects of bufotenine administered to rats," Neuropharmacology. 34(7):799-804 (Jul. 1995).
Gable, R.S. "Comparison of acute lethal toxicity of commonly abused psychoactive substances," Addiction. 99(6):686-696 (Jun. 2004).
Gaivao et al. "Cortisol Modulation by Ayahuasca in Patients With Treatment Resistant Depression and Healthy Controls," Front Psychiatry. 9:185 (May 2018) (10 pages).
Galeffi, C. et al., "N,N-Dimethyl-5-Methoxytryptamine, a Component of a Dart Poison of the Yanoma Indians," Journal of Natural Products, vol. 46, pp. 586-587 (1983).
Garcia-Romeu et al. "Clinical applications of hallucinogens: A review," Exp Clin Psychopharmacol. 24(4):229-268 (Aug. 2016).
Garcia-Romeu et al. "Current perspectives on psychedelic therapy: use of serotonergic hallucinogens in clinical interventions," Int Rev Psychiatry. 30(4):291-316 (Nov. 2018) (27 pages).
Gasser et al., "Safety and efficacy of lysergic acid diethylamide-assisted psychotherapy for anxiety associated with life-threatening diseases," J Nerv Ment Dis. 202(7):513-20 (Jul. 2014).
Geiger et al. "Dark Classics in Chemical Neuroscience: Psilocybin," ACS Chern Neurosci. 9(10):2438-2447 (Oct. 2018).
Gessner et al. "Pharmacological actions of some methoxyindolealkylamines," Nature. 190(4771 ):179-180 (Apr. 1961).
Geyer et al. "A characteristic effect of hallucinogens on investigatory responding in rats," Psychopharmacology (Berl). 65(1 ):35-40 (Sep. 1979).
Geyer et al. "Opposite effects of intraventricular serotonin and bufotenin on rat startle responses," Pharmacol Biochem Behav. 3(4):687-691 (Jul.-Aug. 1975).
GH Research, "GH Research Announces Primary Endpoint Met in Phase 2b Trial with GH001 in TRD Demonstrating—15.5 Point Placebo-adjusted MADRS Reduction," Globe Newswire, Press release, Dubline IE, Feb. 3, 2025, 2 pages.
GH Research, "GH Research to Announce IND Status for GH001," Globe Newswire, Press release, Dublin, IE, Jan. 2, 2026, 1 page.
Ghuran et al. "The cardiac complications of recreational drug use," West J Med. 173(6):412-415 (Dec. 2000).
Gibbons et al., "Development of a Computerized Adaptive Test for Depression," Arch Gen Psvchiatry, (Nov. 2012); 69(11): 1104-1112, doi: 10.1001/archgenpsychiatry.2012.14.
Gillin JC et al., "Evidence for and against the involvement of N, N-dimethyl-tryptamine (DMT) and 5-methoxy-N,N-dimethyltryptamine (5-MeO-DMT) in schizophrenia." 12(4):12-13 (1976).
Glasser, "Some Pharmacological Actions of D-Lysergic Acid Methyl Carbinolamide," Nature, vol. 189, pp. 313-314(1961).
Glennon et al. "Hallucinogens as a discriminative stimuli: generalization of DOM to a 5-methoxy-N, N-dimethyltryptamine stimulus," Life Sci. 24(11):993-997 (Mar. 1979).
Glennon et al., "The electronic and serotonin receptor binding affinity properties of N,N-dimethyltryptamine analogs," 18(3):453-465 (1977) (Abstract only).
Glennon, R.A. et al., "Serotonin Receptor Binding Affinities of Tryptamine Analogues," Journal of Medicinal Chemistry, vol. 22, pp. 428-432 (1979).
"Global Investors Back Psychedelic Medicine Start-Up With $3.8m Series A Round," Beckley Psytech Press Release Jun. 30, 2020 (9 pages).
Goethe et al. "Selective serotonin reuptake inhibitor discontinuation: side effects and other factors that influence medication adherence," J Clin Psychopharmacol. 27(5):451-458 (Oct. 2007).
Golub, T. R., et al., "Molecular classification of cancer: class discovery and class prediction by gene expression monitoring", Science (1999); 286: 531-537.
Goodwin et al., "Psilocybin for treatment resistant depression in patients taking a concomitant SSRI medication," Neuropsychopharmacology. 48:1492-1499 (Jul. 2023).
Gouzoulis-Mayfrank et al. "Neurometabolic effects of psilocybin, 3,4-methylenedioxyethylamphetamine (MDE) and d-methamphetamine in healthy volunteers. A double-blind, placebo-controlled PET study with [18F]FDG," Neuropsychopharmacology. 20(6):565-581 (Jun. 1999).
Gouzoulis-Mayfrank et al. "Psychopathological, neuroendocrine and autonomic effects of 3,4-methylenedioxyethylamphetamine (MDE), psilocybin and d-methamphetamine in healthy volunteers. Results of an experimental double-blind placebo-controlled study," Psychopharmacology (Berl). 142(1 ):41-50 (Feb. 1999).
Graeff et al. "The dual role of serotonin in defense and the mode of action of antidepressants on generalized anxiety and panic disorders," Cent Nerv Syst Agents Med Chern. 10(3):207-217 (Sep. 2010).
Grahame-Smith. "Inhibitory effect of chlorpromazine on the syndrome of hyperactivity produced by L-tryptophan or 5-methoxy-N,N-dimethyltryptamine in rats treated with a monoamine oxidase inhibitor," Br J Pharmacol. 43(4):856-864 (Dec. 1971).
Grandjean et al. "Psilocybin exerts distinct effects on resting state networks associated with serotonin and dopamine in mice," Neuroimage. 225:117456 (Jan. 2021) (8 pages).
Gray et al.,"Antidepressant Treatment Reduces Serotonin-1A Autoreceptor Binding in Major Depressive Disorder," Biol Psychiatry. 74(1 ):26-31 (2013) (13 pages).
Greenan et al., "Preparation and Characterization of Novel Crystalline Solvates and Polymorphs of Psilocybin and Identification of Solid Forms Suitable for Clinical Development," ResearchGate (Feb. 2020) (29 pages).
Grieshaber et al., "The detection of psilocin in human urine," J Forensic Sci. 46(3):627-30 (2001).
Griffiths et al., "Mystical-type experiences occasioned by psilocybin mediate the attribution of personal meaning and spiritual significance 14 months later," Journal of Psychopharmacology. 22(6):621-32 (2008).
Griffiths et al. "Psilocybin can occasion mystical-type experiences having substantial and sustained personal meaning and spiritual significance," Psychopharmacology (Berl). 187(3):268-283 (Aug. 2006) (17 pages).
Griffiths et al., "Psilocybin occasioned mystical-type experiences: immediate and persisting dose-related effects," Psychopharmacology (Berl). 218(4):649-665 (Dec. 2011) (27 pages).
Griffiths et al., "Psilocybin-occasioned mystical-type experience in combination with meditation and other spiritual practices produces enduring positive changes in psychological functioning and in trait measures of prosocial attitudes and behaviors," Journal of Psychopharmacology. 32(1 ):49-69 (Oct. 2017).
Grob et al., "Pilot study of psilocybin treatment for anxiety in patients with advanced-stage cancer," Arch Gen Psychiatry. 68(1 ):71-78 (Jan. 2011).
Guchhait, R. B., "Biogenesis of 5-methoxy-N, N-dimethyltryptamine in human pineal gland," Journal of Neurochemistry. 26:187-90 (1976).
Gudelsky et al. "Suppression of the hypo- and hyperthermic responses to 5-HT agonists following the repeated administration of monoamine oxidase inhibitors," Psychopharmacology (Berl). 90(3):403-407 (1986).
Guest, "Electroencephalographic and behavioral effects of 4-phosphoryloxy N, N-dimethyltryptamine (psilocybin) on the New Zealand albino rabbit," Thesis. 1977 (50 pages).
Gukasyan et al., "Attenuation of psilocybin mushroom effects during and after SSRI/SNRI antidepressant use," Journal of Psychopharmacology. 37(7)707-716 (Jun. 2023).
Gupta et al., "Salts of Therapeutic Agents: Chemical, Physicochemical, and Biological Considerations," Molecules. 23(7): (15 pages) (2018).
Gupta, S. P "QSAR studies on drugs acting at the central nervous system," Chemical Reviews, vol. 89, No. 8, pp. 1765-1800 (1989).
Haberzettl et al. "Animal models of the serotonin syndrome: A systematic review," Behav Brain Res. 256:328-345 (Nov. 2013).
Hackl et al. "Psilocybin Therapy of Psychiatric Disorders Is Not Hampered by hERG Potassium Channel-Mediated Cardiotoxicity," Int J Neuropsychopharmacol. 25(4):280-282 (Apr. 2022).

(56) References Cited

OTHER PUBLICATIONS

Haijen et al. "Predicting responses to psychedelics: a prospective study." Frontiers in Pharmacology. Nov. 2018;9:897, 20 pages. doi: 10.3389/fphar.2018.00897.
Halberstadt, Adam L., "Behavioral and pharmacokinetic interactions between monoamine oxidase inhibitors and the hallucinogen 5-methoxy-N, N-dimethyltryptamine," Pharmacol Biochem Behav. 143:1-10 (Apr. 2016) (29 pages).
Halberstadt, A.L., et al., "Pharmacological Characterization of the LSD Analog N-ethyl-n-cyclopropyl Lysergamide (ECPLA)," Psychopharmacology, Feb. 2019, vol. 236, pp. 799-808.
Halberstadt et al., "Behavioral effects of alpha, alpha, beta, beta-tetradeutero-5-MeO-DMT in rats: comparison with 5-MeO-DMT administered in combination with a monoamine oxidase inhibitor," Psychopharmacology (Berl). 221(4):709-718 (Jun. 2012) (17 pages).
Halberstadt et al. "Differential contributions of serotonin receptors to the behavioral effects of indoleamine hallucinogens in mice," J Psychopharmacol. 25(11):1548-1561 (Nov. 2011).
Halberstadt et al., "LSD but not lisuride disrupts prepulse inhibition in rats by activating the 5-HT2A receptor," Psychopharmacology. 208:179-89 (Nov. 2009).
Halberstadt et al. "Multiple receptors contribute to the behavioral effects of indoleamine hallucinogens," Neuropharmacology. 61 (3):364-381 (Sep. 2011) (42 pages).
Halberstadt. "Recent advances in the neuropsychopharmacology of serotonergic hallucinogens," Behav Brain Res. 277:99-120 (Jan. 2015).
Halpern et al. "A Review of Hallucinogen Persisting Perception Disorder (HPPD) and an Exploratory Study of Subjects Claiming Symptoms of HPPD," Curr Top Behav Neurosci. 36:333-360 (2018) (28 pages).
Hanks et al. "Animal models of serotonergic psychedelics," ACS Chern Neurosci. 4(1):33-42 (Jan. 2013).
Haridy, Rich, "The start-up behind a magic mushroom nose spray for psychedelic microdosing," New Atlas. Dec. 5, 2019 (12 pages).
Hartogsohn. "Set and setting, psychedelics and the placebo response: An extra-pharmacological perspective on psychopharmacology," J Psychopharmacol. 30(12):1259-1267 (Dec. 2016).
Hasler et al. "Acute psychological and physiological effects of psilocybin in healthy humans: a double-blind, placebo-controlled dose-effect study," Psychopharmacology (Berl). 172(2): 145-156 (Mar. 2004).
Hasler et al. "Determination of psilocin and 4-hydroxyindole-3-acetic acid in plasma by HPLC-ECD and pharmacokinetic profiles of oral and intravenous psilocybin in man," Pharma Acta Helv. 72(3):175-184 (Jun. 1997).
Hasler et al. "Renal excretion profiles of psilocin following oral administration of psilocybin: a controlled study in man," J Pharm Biomed Anal. 30(2):331-339 (Sep. 2002).
Heal et al. "Evaluating the abuse potential of psychedelic drugs as part of the safety pharmacology assessment for medical use in humans," Neuropharmacology. 142:89-115 (Nov. 2018).
Heinze et al. "The comparative behavioral effects of N,N-dimethyltryptamine and N,N-diethyltryptamine in primate dyads," Biol Psychiatry. 18(7):829-836 (Jul. 1983).
Helsley et al. "A comparison of N, N-dimethyltryptamine, harmaline, and selected congeners in rats trained with LSD as a discriminative stimulus," Prog Neuropsychopharmacol Biol Psychiatry. 22(4):649-663 (May 1998).
Hendricks et al., "Classic psychedelic use is associated with reduced psychological distress and suicidality in the United States adult population," Journal of Psychopharmacology. 29(3):280-8 (Jan. 2015).
Henriques et al., "Spray dried powders for nasal delivery: Process and formulation considerations," Eur J Pharm Biopharm. 176:1-20 (May 2022).
Hibicke et al., "Psychedelics, but Not Ketamine, Produce Persistent Antidepressant-like Effects in a Rodent Experimental System for the Study of Depression," ACS Chern Neurosci. 11(6):864-871 (Mar. 2020).
Hicks et al., "Clinical Pharmacogenetics Implementation Consortium (CPIC) Guideline for CYP2D6 and CYP2C19 Genotypes and Dosing of Selective Serotonin Reuptake Inhibitors," Clincal Pharmacology & Therapeutics. 98(2):127-134 (Aug. 2015).
Hintzen et al., "The pharmacology of LSD: a critical review," ISBN 13: 9780199589821 (2009) (225 pages).
Hirschfeld et al. "Dose-response relationships of psilocybin-induced subjective experiences in humans," J Psychopharmacol. 35(4):384-397 (Apr. 2021—ePub Mar. 4, 2021) (14 pages).
Hitt et al. "Toad toxicity," N Engl J Med. 314(23):1517-1518 (Jun. 1986) (3 pages).
Hollister. "Clinical, biochemical and psychologic effects of psilocybin," Arch Int Pharmacodyn Ther. 130:42-52 (Feb. 1961).
Hollister et al. "Comparison of three psychotropic drugs (psilocybin, JB-329, and IT-290) in volunteer subjects," J Nerv Ment Dis. 131:428-434 (Nov. 1960).
Holmstedt et al. "Chemical constituents and pharmacology of South American snuffs," Psychopharmacol Bull. 4(3):16 (Dec. 1967).
Honeycomb, "Intro," 5 Hive Forum. [Available at https://forums.5meodmt.org/index.php/topic,50868.msg55861.html#msg55861] (Feb. 2019) (2 pages).
Hopf et al. "Autoradiographic studies on the distribution of psychoactive drugs in the rat brain. 3. 14C-psilocin," Psychopharmacologia. 16(3):201-222 (1969).
Hopf et al. "Distribution patterns of 14-C-psilocin in the brains of various animals," Act Nerv Super (Praha). 16(1 ):64-66 (Mar. 1974).
Horita et al. "Dephosphorylation of psilocybin in the intact mouse," Toxicol Appl Pharmacol. 4:730-737 (Nov. 1962).
Horita et al. "The enzymic dephosphorylation and oxidation of psilocybin and psilocin by mammalian tissue homogenates," Biochem Pharmacol. 7:47-54 (Jul. 1961).
Hoshino et al., "Uber Die Synthese Des Bufotenin-Methyl-Athers (5-Methoxy-N-Dimethyl-Tryptamin) Und Bufotenins (Synthesen in Der Indol-Gruppe. XV)," Bulletin of the Chemical Society of Japan. 11 (3):221-224 (Mar. 1936) (8 pages).
Hróbjartsson et al., "Observer bias in randomized clinical trials with measurement scale outcomes: a systematic review of trials with both blinded and nonblinded assessors," CMAJ, (Mar. 5, 2013); 185(4):E201-11. doi: 10.1503/cmaj.120744. Epub Jan. 28, 2013.
Huang et al. "Drug discrimination and receptor binding studies of N-isopropyl lysergamide derivatives." Pharmacology Biochemistry and Behavior. Mar. 1994;47(3):667-673. doi: 10.1016/0091-3057(94)90172-4.
ICD-10 (The ICD-10 Classification of Mental and Behavioral Disorders: Diagnostic Criteria for Research, Geneva: World Health Organization, 1993).
Illum et al., "The effect of blood sampling site and physicochemical characteristics of drugs on bioavailability after nasal administration in the sheep model," Pharm Res. 20(9):1474-84 (Sep. 2003).
Inserra et al. "Psychedelics in Psychiatry: Neuroplastic, Immunomodulatory, and Neurotransmitter Mechanisms," Pharmacol Rev. 73(1):202-277 (Jan. 2021).
International Search Report and Written Opinion for International Application No. PCT/GB2023/052179, mailed Sep. 27, 2023 (14 pages).
International Search Report for International Application No. PCT/GB2022/053208, mailed Apr. 3, 2023 (6 pages).
International Search Report in International Application No. PCT/GB2021/051475, mailed Sep. 16, 2021 (10 pages).
International Search Report in International Application No. PCT/GB2021/051476, mailed Sep. 15, 2021 (12 pages).
"Investors think mind-bending drug DMT could rival psilocybin as a cost-effective psychedelic treatment for conditions like depression. 3 VCs explain why its fast-acting properties are appealing," Beckley Psytech Press Release May 30, 2021 (3 pages).
Irwin, "Comprehensive observational assessment: la. A systematic, quantitative procedure for assessing the behavioral and physiologic state of the mouse," Psychopharmacologia. 13(3):222-57 (Sep. 1968).
Isaac et al., "The God Molecule: 5-MeO-DMT and the Spiritual Path to Divine Light," Divine Arts. Back cover, pp. 99-100, 120 (Nov. 2016) (3 pages).

(56) References Cited

OTHER PUBLICATIONS

Isbell et al. "Studies on lysergic acid diethylamide (LSD-25). I. Effects in former morphine addicts and development of tolerance during chronic intoxication," AMA Arch Neurol Psychiatry. 76(5):468-478 (Nov. 1956).
Isbister et al. "The pathophysiology of serotonin toxicity in animals and humans: implications for diagnosis and treatment," Clin Neuropharmacol. 28(5):205-214 (Sep.-Oct. 2005).
Ishii et al. "Studies on lysergic acid diethylamide and related compounds. IX. Microbial transformation of amides related to lysergic acid diethylamide by *Streptomyces roseochromogenes*." Chemical and Pharmaceutical Bulletin. Dec. 1979;27(12):3029-3038. doi.org/10.1248/cpb.27.3029.
Jann, "Psilocybin Revisited: The Science Behind the Drug and Its Surprising Therapeutic Potential," Psychiatric Times. 38(3). Available [https://www.psychiatrictimes.com/view/psilocybin- revisited-science-behind-drug-surprising-therapeutic-potential Accessed Apr. 17, 2025 (Mar. 2021) (17 pages).
Jiang et al. "Development of a mechanism-based pharmacokinetic/pharmacodynamic model to characterize the thermoregulatory effects of serotonergic drugs in mice," Acta Pharm Sin B. 6(5):492-503 (Sep. 2016).
Jiang et al., "Modification of 5-methoxy-N,N-dimethyltryptamine-induced hyperactivity by monoamine oxidase A inhibitor harmaline in mice and the underlying serotonergic mechanisms," Pharmacol Rep. 68(3):608-15 (Jun. 2016).
Jiang et al. "Pharmacokinetic interactions between monoamine oxidase A inhibitor harmaline and 5-methoxy-N,N-dimethyltryptamine, and the impact of CYP2D6 status," Drug Metab Dispos. 41 (5):975-986 (May 2013).
Jiang et al. "Potentiation of 5-methoxy-N,N-dimethyltryptamine-induced hyperthermia by harmaline and the involvement of activation of 5-HT1A and 5-HT2A receptors," Neuropharmacology. 89:342-351 (Feb. 2015) (24 pages).
Jo et al. "Toxicological profiles of poisonous, edible, and medicinal mushrooms," Mycobiology. 42(3):215-220 (Sep. 2014) (7 pages).
Johansen et al. "Psychedelics not linked to mental health problems or suicidal behavior: a population study," J Psychopharmacol. 29(3):270-279 (Mar. 2015) (10 pages).
Johnson et al., "Classic psychedelics: An integrative review of epidemiology, therapeutics, mystical experience, and brain network function," Pharmacol Ther. 197:83-102 (May 2019).
Johnson et al. "Emetic activity of reduced lysergamides." Journal of Medicinal Chemistry (1973); 16(5):532-537. doi: 10.1021/jm00263a028.
Johnson et al., "Human hallucinogen research: guidelines for safety," J Psychopharmacol. 22(6):603-20 (Jul. 2008).
Johnson et al., "Long-term follow-up of psilocybin-facilitated smoking cessation," Am J Drug Alcohol Abuse. 43(1 ):55-60 (Jul. 2016) (7 pages).
Johnson et al.,"Pilot study of the 5-HT2AR agonist psilocybin in the treatment of tobacco addiction," J Psychopharmacol. 28(11):983-92 (Nov. 2014).
Johnson et al. "Psilocybin dose-dependently causes delayed, transient headaches in healthy volunteers," Drug Alcohol Depend. 123(1-3):132-140 (Jun. 2012) (20 pages).
Johnson et al. "Psychometric Properties of the General Anxiety Disorder 7-Item (GAD-7) Scale in a Heterogeneous Psychiatric Sample," Front Psychol. 10:1713 (Aug. 2019) (8 pages).
Johnson et al. "The abuse potential of medical psilocybin according to the 8 factors of the Controlled Substances Act," Neuropharmacology. 142:143-166 (Nov. 2018).
Johnson, F.N. et al., "Emetic Activity of Reduced Lysergamides," Journal of Medicinal Chemistry, vol. 16, pp. 532-537 (1973).
Johnson, Matthew W., "Psychiatry might need some psychedelic therapy," Int Rev Psychiatry. 30(4):285-290 (Dec. 2018) (7 pages).
Johnstad, "Powerful substances in tiny amounts: An interview study of psychedelic microdosing." Nordic Studies on Alcohol and Drugs. 35(1 ):39-51 (Feb. 2018).
Johnston et al., "The burden of treatment-resistant depression: A systematic review of the economic and quality of life literature," J Affect Disord. 242:195-210 (Jan. 2019).
Jonas et al., "Pharmacotherapy for adults with alcohol use disorders in outpatient settings: a systematic review and meta-analysis," JAMA. May 14, 2014; 311(18): 1889-900. doi: 10.1001/jama.2014.3628.
Jones et al. "The ever-changing roles of serotonin." The International Journal of Biochemistry & Cell Biology. 125:105776 (May 2020) (5 pages).
Jorgensen, "Studies on the neuroendocrine role of serotonin," Dan Med Bull. 54(4):266-88 (Nov. 2007).
Kaertner et al., "Positive expectations predict improved mental-health outcomes linked to psychedelic microdosing," Sci Rep. (Jan. 21, 2021); 11(1):1941. doi: 10.1038/s41598-021-81446-7.
Kalberer et al., "The fate of psilocin in the rat," Biochem Pharmacol. 11:261-9 (Apr.-May 1962).
Kalfas et al., "Psychedelics for treatment resistant depression: are they game changers?," Expert Opin Pharmacother. 24(18):2117-2132 (Nov. 2023) (17 pages).
Kampermann et al., "Physicians' beliefs about placebo and nocebo effects in antidepressants—an online survey among German practitioners," PLoS One, (May 31, 2017); 12(5): e0178719. doi: 10.1371/journal.pone.0178719. eCollection 2017, 11 pages.
Kargbo et al., "Direct Phosphorylation of Psilocin Enables Optimized cGMP Kilogram-Scale Manufacture of Psilocybin," ACS Omega. 5(27): 16959-16966 (Jul. 2020).
Kargbo et al., "Psilocybin: Characterization of the Metastable Zone Width (MSZW), Control of Anhydrous Polymorphs, and Particle Size Distribution (PSD)," ACS Omega. 7(6): 5429-5436 (with supporting information) (Feb. 2022) (54 pages).
Kargbo, "Improved 5-HT2 Selective Receptor Modulators for the Treatment of Psychological Disorders," ACS Med Chern Lett. 12(12):1876-1878 (Nov. 2021).
Kast, "Attenuation of anticipation: a therapeutic use of lysergic acid diethylamide," Psychiatr Q. 41 (4):646-57 (Oct. 1967).
Kast et al., "Study of Lysergic Acid Diethylamide as an Analgesic Agent," Anesth Analg. 43(3):285-91 (May-Jun. 1964).
Katzman, Martin A., "Aripiprazole: A clinical review of its use for the treatment of anxiety disorders and anxiety as a comorbidity in mental illness," Journal of Affective Disorders. 128S1 :S11-20 (Jan. 2011).
Kaumann et al., "5-hydroxytryptamine receptors in the human cardiovascular system," Pharmacol Ther. 111 (3):674-706 (Sep. 2006).
Keenan et al., "Standard morphologic evaluation of the heart in the laboratory dog and monkey," Toxicol Pathol. 34(1):67-74 (2006).
Kennedy, "Core symptoms of major depressive disorder: relevance to diagnosis and treatment," Dialogues Clin Neurosci. 10(3):271-7 (2008).
Klaassen et al., "Neuroendocrine response to meta-chlorophenylpiperazine and ipsapirone in relation to anxiety and aggression," Psychiatry Res. 113(1-2):29-40 (Dec. 2002).
Klein et al., "Investigation of the Structure-Activity Relationships of Psilocybin Analogues." ACS Pharmacol. Transl. Sci. 2021, 4, 533-542.
Knoth et al., "Effect of inadequate response to treatment in patients with depression," Am J Manag Care. 16(8):e188-96 (Aug. 2010).
Knudsen, "Sustained effects of single doses of classical psychedelics in humans," Neuropsychopharmacology. 48(1 ):145-150 (Jun. 2022) (6 pages).
Ko et al., "Lethal ingestion of Chinese herbal tea containing ch'an su," West J Med. 164(1)71-5 (Jan. 1996).
Kolaczynska et al., "Development and validation of an LC-MS/MS method for the bioanalysis of psilocybin's main metabolites, psilocin and 4-hydroxyindole-3-acetic acid, in human plasma," J Chromatogr B Analyt Technol Biomed Life Sci. 1164:122486 (Feb. 2021) (10 pages).
Kometer et al., "Activation of serotonin 2A receptors underlies the psilocybin-induced effects on alpha oscillations, N170 visual-evoked potentials, and visual hallucinations," J Neurosci.33(25):10544-51 (Jun. 2013).

(56) References Cited

OTHER PUBLICATIONS

Kometer et al., "Psilocybin-induced spiritual experiences and insightfulness are associated with synchronization of neuronal oscillations," Psychopharmacology (Berl). 232(19):3663-76 (Aug. 2015) (14 pages).
Kooijman et al., "Are psychedelics the answer to chronic pain: A review of current literature," Pain Pract. 23(4): 447-458 (Apr. 2023).
Kostakis et al., "Sudden death associated with intravenous injection of toad extract," Forensic Sci Int. 188(1-3)e1-5 (Jul. 2009).
Kraehenmann et al., "Psilocybin-Induced Decrease in Amygdala Reactivity Correlates with Enhanced Positive Mood in Healthy Volunteers," Biol Psychiatry. 78(8):572-81 (Oct. 2015).
Kratochvil, "Solid Forms of Pharmaceutical Molecules," chapter in book 'Glassy, Amorphous and Nano-Crystalline Materials,' Springer Science & Business Media, eds Sestak et al., Oct. 2010, pp. 129-140.
Krebs et al., "Lysergic acid diethylamide (LSD) for alcoholism: meta-analysis of randomized controlled trials," J Psychopharmacol. 26(7):994-1002 (Jul. 2012) (10 pages).
Krebs et al., "Over 30 million psychedelic users in the United States," F1000Res. 2:98 (Mar. 2013).
Krebs et al., "Psychedelics and mental health: a population study," PLoS One. 8(8):e63972 (Aug. 2013) (9 pages).
Krebs-Thomson et al., "The roles of 5-HT1A and 5-HT2 receptors in the effects of 5-MeO-DMT on locomotor activity and prepulse inhibition in rats," Psychopharmacology (Berl). 189(3):319-29 (Dec. 2006).
Kruszewski et al., "Cluster headache and SUNCT: similarities and differences," J Headache Pain. 2(2):57-66 (Nov. 2001).
Kurland et al., "Psychedelic drug assisted psychotherapy in patients with terminal cancer," Journal of Thanatology. 2(1-2):644-691 (1972) (48 pages).
Kurland, "LSD in the supportive care of the terminally ill cancer patient," J Psychoactive Drugs. 17(4):279-90 (Oct.-Dec. 1985).
Kuypers et al., "Ayahuasca enhances creative divergent thinking while decreasing conventional convergent thinking," Psychopharmacology (Berl). 233(18):3395-403 (Jul. 2016) (9 pages).
Kyzar et al., "Psychedelic Drugs in Biomedicine," Trends Pharmacol Sci. 38(11 ):992-1005 (Nov. 2017).
Lala P.K., et al., "Role of Nitric Oxide in Tumor Progression: Lessons from Experimental Tumors," Cancer and Metastasis Reviews, 1998, vol. 17, pp. 91-106.
Lalley, "Inhibition of phrenic and sympathetic vasomotor neurons in cats by the serotonin analog 5-methoxy-N,N-dimethyltryptamine," J Pharmacol Exp Ther. 220(1):39-48 (Jan. 1982).
Lambru et al., "Sunct and Suna: medical and surgical treatments," Neurol Sci. 34 Suppl 1 :S75-81 (May 2013).
Lancelotta et al., "Use of Benefit Enhancement Strategies among 5-Methoxy-N,N-Dimethyltryptamine (5-MeO-DMT) Users: Associations with Mystical, Challenging, and Enduring Effects," J Psychoactive Drugs. 52(3):273-281 (Mar. 2020) (10 pages).
Lanzenberger et al., "Reduced serotonin-1 A receptor binding in social anxiety disorder," Biol Psychiatry. 61 (9):1081-9 (May 2007).
Larson, "Acute and chronic effects of LSD and 5-MeODMT on raphe-evoked dorsal root potentials in the cat," Life Sci. 34(12):1193-201 (Mar. 1984).
Law et al., "14C-Psilocin tissue distribution in pregnant rats after intravenous administration," Functional Foods in Health and Disease. 4(6):232-244 (Jun. 2014).
"Learning from 50 years of psychedelic progress," Psytech Press Release Oct. 19, 2020 (6 pages).
Lebedev et al., "LSD-induced entropic brain activity predicts subsequent personality change," Hum Brain Mapp. 37(9):3203-13 (May 2016).
Lee et al., "Examining cognitive function across the lifespan using a mobile application," Computers in Human Behavior. 28(5):1934-1946 (2012) (14 pages).
Leonard et al., "Does getting high hurt? Characterization of cases of LSD and psilocybin-containing mushroom exposures to national poison centers between 2000 and 2016," J Psychopharmacol. 32(12):1286-1294 (Dec. 2018).
Leone et al., "Deep brain stimulation to relieve drug-resistant Sunct," Ann Neurol. 57(6):924-7 (Jun. 2005).
Lerer et al., "Variability of 5-HT2C receptor cys23ser polymorphism among European populations and vulnerability to affective disorder," Mol Psychiatry. 6(5):579-85. (Sep. 2001).
Li et al., "Association between antidepressant resistance in unipolar depression and subsequent bipolar disorder: cohort study," Br J Psychiatry. 200(1 ):45-51 (Jan. 2012).
Lieberman et al., "Lisuride in Parkinson disease: efficacy of lisuride compared to levodopa," Neurology. 31(8):961-5. Abstract (Aug. 1981).
Lii et al., "Randomized trial of ketamine masked by surgical anesthesia in patients with depression," Nat Ment Health. (Nov. 2023); 1(11): 876-886. doi: 10.1038/s44220-023-00140-x. Epub Oct. 19, 2023.
Lim et al., "A fatal case of 'magic mushroom' ingestion in a heart transplant recipient," Intern Med J. 42(11 ):1268-9 (Nov. 2012).
Lindenblatt et al., "Quantitation of psilocin in human plasma by high-performance liquid chromatography and electrochemical detection: comparison of liquid-liquid extraction with automated on-line solid-phase extraction," J Chromatogr B Biomed Sci Appl. 709(2):255-63 (May 1998).
Liu et al., "Decrease in the descending inhibitory 5-HT system in rats with spinal nerve ligation," Brain Res. 1330:45-60 (Mar. 2010).
Liu et al., "Particle Size Distribution Analysis of OTC Aerosol or Powder Drug Products With Potential for Inadvertent Inhalation Exposure to Consumers," J Pharm Sci. Apr. 2019;108(4):1506-1511. doi: 10.1016/j.xphs.2018.10.066. Epub Nov. 20, 2018.
Liu et al., "Roles of 5-hydroxytryptamine (5-HT) receptor subtypes in the inhibitory effects of 5-HT on C-fiber responses of spinal wide dynamic range neurons in rats," J Pharmacol Exp Ther. 321 (3):1046-53 (Jun. 2007).
Loscher et al., "Pharmacodynamic effects of serotonin (5-HT) receptor ligands in pigs: stimulation of 5-HT2 receptors induces malignant hyperthermia," Naunyn Schmiedebergs Arch Pharmacol. 341 (6):483-93 (Jun. 1990).
Lowe et al., "The Therapeutic Potential of Psilocybin," Molecules. 26(10):2948 (May 2021) (33 pages).
Loyd et al., "Serotonergic neuromodulation of peripheral nociceptors," Semin Cell Dev Biol. 24(1 ):51-7 (Jan. 2013) (15 pages).
Lucki et al., "Differential actions of serotonin antagonists on two behavioral models of serotonin receptor activation in the rat," J Pharmacol Exp Ther. 228(1 ):133-9 (Jan. 1984).
Luethi et al., "Cytochrome P450 enzymes contribute to the metabolism of LSD to nor-LSD and 2-oxo-3-hydroxy-LSD: Implications for clinical LSD use," Biochem Pharmacol. 164:129-138 (Apr. 2019).
Luethi et al. "Monoamine receptor interaction profiles of 4-aryl-substituted 2,5-dimethoxyphenethylamines (2C-BI derivatives)," Eur J Pharmacol. 855:103-111 (Jul. 2019) (36 pages).
Ly et al., "Psychedelics Promote Structural and Functional Neural Plasticity," Cell Rep. 23(11):3170-3182 (Jun. 2018) (25 pages).
Lyness et al. "The relationship of medical comorbidity and depression in older, primary care patients," Psychosomatics. 47(5):435-439 (Sep.-Oct. 2006).
Lyons et al., "Increased nature relatedness and decreased authoritarian political views after psilocybin for treatment-resistant depression," J Psychopharmacol. 32(7):811-819 (Jul. 2018) (9 pages).
Lyons T. et al., "Human brains change after first psilocybin use," BiorXiv, Oct. 15, 2024; 23 pages.
Lyttle et al. "Bufo toads and bufotenine: fact and fiction surrounding an alleged psychedelic," J Psychoactive Drugs. 28(3):267-290 (Jul.-Sep. 1996).
Machado-Vieira et al. "The Timing of Antidepressant Effects: A Comparison of Diverse Pharmacological and Somatic Treatments," Pharmaceuticals (Basel). 3(1 ):19-41 (Jan. 2010).

(56) References Cited

OTHER PUBLICATIONS

MacLean et al., "Mystical experiences occasioned by the hallucinogen psilocybin lead to increases in the personality domain of openness," J Psychopharmacol. 25(11):1453-61 (Nov. 2011) (16 pages).
Madsen et al. "A single psilocybin dose is associated with long-term increased mindfulness, preceded by a proportional change in neocortical 5-HT2A receptor binding," Eur Neuropsychopharmacol. 33:71-80 (Apr. 2020).
Madsen et al. "Psilocybin-induced changes in brain network integrity and segregation correlate with plasma psilocin level and psychedelic experience," Eur Neuropsychopharmacol. 50:121-132 (Sep. 2021—ePub Jul. 8, 2021 ) (12 pages).
Malcolm et al., "Serotonin toxicity of serotonergic psychedelics," Psychopharmacology (Berl). 239(6):1881-1891 (Jul. 2021) (11 pages).
Malik et al., "Phase 1 Study Results on the Effects of 5-MeO-DMT Benzoate on Facial Emotion Processing in Psychedelic-Naive Healthy Subjects," Neuroscience Applied 2. P.0097:45-46 (Dec. 2023) (2 pages).
Malik et al., "Phase 1 study results on the effects of 5-MeO-DMT. benzoate (BPL-003) on facial emotion processing in psychedelic-naive healthy subjects," Beckley Psytech. Poster No. P.0097. Presented: Sep. 30, 2023 (1 page).
Malitz et al. "Some observations on psilocybin, a new hallucinogen, in volunteer subjects," Compr Psychiatry. 1:8-17 (Feb. 1960).
Manevski et al. "Glucuronidation of psilocin and 4-hydroxyindole by the human UDP-glucuronosyltransferases," Drug Metab Dispos. 38(3):386-395 (Mar. 2010).
Marek et al., "The selective 5-HT2A receptor antagonist M100907 enhances antidepressant-like behavioral effects of the SSRI fluoxetine," Neuropsychopharmacology. 30(12):2205-2015 (Dec. 2005).
Markel et al. "LSD flashback syndrome exacerbated by selective serotonin reuptake inhibitor antidepressants in adolescents," J Pediatr. 125(5):817-819 (Nov. 1994).
Martinotti et al. "Hallucinogen Persisting Perception Disorder: Etiology, Clinical Features, and Therapeutic Perspectives," Brain Sci. 8(3):47 (Mar. 2018) (18 pages).
Mason et al. "Alcohol Use Disorder: The Role of Medication in Recovery," Alcohol Res. 41(1):07 (Jun. 2021) (17 pages).
Matharu et al., "Sunct syndrome responsive to intravenous lidocaine," Cephalalgia. 24(11):985-92 (Nov. 2004).
Matreja P., et al., "Effectiveness and acceptability of sertraline and citalopram in major depressive disorder: pragmatic randomized open-label comparison", Human Psychopharmacology. Clinical and Experimental, John Wiley & Sons Ltd, XX, vol. 22, No. 7, Jul. 24, 2007 (Jul. 24, 2007), pp. 477-482.
Matsingos et al., "Hype or hope? High placebo response in major depression treatment with ketamine and esketamine: a systematic review and meta-analysis," Front Psychiatry. (Mar. 8, 2024): 15: 1346697. doi: 10.3389/fpsyt.2024.1346697. eCollection 2024.
Matsumoto et al., "Suppressive effect of mitragynine on the 5-methoxy-N,N-dimethyltryptamine-induced head-twitch response in mice," Pharmacol Biochem Behav. 57(1-2):319-23 (May-Jun. 1997).
Matsushima et al., "Historical overview of psychoactive mushrooms," Inflammation and Regeneration. 29(1 ):47-58 (2009).
May et al., "Functional magnetic resonance imaging in spontaneous attacks of Sunct: shortlasting neuralgiform headache with conjunctival injection and tearing," Ann Neurol. 46(5):791-4 (Nov. 1999).
May et al., "Hypothalamic activation in cluster headache attacks," Lancet. 352(9124):275-8 (Jul. 1998).
McAllister-Williams et al., "Multiple-therapy-resistant major depressive disorder: a clinically important concept," Br J Psychiatry. 212(5):274-278 (May 2018).
McCabe et al., "The relationship between working memory capacity and executive functioning: evidence for a common executive attention construct," Neuropsychology. 24(2):222-243 (Mar. 2010) (38 pages).
McCrone et al., "The economic cost of treatment-resistant depression in patients referred to a specialist service," J Ment Health. 27(6):567-573 (Dec. 2017).
Mcgirr et al. "A systematic review and meta-analysis of randomized, double-blind, placebo-controlled trials of ketamine in the rapid treatment of major depressive episodes," Psychol Med. (Mar. 2015); 45(4): 693-704. doi: 10.1017/S0033291714001603. Epub Jul. 10, 2014.
McIntyre, "Serotonin 5-HT2B receptor agonism and valvular heart disease: implications for the development of psilocybin and related agents," Expert Opin Drug Saf. 22(10):881-883 (Jul.-Dec. 2023).
Mckenna et al., "Differential interactions of indolealkylamines with 5-hydroxytryptamine receptor subtypes", Neuropharmacology (1990); 29(3): 193-198. doi: 10.1016/0028-3908(90)90001-8.
McLeod et al., Bufotenine reconsidered. Acta psychiatrica Scandinavica. 72(5): 447-50 (Nov. 1985).
Medline Plus, "Cancer" [online] National Library of Medicine, [retrieved online Jul. 6, 2007 from www.nlm.nih.gov/medlineplus/cancer.html], 10 pages.
Meltzer et al., Effects of pirenperone and ketanserin on rat prolactin secretion in vivo and in vitro. European journal of pharmacology. 92(1-2): 83-9 (Aug. 1983).
Meltzer et al., Stimulation of rat prolactin secretion by indolealkylamine hallucinogens. Psychopharmacology. 56(3): 255-9 (Apr. 1978).
Merriam-Webster, "Prodrug", in Merriam-Webster.com dictionary, [Retrieved Mar. 7, 2026, from https://www.merriam-webster.com/dictionary/prodrug], (Year: 2026), 8 pages.
Mertens et al., Therapeutic mechanisms of psilocybin: Changes in amygdala and prefrontal functional connectivity during emotional processing after psilocybin for treatment-resistant depression. Journal of psychopharmacology (Oxford, England). 34(2): 167-180 (Feb. 2020) (14 pages).
Messa et al., "5-HT(2A) receptor binding is reduced in drug-naive and unchanged in SSRI-responder depressed patients compared to healthy controls: a PET study," Psychopharmacology (Berl). 167(1 ):72-8 (Mar. 2003) (8 pages).
Metzner, Ralph, "The Toad and the Jaguar: A Field Report of Underground Research on a Visionary Medicine: Bufo Alvarius and 5-Methoxy-Dimethyltryptamine." Regent Press for Green Earth Foundation (2013) (94 pages).
Meyer et al., "The effect of paroxetine on 5-HT(2A) receptors in depression: an [(18)F]setoperone PET imaqinq study," Am J Psychiatry. 158(1 ):78-85 (Jan. 2001).
Migliaccio et al., "Comparison of solution conformational preferences for the hallucinogens bufotenin and psilocin using 360-MHz proton NMR spectroscopy," J Med Chern. 24(2):206-9 (Feb. 1981).
Mitsuma et al., "Effects of serotonergic system on hypothalamic-pituitary-thyroid axis in rats," Horm Metab Res. 15(7):346-349 (Jul. 1983).
Moldavan et al. "The effect of Psilocybe cubensis extract on hippocampal neurons in vitro," Fiziol Zh (1994). 47(6):15-23 (2001).
Monson et al. "MDMA-facilitated cognitive-behavioural conjoint therapy for posttraumatic stress disorder: an uncontrolled trial." European Journal of Psychotraumatology. Dec. 31, 2020;11(1):1840123, 7 pages. doi: 10.1080/20008198.2020.1840123.
Monte et al. "Stereoselective LSD-like activity in a series of d-lysergic acid amides of (R)-and (S)-2-aminoalkanes." Journal of Medicinal Chemistry. Mar. 1995;38(6):958-966. doi: 10.1021/jm00006a015.
Montgomery et al. "A new depression scale designed to be sensitive to change." The British Journal of Psychiatry. Apr. 1979;134(4):382-389. doi: 10.1192/bjp.134.4.382.
Mor et al., "Melatonin receptor ligands: synthesis of new melatonin derivatives and comprehensive comparative molecular field analysis (CoMFA) study," J Med Chern. 41:3831-3844 (Sep. 1998).
Moreno et al. "Safety, tolerability, and efficacy of psilocybin in 9 patients with obsessive-compulsive disorder," J Clin Psychiatry. 67(11 ):1735-1740 (Nov. 2006).
Moriguchi I., et al., Simple Method of Calculating Octanol/Water Partition Coefficient.Chem. Pharm. Bull, Jan. 1992, 40, 127-130.
Morley et al. "New approved and emerging pharmacological approaches to alcohol use disorder: a review of clinical studies," Expert Opin Pharmacother. 22(10):1291-1303 (Jul. 2021) (14 pages).

(56) References Cited

OTHER PUBLICATIONS

Moser et al. "The effect of benzodiazepines on the 5-HT agonist-induced head-twitch response in mice," Eur J Pharmacol. 151(2):223-231 (Jul. 1988).
Moser, P.C. "The effect of putative 5-HT1A receptor antagonists on 8-OH-DPAT-induced hypothermia in rats and mice," Eur J Pharmacol. 193(2):165-172 (Feb. 1991).
Murphy et al., "Therapeutic Alliance and Rapport Modulate Responses to Psilocybin Assisted Therapy for Depression," Front Pharmacol, (Mar. 31, 2022): 12: 788155. doi: 10.3389/fphar.2021.788155. eCollection 2021. 19 pages.
Murphy-Beiner et al. "Ayahuasca's 'afterglow': improved mindfulness and cognitive flexibility in ayahuasca drinkers," Psychopharmacology (Berl). 237(4): 1161-1169 (Jan. 2020).
Muthukumaraswamy et al. "Broadband cortical desynchronization underlies the human psychedelic state," J Neurosci. 33(38):15171-15183 (Sep. 2013).
Muttoni et al. "Classical psychedelics for the treatment of depression and anxiety: A systematic review," J Affect Disord. 258:11-24 (Nov. 2019).
"My first 5MeODMT Experience—12mg (vaporized)," Reddit, Sep. 2019, [Available online at URL: https://www.reddit.eom/r/5MeODMT/comments/dai2dp/myJirst_5meodmt_experience_12mg_vaporized/?share_id=2OegQvv7bxUmdqaFM0in_&utm_content=2&utm_medium=ios_app&utm_name=ioscss&utmsource=share&utmterm=10], (8 pages).
"My journey with 5MEODMT," Reddit. Available [https://www.reddit.eom/r/5MeODMT/comments/t592jk/myjourney_with_5meodmt/ (Mar. 2022) (2 pages).
Nagai et al., "The effects of non-medically used psychoactive drugs on monoamine neurotransmission in rat brain," Eur J Pharmacol. 559(2-3):132-7 (Dec. 2006).
Nakahara et al. "Studies on lysergic acid diethylamide and related compounds. 3. Improvement of amidation of lysergic acid (author's transl)." Yakugaku zasshi: Journal of the Pharmaceutical Society of Japan. Mar. 1974;94(3):407-412. doi: 10.1248/yakushi1947.94.3_407.
Nakamura et al., "Effects in animal models of depression of lisuride alone and upon coadministration with antidepressants," Folia pharmacol iapon. 94(1 ):81-9 (English language abstract) (Jul. 1989).
Narasimhachari et al., "Urinary studies of schizophrenics and controls," Biol Psychiatry. 3(1 ):9-20 (1971) (13 pages).
Nau Jr. et al. "Serotonin 5-HT2 receptor activation prevents allergic asthma in a mouse model," Am J Physiol Lung Cell Mol Physiol. 308(2):L191-198 (Jan. 2015).
Nau Jr. et al. "Serotonin 5-HT2A receptor activation blocks TNF-alpha mediated inflammation in vivo," PLoS One. 8(10):e75426 (Oct. 2013) (8 pages).
NCT00006206, "Combine: Effect of Combined Pharmacotherapies and Behavioral Interventions," [clinical trial registry], ClinicalTrials.gov, Sponsor: University of North Carolina, Chapel Hill, (first posted Sep. 12, 2000), last update posted May 3, 2010, [retrieved from the internet on Feb. 11, 2026 from https://clinicaltrials.gov/study/NCT00006206], 12 pages.
NCT05548075, "Psilocybin in Patients With Fibromyalgia: EEG-measured Brain Biomarkers of Action (Psilopain)." [Clinical trial registry], (Sep. 21, 2022), last updated Jan. 19, 2024, [retrieved from https://clinicaltrials.gov/study/NCT05548075]; 21 pages.
NCT05870540, "A Quadruple Masked, Dose-Finding Study to Evaluate the Efficacy and Safety of Intranasal BPL-003, With Open Label Extension, in Patients With Treatment-Resistant Depression," [clinical trial registry] ClinicalTrials.gov, Sponsor Beckley Psytech Limited, (first posted May 23, 2023), last update posted Jul. 18, 2025, [retrieved from the internet on Feb. 11, 2025 from https://clinicaltrials.gov/study/NCT05870540], 14 pages.
Neumeister et al. "Reduced serotonin type 1A receptor binding in panic disorder," J Neurosci. 24(3):589-591 (Jan. 2004).
"New psychedelic medicine COO looks to boost pharma and biotech collaborations," Beckley Psytech Press Release Feb. 22, 2021 (4 pages).
Nguyen et al., "Epidemiology and Economic Burden of Serotonin Syndrome With Concomitant Use of Serotonergic Agents: A Retrospective Study Utilizing Two Large US Claims Databases," Prim Care Companion CNS Disord. 19(6):17m02200 (Dec. 2017) (9 pages).
Nichols et al. "Molecular genetic responses to lysergic acid diethylamide include transcriptional activation of MAP kinase phosphatase-1, C/EBP-beta and ILAD-1, a novel gene with homology to arrestins," J Neurochem. 90(3):576-584 (Aug. 2004).
Nichols et al. "Psychedelics as Medicines: An Emerging New Paradigm," Clin Pharmacol Ther. 101(2):209-219 (Feb. 2017).
Nichols, "Psychedelics," Pharmacol Rev. 68(2):264-355 (Apr. 2016).
Nonaka et al., "In vitro screening of psychoactive drugs by [(35)S]GTPgammaS binding in rat brain membranes," Biol Pharm Bull. 30(12):2328-33 (Dec. 2007).
Nutt et al. "Drug harms in the UK: a multicriteria decision analysis," Lancet. 376(9752):1558-1565 (Nov. 2010) (9 pages).
Nutt et al. "Psychedelic Psychiatry's Brave New World," Cell. 181 (1):24-28 (Apr. 2020).
Nutt et al., "The Current Status of Psychedelics in Psychiatry," JAMA Psychiatry. 78(2):121-122 (Jul. 2020) (2 pages).
Obreshkova, Danka et al., "Pharmaco-toxicological aspects and analysis of phenylalkylamine and indolylallkylamine hallucinogens (Review)." Pharmacia. 64(1):32-47 (Mar. 2017) (17 pages).
Orsolini et al. The 'Endless Trip' among the NPS Users: Psychopathology and Psychopharmacology in the Hallucinogen-Persisting Perception Disorder. A Systematic Review. Front Psychiatry. 8(240) (Nov. 2017) (10 pages).
Ortiz Bernal et al., "Reactivations after 5-methoxy-N,N-dimethyltryptamine use in naturalistic settings: An initial exploratory analysis of the phenomenon's predictors and its emotional valence," Front Psychiatry. 13: 1049643 (Nov. 2022) doi: 10.3389/fpsyt.2022.1049643, eCollection 2022, (13 pages).
P. Ertl, A. Schuffenhauer, Estimation of synthetic accessibility of drug-like molecules based on molecular complexity and fragment contributions. J. Cheminform. 1, 8 (2009).
Pahnke et al., "Implications of LSD and experimental mysticism," Journal of Psychedelic Drugs Drugs. 3(1 ):92-108 (Sep. 1970) (18 pages).
Palamar et al., Self-reported use of novel psychoactive substances in a US nationally representative survey: Prevalence, correlates, and a call for new survey methods to prevent underreporting. Drug Alcohol Depend. 156:112-119 (Nov. 2015) (21 pages).
Palamar et al., Use of new and uncommon synthetic psychoactive drugs among a nationally representative sample in the United States, 2005-2017. Human psychopharmacology. 34(2):e2690 (Mar. 2019)(22 pages).
Pandey et al., Regional distribution and relative abundance of serotonin(2c) receptors in human brain: effect of suicide. Neurochemical research. 31 (2):167-76 (Feb. 2006).
Papakostas et al., "Does the probability of receiving placebo influence clinical trial outcome? A meta-regression of double-blind, randomized clinical trials in MDD," Eur Neuropsychopharmacol, (Jan. 2009); 19(1): 34-40. doi: 10.1016/j.euroneuro.2008.08.009. Epub Sep. 26, 2008.
Papoian et al., "Regulatory Forum Review: Utility of in vitro secondary pharmacology data to assess risk of drug-induced valvular heart disease in humans: regulatory considerations." Toxicol. Pathol 45(3):381-388 (Apr. 2017).
Pardo et al., "Localization of a human system for sustained attention by positron emission tomography," Nature. 349(6304):61-4 (Jan. 1991) (5 pages).
Passie et al., "The pharmacology of lysergic acid diethylamide: a review," CNS Neurosci Ther. 14(4):295-314 (Nov. 2008) (20 pages).
Passie et al., "The pharmacology of psilocybin." Addiction biology 7(4):357-364 (Oct. 2002) (9 pages).
Patocka et al., "Chemistry and toxicology of major bioactive substances in Inocybe mushrooms." Iot J Mol Sci 22:2218 (Feb. 2021) (13 pages).
PCT Application No. PCT/GB2023/052977, International Preliminary Report on Patentability, mailed May 22, 2025, Applicant: Beckley Psytech Limited, 9 pages.

(56) References Cited

OTHER PUBLICATIONS

PCT Application No. PCT/GB2023/052977, International Search Report and Written Opinion mailed Aug. 2, 2024, Applicant: Beckley Psytech Limited, 11 pages.
PCT Application No. PCT/GB2025/052099, International Search Report and Written Opinion mailed Dec. 22, 2025, Applicant Beckley Psytech Limited. et al.; 21 pages.
PCT Application No. PCT/GB2025/052100, International Search Report and Written Opinion mailed Dec. 19, 2025, Applicant Beckley Psytech Limited. et al.; 19 pages.
PCT Application No. PCT/GB2025/052102, International Search Report and Written Opinion mailed Dec. 19, 2025, Applicant Beckley Psytech Limited. et al.; 19 pages.
PCT Application No. PCT/US2024/038804, International Preliminary Report mailed Jan. 29, 2026, Applicant Atai Therapeutics Inc; 10 pages.
PCT Application No. PCT/US2024/039503, International Preliminary Report mailed Feb. 5, 2026, Applicant Atai Therapeutics, Inc; 13 pages.
Pei et al., "Uncoupling the dopamine D1-D2 receptor complex exerts antidepressant-like effects." Nature medicine 16(12):1393-1395 (Dec. 2010) (4 pages).
Peill et al., "Validation of the Psychological Insight Scale: A new scale to assess psychological insight following a psychedelic experience," J Psychopharmacol. (Jan. 2022); 36(1): 31-45. doi: 10.1177/02698811211066709. Epub Jan. 5, 2022.
Pellegrini et al., "Single-dose (10 mg) psilocybin reduces symptoms in adults with obsessive-compulsive disorder: A pharmacological challenge study," Compr Psychiatry. (Oct. 2025): 142: 152619. doi: 10.1016/j.comppsych.2025.152619. Epub Jul. 1, 2025.
Penn et al., "The drugs don't work? antidepressants and the current and future pharmacological management of depression," Ther Adv Psychopharmacol. 2(5):179-88 (Oct. 2012).
PharmaTher Holdings Ltd. Dec. 14, 2021. PharmaTher Announces Positive Research Results for LSD Microneedle Patch. Press Release. URL:https://psychedelicinvest.com/pharmather-announces-positive-research-results-for-lsd- microneedle-patch/ (11 pages).
Pokorny et al., "Effect of Psilocybin on Empathy and Moral Decision-Making," Int J Neuropsychopharmacol. 20(9):747-757 (Sep. 2017) (38 pages).
Pollan, M. "How to change your mind: what the new science of psychedelics teaches us about consciousness, dying, addiction, depression, and transcendence," New York: Penguin Press, May 2018, 456 pages.
Pompeiano et al., "Distribution and cellular localization of mRNA coding for 5-HT1A receptor in the rat brain: correlation with receptor binding," J Neurosci. 12(2):440-53 (Feb. 1992) (14 pages).
"Spotlight on Beckley Psytech and psilocybin," Beckley Psytech Press Release Mar. 22, 2021 (5 pages).
"Spotlight on the psychedelic experience," Beckley Psytech Press Release Jun. 9, 2021 (5 pages).
Prakash et al., "Fatal serotonin syndrome: a systematic review of 56 cases in the literature," Clin Toxicol (Phila). 59(2):89-100 (Feb. 2021—ePub Nov. 16, 2020) (13 pages).
"Spravato (esketamine) nasal spray, CHI." Janssen Pharmaceuticals, prescribing information. Jul. 2020 (15 pages).
Price et al., "International pooled patient-level meta-analysis of ketamine infusion for depression: In search of clinical moderators," Mol Psychiatry. (Dec. 2022); 27(12):5096-5112. doi: 10.1038/s41380-022-01757-7. Epub Sep. 7, 2022.
Probst-Schendzielorz et al., "Effect of Cytochrome P450 polymorphism on the action and metabolism of selective serotonin reuptake inhibitors," Expert Opin Drug Metab Toxicol. 11 (8):1219-32 (Jun. 2015) (14 pages).
Prochazkova et al., "Exploring the effect of microdosing psychedelics on creativity in an open-label natural setting," Psychopharmacology (Berl). 235(12):3401-3413 (Dec. 2018) (13 pages).
Protzko et al., "Decline Effects: Types, Mechanisms, and Personal Reflections." In: Lilienfeld and Waldman, eds "Psychological Science Under Scrutiny: Recent Challenges and Proposed Solutions," West Sussex, UK, John Wiley & Sons, Inc. (2017). 85-107.
"Psychedelic Compounds Chemical and Physical Properties," [available online at: https://wiki.dmt-nexus.me/Psychedelic_Compounds_Chemical_and_Physical_Properties, last modified on May 19, 2023], (18 pages).
Psytech, "Meet our new scientific advisors," Psytech Press Release Nov. 6, 2020 (4 pages).
PubChem CID: 43608479, "N-[2-(1 H-indol-3-yl)ethyl]oxan-4-amine," [chemical database], National Library of Medicine, 2009, [publicly available online at URL: https://pubchem.ncbi.nlm.nih.gov/compound/43608479, retrieved Oct. 25, 2024], (7 pages).
Pubchem, Substance Record for CID 1832, Modify Date: Jul. 13, 2024. [https://pubchem.ncbi.nlm.nih.gov/compound/MeODMT Retrieved on Jul. 19, 2024 (54 pages).
Quitkin et al., "Identification of true drug response to antidepressants. Use of pattern analysis," Arch Gen Psychiatry. Aug. 1984; 41(8): 782-6. doi: 10.1001/archpsyc.1984.01790190056007.
Raff et al., "Renal failure after eating "magic" mushrooms," CMAJ. 147(9): 1339-41 (Nov. 1992) (3 pages).
Raison et al. "Single-dose psilocybin treatment for major depressive disorder: a randomized clinical trial." JAMA. Sep. 2023;330(9):843-853. doi: 10.1001/jama.2023.14530.
Ramage et al., "5-hydroxytryptamine and cardiovascular regulation," Trends Pharmacol Sci. 29(9):472-81 (Sep. 2008).
Rambousek et al., "The effect of psilocin on memory acquisition, retrieval, and consolidation in the rat," Front Behav Neurosci. 8(180) (May 2014) (7 pages).
Raval et al., "A Single Dose of Psilocybin Increases Synaptic Density and Decreases 5-HT2A Receptor Density in the Pig Brain," Int J Mol Sei. 22(835) (Jan. 2021) (14 pages).
Reckweg et al., "The clinical pharmacology and potential therapeutic applications of 5-methoxy-N,N-dimethyltryptamine (5-MeO-DMT)," Journal of Neurochemistry. 162(1):128-46 (Feb. 2022).
Reddit, "5-MEO and suddenly I quit smoking," [online forum] forum thread, Jun. 2019, [Retrieved Nov. 27, 2023. from URL: https://www.reddit.com/r/5MeODMT/comments/bzcn8v/5meo_and_suddenly_i_quit_smoking/], 3 pages.
Reddit, Addictions helped by 5meoDMT?, [online forum], forum thread, Jan. 2021 [Retrieved Nov. 27, 2023, Available at URL: https://www.reddit.com/r/5MeODMT/comments/kwovOn/addictions_helped_by_5meodmt/?utm_source =share&utm medium=web2x &context=3], 2 pages.
Reddit, "Bufo 5-MEO-DMT has practically cured me of my anxiety, insomnia and of childhood traumas," Jun. 2021, [Available online at URL: https://www.reddit.com/r/5MeODMT/comments/nvi049/bufo_5meodmt_has_practically_cured_me_of_my/], 15 pages.
Reddit, "Opinion on 5MeODMT+Ketamine therapy," [online], Reddit, Jan. 2020, [Retrieved Nov. 27, 2023, Available at URL: https://www.reddit.com/r/5MeODMT/comments/epukgs/comment/femkolp/?utm_source=share&utmmedium=web2x&context=3], (2 pages).
Registry No. 2761182-82-3, File Registry on STN, entered STN: Mar. 3, 2022 (2 pages).
"Results from Beckley Psytechs Phase IIa study of BPL-003 (intranasal 5-MeO-DMT benzoate) for Alcohol Use Disorder to be presented at CPDD 2025." Jun. 12, 2025https://www.beckleypsytech.com/posts/results-from-phase-iia-study-of-bpl-003-for-aud-to-be- presented-at-cpdd-2025.
Richards et al., "LSD-assisted psychotherapy and the human encounter with death," Journal of Transpersonal Psychology, 4(2):121-150 (1972).
Richards et al., "The peak experience variable in DPT-assisted psychotherapy with cancer patients," Journal of Psychedelic Drugs, 9(1 ): 1-10 (Jan.-Mar. 1977) (11 pages).
Richards, "Psychedelic drug-assisted psychotherapy with persons suffering from terminal cancer," J Altered States of Consciousness. 5(4):309-319 (1980).
Rickli et al. "Receptor interaction profiles of novel psychoactive tryptamines compared with classic hallucinogens." European Neuropsychopharmacology. Aug. 2016;26(8):1327-1337. doi: 10.1016/j.euroneuro.2016.05.001.

(56) References Cited

OTHER PUBLICATIONS

Riga et al., "The natural hallucinogen 5-MeO-DMT, component of Ayahuasca, disrupts cortical function in rats: reversal by antipsychotic drugs," Int J Neuropsychopharmacol. 17(8):1269-82 (Aug. 2014) (14 pages).
Riga et al., "The serotonergic hallucinogen 5-methoxy-N,N-dimethyltryptamine disrupts cortical activity in a regionally-selective manner via 5-HT(1 A) and 5-HT(2A) receptors," Neuropharmacology. 101:370-8 (Feb. 2016) (26 pages).
Robert et al., "Paraventricular hypothalamic regulation of trigeminovascular mechanisms involved in headaches," J Neurosci. 33(20):8827-40 (May 2013) (14 pages).
Roberts et al., "Intranasal 5-MeO-DMT (BPL-003) safety, pharmacokinetics and psychedelic effects in healthy volunteers," Beckley Psytech. Poster No. P.0639. Presented: 6th ECNP Congress, Barcelona, Spain, Oct. 7-10, 2023 (1 page).
Roberts et al., "Intranasal 5-Methoxy-N,N-Dimethyltryptamine Safety, Pharmacokinetics and Psychedelic Effects in Healthy Volunteers," Neuroscience Applied 2. P.0639:6-7 (2 pages).
Roberts et al., "Rapid antidepressant effect of intranasal BPL-003 (5-methoxy-N,N-dimethyltryptamine) in treatment-resistant patients: a Phase 2a open-label study," Beckley Psytech, Poster No. P2440, 37th ECNP Congress, Milan, Italy, Sep. 21-24, 2024, 1 page.
Roberts et al. "Rapid antidepressant effect of intranasal BPL-003 (5-methoxy-N,N-dimethyltryptamine) in treatment-resistant patients: a Phase 2a open-label study," (Sep. 2024) (2 pages).
Robertson, Dr. Donald L., "Supersaturated Solution," modified Oct. 18, 2010 (1 page).
Roseman et al., "Emotional breakthrough and psychedelics: Validation of the Emotional Breakthrough Inventory," J Psychopharmacol. 33(9):1076-1087 (Sep. 2019).
Roseman et al., "Increased amygdala responses to emotional faces after psilocybin for treatment-resistant depression," Neuropharmacology. Nov. 2018: 142: 263-269. doi: 10.1016/j.neuropharm.2017.12.041. Epub Dec. 27, 2017.
Ross et al., "Rapid and sustained symptom reduction following psilocybin treatment for anxiety and depression in patients with life-threatening cancer: a randomized controlled trial," J Psychopharmacol. 30(12):1165-1180 (Dec. 2016).
Rossi et al., "Serotonin-1 A receptor function in the dorsal raphe nucleus following chronic administration of the selective serotonin reuptake inhibitor sertraline," J Neurochem. 105(4): 1091-9 (May 2008).
Roth et al., "The Multiplicity of Serotonin Receptors: Uselessly Diverse Molecules or an Embarrassment of Riches?" 6(4):252-262 (Aug. 2000).
Rothman et al. "Evidence for possible involvement of 5-HT(2B) receptors in the cardiac valvulopathy associated with fenfluramine and other serotonergic medications," Circulation. 102(23):2836-2841 (Dec. 2000) (7 pages).
Rucker et al., "Intranasal 5-MeO-DMT (BPL-003) Safety, PK, and effect on altered states of consciousness in healthy volunteers," Beckley Psytech. Poster No. T152. Presented: SOBP Annual Meeting, San Diego, California, Apr. 27-29, 2023 (1 page).
Rucker et al., "Low-dose psilocybin in short-lasting unilateral neuralgiform headache attacks: results from an open-label phase Ib ascending dose study," Headache. 64:1309-1317 (Sep. 2024—ePub Sep. 20, 2024).
Rucker et al., "Phase 1, placebo-controlled, single ascending dose trial to evaluate the safety, pharmacokinetics and effect on altered states of consciousness of intranasal BPL-003 (5- methoxy- N,N-dimethyltryptamine benzoate) in healthy participants," J. Psychopharmacol. Clinical Trial 38(8): 712-723 (Aug. 2024—ePub Apr. 14, 2024).
Rucker et al. "Psychiatry & the psychedelic drugs. Past, present & future," Neuropharmacology. 142:200-218 (Nov. 2018) (19 pages).
Rucker, James J.H. "Psychedelic drugs should be legally reclassified so that researchers can investigate their therapeutic potential," BMJ. 350:h2902 (May 2015) (2 pages).
Rush et al., "Acute and longer-term outcomes in depressed outpatients requiring one or several treatment steps: a STAR'D report," Am J Psychiatry. 163(11 ):1905-17 (Nov. 2006).
Rush et al., "The 16-Item Quick Inventory of Depressive Symptomatology (QIDS), clinician rating (QIDS-C), and self-report (QIDS-SR): a psychometric evaluation in patients with chronic major depression," Biol Psychiatry. 54(5):573-83 (Sep. 2003).
Russ et al., "States and traits related to the quality and consequences of psychedelic experiences," Psychology of Consciousness: Theory, Research, and Practice, 6(1):1-21 (Dec. 2018).
Sager et al., "Fluoxetine and norfluoxetine-mediated complex drug-drug interactions: in vitro to in vivo correlation of effects on CYP2D6, CYP2C19, and CYP3A4," Clin Pharmacol Ther. 95(6):653-62 (Jun. 2014) (25 pages).
Sakashita et al. "Effect of psilocin on extracellular dopamine and serotonin levels in the mesoaccumbens and mesocortical pathway in awake rats," Biol Pharm Bull. 38(1):134-138 (2015).
Sakloth et al. "Effects of acute and repeated treatment with serotonin 5-HT2A receptor agonist hallucinogens on intracranial self-stimulation in rats," Exp Clin Psychopharmacol. 27(3):215-226 (Jun. 2019) (23 pages).
Salmi et al. "Evidence for functional interactions between 5-HT1A and 5-HT2A receptors in rat thermoregulatory mechanisms," Pharmacol Toxicol. 82(3):122-127 (Mar. 1998).
Sampedro et al., "Assessing the Psychedelic "After-Glow" in Ayahuasca Users: Post-Acute Neurometabolic and Functional Connectivity Changes Are Associated with Enhanced Mindfulness Capacities," Int J Neuropsychopharmacol. 20(9):698-711 (Sep. 2017) (55 pages).
Sanches et al., "Antidepressant Effects of a Single Dose of Ayahuasca in Patients With Recurrent Depression: A Spect Study," J Clin Psychopharmacol. 36(1 ):77-81 (Feb. 2016).
Sanchez et al. "Assessment of relative efficacies of 5-HT1A receptor ligands by means of in vivo animal models," Eur J Pharmacol. 315(3):245-254 (Nov. 1996).
Sanders-Bush et al. "Metabolism of bufotenine-2'-14C in human volunteers," Life Sci. 19(9):1407-1411 (Nov. 1976) (5 pages).
Sani et al., "High-frequency measurement of depressive severity in a patient treated for severe treatment-resistant depression with deep-brain stimulation," Transl Psychiatry. Aug. 15, 2017; 7(8): e1207. doi: 10.1038/tp.2017.145, 6 pages.
Santana et al. "Expression of serotoninl A and serotonin2A receptors in pyramidal and GABAergic neurons of the rat prefrontal cortex," Cereb Cortex. 14(10):1100-1109 (Oct. 2004).
Santini et al., "The association between social relationships and depression: a systematic review," J Affect Disord. 175:53-65 (Apr. 2015).
Sard, H., SAR of psilocybin analogs: Discovery of a selective 5-HT2C agonist. Bioorganic and Medicinal Chemistry Letters, 15(20), 4555-4559 (Oct. 15, 2005).
Schartner et al., "Increased spontaneous MEG signal diversity for psychoactive doses of ketamine, LSD and psilocybin," Sci Rep. Apr. 19, 2017: 7: 46421. doi: 10.1038/srep46421. 12 pages.
Schindler et al. "Indoleamine Hallucinogens in Cluster Headache: Results of the Clusterbusters Medication Use Survey," J Psychoactive Drugs. 47(5):372-381 (Nov.-Dec. 2015) (11 pages).
Schindler et al. "Neuroendocrine Associations Underlying the Persistent Therapeutic Effects of Classic Serotonergic Psychedelics," Front Pharmacol. 9(177) (Mar. 2018) (16 pages).
Schlemmer et al., "A primate model for the study of hallucinogens," Pharmacol Biochem Behav. 24(2):381-92 (Feb. 1986).
Schlemmer et al., "Evidence for dopamine mediation of submissive gestures in the stumptail macaque monkey," Pharmacol Biochem Behav. 14 Suppl 1:95-102 (1981).
Schlemmer et al., "The effect of a hallucinogen, 5-methoxy N,N-dimethyltryptamine, on primate social behavior," Commun Psychopharmacol. 1 (2):105-18 (1977).
Schmid et al. "Long-lasting subjective effects of LSD in normal subjects." Psychopharmacology. Feb. 2018;235:535-545. doi: 10.1007/s00213-017-4733-3.
Schneller et al., "Synthesis of 4-Amino-1 H-pyrrolo[2,3-b]pyridine (1,7-Dideazaadenine) and 1H- Pyrrolo[2,3-bjpyridin-4-ol (1,7-Dideazahypoxantine)," J Org Chem. 45(20):4045-8 (1980).

(56) References Cited

OTHER PUBLICATIONS

Schreiber et al. "Neuronal circuits involved in the anxiolytic effects of the 5-HT1A receptor agonists 8-OH-DPAT ipsapirone and buspirone in the rat," Eur J Pharmacol. 249(3):341-351 (Nov. 1993).
Schultes et al., "Plants of the Gods: Their Sacred, Healing, and Hallucinogenic Powers," Healing Arts Press (2001) (208 pages).
Schultes, "Fifteen years of study of psychoactive snuffs of South America: 1967-1982—a review," J Ethnopharmacol. 11(1):17-32 (Jun. 1984).
Scott et al. "Illicit substance use in pregnancy—a review," Obstet Med. 3(3):94-100 (Sep. 2010).
Scotton et al., "Serotonin Syndrome: Pathophysiology, Clinical Features, Management, and Potential Future Directions," Int J Tryptophan Res. 12:1178646919873925 (Sep. 2019) (14 pages).
Screen Captures of Psychedelics Today YouTube video Transcript: "Rafael Lancelotta—Exploring 5-MeO-DMT" [https://www.youtube.com/watch?v=kEp-Az9ibLM uploaded on May 10, 2018 (53 Pages).
Screen Captures of Yann WithAyahuasca YouTube video Transcript: "Can you Bad Trip on Bufo Alvarius / Sapito? Against depression : Ayahuasca or Bufo Alvarius?" [https://www.youtube.com/watch?v=4GcU2outMFs uploaded on May 25, 2017 (9 Pages).
Sepeda et al. "Inhaled 5-methoxy-N,N-dimethyltryptamine: Supportive context associated with positive acute and enduring effects," Journal of Psychedelic Studies. 4(2):114-122 (Jun. 2020).
Sewell et al. "Response of cluster headache to psilocybin and LSD," Neurology. 66(12): 1920-1922 (Jun. 2006) (5 pages).
Sexton et al. "Population Survey Data Informing the Therapeutic Potential of Classic and Novel Phenethylamine, Tryptamine, and Lysergamide Psychedelics," Front Psychiatry. 10:896 (Feb. 2020) (27 pages).
Sexton et al., "Prevalence and epidemiological associates of novel psychedelic use in the United States adult population," J Psychopharmacol. 33(9) :1058-1067 (Sep. 2019) (10 pages).
Sheehan et al., "The Mini-International Neuropsychiatric Interview (M.I.N.L): the development and validation of a structured diagnostic psychiatric interview for DSM-IV and ICD-10," J Clin Psychiatry. 59 Suppl 20:22-33 (1998).
Shelton et al., "Olanzapine/fluoxetine combination for treatment-resistant depression: a controlled study of SSRI and nortriptyline resistance," J Clin Psychiatry. 66(10):1289-97 (Oct. 2005).
Shen et al., "Development of a LC-MS/MS method to analyze 5-methoxy-N,N-dimethyltryptamine and bufotenine, and application to pharmacokinetic study," Bioanalysis. 1(1):87-95 (Apr. 2009).
Shen et al. "Effects of monoamine oxidase inhibitor and cytochrome P450 2D6 status on 5-methoxy-N,N-dimethyltryptamine metabolism and pharmacokinetics," Biochem Pharmacol. 80(1):122-128 (Jul. 2010).
Shen et al., "Psychedelic 5-methoxy-N,N-dimethyltryptamine: metabolism, pharmacokinetics, drug interactions, and pharmacological actions," Gurr Drug Metab. 11 (8):659-66 (18 pages) (Oct. 2010).
Sherwood et al. "An Improved, Practical, and Scalable Five-Step Synthesis of Psilocybin," Synthesis. 52(5):688-694 (Jan. 2020) (7 pages).
Sherwood et al., "Psilocybin: crystal structure solutions enable phase analysis of prior art and recently patented examples," Acta Crystallogr C Struct Chern. 78(Pt 1):36-55 (Jan. 2022).
Shulgin, A. et al. TiHKAL: The Continuation. #38. 5-MEO-DMT. Tryptamine, 5-Methoxy-N,N-Dimethyl; Indole, 5-Methoxy-3-[2-(Dimethylamino)Ethyl]; 5-Methoxy-N,N-Dimethyltryptamine; 5-Methoxy-3-[2-(Dimethylamino)Ethyl]Indole; N,N,O-Trimethylserotonin; N,N,O-TMS; Bufotenine Methyl Ether; O-Methylbufotenine; Omb.
Shulgin, "Bufotenine," J Psychoactive Drugs. 13(4):389 (Jul. 1981) (2 pages).
Shulgin, "Psilocybin," J Psychedelic Drugs. 12(1 ):79 (Jan.-Mar. 1980) (2 pages).
Sills et al. "Development of selective tolerance to the serotonin behavioral syndrome and suppression of locomotor activity after repeated administration of either 5-MeODMT or mCPP," Life Sciences. 36(26):2463-2469 (Jul. 1985).
Silva et al., "Facilitatory role of serotonin (5-HT) in the control of thyrotropin releasing hormone/thyrotropin (TRH/TSH) secretion in rats," Brazilian Journal of Medical and Biological Research. 29(5):677-83 (1996).
Singh et al., "Sertraline", NCBI Bookshelf, Feb. 13, 2023, 4 pages.
Singh, J. B. et al., "A Double-Blind, Randomized, Placebo-Controlled, Dose-Frequency Study of Intravenous Ketamine in Patients With Treatment-Resistant Depression," Am J Psychiatry, 2016; 173:816-826; doi: 10.1176/appi.ajp.2016.16010037.
Singh, S.K. et al., "An ab Initio Study of the Effect of Substituents on the n * Interactions between 7Azaindole and 2,6 Difluorosubstituted Pyridines," The Journal of Physical Chemistry A, vol. 120, pp. 6258-6269 (2016).
Sitaram et al., "In vivo metabolism of 5-methoxy-N,N-dimethyltryptamine and N,N-dimethyltryptamine in the rat," Biochem Pharmacol. 36(9): 1509-12 (May 1987).
Sitaram et al., "Observations on the metabolism of the psychotomimetic indolealkylamines: implications for future clinical studies," Biol Psychiatry. 28(10):841-8 (Nov. 1990).
Sjaastad et al. "The rare, unilateral headaches. Vg study of headache epidemiology," J Headache Pain. 8(1 ):19-27 (Feb. 2007).
Sklerov et al. "A fatal intoxication following the ingestion of 5-methoxy-N,N-dimethyltryptamine in an ayahuasca preparation," J Anal Toxicol. 29(8):838-41 (Nov./Dec. 2005).
Sloshower et al., "Psilocybin-assisted therapy for major depressive disorder: An exploratory placebo-controlled, fixed-order trial," J Psychopharmacol. 37(7):698-706 (Jul. 2023).
Small Pharma Reports Positive Top-line Data from SPL026 (DMT)-SSRI Drug Interaction Study in Patients with Major Depressive Disorder [Press release], Sep. 26, 2023.https://www.biospace.com/small-pharma-reports-positive-top-line-results-from-phase-lia-trial-of- spl026-in-major-depressive-disorder.
Smith et al., "Differential effects of 5-hydroxytryptamine1 a selective drugs on the 5-HT behavioral syndrome," Pharmacol Biochem Behav. 24(6):1513-9 (Jun. 1986).
Snaith et al., "A scale for the assessment of hedonic tone the Snaith-Hamilton Pleasure Scale," Br J Psychiatry. 167(1 ):99-103 (Jul. 1995).
Sohlberg, E. et al., "The impact of the site of blood sampling on pharmacokinetic parameters following sublingual dosing to dogs," Journal of Pharmacological and Toxicological Methods, vol. 67, pp. 1-4 (2013).
Soler et al., "Exploring the therapeutic potential of Ayahuasca: acute intake increases mindfulness-related capacities," Psychopharmacology (Berl). 233(5):823-9 (Nov. 2015).
Spain et al. "Neurovascular and neuroimaging effects of the hallucinogenic serotonin receptor agonist psilocin in the rat brain," Neuropharmacology. 99:210-20 (Jul. 2015).
Spencer et al., "Serotonin receptor subtype mediation of the interoceptive discriminative stimuli induced by 5-methoxy-N,N-dimethyltryptamine," Psychopharmacology (Berl). 93(2):158-66 (1987).
Spindelegger et al., "Influence of escitalopram treatment on 5-HT 1A receptor binding in limbic regions in patients with anxiety disorders," Mol Psychiatry. 14(11):1040-50 (Nov. 2009) (12 pages).
Sprenger et al. "Specific hypothalamic activation during a spontaneous cluster headache attack," Neurology. 62(3):516-7 (Feb. 2004) (3 pages).
Spriggs et al., Study Protocol for "Psilocybin as a Treatment for Anorexia Nervosa: A Pilot Study," Front Psychiatry. Oct. 20, 2021: 12: 735523. doi: 10.3389/fpsyt.2021.735523. eCollection 2021, 16 pages.
Squires, "Evidence that 5-methoxy-N, N-dimethyl tryptamine is a specific substrate for MAO-A in the rat: implications for the indoleamine dependent behavioural syndrome," J Neurochem. 24(1):47-50 (Jan. 1975).
Sternbach, "The serotonin syndrome," Am J Psychiatry. 148(6):705-13 (Jun. 1991).
Stoll, A. et al., "49. Amide der stereoisomeren Lysergsuren und Dihydro-lysergsuren," Helvetica Chimica Acta, vol. 38, pp. 421-433 (1955).

(56) References Cited

OTHER PUBLICATIONS

Stoll et al. "Amide der stereoisomeren Lysergsäuren und Dihydrolysergsäuren. 38. Mitteilung über Mutterkornalkaloide." Helvetica Chimica Acta. 1955;38(2):421-433; 26 pages with English machine translation.
Strassman, "Human hallucinogen interactions with drugs affecting serotonergic neurotransmission," Neuropsychopharmacology. 7(3):241-3 (Nov. 1992) (4 pages).
Studerus et al. "Acute, subacute and long-term subjective effects of psilocybin in healthy humans: a pooled analysis of experimental studies," J Psychopharmacol. 25(11 ):1434-1452 (Nov. 2011) (20 pages).
Studerus et al. "Prediction of psilocybin response in healthy volunteers," PLoS One. 7(2):e30800 (Feb. 2012) (12 pages).
Sugrue, M.F. "A study of the role of noradrenaline in behavioral changes produced in the rat by psychotomimetic drugs," Br J Pharmacol. 35(2):243-252 (Feb. 1969).
Suzuki et al., "Characterization of eight biogenic indoleamines as substrates for type A and type B monoamine oxidase," Biochem Pharmacol. 30(11 ):1353-8 (Jun. 1981).
Swainson et al. "Esketamine for treatment resistant depression," Expert Rev Neurother. 19(10):899-911 (Oct. 2019) (14 pages).
Szabo et al., Psychedelic N,N-dimethyltryptamine and 5-methoxy-N,N-dimethyltryptamine modulate innate and adaptive inflammatory responses through the sigma-1 receptor of human monocyte-derived dendritic cells. PLoS One 9(8):e106533 (2014).
Szigeti et al., "Expectancy Effects in Psychedelic Trials," Biol Psychiatry Cogn Neurosci Neuroimaging, (May 2024); 9(5): 512-521, doi: 10.1016/j.bpsc.2024.02.004. Epub Feb. 20, 2024.
Tao et al. "Changes in intensity of serotonin syndrome caused by adverse interaction between monoamine oxidase inhibitors and serotonin reuptake blockers," Neuropsychopharmacology. 39(8):1996-2007 (Jul. 2014).
Tap S., "The potential of 5-methoxy-N,N-dimethyltryptamine in the treatment of alcohol use disorder: A first look at therapeutic mechanisms of action", Addiction Biology, Abingdon Carfax Publishing, Abingdon, GB, vol. 29, No. 4, Apr. 10, 2024 (Apr. 10, 2024) , pp. 1-14.
Teague, S. J., et al., "The Design of Leadlike Combinatorial Libraries," Communications, Angew. Chem. Int. Ed., 1999, 38, No. 24, pp. 3743-3748.
The Third Wave, The Ultimate Guide to 5-MEO-DMT, [https://web.archive.org/web/20200513112802/https://thethirdwave.co/psychedelics/5-meo-dmt/], Retrieved on Mar. 27, 2026, 14 pages.
"Thermal Applications Note: Purge Gas Recommendations for use in Modulated DSC," TA Instruments: Thermal Analysis & Rheology (3 pages).
Thermo Scientific, "Cimarec+ stirrers, hotplates, and stirring hotplates: Operating Manual and Parts List," Thermo Scientific, Feb. 2017, (32 pages).
"This psychedelic medicine company wants to treat psychiatric and neurological disorders," Psytech Press Release Dec. 21, 2020 (5 pages).
Thundiyil et al. "Evolving epidemiology of drug-induced seizures reported to a Poison Control Center System," J Med Toxicol. 3(1 ):15-19 (Mar. 2007).
Timmermann et al., "Exploring 5-MeO-DMT as a pharmacological model for deconstructed consciousness," Neuroscience of Consciousness, (Apr. 19, 2025); 2025(1): niaf007, doi: 10.1093/nc/niaf007. eCollection 2025, 8 pages.
Timmermann et al., "Human brain effects of DMT assessed via EEG-fMRI," Proc Natl Acad Sci USA, (Mar. 28, 2023); 120(13): e2218949120. doi: 10.1073/pnas.2218949120. Epub Mar. 20, 2023, 12 pages.
Tittarelli et al. "Recreational use, analysis and toxicity of tryptamines," Curr Neuropharmacol. 13(1):26-46 (Jan. 2015).
Todd et al., "A Monoclonal Antibody TrkB Receptor Agonist as a Potential Therapeutic for Huntington's Disease," PLoS ONE. 9(2):e87923 (Feb. 2014) (13 pages).
Transcript of Interview, Rafael Lancelotta, "Exploring 5-MeO-DMT," Psychedelics Today, Nov. 21, 2017 (20 Pages).
"Strategic Investment in Beckley Psytech," atai Life Sciences Investor Deck. Conference call, Thursday, Jan. 4, 2024 (17 pages).
Trauninger et al. "Methylprednisolone therapy for short-term prevention of SUNCT syndrome," Cephalalgia. 30(6)735-739 (Jun. 2010).
Tricklebank et al., "Subtypes of the 5-HT receptor mediating the behavioural responses to 5-methoxy-N,N-dimethyltryptamine in the rat," Eur J Pharmacol. 117(1 ):15-24 (Oct. 1985).
Trulson et al. "Development of tolerance to repeated administration of 5-methoxy-N,N-dimethyltryptamine in rats," Eur J Pharmacol. 108(1):33-37 (Jan. 1985).
Turner et al. "Effect of some indolealkylamines on man," AMA Arch Neurol Psychiatry. 81(1 ):121-129 (Jan. 1959).
Turton et al., "A qualitative report on the subjective experience of intravenous psilocybin administered in an fMRI environment," Gurr Drug Abuse Rev. 7(2):117-127 (2014) (11 pages).
Tyls et al., "Psilocybin-summary of knowledge and new perspectives," Eur Neuropsychopharmacol. 24(3): 342-56 (Mar. 2014).
Ullmer et al., "Expression of serotonin receptor mRNAs in blood vessels," FEBS Lett. 370(3):215-21 (Aug. 1995).
U.S. Appl. No. 17/941,410, filed Sep. 9, 2022 (189 pages).
U.S. Appl. No. 18/065,030, filed Dec. 13, 2022 (57 pages).
U.S. Appl. No. 18/162,976, filed Feb. 1, 2023 (176 pages).
U.S. Appl. No. 19/479,001, filed Oct. 27, 2025, Inventor: Feilding-Mellen, Cosmo et al.
U.S. Appl. No. 17/660,981, Non-Final Office Action mailed Jul. 18, 2022; Inventor Feilding-Mellen, Cosmo et al.; 12 pages.
U.S. Appl. No. 17/660,981, Notice of Allowance Action mailed Aug. 24, 2022; Inventor Feilding-Mellen, Cosmo et al.; 8 pages.
U.S. Appl. No. 18/229,041, Non-Final Office Action mailed Jan. 29, 2024; Inventor Gray, Jason.; 6 pages.
U.S. Appl. No. 18/229,041, Notice of Allowance mailed Mar. 14, 2024; Inventor Gray, Jason.; 7 pages.
U.S. Appl. No. 18/229,041, Restriction Requirement mailed Nov. 15, 2023; Inventor Gray, Jason.; 8 pages.
U.S. Appl. No. 19/129,744, filed May 14, 2025, Inventor: Feilding-Mellen, Cosmo.
U.S. Appl. No. 19/273,755, filed Jul. 18, 2025, Inventor: Feilding-Mellen, Cosmo et al.
U.S. Appl. No. 19/273,755, Non-final Office Action mailed Sep. 24, 2025; Inventor Feilding-Mellen, Cosmo et al.; 25 pages.
U.S. Appl. No. 19/273,890, filed Jul. 18, 2025, inventor: Feilding-Mellen et al.
U.S. Appl. No. 19/429,204, filed Dec. 22, 2025, Inventor Fawaz et al.
U.S. Appl. No. 19/502,719, filed Jan. 15, 2026, inventor: Khan et al.
U.S. Appl. No. 19/505,206, filed Jan. 23, 2026, inventor: Short et al.
U.S. Department of Health and Human Services, "Major Depressive Disorder: Developing Drugs for Treatment Guidance for Industry, Draft Guidance." [Online] FDA, (Jun. 2018), [accessed online on Jan. 6, 2026 from https://www.fda.gov/regulatory-information/search-fda-guidancedocuments/majordeppressive-disorder-developing-drugs-treatment]; 11 pages.
U.S. Department of Health and Human Services, "Psychedelic Drugs: Considerations for Clinical Investigations," Draft Guidance, U.S. Department of Health and Human Services, Food and Drug Administration, Center for Drug Evaluation and Research (CDER), Jun. 5, 2023; 14 pages.
Uthaug et al. "A comparison of reactivation experiences following vaporization and intramuscular injection (IM) of synthetic 5-methoxy-N,N-dimethyltryptamine (5-MeO-DMT) in a naturalistic setting," Journal of Psychedelic Studies. 4(2): 104-13 (Mar. 2020).
Uthaug, M.V., "The Ethical and Ecological Considerations of Inhaling Bufotoxins from Incilius Alvarius," Psychedelics Today, [https://psychedelicstoday.com/2018/10/03/ethics-ecology- bufotoxins/ dated Oct. 3, 2018 (9 Pages).
"Vacuum for Laboratories: Vacuu-Lan Local Vacuum Networks," Vacuubrand (2019) (16 pages).

(56) References Cited

OTHER PUBLICATIONS

Van De Kar et al., "5-HT2A receptors stimulate ACTH, corticosterone, oxytocin, renin, and prolactin release and activate hypothalamic CRF and oxytocin-expressing cells," J Neurosci. 21(10):3572-3579 (May 2001).

Van Went, G.F. "Mutagenicity testing of 3 hallucinogens: LSD, psilocybin and delta9-THC, using the micronucleus test," Experientia. 34(3):324-325 (Mar. 1978).

Vangveravong et al., "Synthesis and serotonin receptor affinities of a series of trans-2-(indol-3-yl)cyclopropylamine derivatives," J Med Chem. 41 (25):4995-5001 (Dec. 3, 1998).

Vaupel et al. "The inhibition of food intake in the dog by LDS, mescaline, psilocin, d-amphetamine and phenylisopropylamine derivatives," Life Sci. 24(26):2427-2431 (Jun. 1979).

Vigerelli et al. "Biological Effects and Biodistribution of Bufotenine on Mice," Biomed Res Int. 2018:1032638 (May 2018) (11 pages).

Vizeli et al., "Genetic influence of CYP2D6 on pharmacokinetics and acute subjective effects of LSD in a pooled analysis," Sci Rep. 11 (1 ):10851 (May 2021) (9 pages).

Vogel et al. "Structure-activity-relationships of certain hallucinogenic substances based on brain levels," Life Sci. 20(10):1629-1635 (May 1977).

Vollenweider et al. "5-HT modulation of dopamine release in basal ganglia in psilocybin-induced psychosis in man—a PET study with [11C]raclopride," Neuropsychopharmacology. 20(5):424-433 (May 1999).

Vollenweider et al. "Positron emission tomography and fluorodeoxyglucose studies of metabolic hyperfrontality and psychopathology in the psilocybin model of psychosis," Neuropsychopharmacology. 16(5):357-372 (May 1997).

Von Rotz et al., "Single-dose psilocybin-assisted therapy in major depressive disorder: A placebo-controlled, double-blind, randomised clinical trial," EClinicalMedicine. 56:101809 (Feb. 2023) (11 pages).

Wall et al., "Reduced Brain Responsiveness to Emotional Stimuli With Escitalopram But Not Psilocybin Therapy for Depression," Am J Psychiatry. Jun. 1, 2025; 182(6):569-582. doi: 10.1176/appi.ajp.20230751. Epub May 7, 2025.

Wallach, "Endogenous hallucinogens as ligands of the trace amine receptors: a possible role in sensory perception," Med Hypotheses. 72(1 ):91-4 (Jan. 2009).

Watts et al., "Patients accounts of increased connectedness and acceptance after psilocybin for treatment-resistant depression," Journal of Humanistic Psychology, 57(5):520-564 (2017) (45 pages).

"Wearable technology can revolutionise our clinical research," Beckley Psytech Press Release Mar. 2, 2021 (5 pages).

Whiteford et al., "Estimating remission from untreated major depression: a systematic review and meta-analysis," Psychol Med. (Aug. 2013); 43(8): 1569-85.

Wikipedia, "Seed crystal," [online dictionary], [Available at URL: https://web.archive.org/web/2O2O12O92O2659/https:/en.wikipedia.o rg/wiki/Seedcrystal], last modified Mar. 29, 2020, (2 pages).

Wildman et al. "Prediction of Physiochemical Parameters by Atomic Contributions", J. Chem. Inf. Comput Sci., 1999, vol. 39, No. 5, p. 868-873.

"Will 5meo help my addiction issues?," Reddit. Available[https://www.reddit.com/r/5MeODMT/comments/q3v3bt/comment/hfuxvjo/?utm_source=share&ut m medium=web2x&context=3 (Oct. 2021) (1 page).

Williams et al. "Depression and pain: an overview," Acta Neuropsychiatr. 18(2):79-87 (Apr. 2006).

Williams et al., "'Equal-unblinding' meta-analysis of psychedelic therapy vs. antidepressants for the treatment of depression," University of California, Los Angeles, CA, Jun. 2025, 34 pages.

Williams et al. "Microvascular decompression of the trigeminal nerve in the treatment of Sunct and Suna," J Neurol Neurosurg Psychiatry. 81 (9):992-996 (May 2010) (5 pages).

Williams et al., "Precision psychiatry: a neural circuit taxonomy for depression and anxiety," Lancet Psychiatry, May 2016; 3(5):472-80.

Williams et al. "Sunct and Suna: clinical features and medical treatment," J Clin Neurosci. 15(5):526-534 (May 2008).

Willins et al. "Direct injection of 5-HT2A receptor agonists into the medial prefrontal cortex produces a head-twitch response in rats," J Pharmacol Exp Ther. 282(2):699-706 (Aug. 1997).

Winne et al., "Anxiety-like behavior induced by salicylate depends on age and can be prevented by a single dose of 5-MeO-DMT," Exp Neurol. 326:113175 (Jan. 2020) (1 page).

Wolfson et al., "MDMA-assisted psychotherapy for treatment of anxiety and other psychological distress related to life-threatening illnesses: a randomized pilot study," Scientific Reports, vol. 10:20442, Published Nov. 24, 2020, 15 pages.

"Woman who has suffered with a non-stop headache for eight years fulfils dream of becoming a mum," Beckley Psytech Press Release Mar. 2, 2021 (8 pages).

Wordsworth, R., "LSD doesn't just treat mental illness, 'it could actually heal the brain': Research into psychedelic compounds has had phenomenal success and should no longer by ignored," Wired.co.uk, [https://web.archive.Org/web/20230510125630/https://www.wired.co.uk/article/khaliya-mental' health dated Mar. 9, 2017 (3 Pages).

World Health Organization, "Depression," Jan. 30, 2020. Available [https://www.who.int/news- room/fact-sheets/detail/depression (3 pages).

Written Opinion for International Application No. PCT/GB2022/053208, mailed Apr. 3, 2023 (9 pages).

Wyler et al. "Serotonergic Control of Metabolic Homeostasis," Front Cell Neurosci. 11:277 (Sep. 2017) (9 pages).

Yaden et al. "The Subjective Effects of Psychedelics Are Necessary for Their Enduring Therapeutic Effects," ACS Pharmacol Transl Sci. 4(2):568-572 (Dec. 2020).

Yang et al., "Effect of clinically relevant doses of vortioxetine and citalopram on serotonergic PET markers in the nonhuman primate brain," Neuropsychopharmacology. 44(10):1706-1713 (Sep. 2019).

Yazar-Klosinski, B.B. et al., "Potential Psychiatric Uses for MDMA," Developments, vol. 101, pp. 194-196 (2017).

Young et al., "Discriminative stimulus properties of the hallucinogenic agent DOM," Communications in Psychopharmacology. 4:501-6 (1980).

Younger et al., "Development of the Stanford Expectations of Treatment Scale (SETS): a tool for measuring patient outcome expectancy in clinical trials," Clin Trials. 9(6):767-76 (Dec. 2012).

Yu et al., "Screening for endogenous substrates reveals that CYP2D6 is a 5-methoxyindolethylamine O-demethylase," Pharmacogenetics. 13(6):307-19 (Jun. 2003).

Yu et al. "Serotonin 5-hydroxytryptamine(2A) receptor activation suppresses tumor necrosis factor-alpha-induced inflammation with extraordinary potency," J Pharmacol Exp Ther. 327(2):316-323 (Nov. 2008).

Zanardi et al., "Increased 5-hydroxytryptamine-2 receptor binding in the frontal cortex of depressed patients responding to paroxetine treatment: a positron emission tomography scan study," J Clin Psychopharmacol. 21 (1 ):53-8 (Feb. 2001).

Zarate et al., "A Randomized Trial of an N-methyl-d-aspartate Antagonist in Treatment-Resistant Major Depression," Arch Gen Psychiatry. Aug. 2006; 63(8): 856-64. doi: 10.1001/archpsyc.63.8.856.

Zhuk et al. "Research on acute toxicity and the behavioral effects of methanolic extract from psilocybin mushrooms and psilocin in mice," Toxins (Basel). 7(4):1018-1029 (Mar. 2015).

COMPOSITIONS OF MATTER AND PHARMACEUTICAL COMPOSITIONS

CROSS-REFERENCES TO RELATED APPLICATIONS

This application is a continuation of U.S. patent application Ser. No. 19/358,021, filed Oct. 14, 2025, which is a continuation of U.S. patent application Ser. No. 19/173,537, filed Apr. 8, 2025, which issued as U.S. Pat. No. 12,472,163, which is a continuation of U.S. patent application Ser. No. 18/744,484, filed Jun. 14, 2024, which issued as U.S. Pat. No. 12,396,982, which is a continuation of U.S. patent application Ser. No. 18/229,286, filed on Aug. 2, 2023, which issued as U.S. Pat. No. 12,053,453, which is a continuation of U.S. patent application Ser. No. 17/314,107, filed May 7, 2021, which issued as U.S. Pat. No. 11,759,452, and which claims the benefit of U.S. Provisional Application 63/021,866 filed May 8, 2020, U.S. Provisional Application 63/106,516 filed Oct. 28, 2020 and U.S. Provisional Application 63/134,805 filed Jan. 7, 2021. All of which are incorporated by reference herein in their entireties.

FIELD OF THE DISCLOSURE

The present invention relates to novel indole compounds, the administration of psilocybin, psilocybin chemical analogues, and novel indole chemical compounds; and pharmaceutical compositions, methods of preparing the pharmaceutical compositions and methods of treating neurological diseases or disorders using the analogues and novel compounds.

BACKGROUND OF THE INVENTION

Psychoactive drugs are compounds that affect behavior, mood, thoughts, or perception. Psychoactive drugs include antipsychotics, anti-anxiety agents, stimulants, reuptake inhibitors, monoamine oxidase inhibitors (MAOI), tricyclic antidepressants and mood stabilizers. Some of these compounds have historically been used for off label psychoactive activity and are now being investigated for positive clinical efficacy. In addition to potential therapeutic efficacy, these drugs must be investigated for all relevant pharmaceutical characteristics, including minimum and maximum dosing thresholds and the most efficacious delivery system.

Indole compounds represent a diverse class of compounds with broad biomedical potential across many targets including cancer, cardiovascular, gastrointestinal, and a wide range of neurological disorders. During in vivo biosynthesis, the amino acid tryptophan precursor of serotonin has been the scaffold of choice for many drugs containing the heterocyclic indole backbone. Serotonin (5-HT) supports many important bodily functions including mood, sleep, appetite, intestinal motility, and sexual health. The serotonergic system consists of a class of G-coupled protein receptors, 5-$HT_1$ through 5-$HT_7$ as well as their subtypes (1A, 2A, 2B, etc.), which modulate the range of these biological pathways.

Most serotonergic targeting therapeutics are antidepressants either as selective reuptake inhibitors (collectively SSRIs), direct 5-HT modulators (atypical) or in combination with norepinephrine inhibitors (SNRIs). While still not fully understood, the general mechanism of action of the approved therapeutics relies on increasing the concentration of the monoamines, 5-HT and norepinephrine, in the post-synaptic receptors to restore synaptic balance. However these medications generally lack efficacy (being only 20-30% effective over placebo), have considerable side effects, and have a delayed onset of weeks to months.

Sigma-1 receptor (σ receptors) are intracellular receptors expressed in specific regions of the brain. Modulation, and agonism, of Sigma-1 ($\sigma_1$) has been shown to have positive impacts on locomotion, mood disorders, increases of brain-derived neurotrophic factor (BDNF), neuronal growth, and neurogenesis. Diverse classes of psychotropic drugs, including antipsychotics, antidepressants, selective serotonin reuptake inhibitors (SSRI's) and motor neuron drugs bind to the (Q1) receptor. Binding of the SSRI's to the σ1 receptor may mediate the serotonin independent actions of this class of drugs. The hallucinogen N,N-dimethyltryptamine (DMT) is an endogenous σ1 receptor regulator.

Psilocybin is an indole alkaloid and a naturally occurring psychoactive prodrug that is produced by more than 200 species of mushrooms. Psilocybin is a prodrug that is dephosphorylated in vivo via oral dosing to produce the active compound psilocin. Psilocybin and psilocin are both indole compounds and are known to be potent 5-HT agonists and can cross the blood-brain barrier. The therapeutic implications of psilocybin are broad with active clinical studies targeting depression, anxiety, migraines, addiction, dementias, Alzheimer's disease, eating disorders, obsessive compulsive disorder, and palliative care.

Magic Mushrooms is a common term for a group of over 200 species of naturally occurring mushrooms that contains psilocybin and active psilocybin chemical analogues and combinations thereof. Similarly, other naturally-occurring psychedelic indole compounds include N,N-dimethyltryptamine (DMT), 5-methoxy-DMT (5-MeO-DMT), lysergamides (e.g. LSD), and ibogaine. The raw fruit as well as extracts containing these natural products have been orally consumed for their psychoactive effects. Exact dose response activity has been difficult to quantify because of the variability of the individual response, the difficulty in measuring the potency of the natural organisms and extracts, and the different inherent potencies and ratio of the different analogues and combinations thereof. This is only exacerbated by the interplay of serotonin receptors activities as well as Sigma-1 ($\sigma_1$) receptors, especially for compounds like DMT. Specifically for neurodegenerative diseases and cognitive function, agonists of the 01 receptor (e.g. DMT) are shown to enhance brain plasticity with key roles in memory and learning.

Psilocybin and it's known analogues have been synthesized and bioengineered. In the mid-twentieth century, Sandoz Pharmaceuticals briefly marketed an oral formulation of psilocybin for adjuvant therapy in psychotherapy. The product was soon removed from the market due to the unpredictability of individual response to the dosage form. As of 2020, the U.S. Drug Enforcement Agency has classified psilocybin as a Schedule 1 drug having a high potential for abuse, no approved medical use and a lack of accepted safety for use under medical supervision.

Dosing and assessing pharmaceutical efficacy for these compounds has proven to be difficult. One reason is that plasma concentration-time curves are highly variable. Additionally, psilocybin and especially DMT is subject to first pass metabolism of the oral dosage forms, which reduces availability of active pharmaceutical ingredient before it has entered the systemic circulation. Also, there are wide individual variances in the renal excretion of the compounds. Further, the pH and monoamine oxidase (MAO) enzymatic cleavage of psilocybin to the active pharmaceutical ingredient psilocin after oral delivery can also be a determining factor for the pharmacodynamics. Consequently, research into optimal dosage to treat various neurological disorders has not been rigorously pursued.

A 2016 Johns Hopkins study reported that relatively large doses such as 0.2 mg/kg dosing regimens are needed to induce psychedelic effects, which correlate to blood plasma concentrations between 4-8 ng/ml. The in vivo half-life for psilocin is about 50 minutes and leads to psychedelic experiences lasting 4-6 hours in which trained professionals monitor subjects in a clinical setting. Psychotherapy is performed before and after psychedelic doses to ready the patient and integrate the experiential outcome into a personal response to ameliorate depressive thoughts and actions, with the drug merely acting as a holistic tool. However, in-patient therapies incur significant costs for the patient and time on the care provider, not to mention the increased risk for adverse events while a patient is under the influence of a psychedelic drug.

Additionally, the positive psychological effects were seen with increasing doses, but the negative side effects of anxiety, negative ideation, nausea, and headaches also increased as doses increased. Consequently, professional monitoring of the patients is necessary before, during and after the psychedelic session. Recently, microdosing has been used to dose psychedelic substances in very small, sub-perceptual amounts. Psychedelic substances that have been microdosed include LSD (lysergic acid diethylamide), cannabis and psilocybin analogues. Reports of microdosing substances such as DMT and 5-MeO-DMT are scant since their lack of bioavailability and short half-life makes their dosing challenging. Microdosing has been reported to have the beneficial therapeutic effects of improving mood, intellectual focus, energy levels, and creativity without the disabling hallucinogenic effects.

Microdosing of a psychedelic substance largely reduces psychotropic effects and anecdotally dosing is usually one-tenth ($1/10^{th}$) of a psychedelic dose. Many clinical investigations of psychedelics to alleviate depression and PTSD omit participants with a history of heart trouble, psychosis, and schizophrenia since the intense psychotropic effects can exacerbate these conditions microdosing could alleviate these issues. Treatments that are devoid of psychedelic effects would make the administration of the drugs in a clinical setting unnecessary, opening more traditional, flexible, and affordable drug regimens. Microdosing reports have noted improved cognitive benefits such as productivity, creativity, and abstract thinking; coupling evidence suggesting psychedelics reduce neuroinflammation and increase neuroplasticity and neuronal connections could lead to effective treatments for dementia, Alzheimer's disease, and other neurocognitive disorders.

Transdermal and nasal application of active pharmaceutical ingredients has many benefits when used for psychoactive drugs. In particular, psilocin is the product of the conversion of psilocybin, which is a prodrug that is transformed to psilocin in the gastrointestinal tract. By avoiding the gastrointestinal tract through transdermal application of psilocin problems with absorption and food interactions can be avoided. As therapeutic effects of orally-dosed DMT can only be realized with co-administration of MAOIs, transdermal systems offer a new delivery method with reduced metabolism and improved pharmacokinetic/pharmacodynamic (PK/PD) properties. Other benefits of transdermal dosing include avoiding of the first pass metabolism; providing multi-day therapy by single application thereby improving patient compliance; and extending the activity of drugs having short half-life through the reservoir of drug present in the delivery system and its controlled release characteristics.

Systemic delivery of pharmaceutical ingredients by administration to the nasal mucosa can be advantageous. Nasal delivery allows for avoidance of intestinal metabolism and first pass metabolism. Additionally, nasal delivery of systemic drugs can bypass the blood brain barrier and enter the brain via the olfactory and trigeminal nerve pathways, which can be advantageous for pharmaceutical dosing of diseases of the central nervous system. An additional benefit of nasal dosing is the rapid systemic absorption through the nasal mucosa; pairing this with a short half-life compound like DMT could have significant clinical advantages over longer acting psychedelics.

Oral delivery of drugs is often preferred over various other drug administration routes because of ease of ingestion, pain avoidance, good patient compliance and compounding history. However, many problems are still associated with oral delivery such as poor solubility of drugs in aqueous environments, taste, stability of the drug with the formulation excipients, varied dissolution rates, unknown gastrointestinal absorption issues and food effects. Oral pharmaceutical formulations are recognized as a scientific endeavor that requires specific knowledge of the field in general, and innovative design.

Recent studies on psilocybin and its psilocybin analogues and combinations thereof, have been reported to have efficacy in models and small clinical trials of post-treatment Lyme disease syndrome, dementias, Alzheimer's disease, post-traumatic stress disorder, anorexia nervosa, depression and anxiety, abuse disorders including opioid addiction, alcohol addiction, nicotine addiction, cannabinoid addiction, headache, central nervous system inflammation, dementia, and disorders of cognition and memory. These promising experimental reports using psilocybin and its analogues demonstrate an immediate need to determine a formulation to permit the most advantageous dosing amount and dosing period; improved pharmacokinetic (PK) profiles, pharmacodynamic (PD) profiles, or safety profiles; evaluation of the benefits of long term or maintenance therapies; development of treatment regimens that maximize biological efficacy for treating diseases; and the use of these compounds in other potential advantageous benefits. Additionally, there is a need for development of novel, safe and effective exogenous serotonergic and/or Sigma-1 modulators for the treatment of neurological, mood and abuse disorders or diseases.

SUMMARY

Provided herein are novel indole compounds that have biological efficacy and increased clinical safety.

These compounds include the compounds of Structure (1) or pharmaceutically acceptable salts or solvates thereof:

Structure (1)

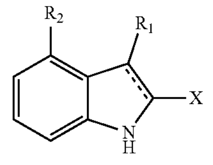

wherein:

X is H, $CF_3$, or a halogen that is selected from the group consisting of F, Cl, Br, I, and astatine; $R_1$ comprises an aliphatic substituent with a primary, secondary, tertiary, or quaternary amine; $R_2$ is hydrogen, hydroxyl, ester, ether, aldehyde, acid, amide, thiol, sulfones, sulfonamide or combinations thereof.

A further aspect of the present invention is a compound according to Structure (1), as described above, that is selected from the group consisting of:

TABLE (1)

| NOVEL INDOLE COMPOUNDS |
|---|
| 2-bromo-3-[2-(dimethylamino)ethyl]-1H-indol-4-ol |
| 2-fluoro-3-[2-(dimethylamino)ethyl]-1H-indol-4-ol |
| 2-chloro-3-[2-(dimethylamino)ethyl]-1H-indol-4-ol |
| 2-iodo-3-[2-(dimethylamino)ethyl]-1H-indol-4-ol |
| 3-[2-(dimethylamino)ethyl]-2-trifluoromethyl-1H-indol-4-ol |
| 2-bromo-3-[2-(dimethylamino)ethyl]-1H-indol-4-yl dihydrogen phosphate |
| 2-fluoro-3-[2-(dimethylamino)ethyl]-1H-indol-4-yl dihydrogen phosphate |
| 2-chloro-3-[2-(dimethylamino)ethyl]-1H-indol-4-yl dihydrogen phosphate |
| 2-iodo-3-[2-(dimethylamino)ethyl]-1H-indol-4-yl dihydrogen phosphate |
| 3-[2-(dimethylamino)ethyl]-2-trifluoromethyl-1H-indol-4-yl dihydrogen phosphate |
| 2-bromo-3-[2-(dimethylammonio)ethyl]-1H-indol-4-yl hydrogen phosphate |
| 2-fluoro-3-[2-(dimethylammonio)ethyl]-1H-indol-4-yl hydrogen phosphate |
| 2-chloro-3-[2-(dimethylammonio)ethyl]-1H-indol-4-yl hydrogen phosphate |
| 2-iodo-3-[2-(dimethylammonio)ethyl]-1H-indol-4-yl hydrogen phosphate |
| 3-[2-(dimethylammonio)ethyl]-2-trifluoromethyl-1H-indol-4-yl hydrogen phosphate |
| 2-(2-bromo-1H-indol-3-yl)-N,N-dimethylethan-1-amine |
| 2-(2-fluoro-1H-indol-3-yl)-N,N-dimethylethan-1-amine |
| 2-(2-chloro-1H-indol-3-yl)-N,N-dimethylethan-1-amine |
| 2-(2-iodo-1H-indol-3-yl)-N,N-dimethylethan-1-amine |
| N N-dimethyl-2-(2-trifluoromethyl-1H-indol-3-yl)ethan-1amine |
| 3-[2-(dimethylamino)ethyl]-1H-indol-4-yl acetate |
| 2-bromo-3-[2-(dimethylamino)ethyl]-1H-indol-4-yl acetate |
| 2-fluoro-3-[2-(dimethylamino)ethyl]-1H-indol-4-yl acetate |
| 2-chloro-3-[2-(dimethylamino)ethyl]-1H-indol-4-yl acetate |
| 2-iodo-3-[2-(dimethylamino)ethyl]-1H-indol-4-yl acetate |
| 3-[2-(dimethylamino)ethyl]-2-trifluoromethyl-1H-indol-4-yl acetate |
| 3-[2-(dimethylamino)ethyl]-1H-indol-4-yl propionate |
| 2-bromo-3-[2-(dimethylamino)ethyl]-1H-indol-4-yl propionate |
| 2-fluoro-3-[2-(dimethylamino)ethyl]-1H-indol-4-yl propionate |
| 2-chloro-3-[2-(dimethylamino)ethyl]-1H-indol-4-yl propionate |
| 2-iodo-3-[2-(dimethylamino)ethyl]-1H-indol-4-yl propionate |
| 3-[2-(dimethylamino)ethyl]-2-trifluoromethyl-1H-indol-4-yl propionate |
| 3-[2-(dimethylamino)ethyl]-1H-indol-4-yl butyrate |
| 2-bromo-3-[2-(dimethylamino)ethyl]-1H-indol-4-yl butyrate |
| 2-fluoro-3-[2-(dimethylamino)ethyl]-1H-indol-4-yl butyrate |
| 2-chloro-3-[2-(dimethylamino)ethyl]-1H-indol-4-yl butyrate |
| 2-iodo-3-[2-(dimethylamino)ethyl]-1H-indol-4-yl butyrate |
| 3-[2-(dimethylamino)ethyl]-2-trifluoromethyl-1H-indol-4-yl butyrate |
| 3-[2-(dimethylamino)ethyl]-1H-indol-4-yl pentanoate |
| 2-bromo-3-[2-(dimethylamino)ethyl]-1H-indol-4-yl pentanoate |
| 2-fluoro-3-[2-(dimethylamino)ethyl]-1H-indol-4-yl pentanoate |
| 2-chloro-3-[2-(dimethylamino)ethyl]-1H-indol-4-yl pentanoate |
| 2-iodo-3-[2-(dimethylamino)ethyl]-1H-indol-4-yl pentanoate |
| 3-[2-(dimethylamino)ethyl]-2-trifluoromethyl-1H-indol-4-yl pentanoate |
| 3-[2-(dimethylamino)ethyl]-1H-indol-4-yl hexanoate |
| 2-bromo-3-[2-(dimethylamino)ethyl]-1H-indol-4-yl hexanoate |
| 2-fluoro-3-[2-(dimethylamino)ethyl]-1H-indol-4-yl hexanoate |
| 2-chloro-3-[2-(dimethylamino)ethyl]-1H-indol-4-yl hexanoate |
| 2-iodo-3-[2-(dimethylamino)ethyl]-1H-indol-4-yl hexanoate |
| 3-[2-(dimethylamino)ethyl]-2-trifluoromethyl-1H-indol-4-yl hexanoate |
| 3-[2-(dimethylamino)ethyl]-1H-indol-4-yl heptanoate |
| 2-bromo-3-[2-(dimethylamino)ethyl]-1H-indol-4-yl heptanoate |
| 2-fluoro-3-[2-(dimethylamino)ethyl]-1H-indol-4-yl heptanoate |
| 2-chloro-3-[2-(dimethylamino)ethyl]-1H-indol-4-yl heptanoate |
| 2-iodo-3-[2-(dimethylamino)ethyl]-1H-indol-4-yl heptanoate |
| 3-[2-(dimethylamino)ethyl]-2-trifluoromethyl-1H-indol-4-yl heptanoate |
| 3-[2-(dimethylamino)ethyl]-1H-indol-4-yl octanoate |
| 2-bromo-3-[2-(dimethylamino)ethyl]-1H-indol-4-yl octanoate |
| 2-fluoro-3-[2-(dimethylamino)ethyl]-1H-indol-4-yl octanoate |
| 2-chloro-3-[2-(dimethylamino)ethyl]-1H-indol-4-yl octanoate |
| 2-iodo-3-[2-(dimethylamino)ethyl]-1H-indol-4-yl octanoate |
| 3-[2-(dimethylamino)ethyl]-2-trifluoromethyl-1H-indol-4-yl octanoate, |
| 3-[2-(dimethylamino)ethyl]-1H-indol-4-yl nonanoate |
| 2-bromo-3-[2-(dimethylamino)ethyl]-1H-indol-4-yl nonanoate |
| 2-fluoro-3-[2-(dimethylamino)ethyl]-1H-indol-4-yl nonanoate |
| 2-chloro-3-[2-(dimethylamino)ethyl]-1H-indol-4-yl nonanoate |
| 2-iodo-3-[2-(dimethylamino)ethyl]-1H-indol-4-yl nonanoate |
| 3-[2-(dimethylamino)ethyl]-2-trifluoromethyl-1H-indol-4-yl nonanoate |
| 3-[2-(dimethylamino)ethyl]-1H-indol-4-yl decanoate |
| 2-bromo-3-[2-(dimethylamino)ethyl]-1H-indol-4-yl decanoate, |
| 2-fluoro-3-[2-(dimethylamino)ethyl]-1H-indol-4-yl decanoate, |
| 2-chloro-3-[2-(dimethylamino)ethyl]-1H-indol-4-yl decanoate, |
| 2-iodo-3-[2-(dimethylamino)ethyl]-1H-indol-4-yl decanoate |
| 3-[2-(dimethylamino)ethyl]-2-trifluoromethyl-1H-indol-4-yl decanoate |
| 3-[2-(dimethylamino)ethyl]-1H-indol-4-yl undecanoate |
| 2-bromo-3-[2-(dimethylamino)ethyl]-1H-indol-4-yl undecanoate |
| 2-fluoro-3-[2-(dimethylamino)ethyl]-1H-indol-4-yl undecanoate |
| 2-chloro-3-[2-(dimethylamino)ethyl]-1H-indol-4-yl undecanoate |

TABLE (1)-continued

| NOVEL INDOLE COMPOUNDS |
|---|
| 2-iodo-3-[2-(dimethylamino)ethyl]-1H-indol-4-yl undecanoate |
| 3-[2-(dimethylamino)ethyl]-2-trifluoromethyl-1H-indol-4-yl undecanoate |
| 3-[2-(dimethylamino)ethyl]-1H-indol-4-yl dodecanoate |
| 2-bromo-3-[2-(dimethylamino)ethyl]-1H-indol-4-yl dodecanoate |
| 2-fluoro-3-[2-(dimethylamino)ethyl]-1H-indol-4-yl dodecanoate |
| 2-chloro-3-[2-(dimethylamino)ethyl]-1H-indol-4-yl dodecanoate |
| 2-iodo-3-[2-(dimethylamino)ethyl]-1H-indol-4-yl dodecanoate |
| 3-[2-(dimethylamino)ethyl]-2-trifluoromethyl-1H-indol-4-yl dodecanoate |
| 2-(4-methoxy-1H-indol-3-yl)-N,N-dimethylethan-1-amine |
| 2-(2-bromo-4-methoxy-1H-indol-3-yl)-N N-dimethylethan-1-amine |
| 2-(2-fluoro-4-methoxy-1H-indol-3-yl)-N,N-dimethylethan-1-amine |
| 2-(2-chloro-4-methoxy-1H-indol-3-yl)-N,N-dimethylethan-1-amine |
| 2-(2-iodo-4-methoxy-1H-indol-3-yl)-N,N-dimethylethan-1-amine |
| 2-(4-methoxy-2-trifluoromethyl-1H-indol-3-yl)-N,N-dimethylethan-1-amine |
| 1-[3-[2-(dimethylamino)ethyl]-1H-indol-4-yl]ethan-1-one |
| 1-[2-bromo-3-[2-(dimethylamino)ethyl]-1H-indol-4-yl]ethan-1-one |
| 1-[2-fluoro-3-[2-(dimethylamino)ethyl]-1H-indol-4-yl]ethan-1-one, |
| 1-[2-chloro-3-[2-(dimethylamino)ethyl]-1H-indol-4-yl]ethan-1-one |
| 1-[2-iodo-3-[2-(dimethylamino)ethyl]-1H-indol-4-yl]ethan-1-one |
| 1-[3-[2-(dimethylamino)ethyl]-2-trifluoromethyl-1H-indol-4-yl]ethan-1-one |
| 3-[2-(dimethylamino)ethyl]-1H-indole-4-carboxylic acid |
| 2-bromo-3-[2-(dimethylamino)ethyl]-1H-indole-4-carboxylic acid |
| 2-fluoro-3-[2-(dimethylamino)ethyl]-1H-indole-4-carboxylic acid |
| 2-chloro-3-[2-(dimethylamino)ethyl]-1H-indole-4-carboxylic acid |
| 2-iodo-3-[2-(dimethylamino)ethyl]-1H-indole-4-carboxylic acid |
| 3-[2-(dimethylamino)ethyl]-2-trifluoromethyl-1H-indole-4-carboxylic acid |
| 3-[2-(dimethylamino)ethyl]1H-indole-4 methyl carboxylate |
| 2-bromo-3-[2-(dimethylamino)ethyl]1H-indole-4 methyl carboxylate |
| 2-fluoro-3-[2-(dimethylamino)ethyl]1H-indole-4 methyl carboxylate |
| 2-chloro-3-[2-(dimethylamino)ethyl]1H-indole-4 methyl carboxylate |
| 2-iodo-3-[2-(dimethylamino)ethyl]1H-indole-4 methyl carboxylate |
| 3-[2-(dimethylamino)ethyl]-2-trifluoromethyl-1H-indole-4 methyl carboxylate |
| 3-[2-(dimethylamino)ethyl]1H-indole-4 ethyl carboxylate |
| 2-bromo-3-[2-(dimethylamino)ethyl]1H-indole-4 ethyl carboxylate |
| 2-fluoro-3-[2-(dimethylamino)ethyl]1H-indole-4 ethyl carboxylate |
| 2-chloro-3-[2-(dimethylamino)ethyl]1H-indole-4 ethyl carboxylate |
| 2-iodo-3-[2-(dimethylamino)ethyl]1H-indole-4 ethyl carboxylate |
| 3-[2-(dimethylamino)ethyl]-2-trifluoromethyl-1H-indole-4 ethyl carboxylate |
| 3-[2-(dimethylamino)ethyl]1H-indole-4 propyl carboxylate |
| 2-bromo-3-[2-(dimethylamino)ethyl]1H-indole-4 propyl carboxylate |
| 2-fluoro-3-[2-(dimethylamino)ethyl]1H-indole-4 propyl carboxylate |
| 2-chloro-3-[2-(dimethylamino)ethyl]1H-indole-4 propyl carboxylate |
| 2-iodo-3-[2-(dimethylamino)ethyl]1H-indole-4 propyl carboxylate |
| 3-[2-(dimethylamino)ethyl]-2-trifluoromethyl-1H-indole-4 propyl carboxylate |
| 3-[2-(dimethylamino)ethyl]1H-indole-4 butyl carboxylate |
| 2-bromo-3-[2-(dimethylamino)ethyl]1H-indole-4 butyl carboxylate |
| 2-fluoro-3-[2-(dimethylamino)ethyl]1H-indole-4 butyl carboxylate |
| 2-chloro-3-[2-(dimethylamino)ethyl]1H-indole-4 butyl carboxylate |
| 2-iodo-3-[2-(dimethylamino)ethyl]1H-indole-4 butyl carboxylate |
| 3-[2-(dimethylamino)ethyl]-2-trifluoromethyl-1H-indole-4 butyl carboxylate |
| 3-[2-(dimethylamino)ethyl]1H-indole-4 pentyl carboxylate |
| 2-bromo-3-[2-(dimethylamino)ethyl]1H-indole-4 pentyl carboxylate |
| 2-fluoro-3-[2-(dimethylamino)ethyl]1H-indole-4 pentyl carboxylate |
| 2-chloro-3-[2-(dimethylamino)ethyl]1H-indole-4 pentyl carboxylate |
| 2-iodo-3-[2-(dimethylamino)ethyl]1H-indole-4 pentyl carboxylate |
| 3-[2-(dimethylamino)ethyl]-2-trifluoromethyl-1H-indole-4 pentyl carboxylate |
| 3-[2-(dimethylamino)ethyl]1H-indole-4 hexyl carboxylate |
| 2-bromo-3-[2-(dimethylamino)ethyl]1H-indole-4 hexyl carboxylate |
| 2-fluoro-3-[2-(dimethylamino)ethyl]1H-indole-4 hexyl carboxylate |
| 2-chloro-3-[2-(dimethylamino)ethyl]1H-indole-4 hexyl carboxylate |
| 2-iodo-3-[2-(dimethylamino)ethyl]1H-indole-4 hexyl carboxylate |
| 3-[2-(dimethylamino)ethyl]-2-trifluoromethyl-1H-indole-4 hexyl carboxylate |
| 3-[2-(dimethylamino)ethyl]1H-indole-4 heptyl carboxylate |
| 2-bromo-3-[2-(dimethylamino)ethyl]1H-indole-4 heptyl carboxylate |
| 2-fluoro-3-[2-(dimethylamino)ethyl]1H-indole-4 heptyl carboxylate |
| 2-chloro-3-[2-(dimethylamino)ethyl]1H-indole-4 heptyl carboxylate |
| 2-iodo-3-[2-(dimethylamino)ethyl]1H-indole-4 heptyl carboxylate |
| 3-[2-(dimethylamino)ethyl]-2-trifluoromethyl-1H-indole-4 heptyl carboxylate |
| 3-[2-(dimethylamino)ethyl]1H-indole-4 octyl carboxylate |
| 2-bromo-3-[2-(dimethylamino)ethyl]1H-indole-4 octyl carboxylate |
| 2-fluoro-3-[2-(dimethylamino)ethyl]1H-indole-4 octyl carboxylate |
| 2-chloro-3-[2-(dimethylamino)ethyl]1H-indole-4 octyl carboxylate |
| 2-iodo-3-[2-(dimethylamino)ethyl]1H-indole-4 octyl carboxylate |
| 3-[2-(dimethylamino)ethyl]-2-trifluoromethyl-1H-indole-4 octyl carboxylate |
| 3-[2-(dimethylamino)ethyl]1H-indole-4 nonyl carboxylate |
| 2-bromo-3-[2-(dimethylamino)ethyl]1H-indole-4 nonyl carboxylate |
| 2-fluoro-3-[2-(dimethylamino)ethyl]1H-indole-4 nonyl carboxylate |
| 2-chloro-3-[2-(dimethylamino)ethyl]1H-indole-4 nonyl carboxylate |

TABLE (1)-continued

| NOVEL INDOLE COMPOUNDS |
|---|
| 2-iodo-3-[2-(dimethylamino)ethyl]1H-indole-4 nonyl carboxylate |
| 3-[2-(dimethylamino)ethyl]-2-trifluoromethyl-1H-indole-4 nonyl carboxylate |
| 3-[2-(dimethylamino)ethyl]1H-indole-4 decyl carboxylate |
| 2-bromo-3-[2-(dimethylamino)ethyl]1H-indole-4 decyl carboxylate |
| 2-fluoro-3-[2-(dimethylamino)ethyl]1H-indole-4 decyl carboxylate |
| 2-chloro-3-[2-(dimethylamino)ethyl]1H-indole-4 decyl carboxylate |
| 2-iodo-3-[2-(dimethylamino)ethyl]1H-indole-4 decyl carboxylate |
| 3-[2-(dimethylamino)ethyl]-2-trifluoromethyl-1H-indole-4 decyl carboxylate |
| 3-[2-(dimethylamino)ethyl]1H-indole-4 undecyl carboxylate |
| 2-bromo-3-[2-(dimethylamino)ethyl]1H-indole-4 undecyl carboxylate |
| 2-fluoro-3-[2-(dimethylamino)ethyl]1H-indole-4 undecyl carboxylate |
| 2-chloro-3-[2-(dimethylamino)ethyl]1H-indole-4 undecyl carboxylate |
| 2-iodo-3-[2-(dimethylamino)ethyl]1H-indole-4 undecyl carboxylate |
| 3-[2-(dimethylamino)ethyl]-2-trifluoromethyl-1H-indole-4 undecyl carboxylate |
| 3-[2-(dimethylamino)ethyl]1H-indole-4 dodecyl carboxylate |
| 2-bromo-3-[2-(dimethylamino)ethyl]1H-indole-4 dodecyl carboxylate |
| 2-fluoro-3-[2-(dimethylamino)ethyl]1H-indole-4 dodecyl carboxylate |
| 2-chloro-3-[2-(dimethylamino)ethyl]1H-indole-4 dodecyl carboxylate |
| 2-iodo-3-[2-(dimethylamino)ethyl]1H-indole-4 dodecyl carboxylate |
| 3-[2-(dimethylamino)ethyl]-2-trifluoromethyl-1H-indole-4 dodecyl carboxylate |
| 1-[3-[2-(dimethylamino)ethyl]-1H-indol-4-yl]-N-methylmethanesulfonamide |
| 1-[2-bromo-3-[2-(dimethylamino)ethyl]-1H-indol-4-yl]-N-methylmethanesulfonamide |
| 1-[2-fluoro-3-[2-(dimethylamino)ethyl]-1H-indol-4-yl]-N-methylmethanesulfonamide |
| 1-[2-chloro-3-[2-(dimethylamino)ethyl]-1H-indol-4-yl]-N-methylmethanesulfonamide |
| 1-[2-iodo-3-[2-(dimethylamino)ethyl]-1H-indol-4-yl]-N-methylmethanesulfonamide |
| 1-[3-[2-(dimethylamino)ethyl]-2-trifluoromethyl-1H-indol-4-yl]-N-methylmethanesulfonamide |

and any salt forms thereof.

In another aspect of this invention, are the compounds of Structure (2) or pharmaceutically acceptable salts or solvates thereof:

Structure (2)

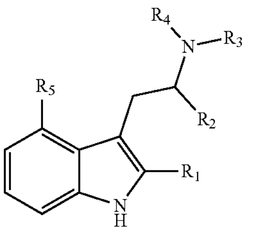

wherein $R^1$ is selected from the group consisting of H, F, Cl, Br, I, or $CF_3$; $R_2$ or $CH_3$; $R_3$ and $R_4$ are each independently optionally selected from the group consisting of H, $CH_3$, $C_2H_5$, $(H_3C)_2CH$, or $H_2C{=}CH{-}CH_2$; wherein $R^5$ is selected from the group consisting of $OCH_3$, $OCOCH_3$, O-phosphate, O-polyethylene glycol (PEG), $O{-}(CH_2)_2(COOH)_2$ (succinate), $O{-}(CH_2)_2$ (COOH) (hemi-succinate), and $CH_2SO_2NHCH_3$ (sulfonamide); wherein when $R_1$ is H then $R_5$ is $CH_2SO_2NHCH_3$.

Specific compounds of Structure (2) are 2-chloro-3-(2-(dimethylamino)ethyl)-1H-indol-4-yl acetate, 2-bromo-3-(2-(dimethylamino)ethyl)-1H-indol-4-yl acetate, 2-chloro-3-(2-(dimethylamino)ethyl)-1H-indol-4-yl hydrogen phosphate, 2-bromo-3-(2-(dimethylamino)ethyl)-1H-indol-4-yl hydrogen phosphate, 2-bromo-3-(2-(dimethylamino)ethyl)-1H-indol-4-ol, 2-chloro-3-(2-(dimethylamino)ethyl)-1H-indol-4-ol, 2-(2-chloro-4-methoxy-1H-indol-3-yl)-N,N-dimethylethan-1-amine, 2-(2-bromo-4-methoxy-1H-indol-3-yl)-N,N-dimethylethan-1-amine. Other specific compounds of Structure (2) are of particular interest are 1-(2-chloro-3-(2-(dimethylamino)ethyl)-1H-indol-4-yl)-N-methylmethanesulfonamide, and 1-(3-(2-(dimethylamino)ethyl)-1H-indol-4-yl)-N-methylmethanesulfonamide Another aspect of this invention, are the compounds of Structure (3) or pharmaceutically acceptable salts or solvates thereof:

Structure (3)

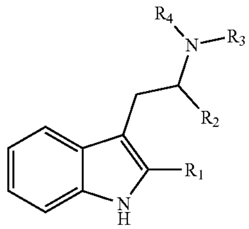

wherein $R^1$ is selected from the group consisting of F, Cl, Br, I, or $CF_3$; $R_2$ is $CH_3$; $R_3$ and $R_4$ are each independently optionally selected from the group consisting of H, $CH_3$, $C_2H_5$, $(H_3C)_2CH$, or $H_2C{-}CH{-}CH_2$ Specific compounds of Structure (3) are 2-(2-chloro-1H-indol-3-yl)-N,N-dimethylethan-1-amine, 2-(2-chloro-1H-indol-3-yl)-N,N-dimethylethan-1-amine, (R)-1-(2-chloro-1H-indol-3-yl) propan-2-amine, (R)-1-(2-chloro-1H-indol-3-yl)-N-methylpropan-2-amine, (R)-1-(2-chloro-1H-indol-3-yl)-N,N-dimethylpropan-2-amine, (S)-1-(2-chloro-1H-indol-3-yl)-N,N-dimethylpropan-2-amine, (S)-1-(2-chloro-1H-indol-3-yl) propan-2-amine, (S)-1-(2-chloro-1H-indol-3-yl)-N-methylpropan-2-amine, (R)-1-(2-bromo-1H-indol-3-yl) propan-2-amine, (R)-1-(2-bromo-1H-indol-3-yl)-N-methylpropan-2-amine, (R)-1-(2-bromo-1H-indol-3-yl)-N,N-dimethylpropan-2-amine, (S)-1-(2-bromo-1H-indol-3-yl)-N,N-dimethylpropan-2-amine, (S)-1-(2-bromo-1H-indol-3-yl) propan-2-amine, (S)-1-(2-bromo-1H-indol-3-yl)-N-methylpropan-2-amine, 2-(2-chloro-1H-indol-3-yl)-N,N-diethylethan-1-amine, N-(2-(2-chloro-1H-indol-3-yl) ethyl)-N-isopropylpropan-2-amine, N-(2-(2-chloro-1H-indol-3-yl)ethyl)-N-vinylethenamine, 2-(2-bromo-1H-indol-3-yl)-N,N-diethylethan-1-amine, N-(2-(2-bromo-1H-indol-3-yl)ethyl)-N-isopropylpropan-2-amine, or N-(2-(2-bromo-1H-indol-3-yl)ethyl)-N-isopropylpropan-2-amine.

Provided herein are pharmaceutical compositions wherein the compositions are designed to release the active pharmaceutical ingredients as described herein into the bloodstream through the application of the active pharmaceutical ingredient transdermally to the skin and nasal passages. These pharmaceutical compositions are transdermal or nasal pharmaceutical formulations. The active pharmaceutical ingredient may be applied by sprayable liquids, gels, creams, lotions, ointments, transdermal patch and the like.

In one embodiment, the transdermal pharmaceutical and nasal compositions of active pharmaceutical ingredients may be the compounds as described by Structures (1), (2), (3), and the compounds listed in Table (1) and any ionic or salt forms thereof.

In certain embodiments, the psilocybin analogues and combinations hereof, include any compound that is structurally related to psilocybin and functionally mimics and/or antagonizes the action of serotonin. In another embodiment the active pharmaceutical ingredient comprises psilocybin an active analogues and combinations thereof. Active analogues and combinations thereof of psilocybin include but are not limited have the compounds listed in Table (2) Psilocybin Analogues.

TABLE (2)

| Psilocybin and Psilocybin Analogs |
|---|
| psilocybin |
| psilocin |
| 4-hydroxy-indole-3-acetic acid |
| 4-hydroxy-indole-3-acetaldehyde |
| 4-hydroxytryptophol |
| 4-hydroxytryptophan |
| norpsilocin |
| aeruginascin |
| baeocystin |
| norbaeocystin |
| 4-hydroxy-N-methyl-N-ethyltryptamine (4-OH—MET) |
| 4-hydroxydiethyltryptamine (4-OH—DET) |
| 4-hydroxy-N,N-dipropyltryptamine (4-OH—DPT |
| 4-hydroxy-N,N-diisopropyltryptamine (4-OH—DiPT |
| N,N-dimethyltryptamine (DMT) |
| Indole-3-acetic acid |
| N,N-dimethyltryptamine-N-oxide (DMT—NO) |
| lysergic acid diethylamide (LSD) |
| O-acetylpsilocin (4-AcO—DMT) |
| 5-methoxy-N,N-dimethyltryptamine (5-MeO—DMT |
| ibogaine |
| bufotenin (5-OH—DMT) |

Provided herein is the manufacture of a transdermal or nasal medicament using as the active pharmaceutical ingredient the novel compounds and described by Structure (1), (2), and (3), the novel compounds listed of Table (1), and the psilocybin analogues of Table (2) and salts or solvates thereof for the treatment of neurological, mood, and abuse disorders or disease.

The transdermal and nasal pharmaceutical compositions of the present invention provide a composition as described for use in a medicine to treat, manage or prevent a disease.

In another embodiment, the pharmaceutical compositions are designed for oral delivery into the human systemic circulation with quick onset and duration.

In another embodiment, the pharmaceutical compositions are designed for extended release into the human systemic circulation via oral delivery, preferably providing a once daily dose.

The oral pharmaceutical compositions described herein may be designed for modified time release of the active pharmaceutical ingredients into the human systemic circulation for extended duration. The composition may be comprised of solid, semisolid, liquid, or flexible delivery systems and administered via sublingual, buccal, or oral administration. The active pharmaceutical ingredient may be supplied within a tablet, capsule, soft gels, strip, sublingual strip, wafer, solution, suspensions.

In one embodiment, the oral pharmaceutical compositions contain the active pharmaceutical ingredient of the novel compounds and described by Structures (1), (2), (3), the novel compounds of Table (1), and the psilocybin analogues of Table (2) or salts or solvates thereof. Combinations of psilocybin analogues and/or the novel indole compounds as the active pharmaceutical ingredient of pharmaceutical formulations is also part of the present invention.

The present invention provides a composition as described for use in the treatment, management, or prevention of a neurological, mood, or abuse disorders or disease wherein the disorder may be depression, central nervous system inflammation, addiction, headache, or dementia, or disorders of cognition and memory.

The present invention provides for the combination of the topical, nasal, or oral application of the compounds and analogues described herein in combination with active pharmaceutical ingredients that have been approved by regulatory authority for the treatment, management or preventions of neurological, mood and abuse disorders or disease. The approved active pharmaceutical ingredients may be delivered to a patient in need by any delivery system approved by the regulatory authorities. In one aspect of the present invention, the approved active pharmaceutical ingredient for use in combination with the novel indoles or the psilocybin analogues is a MAOI. In another aspect of the present invention the approved active pharmaceutical ingredient is a 5-HT antagonist.

Also provided herein are novel synthesis pathways to provide the novel indole compounds of Structure (1), (2), and (3), and to the novel compounds of Table (1) and the psilocybin analogues of Table (2). The novel synthesis of the described compounds is described in the specific examples and as described herein.

DETAILED DESCRIPTION

Figure 1:
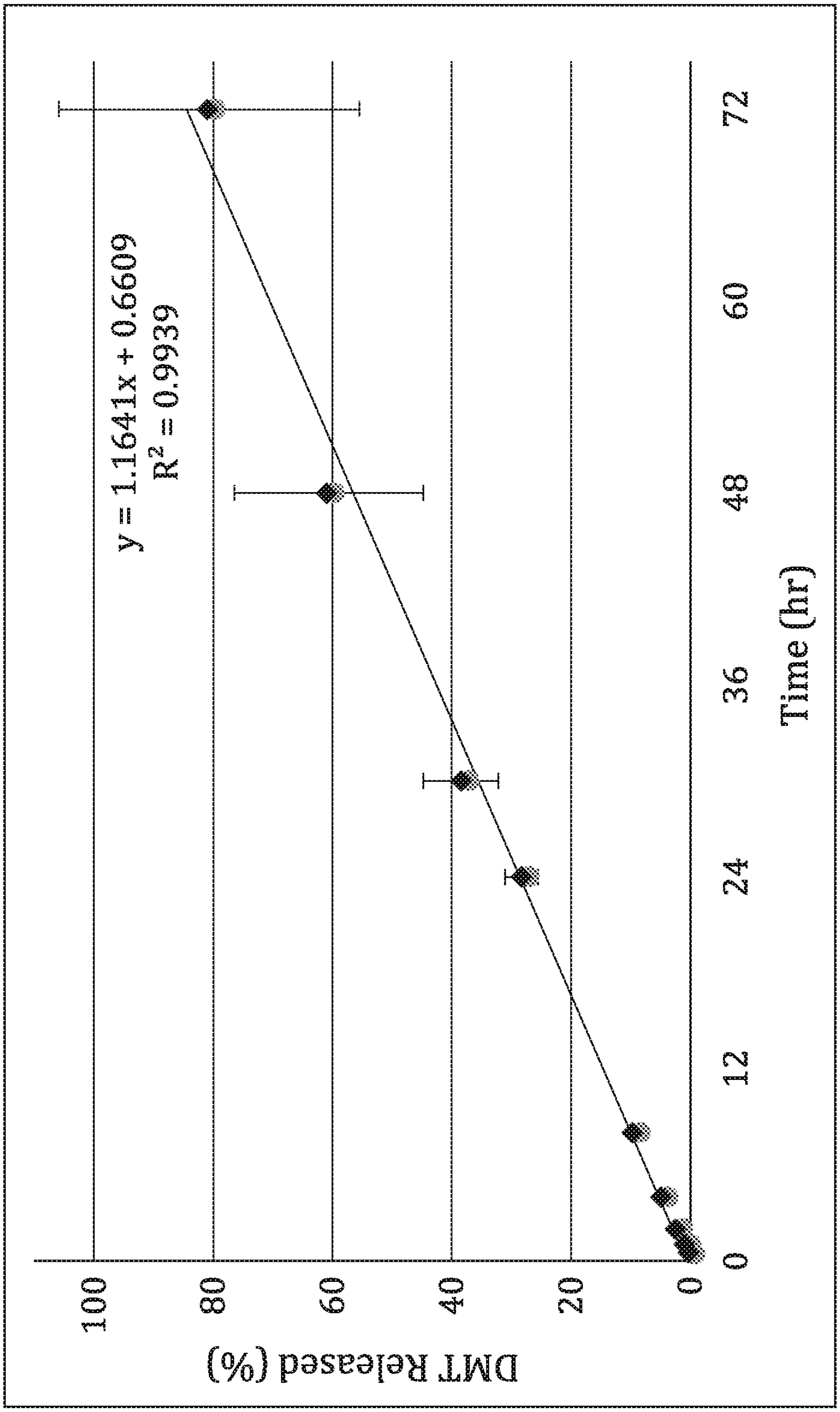
FIG. 1 demonstrates the drug release of DMT transdermal patches from Example 1. The results are averaged (n=3) as assessed by Franz cell diffusion model.
Figure 2:
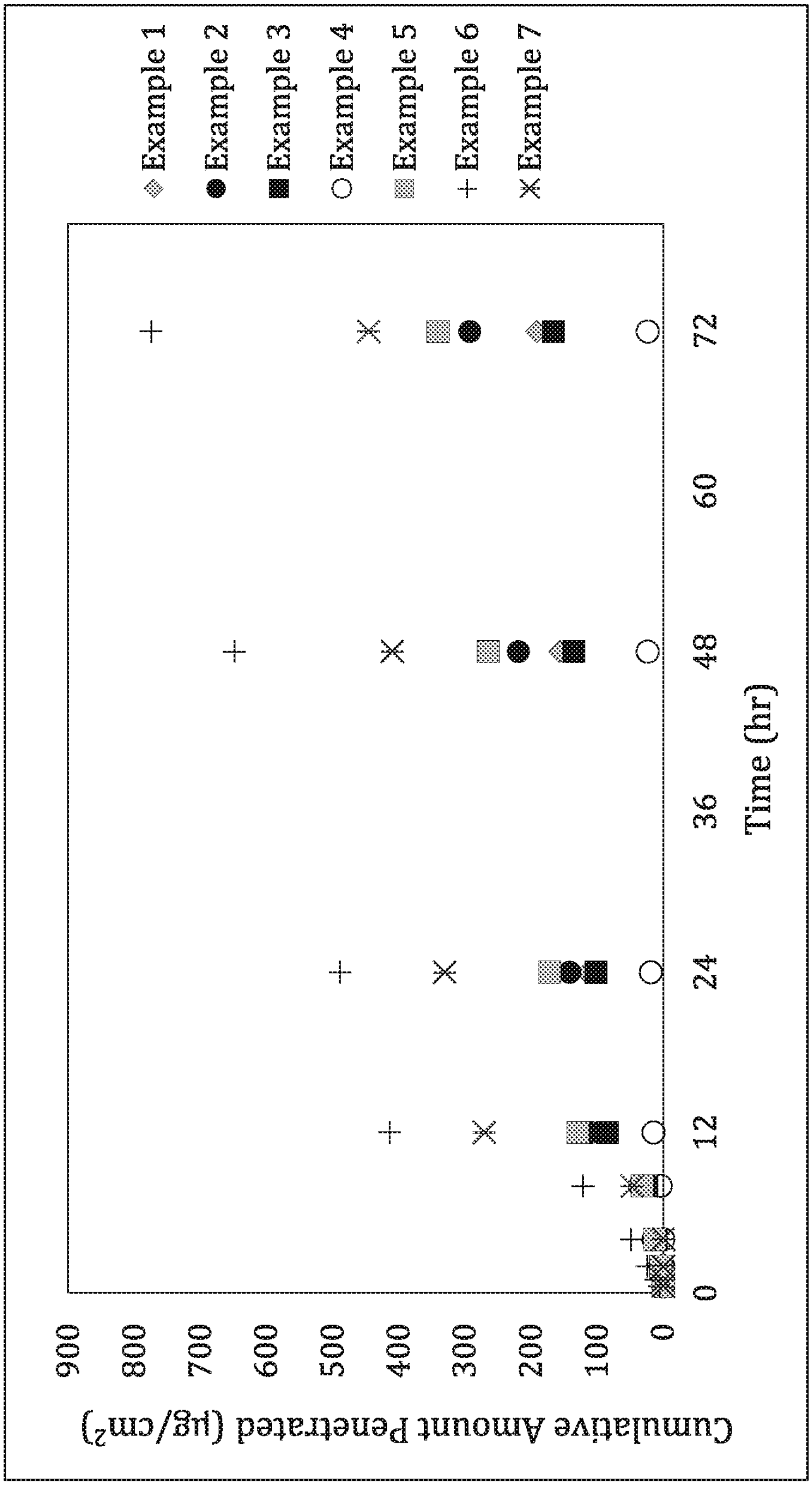
FIG. 2 demonstrates the diffusion rate of the transdermal formulation by the Franz cell model.

Unless defined otherwise, all technical and scientific terms used herein have the same meaning as commonly understood by one of ordinary skill in the art.

As used in the specification and the accompanying claims the indefinite articles “a” and “an” and the definite article “the” include plural as well as singular referents, unless the context clearly dictates otherwise.

The term “about” or “approximately” means an acceptable error for a particular value as determined by one of ordinary skill in the art, which depends in part on how the value is measured or determined. In certain embodiments, the term “about” or “approximately” means within 1, 2, 3 or 4 standard deviations. In certain embodiments, the term “about” or “approximately” means with 30%, 20%, 15%, 10%, 9%, 8%, 7%, 6%, 5%, 4%, 3%, 2%, 1%, 0.5%, 0.1%, or 0.05%, of a given value or range.

As used herein, and unless otherwise specified, the terms "treat," "treating" and "treatment" refer to the eradication or amelioration of a disease or disorder, or of one or more symptoms associated with the disease or disorder. In certain embodiment the terms refer to minimizing the spread or worsening of the disease or disorder resulting from the administration of one or more prophylactic or therapeutic agents to a subject with such disease or disorder. In some embodiments the terms refer to the administration of a compound or dosage form provided herein, with or without one or more additional active agent(s), after the onset of symptoms of a particular disease.

As used herein, and unless otherwise specified, the term "Abuse Disorder" is a disorder or disease that affects a person's brain and behavior and leads to an inability to control the use of a legal or illegal drug or medication. Prescription medicines, non-prescription medicines, and non-approved drugs may all be abused drugs. Drugs and medication may also include substances such as amphetamines, opioids, cocaine, barbiturates, alcohol, marijuana, and nicotine.

As used herein, and unless otherwise specified, the term "Mood Disorder" is a group of conditions where a disturbance in the person's mood is the underlying feature. Mood disorders may be groups of mania (elevated mood disorders) or hypomania (depression). The classification is in the Diagnostic and Statistical Manual of Mental Disorders (DSM) and the International Classification of Diseases (ICD).

As used herein, and unless otherwise specified, the term "Neurological Disorder" refers to diseases of the central and peripheral nervous system e.g., the brain, spinal cord, cranial nerves, peripheral nerves, nerve roots, autonomic nervous system, neuromuscular junction, and muscles. These disorders include epilepsy, Alzheimer's disease and other dementias, cerebrovascular diseases including stroke, migraine, cluster headaches and other headache disorders, multiple sclerosis, Parkinson's disease, neuroinfections, brain tumors, traumatic disorders of the nervous system due to head trauma, and traumatic disorders due to traumatic or terrifying experiences (Posttraumatic Stress Disorder e.g. PTSD) and neurological disorders as a result of malnutrition and substance abuse. The substance abused may be any number of addictive substances, especially alcohol and drugs and combinations thereof. Many bacterial (e.g., Mycobacterial tuberculosis, *Neisseria meningitides*), viral (e.g. Human Immunodeficiency Virus (HIV), Lyme Disease, Enteroviruses, West Nile Virus, Zika), fungal (e.g., *Cryptococcus, Aspergillus*), and parasitic (e.g., malaria, Chagas) infections can affect the nervous system. Neurological symptoms may occur due to the infection itself, or due to an immune response.

As used herein, and unless otherwise specified, the terms "prevent," "preventing" and "prevention" refer to the prevention of the onset, recurrence or spread of a disease or disorder or of one or more symptoms thereof. In certain embodiments, the terms refer to the treatment with or administration of a compounder dosage form provided herein, with or without one or more other additional active agent(s), prior to the onset of symptoms, particularly to a subject at risk of diseases or disorders provided herein. The terms encompass the inhibition or reduction of a symptom of the particular disease. Subjects with familial history of a disease in particular are candidates for preventive regimes in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

As used herein, and unless otherwise specified, a "prophylactically effective amount" of a compound is an amount sufficient to prevent a disease or disorder or prevent its recurrence. A prophylactically effective amount of a compound means an amount of therapeutic agent, alone or in combination with one or more other agent(s), that provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of a therapeutic agent, alone or in combination with one or more other agent(s), that provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein the term, and unless otherwise specified, an "Active Pharmaceutical Ingredient (API)" is any substance or mixture of substances intended to be used in the manufacture of a drug (medicinal) product and that, when used in the production of a drug, becomes an active ingredient of the drug product. Such substances are intended to affect the diagnosis, cure, mitigation, treatment, or prevention of disease or to affect the structure or function of the body.

As used herein, and unless otherwise specified, the term "Drug Product" is a finished dosage form, for example, an oral, nasal or transdermal formulation, that contains an active pharmaceutical ingredient, generally, but not necessarily in association with inactive ingredients.

The terms "composition," "formulation," and "dosage form," as used herein are intended to encompass compositions comprising the specified ingredient(s) (in the specified amounts, if indicated), as well as any product(s) that result, directly or indirectly, from combination of the specified ingredient(s) in the specified amount(s). By "pharmaceutical" or "pharmaceutically acceptable" it is meant that any diluent(s), excipient(s), absorption enhancer(s), or carrier(s) in the composition, formulation, or dosage form are compatible with the other ingredient(s) and not deleterious to the recipient thereof. Unless indicated otherwise, the terms “composition,” “formulation,” and “dosage form” are used herein interchangeably.

As used herein, the term “transdermal” relates to, being, or supplying a medication in a form for absorption through the skin into the bloodstream.

As used herein, the term “nasal” relates to, being or supplying a medication in a form for absorption through the nasal mucosa. Nasal delivery may be affected through a wide range of dosage forms including but not limited to solutions, gels, suspensions, emulsions, liposomes and microparticles.

As used herein “oral” relates to a medication in a form for absorption through the oral mucosal, sublingual, buccal, esophageal, gastric, or intestinal membranes. The term “capsule” refers to an oral composition in which the API and inactive ingredients are contained as a solid, liquid or semisolid within an outer shell comprised of gelatin, polymerized cellulose, or other suitable material. A capsule is intended to be swallowed wherein the composition will dissolve and release the API for systemic absorption through the esophageal, gastric, or intestinal lining.

The terms “tablet” and “wafer” includes spherical, round, oval, triangular, diamond, bullet, or oblong shaped oral compositions which contain the API, inactive ingredients, and optionally a saliva stimulant, which are formed with direct compression of a powdered formulation. Upon entry into the mouth, the compositions will dissolve and release the API for systemic absorption through the buccal, sublingual, esophageal, gastric, or intestinal lining.

The terms “strip” or “oral strip” includes square, rectangular, triangular, rounded, circular or oblong shaped oral compositions that contain the API, inactive ingredients, and optionally a saliva stimulant, that form a pliable matrix. Upon entry into the mouth, commonly placed under the tongue, the composition will dissolve and release the API for systemic absorption through the buccal, sublingual, esophageal, gastric, or intestinal lining.

As used herein “immediate release” is defined as the formulation of an active pharmaceutical ingredient(s) drug taken orally, nasally or transdermally that results in the rapid absorption of the drug into the blood after administration. Immediate release may be measured in vitro using the FDA Industry guidance on dissolution and/or permeability testing, or in vivo using blood plasma levels.

As used herein, “modified release” or “extended release” is defined as a formulation of an active pharmaceutical ingredient(s) taken orally, nasally or transdermally that releases the active pharmaceutical ingredients over several hours or days, to maintain a relatively constant plasma concentration of the drug. Such modifications may have a number of objectives, such as maintaining therapeutic activity for an extended time, reducing toxic effects, protecting the active substance against degradation due to low pH, targeting the active substance to a predefined segment of the gastrointestinal tract for local treatment or targeting active substance release at specified time-points. Modified release is measured by the appropriate FDA industry guidelines on modified release formulations.

The term “subject” is defined herein to include animals such as mammals, including, but not limited to, primates (e.g., humans), cows, sheep, goats, horses, dogs, cats, rabbits, rats, mice and the like. In specific embodiments, the subject is a human.

The terms “co-administration,” “in combination with” and “in combination” include the administration of two or more therapeutic agents either simultaneously, concurrently or sequentially within no specific time limits. In one embodiment, the agents are present in the cell or in the subject’s body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, or 4 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The term “psilocybin analogue” is defined herein to include any compound that is structurally related to psilocybin and functionally mimics and/or antagonizes the action of serotonin. Certain embodiments herein provide salts, cocrystals, solvates, isomers, hydrates, ions, zwitterions, complexes, prodrugs, precursors, metabolites, and/or other derivatives of the psilocybin. Certain embodiments herein provide mixtures of two or more of the psilocybin analogues provided herein. As described herein the psilocybin analogues are selected from the group consisting of the compounds as listed in Table (2) and salts and solvates thereof. Certain embodiments herein provide mixtures of two or more of the psilocybin analogues provided herein.

The psilocybin analogues described herein may be synthesized using any method known to one of ordinary skill in the art. Certain of the compounds are known to be able to be provided by application of biological processes to manufactured goods; the compounds are bioengineered.

The psilocybin analogues described herein may be provided by the alcohol or acid-base extraction of the psychoactive compounds from natural source that contain the compounds. The extraction methods are well known to those of skill in the art.

In certain embodiments the inventive formulation uses psilocybin and psilocybin analogues and combinations thereof, that may be derived synthetically or bioengineered; or extracted from naturally occurring mushrooms. Some of the manufacturing processes may be novel, as described herein, others may use techniques that have been well described in the art.

Provided herein are dosage forms, pharmaceutical formulations and compositions comprising an active pharmaceutical ingredient that is either (a) a novel indole of Structure (1), Structure (2), Structure (3), or (b) or a psilocybin analogue. The dosage forms, pharmaceutical formulations and compositions release the active pharmaceutical ingredients into the bloodstream upon transdermal, nasal, or oral administration. In certain embodiments, the psilocybin analogue is psilocin. In certain embodiments, the psilocybin analogue is 4-hydroxytryptophan. In certain embodiments, the psilocybin analogue is 4-hydroxytryptophol. In certain embodiments, the psilocybin analogue is 4-hydroxy-indole-3-acetaldehyde. In certain embodiments, the psilocybin analogue is 4-hydroxy-indole-3-acetic acid. In certain embodiments, the psilocybin analogue is norpsilocin. In certain embodiments, the psilocybin analogue is aeruginascin. In certain embodiments, the psilocybin analogue is baeocystin. In certain embodiment, the psilocybin analogue is norbaeocystin. In certain embodiments, the psilocybin analogue is 4-hydroxy-N-methyl-N-ethyltryptamine (4-OH-MET). In certain embodiment, the psilocybin analogue is 4-hydroxydiethyltryptamine (4-OH-DET). In certain embodiment, the psilocybin analogue is 4-hydroxy-N N-dipropyltryptamine (4-OH-DPT). In certain embodiments, the psilocybin analogue is 4-hydroxy-N,N-diisopropyltryptamine (4-OH-DiPT). In certain embodiments, the psilocybin analogue is N,N-dimethyltryptamine (DMT). In certain embodiments, the psilocybin analogue is indole-3-acetic acid. In certain embodiments, the psilocybin analogue is N,N-dimethyltryptamine-N-oxide (DMT-NO). In certain embodiments, the psilocybin analogue is lysergic acid diethylamide (LSD). In certain embodiments, the psilocybin analogue is O-acetylpsilocin (4-AcO-DMT). In certain embodiments, the psilocybin analogue is 5-meth oxy-N,N-dimethyltryptamine (5-MeO-DMT). In certain embodiments, the psilocybin analogue is bufotenin (5-0H-DMT). In certain embodiments, the psilocybin analogue is ibogaine.

In certain embodiments, exemplary compounds have the structure as shown in Structure (1):

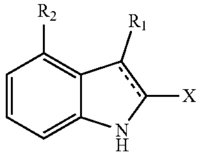

wherein:

X is H, $CF_3$, or a halogen that is selected from the group consisting of F, Cl, Br, I, or astatine; $R_1$ comprises an aliphatic substituent with a primary, secondary, tertiary, or quaternary amine; $R_2$ is hydrogen, hydroxyl, ester, ethers, aldehydes, acids, amides, thiols, sulfones, sulfonamides or combinations thereof.

In certain embodiments, the psilocybin analogues and combinations thereof, provided herein include any compound that is structurally related to psilocybin and functionally mimics and/or antagonizes the action of serotonin.

In certain embodiments, exemplary psilocybin analogues and combinations thereof, are the compounds provided in Table (2):

In certain embodiments, the pharmaceutical formulations and compositions comprising an active pharmaceutical ingredient that is either (a) an in dole of the genus compound of the structures of Structure (1), (2), (3), (b) Table (1), (c) psilocybin analogues, or (d) Table (2) and combinations thereof, can be used in combination with other active agents.

In certain embodiments, the pharmaceutical formulations comprise MAOIs. MAOIs are drugs in a family of enzymes that catalyze the oxidation of monoamines, and certain psilocybin analogues and combinations thereof are known to be enzymatically degraded by MAOIs. The MAOIs, include but are not limited to harmala alkaloids, harmine, harmane, harmaline, hydrazine, iproniazid, isocarboxazid, nialamide, phenelzine, hydracarbazine, tranylcypromine, bifemelane, moclobemide, pirlindole, toloxatone, rasagiline, selegiline, safinamide, and other reversible inhibitors of monoamine oxidase A (RIMAs).

Certain embodiments herein encompass pharmaceutical formulations and compositions comprising an active pharmaceutical ingredient that is either (a) an indole of Structure (1) or (b) psilocybin analogues and combinations thereof, and optionally a monoamine oxidase inhibitor (also known as MAO inhibitors or MAOIs), wherein the formulations and compositions are prepared for transdermal administration.

Certain embodiments herein encompass pharmaceutical formulations and compositions comprising an active pharmaceutical ingredient that is either (a) an indole of Structure (1), Structure (2) or Structure (3), or (b) psilocybin analogues and combinations thereof, and optionally a monoamine oxidase inhibitor (also known as MAO inhibitors or MAOIs), wherein the formulations and compositions are prepared for oral administration. In certain embodiments, 5-HT antagonists can be used as an allosteric modulator or to improve therapeutic benefit of the psilocybin analogues. It is known that certain 5-HT antagonists can reduce pyschoactivity induced by the psilocybin analogues, which can be beneficial for treatment or to reduce side effects. Certain 5-HT antagonists include but are not limited to: ketanserin, clozapine, olanzapine, quetiapine, risperidone, asenapine, cyproheptadine, trazadone, mirtazapine, nefazodone, niaprazine, pizotifen, metergoline, or 2-bromo-LSD (BOL-148).

In certain embodiments, the pharmaceutical formulations and compositions comprising the active pharmaceutical ingredient of (a) an indole of Structure (1), Structure (2) or Structure (3), or (b) psilocybin analogues and combinations thereof are used for treating neurological, mood and abuse disorders. These formulations and compositions may be prepared for transdermal administration.

In certain embodiments, the pharmaceutical formulations and compositions comprising the active pharmaceutical ingredient of (a) an indole of the genus compound of the structures of Structure (1), (2), (3), (b) Table (1), (c) psilocybin analogues, or (d) Table (2) and combinations thereof are used for treating neurological, mood and abuse disorders. These formulations and compositions may be prepared for nasal administration.

In certain embodiments, the pharmaceutical formulations and compositions comprising the active pharmaceutical ingredient of ((a) an indole of the genus compound of the structures of Structure (1), (2), (3), (b) Table (1), (c) psilocybin analogues, or (d) Table (2) and combinations thereof are used for treating neurological, mood and abuse disorders. These formulations and compositions may be prepared for oral administration. Particular embodiments relate to the use an active pharmaceutical ingredient of (a) an indole of the genus compound of the structures of Structure (1), (2), (3), (b) Table (1) (c) psilocybin analogues, or (d) Table (2) and combinations thereof, for the preparation of pharmaceutical formulations and compositions for treating particular medical indications, as provided herein. The pharmaceutical formulations and compositions are intended for the transdermal delivery of the active pharmaceutical ingredient of (a) an indole of the genus compound of the structures of Structure (1), (2), (3), (b) Table (1), (c) psilocybin analogues, or (d) Table (2) and combinations thereof, in subjects in need thereof. Transdermal formulations can be manufactured in the form of sprayable liquids, gels, creams, lotions, ointments, and transdermal patches and are applied topically to the desired area.

Particular embodiments relate to the use an active pharmaceutical ingredient of (a) an indole of the genus compound of the structures of Structure (1), (2), (3), (b) Table (1), (c) psilocybin analogues, or (d) Table (2) and combinations thereof, for the preparation of pharmaceutical formulations and compositions for treating particular medical indications, as provided herein. The pharmaceutical formulations and compositions are intended for the oral delivery of the active pharmaceutical ingredient of (a) an indole of the genus compound of the structures of Structure (1), (2), (3), (b) Table (1), (c) psilocybin analogues, or (d) Table (2) and combinations thereof, in subjects in need thereof. Oral formulations can be manufactured in the form of tablets, capsules, softgels, strips, oral patch's and are intended for oral delivery to patient in need of therapy.

In certain embodiments the pharmaceutical formulations may be formulated for immediate release of the API. In certain embodiments the immediate release formulations are transdermal or nasal compositions In certain embodiments the pharmaceutical formulations may be formulated for immediate release of the API. In certain embodiments the immediate release formulations are oral compositions.

In certain embodiments the pharmaceutical formulations may be formulated for modified release of the API. In certain embodiments the immediate release formulations are transdermal compositions.

In certain embodiments the pharmaceutical formulations may be formulated for modified release of the API. In certain embodiments the immediate release formulations are oral compositions.

In certain embodiments, the transdermal composition comprises a transdermal patch or nasal formulation that delivers the active pharmaceutical ingredient across the skin or mucosal membrane into the bloodstream. In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for transdermal or nasal administration.

In certain embodiments, the formulations of an active pharmaceutical ingredient of (a) an indole of the genus compound of the structures of Structure (1), (2), (3), (b) Table (1), (c) psilocybin analogues, or (d) Table (2) and combinations thereof, effect an immediate release of the active pharmaceutical ingredient into the plasma upon transdermal, nasal or oral administration. In particular embodiments, the formulations comprising an active pharmaceutical ingredient of (a) an indole of the genus compound of the structures of Structure (1), (2), (3), (b) Table (1), (c) psilocybin analogues, or (d) Table (2) and combinations thereof, comprise a therapeutically or prophylactically effective amount of the active pharmaceutical ingredient, and, optionally, one or more excipients.

In certain embodiments of the inventive transdermal, nasal, or oral formulation use psilocybin and psilocybin analogues and combinations thereof, that may be derived synthetically or bioengineered; or extracted from naturally occurring mushrooms that have been well described in the art.

In certain embodiments of the inventive transdermal, nasal or oral formulation use psilocybin and psilocybin analogues and combinations thereof, that may be derived synthetically or bioengineered; or extracted from naturally occurring mushrooms using novel chemical synthesis or extraction techniques as described herein.

In certain embodiments the transdermal pharmaceutical dosage composition is in the form of sprayable liquids, gels, creams, lotions, ointments and transdermal patches, wherein the active pharmaceutical ingredient is infused with inactive ingredients that enhance the delivery properties of the composition and stabilize the active pharmaceutical ingredient.

In one embodiment, penetration enhancers may be an inactive ingredient. The penetration enhancers may include fatty acids and oils that may be, but are not limited to: castor oil, coconut oil, medium chain triglycerides (MCT), jojoba oil, sunflower oil, argan oil, almond oil, olive oil, mineral oil, petroleum jelly, cocoa butter, shea butter, or other esters, triglycerides, or functional derivatives thereof.

In certain embodiments, the surfactants may be used in the transdermal delivery system as emulsifiers and stabilizers can encapsulate drugs for better stability and permeability properties. Surfactants include but are not limited to: polysorbates (e.g. Tween, polysorbate 20), sorbitans (Span), phospholipids (lecithin), lauryl sulfates, betaines, propionates, fatty alcohols and alkanolamides, fatty acid esters, amine oxides, myristates, and azones.

In certain embodiments, co-solvents may be used in the transdermal formulation to improve drug solubility and permeability, while acting as a humectant for better skin feel. Common co-solvents include but are not limited to: alcohols such as ethanol, isopropanol, glycerin, propylene glycol, dipropylene glycol, polyethylene glycol, diethylene monoethyl ether, Cremophores, siloxanes, polyethylenes, and water.

In certain embodiments, thickeners may be used in the transdermal formulation to reduce separation and provide a suitable matrix for modified delivery. Common thickeners include but are not limited to: acrylates, carbomers, cellulose matrices, silicones, carrageenans, gums, resins, polysaccharides, and high melting point waxes and oils such as beeswax, coconut oil, palm oil, soybean oil, stearic acid, rapeseed, cocoa butter, shea butter, gums, rosins, resins, paraffins, and petroleum jelly.

In certain embodiments, tackifiers may be used in the transdermal formulation to increase adhesion for extended wearability. Common tackifiers include but are not limited to gums, resins (natural or modified), carbomers, or other natural or synthetic polymers.

In certain embodiments, preservatives may be used in the transdermal formulation to improve formulation stability and retard microbial growth. Common preservatives include but are not limited to: parabens, sorbates, benzoates, silicas, chlorides, phenols, chlorhexidine, citric acid, triclosan, Vitamin E (or tocopherols), chelators, metals, salts, and alcohols. Lastly the formulation is typically emulsified with a hydrophilic ingredient such as water, or Aloe barbadensis juice.

In certain embodiments, the formulations comprising an active pharmaceutical ingredient of (a) an indole of Structure (1) or (b) psilocybin analogues and combinations thereof effect a controlled release of the active pharmaceutical ingredient transdermally upon administration. In certain embodiments, the formulations comprising the active pharmaceutical ingredient comprise a therapeutically or prophylactically effective amount of the active pharmaceutical ingredient(s) and a drug release controlling component that is capable of controlled and sustained release of the active pharmaceutical ingredients directly into the bloodstream.

In certain embodiments, the transdermal dosage form is a transdermal delivery device. Any device conventional in the art for transdermally delivering a therapeutic agent to a patient can be used for the transdermal delivery of the compositions of the invention and as the transdermal delivery device. For example, the transdermal delivery device can be a reservoir-type transdermal delivery device, a polymer-matrix type transdermal delivery device, or a drug-in-adhesive type transdermal delivery device or a multilaminate type transdermal delivery device. The transdermal delivery device is designed so that when contacted with the patient's skin, the active pharmaceutical ingredient of the present invention is delivered in a therapeutically effective amount.

In certain embodiments, the transdermal delivery device is of the drug-in-adhesive type device comprising the active pharmaceutical ingredient dispersed directly in a pressure-sensitive adhesive matrix. The adhesive matrix is preferably supported on the topside with an impermeable backing film and on the side that faces the skin with an impermeable release liner. To administer the active pharmaceutical ingredient, the release liner is removed to expose the adhesive matrix, and the device is contacted with the skin. The adhesive matrix functions to adhere the device to the skin and, typically, to control the delivery rate of the active pharmaceutical ingredient. Similar to the polymer-matrix design, the drug-in-adhesive design allows the active pharmaceutical ingredient to diffuse out of the adhesive matrix, contact the patient's skin and penetrate the skin. The delivery rate of the active pharmaceutical ingredient is usually determined by the rate of diffusion of the active pharmaceutical ingredient(s) out of the adhesive matrix. Multiple drug-in-adhesive layers can be laminated together between rate-controlling membranes for longer, extended delivery. The delivery rate is such that effective amount of the active pharmaceutical ingredient is delivered to the patient in need of the active pharmaceutical ingredient.

In certain embodiments, a reservoir-type transdermal delivery device preferably comprises a reservoir, usually a liquid, or semisolid located between an impermeable backing film and a rate-controlling membrane that is covered with a pressure-sensitive adhesive skin-contacting layer. The reservoir, which may be a solution or a dispersion, contains the composition of the invention. The transdermal delivery device is preferably supported by the impermeable backing film and the adhesive surface is protected by a release liner. To administer the active pharmaceutical ingredient of the present invention, the release liner is removed to expose the pressure-sensitive adhesive and the pressure-sensitive adhesive is contacted with the skin. The active pharmaceutical ingredient of the present invention is permeable through the rate-controlling membrane, and penetrates through it and the adhesive, contacts the skin, and then penetrates the skin. The delivery rate of the active pharmaceutical invention is usually determined by the rate that the active pharmaceutical ingredient penetrates the rate-controlling membrane.

In certain embodiments, the transdermal delivery device is of the polymer-matrix design. In the polymer-matrix design, the psilocybin analogue and combinations thereof, are dispersed in a polymer matrix that controls the delivery rate of the active pharmaceutical ingredient. Preferably the polymer-matrix reservoir is supported on an impermeable backing layer. An adhesive layer is attached to the surface of the polymer matrix. To administer the active pharmaceutical ingredients the release liner is removed to expose the polymer matrix and the ring of pressure-sensitive adhesive, and the device is contacted with the skin. The adhesive holds the device against the skin so that the polymer matrix directly contacts the skin. When the polymer matrix is contacted with the skin, the active pharmaceutical ingredient (s) diffuse out of the polymer matrix, contacts the patient's skin, and penetrates the skin. The delivery rate of the active pharmaceutical ingredients is usually determined by the rate of diffusion active pharmaceutical ingredient out of the polymer matrix.

Adhesives comprise cross-linking monomeric units or sites can be incorporated into the adhesive polymers. For example, cross-linking monomers can be incorporated into polyacrylate polymers. The cross-linking monomers may, for example, provide sites for cross-linking the polymer matrix after dispersing the psilocybin analogue and combinations thereof, into the polymer. Known adhesives comprise cross-linking monomers for polyacrylate polymers include, for example, polymethacrylic esters of polyols such as butylene diacrylate, butylene dimethacrylate and trimethylol propane trimethacrylate, polyisobutylene type adhesives and silicone. Other monomers that provide cross-linking sites include allyl acrylate, allyl methacrylate, diallyl maleate, silyl ethers, and silanes. Monomers are then polymerized using methods known by those skilled in the art to comprise polyacrylate (acrylics), polysiloxane (silicones), or polyisobutylene (or other rubber) adhesive matrices containing cross-linkers, functional groups, or vinyl acetate to suspend, stabilize, and release the active pharmaceutical ingredient.

In an embodiment of the present invention, the transdermal delivery device may optionally include one or more penetration enhancers, which increase the rate at which the active pharmaceutical ingredients penetrate through the patient's skin. Preferably, the penetration enhancer penetrates the rate-controlling membrane or diffuses out of the polymer matrix or adhesive matrix so that it can contact the patient's skin and improve penetration of active pharmaceutical ingredient as defined herein through the patient's skin. Suitable penetration enhancers for use in the transdermal delivery devices and compositions of the invention include, for example, $C_{2-4}$ alcohols, e.g., ethanol and isopropanol, polyethylene glycol monolaurate, polyethylene glycol-3-lauramide, dimethyl lauramide, polysorbates, sorbitans, fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene. In certain embodiments, the transdermal patches as described herein are used co-administered with penetration enhancers. In certain embodiments, the penetration enhancers may include oils that may be, but are not limited to: castor oil, coconut oil, medium chain triglycerides (MCT), jojoba oil, sunflower oil, argan oil, almond oil, olive oil, mineral oil, petroleum jelly, cocoa butter, and shea butter. Other penetration enhancers for use in transdermal patches include, for example, $C_{2-4}$ alcohols, e.g., ethanol and isopropanol, polyethylene glycol monolaurate, polyethylene glycol-3-lauramide, dimethyl lauramide, polysorbates (Tween), sorbitans (Span), fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene.

In certain embodiments, the delivery rate of the active pharmaceutical ingredient may be delivered in a once a day transdermal patch application. In certain embodiments, the delivery rate of the API may be delivered over the course of 6-12 hours. In certain embodiments, the delivery rate of the API may be delivered over 12-24 hours. In certain embodiments the delivery rate of the API may be delivered over 24-48 hours. In other embodiments, the transdermal patch may be applied once every 2 days; once every 3 days; once every 4 days; once every 5 days; once every 5 days; or once every 7 days. The transdermal patch delivery rate options will facilitate patient dosing compliance while delivering a steady-state systemic safe and effective drug concentrations.

As described herein, certain embodiments provide transdermal formulations of active pharmaceutical ingredient as described herein, useful in methods relating to differing dosage amounts and/or dosage periods; providing alternative pharmacokinetic profiles, pharmacodynamic profiles, and/or safety profiles; permitting long term maintenance therapies; providing for the testing of new indications for the psilocybin analogues; and other potential advantageous benefits. In particular embodiments formulations provided herein (e.g. sprayable liquids, gels, creams, lotions, ointments, or transdermal patch for the dermal delivery of the active pharmaceutical ingredient) comprise the active pharmaceutical ingredients ((a) an indole of the genus compound of the structures of Structure (1), (2), (3), (b) Table (1), (c) psilocybin analogues, or (d) Table (2) alone or in combination) in a specific: pharmaceutically active amount. In particular embodiments, the specific amount of the active pharmaceutical ingredient as disclosed herein, in the formulation is, e.g. about 1 mg, about 2 mg, about 3 mg, about 4 mg, about 5 mg, about 6 mg, about 7 mg, about 8 mg, least about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg about 23 mg, about 24 mg, about 25 mg, about 26 mg, about 27 mg, about 28 mg, about 29 mg, about 30 mg, about 31 mg about 32 mg, about 33 mg, about 34 mg, about 35 mg about 36 mg, about 37 mg, about 38 mg, about 39, about 40 mg, about 45 mg, about 50 mg, about 55 mg, about 60 mg, about 65 mg, about 70 mg, about 75 mg, about 80 mg, about 85 mg, about 90 mg, about 95 mg, or at least 100 mg. In particular embodiments, the specific amount of the psilocybin analogue in the formulation is, e.g., at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least 40 mg, at least 45 mg, at least 50 mg, at least about 55 mg, at least about 60 mg, at least about 65 mg, at least about 70 mg, at least about 75 mg, at least about 80 mg, at least about 85 mg, at least about 90 mg, at least about 95 mg, or at least 100 mg.

In more particular embodiments, the specific amount of the active pharmaceutical ingredient as disclosed herein, in the formulation is, e.g. about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg about 23 mg, about 24 mg, about 25 mg, about 30 mg, about 35 mg, about 40 mg, about 45 mg, about 50 mg, about 55 mg about 60 mg, about 65 mg, about 70 mg, about 75 mg about 80 mg, about 85 mg, about 90 mg, or at least 100 mg.

In more particular embodiments, the specific amount of the active pharmaceutical ingredient in the formulation is, e.g., at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, or at least 100 mg.

In a particular embodiment the active pharmaceutical ingredient in the pharmaceutical formulation is from about 5 mg to 100 mg, or from about 5 mg to 25 mg, or from about 25 mg to 50 mg, or from about 50 mg to 75 mg, or from about 75 mg to 100 mg.

As described herein, certain embodiments provide transdermal formulations of active pharmaceutical ingredient as described herein, relating to the skin application size for transdermal delivery devices. Application area is a crucial metric for determining drug fluxes, to differ dosage, and to provide sufficient area for efficient transdermal delivery. In particular embodiments the API (compounds of (a) are indole of the genus compound of the structures of Structure (1), (2), (3), (b) Table (1), (c) psilocybin analogues, or (d) Table (2) (alone or in combination) is contained within a drug delivery device (e.g. sprayable liquids, gels, creams, lotions, ointments, or transdermal patch) and is applied to the skin of a human or mammal in an area of not more than 1 cm, or at least 2 $cm^2$, at least 3 $cm^2$, at least 4 $cm^2$, at least 5 $cm^2$, at least 6 $cm^2$, at least 7 $cm^2$, at least 8 $cm^2$, at least 9 $cm^2$, at least 10 $cm^2$, at least 15 $cm^2$, at least 20 $cm^2$, at least 25 $cm^2$, at least 30 $cm^2$, at least 35 $cm^2$, at least 40 $cm^2$, at least 45 $cm^2$, at least 50 $cm^2$, at least 60 $cm^2$, at least 70 $cm^2$, at least 80 $cm^2$, at least 90 $cm^2$, or at least 100 $cm^2$ at least 150 $cm^2$, at least 200 $cm^2$, at least 250 $cm^2$, at least 300 $cm^2$, at least 350 $cm^2$, at least 400 $cm^2$, at least 450 $cm^2$, at least 500 $cm^2$, at least 600 $cm^2$, at least 700 $cm^2$, at least 800 $cm^2$, at least 900 $cm^2$, or at least 1000 $cm^2$.

In particular embodiments the API alone or in combination, is contained within a drug delivery device (e.g. sprayable liquids, gels, creams, lotions, ointments, or transdermal patch) and is applied to the skin of a human or mammal in an area of not more than 1 cm, or at least 2 $cm^2$, at least 3 $cm^2$, at least 4 $cm^2$, at least 5 $cm^2$, at least 6 $cm^2$, at least 7 $cm^2$, at least 8 $cm^2$, at least 9 $cm^2$, at least 10 $cm^2$, at least 15 $cm^2$, at least 20 $cm^2$, at least 25 $cm^2$, at least 30 $cm^2$, at least 35 $cm^2$, at least 40 $cm^2$, at least 45 $cm^2$, at least 50 $cm^2$, at least 60 $cm^2$, at least 70 $cm^2$, at least 80 $cm^2$, at least 90 $cm^2$, or at least 100 $cm^2$.

In an embodiment the API alone or in combination is applied to the skin of a human or mammal in an area from about 1 $cm^2$ to 10 $cm^2$, from about 10 $cm^2$ to 40 $cm^2$, from about 40 $cm^2$ to 100 $cm^2$, or more preferably 5 $cm^2$ to 40 $cm^2$ In certain embodiments the active pharmaceutical ingredients are delivered in an oral pharmaceutical formulation composition comprising a capsule or tablet that delivers the API into the bloodstream through the esophageal, gastric, and/or intestinal membranes.

In certain embodiments the oral composition is swallowed and the active pharmaceutical ingredients are further delivered into the bloodstream through the esophageal, gastric, and/or intestinal membranes.

In certain embodiments the oral composition comprises a tablet, wafer, or strip that delivers the active pharmaceutical ingredient into the bloodstream through the sublingual, buccal, or other oral mucosal membrane.

In certain embodiments the oral composition comprises an oral patch or oral film that delivers the active pharmaceutical ingredient into the bloodstream through the sublingual, buccal, or other oral mucosal membrane.

In certain embodiments the oral composition is swallowed, and the active pharmaceutical ingredients are further delivered into the bloodstream through the esophageal, gastric, and/or intestinal membranes.

In certain embodiments the oral composition comprises a powder, solution, or suspension that delivers the active pharmaceutical ingredient into the bloodstream through the sublingual, buccal, or other oral mucosal membrane.

In certain embodiments the oral composition is swallowed, and the active pharmaceutical ingredients are further delivered into the bloodstream through the esophageal, gastric, and/or intestinal membranes.

In certain embodiments, the formulations of active pharmaceutical ingredient of (a) an indole of the genus compound of the structures of Structure (1), (2), (3), (b) Table (1), (c) psilocybin analogues, or (d) Table (2) and combinations thereof, effect an immediate release of the active pharmaceutical ingredient into the plasma upon oral administration. In particular embodiments, the formulations comprising an active pharmaceutical ingredient of (a) an indole of the genus compound of the structures of Structure (1), (2), (3), (b) Table (1) (c) psilocybin analogues, or (d) Table (2) and combinations thereof, comprise a therapeutically or prophylactically effective amount of the active pharmaceutical ingredient, and, optionally, one or more excipients.

In certain embodiments, the formulations of active pharmaceutical ingredient of (a) an indole of (a) an indole of the genus compound of the structures of Structure (1), (2), (3), (b) Table (1), (c) psilocybin analogues, or (d) Table (2) and combinations thereof, effect a modified release of the active pharmaceutical ingredient into the plasma upon oral administration. In particular embodiments, the formulations comprising an active pharmaceutical ingredient of (a) an indole of the genus compound of the structures of Structure (1), (2), (3), (b) Table (1), (c) psilocybin analogues, or (d) Table (2) and combinations thereof, comprise a therapeutically or prophylactically effective amount of the active pharmaceutical ingredient, and, optionally, one or more excipients.

In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for oral administration.

In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for oral administration.

In certain embodiments the oral composition contains inactive ingredients that enhance drug delivery properties and stabilize the active ingredient.

In one embodiment fillers may be included as an inactive ingredient. The fillers can act as matrix to affect the dissolution time or act as binders to improve tablet stability. The fillers may include but are not limited to: starch, citric acid, tartaric acid, bicarbonates, phosphates, polyvinyl pyrrolidone, cellulose (natural and modified), croscarmellose, glycolates, acrylates, acetates, gelatin, gums, alginates, pectin, chitosan, chitin, salts, polysaccharides, mucilages, sugars, sucrose, lactose, and dextrose.

In another embodiment, lubricants may be included as an inactive ingredient. The lubricants act to improve powder flowability or reduce friction on manufacturing parts; these may include but are not limited to: magnesium stearate, talc, stearic acid, and silicon dioxide.

In yet another embodiment, flavorings may be included as an inactive ingredient. The flavorings can mask the taste of bitter agents or improve the taste of the oral composition; these include but are not limited to: sugars, dextrose, sucrose, sucralose, stevia, essential oils, citric acid, and natural or artificial flavorings. Optionally, coloring agents can be included in the powders to improve visual properties or to differentiate product offerings; these coloring agents can be natural or artificial dyes, pigments, chelates, or metals.

In certain embodiments the oral composition contains surfactants that are emulsifiers and stabilizers that can encapsulate drugs for better stability, taste, permeability, and drug release properties. Surfactants include but are not limited to vegetable oils, triglycerides, esters, polysorbates (Tween), sorbitans (Span), phospholipids (e.g. lecithin), lauryl sulfates, betaines, propionates, fatty acids, fatty alcohols, saponins and alkanolamides, amine oxides, cyclodextrins, myristates and azones.

In certain embodiments the oral composition contains co-solvents to improve drug solubility, dissolution, and permeability. Co-solvents include but are not limited to: alcohols such as ethanol, isopropanol, glycerin, propylene glycol, dipropylene glycol, polyethylene glycol, diethylene monoethyl ether, Cremophores, siloxanes, polyethylenes, and water.

In certain embodiments the oral composition contains thickeners to reduce dissolution and provide a suitable matrix for delivery. Thickeners include but are not limited to: acrylates, carbomers, cellulose matrices, silicones, carrageenans, polysaccharides, and high melting point waxes and oils such as beeswax, coconut oil, palm oil, soybean oil, stearic acid, rapeseed, cocoa butter, shea butter, gums, rosins, resins, paraffins, and petroleum jelly.

In certain embodiments the oral composition contains preservatives to improve formulation stability and retard microbial growth. Preservatives include but are not limited to: parabens, sorbates, benzoates, silicas, chlorides, phenols, chlorhexidine, citric acid, triclosan, Vitamin E (or tocopherols), chelators, metals, salts, and alcohols.

In certain embodiments the oral composition contains enteric coatings to modify and extend release within the gastrointestinal tract. Enteric coatings include high melting point waxes, fatty acids, sugars, fibers, and polymers and others.

In another embodiment the oral composition contains inactive ingredients that change the physical properties of the drug delivery system such as pH, solubility, dissolution, hydrophobicity, and stability. Many such compounds are known to those of skill in the art.

In certain embodiments the oral composition contains membrane penetration enhancers to increase systemic delivery. Suitable penetration enhancers for use in the oral composition include, for example, $C_{2-4}$ alcohols, e.g. ethanol and isopropanol, polyethylene glycol monolaurate, polyethylene glycol-3-lauramide, dimethyl lauramide, sorbitans (Span), polysorbates (e.g. Tween, polysorbate 20), fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and triglycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene.

In certain embodiments the active pharmaceutical ingredient of (a) an indole of (a) an indole of the genus compound of the structures of Structure (1), (2), (3), (b) Table (1), (c) psilocybin analogues, or (d) Table (2) and combinations thereof is included in at least one matrix of the oral composition. In another embodiment active pharmaceutical ingredient of ((a) an indole of the genus compound of the structures of Structure (1), (2), (3), (b) Table (1), (c) psilocybin analogues, or (d) Table (2) and combinations thereof is included in at least two matrices of the oral composition. In another embodiment the active pharmaceutical ingredient of (a) an indole of the genus compound of the structures of Structure (1), (2), (3), (b) Table (1), (c) psilocybin analogues, or (d) Table (1) and combinations thereof is included in at least three matrices of the oral composition. In another embodiment the active pharmaceutical ingredient of (a) an indole of (a) an indole of the genus compound of Structure (1), (2), (3), (b) Table (1), (c) psilocybin analogues, or (d) Table (2) and combinations thereof is included in at least four matrices of the oral composition. In yet another embodiment the active pharmaceutical ingredient of (a) an indole of the genus compound of Structure (1), (2), (3), (b) Table (1), (c) psilocybin analogues, or (d) Table (2) and combinations thereof is included in at least five matrices of the oral composition.

In certain embodiments the active pharmaceutical ingredients are single active ingredients. In a preferred embodiment the compounds of (a) an indole of the genus compound of the structures of Structure (1), (2), (3), (b) Table (1), (c) psilocybin analogues, or (d) Table (2) are orally administered in a capsule. In a preferred embodiment the compounds of (a) an indole of the genus compound of Structure (1), (2), (3), (b) Table 1, (c) psilocybin analogues, or (d) Table (2) are orally administered in a tablet. In a preferred embodiment the compounds of (a) an indole of the genus compound of the structures of Structure (1), (2), (3), (b) Table (1), (c) psilocybin analogues, or (d) Table (2) are orally administered in a wafer. In a preferred embodiment the compounds of (a) an indole of the genus compound of the structures of Structure (1), (2), (3), (b) Table (1), (c) psilocybin analogues, or (d) Table (2) is orally administered in a strip. In a preferred embodiment the compounds of (a) an indole of the genus compound of Structure (1), (2), (3), (b) Table (1), (c) psilocybin analogues, or (d) Table (2) is orally administered in a transdermal patch. In a preferred embodiment the compound of (a) an indole of the genus compound of the structures of Structure (1), (2), (3), (b) Table (1), (c) psilocybin analogues, or (d) Table (2) is orally administered in a powder. In a preferred embodiment the compounds of (a) an indole of the genus compound of the structures of Structure (1), (2), (3), (b) Table (1), (c) psilocybin analogues, or (d) Table (2) is orally administered in a suspension. In a preferred embodiment the compounds of (a) an indole of the genus compound of the structures of Structure (1), (2), (3), (b) Table (1), (c) psilocybin analogues, or (d) Table (2) is orally administered in a solution.

In another embodiment mixtures of psilocybin analogues are delivered in the same oral composition as described herein. In a preferred embodiment the compounds of (a) an indole of the genus compound of the structures of Structure (1), (2), (3), (b) Table (1), (c) psilocybin analogues, or (d) Table (2) is orally administered either singularly or in combination with other (a) an indole of the genus compound of the structures of Structure (1), (2), (3), (b) Table (1), (c) psilocybin analogues, or (d) Table (2) in an oral composition as described herein.

In certain embodiments the oral composition contains at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 60 mg, at least 70 mg, at least 80 mg, at least 90 mg, at least 100 mg, at least 120 mg, at least 140 mg, at least 160 mg, at least 180 mg, at least 200 mg, at least 250 mg, at least 300 mg, at least 350 mg, at least 400 mg, at least 450 mg, and/or at least 500 mg of the active pharmaceutical ingredient of (a) an indole of the genus compound of the structures of Structure (1), (2), (3), (b) Table (1), (c) psilocybin analogues, or (d) Table (2) and combinations thereof.

In certain embodiments the systemic drug release of the oral composition containing the active pharmaceutical ingredient of (a) an indole of the genus compound of the structures of Structure (1), (2), (3), (b) Table (1), (c) psilocybin analogues, or (d) Table (2) and combinations thereof occurs with therapeutically active onset of not more than 1 minute, not more than 3 minutes, not more than 5 minutes, not more than 7 minutes, not more than 9 minutes, not more than 11 minutes, not more than 13 minutes, not more than 15 minutes, not more than 17 minutes, not more than 19 minutes, not more than 21 minutes, not more than 23 minutes, not more than 25 minutes, not more than 27 minutes, not more than 30 minutes, not more than 45 minutes, not more than 60 minutes, not more than 90 minutes, not more than 120 minutes, not more than 150 minutes, and not more than 180 minutes.

In certain embodiments the duration of the therapeutic or prophylactic effect of the oral composition containing the active pharmaceutical ingredient of (a) an indole of the genus compound of the structures of Structure (1), (2), (3), (b) Table (1), (c) psilocybin analogues, or (d) Table (2) and combinations thereof sustains for at least 5 minutes, at least 15 minutes, at least 30 minutes, at least 45 minutes, at least 60 minutes, at least 90 minutes, at least 120 minutes, at least 3 hours, at least 4 hours, at least 5 hours, at least 6 hours, at least 8 hours, at least 10 hours, at least 12 hours, at least 18 hours, at least 1 day, at least 2 days, at least 3 days, at least 4 days, at least 5 days, at least 6 days, and at least 1 week.

As described herein, certain embodiments provide oral compositions of active pharmaceutical ingredient as described herein, useful in methods relating to differing dosage amounts and/or dosage periods; providing alternative pharmacokinetic profiles, pharmacodynamic profiles, and/or safety profiles; permitting long term maintenance therapies; providing for the testing of new indications for the psilocybin analogues; and other potential advantageous benefits.

Provided herein are methods of preventing, managing, and treating neurological, mood or addictive disorders including post-treatment Lyme disease syndrome, dementia s, Alzheimer's disease, post-traumatic stress disorder, anorexia nervosa, depression, anxiety, addiction, substance abuse including but not limited to opioid addiction, alcohol addiction, nicotine addiction, cannabinoid addiction, headache, central nervous system inflammation, dementia, cognition and memory by administering psilocybin analogues transdermally, intranasally, or orally.

In certain embodiment the active pharmaceutical ingredients are single active pharmaceutical ingredients. In a preferred embodiment, the compounds of (a) an indole of the genus compound of the structures of Formula (1), (Z), (3), (b) Table (1), (c) psilocybin analogues, or (d) Table (2) delivered in a transdermal patch delivery system. In a preferred embodiment, the active pharmaceutical ingredient is transdermally delivered in a transdermal patch delivery system.

In another embodiment, mixtures of psilocybin analogues are delivered in the same transdermal delivery system. In a preferred embodiment the psilocybin analogue is transdermally delivered either singularly or in combination with other psilocybin analogues in a transdermal patch delivery system.

In another embodiment, the active pharmaceutical ingredients thereof are co-administered with one or more therapeutic agent. The co-administered agent may be MAOI. In another embodiment, a compound from another class of neurologically active agents is co-administered providing for a synergistic therapeutic effect is. Other neurologically active agents include those compounds that fall into the following classes of compounds: antipsychotics, antidepressants, anxiolytics, stimulants, reuptake inhibitors (SSRI or SSNRI), monoamine oxidase inhibitors (MAOI), cognitive-enhancing agents, tricyclic antidepressants, mood stabilizers, NMDA antagonists and 5-HT antagonists.

In yet another embodiment, the (a) an indole of the genus compound of the structures of Structure (1), (2), (3), (b) Table (1), (c) psilocybin analogues, or (d) Table (2), either singularly or in mixtures, are co-administered with one or more therapeutic agents to reduce substance abuse. For the treatment of opioid addiction, other co-administered compounds can include: methadone, buprenorphine, naloxone, naltrexone, and the like. For the treatment of alcoholism, other co-administered compounds can include ethyl alcohol, disulfiram, naltrexone, acamprosate, benzodiazepines, and the like. For the treatment of nicotine addiction, other co-administered compounds can include low dose nicotine, Bupropion, Varenicline and the like.

Provided herein are methods of preventing, managing, treating neurological, mood or addictive disorders including post-treatment Lyme disease syndrome, dementias, Alzheimer's disease, post-traumatic stress disorder, anorexia nervosa, depression, anxiety, addiction, substance abuse including but not limited to opioid addiction, alcohol addiction, nicotine addiction, cannabinoid addiction, headache, central nervous system inflammation, dementia, cognition and memory by administering psilocybin analogues transdermally.

EXAMPLES

Example 1

Purified N,N-dimethyltryptamine (DMT1.8% w/w, wet) was dissolved with a combination of ethyl acetate (7.2% w/w, wet) and ethanol (7.2% w/w, wet) and incorporated into a Duro-Tak 4098 acrylate adhesive (83.8% w/w, wet) and mixed thoroughly. The mixture was formulated to a 150 μm thickness onto the siliconized side of a Scotchpak 9709 release liner. The formulation was dried at 75° C. and laminated onto an occlusive Scotchpak 9733 polyester backing before cutting transdermal patches to a size of 10 $cm^2$. The final transdermal patches were stored within a heat-sealed aluminized pouch to reduce oxidation.

Linear drug release (n=3 transdermal patches) was observed over 72 hours with over 80% DMT released at 72 hours (FIG. 1). Average DMT flux was quantified at 37 $ug/cm^2$*hr over 72 hours.

Example 2

Purified DMT (2.0% w/w, wet) was dissolved in ethanol (8.0% w/w, wet) and incorporated into Duro-Tak 4098 adhesive (90.0% w/w, wet) and mixed thoroughly. The mixture was formulated to a 250 μm thickness onto a release liner. The formulation was dried and laminated onto an occlusive backing before cutting transdermal patches to a size of 10 $cm^2$. The final transdermal patches (6.4% w/w DMT) were stored within a heat-sealed aluminized pouch to reduce oxidation. Average DMT flux was quantified at 43 $\mu g/cm^2$*hr over 72 hours.

Example 3

Purified DMT (2.0% w/w, wet) was dissolved in ethanol (8.1% w/w, wet) and incorporated into silicone adhesives Bio PSA 7-4302 (44.9% w/w, wet) and Bio PSA 7-4202 (44.9% w/w, wet) and mixed thoroughly. The mixture was formulated to a 150 μm thickness onto a release liner. The formulation was dried and laminated onto an occlusive backing before cutting transdermal patches to a size of 10 $cm^2$. The final transdermal patches (3.9% w/w DMT) were stored within a heat-sealed aluminized pouch to reduce oxidation. Average DMT flux was quantified at 31 $\mu g/cm^2$*hr over 48 hours.

Example 4

Purified DMT (2.0% w/w, wet) was dissolved in ethanol (4.0% w/w, wet) and incorporated into a Duro-Tak 6908 polyisobutylene adhesive (94.0% w/w, wet) and mixed thoroughly. The mixture was formulated to a 150 μm thickness onto a release liner. The formulation was dried and laminated onto an occlusive backing before cutting transdermal patches to a size of 10 $cm^2$. The final transdermal patches (5.4% w/w DMT) were stored within a heat-sealed aluminized pouch to reduce oxidation. Average DMT flux was quantified at 7 μg/$cm^2$*hr over 30 hours.

Example 5

Purified DMT (3.8% w/w, wet) was dissolved in ethanol (15.9% w/w, wet) and incorporated into Duro-Tak 4098 adhesive (80.3% w/w, wet) and mixed thoroughly. The mixture was formulated to a 200 μm thickness onto a release liner. The formulation was dried and laminated onto an occlusive backing before cutting transdermal patches to a size of 10 $cm^2$. The final transdermal patches (10.9% w/w DMT) were stored within a heat-sealed aluminized pouch to reduce oxidation. Average DMT flux was quantified at 57 μg/$cm^2$*hr over 48 hours.

Example 6

Purified DMT (4.2% w/w, wet) was dissolved in ethanol (11.2% w/w, wet) and incorporated into a Duro-Tak 4098 acrylate adhesive (77.5% w/w, wet) before isopropyl myristate (7.1% w/w, wet) was added and mixed thoroughly. The mixture was formulated to a 200 μm thickness onto a release liner. The formulation was dried and laminated onto an occlusive backing before cutting transdermal patches to a size of 10 $cm^2$. The final transdermal patches (10.3% w/w DMT) were stored within a heat-sealed aluminized pouch to reduce oxidation. Average DMT flux was quantified at 145 μg/$cm^2$*hr over 48 hours.

Example 7

Purified 4-acetoxy-N,N-dimethyltryptamine (4-AcO-DMT, 3.2% w/w, wet) was dissolved in ethanol (12.4% w/w, wet) and incorporated into a Duro-Tak 4098 acrylate adhesive (84.4 w/w, wet) and mixed thoroughly. The mixture was formulated to a 200 μm thickness onto the siliconized side of a release liner. The formulation was dried and laminated onto an occlusive polyester backing before cutting transdermal patches to a size of 10 $cm^2$. The final transdermal patches (9.0% w/w 4-AcO-DMT) were stored within a heat-sealed aluminized pouch to reduce oxidation. Average 4-AcO-DMT flux was quantified at 98 μg/$cm^2$*hr over 48 hours.

Example 8

A second DIA with excipients listed above will be cast directly onto the backing and laminated onto a rate-controlling membrane. The DIA-coated liner from Example 1 will then be laminated to the backing/DIA/membrane material to form a multi-layered delivery system. The transdermal patch is then die cut to a suitable size.

The DIA cast on the liner, will then be applied directly on the skin, does not require as high of a drug loading as the second DIA. The second DIA acts as a reservoir and will diffuse drugs through the rate-controlling membrane after manufacture until equilibrium between the first DIA is achieved. Once applied, the second DIA will permeate drug in a zero-order rate through the membrane into the skin until drug reservoir is sufficiently depleted.

Example 9

N,N-dimethyltryptamine (DMT) freebase was dissolved in 25 mg/mL acetone. 7 mg/mL fumaric acid was added dropwise to precipitate DMT fumarate. The precipitate was washed with fresh acetone twice and dried under nitrogen.

DMT fumarate (18.0% w/w) was dissolved in deionized water (82.0% w/w) to afford a therapeutically effective aqueous gel vehicle for intranasal absorption at a suitable pH=6. The formulation of DMT fumarate gel can be administered via the nasal cavity in small volumes of between 0.04 and 0.50 mL for therapeutic effects. Potency analysis using tryptamine internal standard quantification revealed DMT freebase concentration of 135.5 mg/mL with no other degradation byproducts after storage for 106 days in dark conditions at room temperature.

Example 10

A Franz Cell apparatus was used to determine API release and permeability through a human skin mimic (Strat-M membrane, Millipore) and to compare patch effectiveness in Examples 1-8. The receiving well (10% ethanol in water) was kept at 32° C. throughout the experiment and all 10 mL were removed per sampling point. Drug flux was determined using the slope of zero-order permeated API over a specified time range. Potency analysis of API was accomplished using LC-MS while tryptamine (50 μg/mL) was added as an internal standard and used to quantify API with UV detection at 280 nm in Examples 1-9.

Example 11

Freebase 4-AcO-DMT (8% w/w) was dissolved in ethanol (4% w/w) and further added was povidone (2% w/w), butylated hydroxytoluene (1% w/w), and FD&C Blue No. 1. This solution was added to Ceolus KG 1000 microcrystalline cellulose (16% w/w) and mannitol (47% w/w) with simultaneous mixing and subsequent drying to form a homogenously coated powder. Further added was Prosolv HD 90 silicified microcrystalline cellulose (20% w/w), Cabosil silicon dioxide (1% w/w), and magnesium stearate (1% w/w) and blended to uniformity. Using a die set and sufficient force, a 250 mg tablet was formed for ingestion of 4-AcO-DMT for therapeutic use.

Example 12: 2-(2-chloro-1H-indol-3-yl)-N,N-dimethylethan-1-amine

A mixture of tryptamine hydrochloride salt (1 g, 5.1 mmol) and N-chlorosuccinimide (NCS, 0.69 g, 5.2 mmol) in acetic acid (50 mL) and formic acid (15 mL) was stirred for approximately 20 minutes. The product, 2-chloro-tryptamine (verified via 2D NMR spectroscopy), was dried and purified, and 211 mg (1.09 mmol) was further reacted with sodium cyanoborohydride (139.26 mg, 2.22 mmol) in methanol (21 mL) and formaldehyde (0.222 mL, 2.75 mmol) under nitrogen at 0° C. and stirred for 2.5 hours. The reaction was quenched with 1.0 M sodium hydroxide (27 mL) and extracted three times with methyl-tert-butyl-ether (MTBE). The residue was dried over sodium sulfate and concentrated down as a light brown oil/solid. Based on the LC-MS, 1H and 13C NMR data, the final product contained majority 2-chloro-N,N-dimethyltryptamine. Product Formula $C_{12}H_{15}N_2Cl$ m/z 222.0924, $[M+H]^+$ 223.0997 $^1H$ NMR (600 MHz, DMSO-$d_6$) δ ppm 2.13 (s, 6H) 2.34-2.38 (m, 2H) 2.68-2.80 (m, 3H) 6.91-6.99 (m, 1H) 7.02 (t, J=7.54 Hz, 2H) 7.20 (d, J=7.99 Hz, 2H) 7.40 (d, J=7.81 Hz, 1H) 11.53 (br s, 1H)

Example 13: 2-(2-bromo-1H-indol-3-yl)-N,N-dimethylethan-1-amine

Previously documented methods were used to synthesize N,N-dimethyltryptamine (2.88 mmol) and dissolved in anhydrous acetonitrile (36 mL, 15 mg/mL) under inert conditions. This was combined with copper (II) bromide (1.93 g, 8.65 mmol) and stirred for 2 hours. The reaction was quenched with 40 ml of water and 100 mL EtOAc was added followed by 40 mL of saturated ammonium carbonate. The organic layer was washed and dried over sodium sulfate, filtered and concentrated down to a light brown oil (302.3 mg). The final major product, 2-bromo-N,N-dimethyltryptamine, was verified via LC-MS, 1D and 2D NMR spectroscopy. Product formula: $C_{12}H_{15}N_2Br$ m/z 266.0419, $[M+H]^+$ 267.0491

$^1H$ NMR (600 MHz, DMSO-$d_6$) δ ppm 2.21 (s, 6H) 2.38-2.47 (m, 2H) 2.73-2.88 (m, 3H) 6.93-7.03 (m, 1H) 7.03-7.11 (m, 1H) 7.28 (br d, J=7.99 Hz, 1H) 7.46-7.51 (m, 1H) 11.61 (br s, 1H)

Example 14: 2-bromo-3-(2-(dimethylamino)ethyl)-1H-indol-4-yl acetate

Previously documented methods were used to synthesize 4-acetoxy-N,N-dimethyltryptamine (14.9 mg, 0.06 mmol) and dissolved in anhydrous acetonitrile (1 mL) under inert conditions. Copper (II) bromide (40.5 mg, 0.18 mmol) was added and the reaction was stirred for 2 hours. Upon work-up, the major product, 2-bromo-4-acetoxy-N,N-dimethyltryptamine was verified via LC-MS and 1D NMR spectroscopy. Product formula: $C_{14}H_{17}N_2O_2Br$m/z 324.0473, $[M+H]^+$ 325.05461H NMR (600 MHz, DMSO-$d_6$) δ ppm 2.21-2.25 (m, 13H) 2.32-2.39 (m, 12H) 2.71-2.75 (m, 3H) 6.74 (d, J=7.63 Hz, 1H) 7.06-7.10 (m, 2H) 7.18 (d, J=8.17 Hz, 2H) 11.91 (s, 1H)

Example 15: 2-(2-chloro-4-methoxy-1H-indol-3-yl)-N,N-dimethylethan-1-amine

Previously documented methods were used to synthesize 4-methoxy-N,N-dimethyltryptamine (130 mg, 0.6 mmol) and dissolved in anhydrous acetonitrile (3.6 mL). Copper (II) chloride (241 mg, 1.8 mmol) was added and stirred overnight under inert atmosphere. Quenched with water (14 mL) and extracted three times with EtOAc and washed with saturated ammonium carbonate. The organic layer was dried over sodium sulfate, filtered and concentrated to an orange semi-solid (38.2 mg, 25% yield).

This was purified via HPLC to produce 2-chloro-4-methoxy-N,N-dimethyltryptamine and verified via LC-MS, 1D and 2D NMR spectroscopy.

Product formula: $C_{13}H_{17}N_2OCl$ m/z 252.1029, $[M+H]^+$ 253.11021H NMR (600 MHz, DMSO-$d_6$) δ ppm 2.27-2.39 (m, 14H) 2.50-2.60 (m, 6H) 2.89-3.05 (m, 5H) 3.84-3.99 (m, 9H) 6.54-6.66 (m, 2H) 6.92 (d, J=8.17 Hz, 1H) 7.03-7.19 (m, 2H) 11.71 (s, 1H)

Example 16: 1-(3-(2-(dimethylamino)ethyl)-1H-indol-4-yl)-N-methylmethanesulfonamide The nitro group of N-methyl-3-nitrobenzenesulfonamide will be reduced via palladium on carbon ($H_2$/Pd/C) in ethanol solvent and aqueous HCl to the subsequent aniline. This product will be treated with sodium nitrite to give the diazonium salt and subsequently reduced to the hydrazine with $SnCl_2$, all at 0° C. The hydrazone will be generated upon condensation with 4,4-dimethyoxy-N,N-dimethylbutylamine in aqueous hydrochloric acid. The final product will be produced via the Fischer indole reaction, where the hydrazone will be reacted with polyphosphoric acid in refluxing chloroform to initiate cyclization.

This compound can be further halogenated at the C-2 position following the Copper (II) halide protocols of previous examples.

Example 17: Computational Analysis

Six distinct receptor models were tested depending on the documented crystal structures in the RCSB Protein Data Bank (PDB) for various serotonin receptors and sigma-1. These receptor structures include 5-$HT_{2A}$, 5-$HT_{2B}$, 5-$HT_{1B}$, and $\sigma_1$ (PDB ID's also shown in column headings).

For each static protein structure, the PDB files of crystal structures containing bound ligands most chemically similar to the tryptamine scaffold were used for most accuracy where possible (e.g. LSD or ergotamine-bound). The overall workflow was performed using various aspects of the Schrodinger software suite. The 3D SMILES for each ligand was uploaded following literature recommended protonation and/or charge for tryptamines and various conformers were generated and minimized using Schrödinger LigPrep. A final list of compounds were screened with Glide scores being generated by Schrödinger Glide including the structures listed in Table 3. Validation of this technique was done by including known agonists of 5-HT and $\sigma_1$ receptors and compared to experimental binding assay data. The docking scores of the known agonists and the experimental data were comparable and within the experimental error for activity. For example, the (+)-LSD enantiomer shows greater activity in vitro at the 5-$HT_{2A}$ receptor than the (−)-LSD enantiomer, and our computationally rendered values show the same trend in activity.

TABLE 3

Virtual Docking Glide Scores of Compounds in Table (1)

| Compound | Name | 6WGT (5-$HT2_A$) | 5TVN (5-$HT2_B$) | 4IAR (5-$HT1_B$) | 5HK2 (Sigma-1) | 5HK1 (Sigma-1) | 4IB4 (5-HT2B) |
|---|---|---|---|---|---|---|---|
| 1 | 2-(2-chloro-1H-indol-3-yl)-N,N-dimethylethan-1-amine | −9.11 | −7.09 | −6.27 | −9.2 | −8.04 | −8.82 |
| 2 | 2-(2-bromo-1H-indol-3-yl)-N,N-dimethylethan-1-amine | −9.12 | −8.85 | −7.19 | −9.39 | −7.4 | −8.91 |
| 3 | 2-chloro-3-(2-(dimethylamino)ethyl)-1H-indol-4-yl acetate | Z-4.92 | −6.39 | −5.31 | −10.74 | −9.08 | −8.79 |
| 4 | 2-bromo-3-(2-(dimethylamino)ethyl)-1H-indol-4-yl acetate | −10.89 | −6.97 | −5.89 | −10.72 | −9.42 | −8.9 |

TABLE 3-continued

| Virtual Docking Glide Scores of Compounds in Table (1) | | | | | | | |
|---|---|---|---|---|---|---|---|
| Compound | Name | 6WGT ($5-HT2_A$) | 5TVN ($5-HT2_B$) | 4IAR ($5-HT1_B$) | 5HK2 (Sigma-1) | 5HK1 (Sigma-1) | 4IB4 (5-HT2B) |
| 5 | 2-chloro-3-(2-(dimethylamino)ethyl)-1H-indol-4-yl hydrogen phosphate | −9.28 | −3.54 | −5.94 | −7.5 | −10.56 | −8.48 |
| 6 | 2-bromo-3-(2-(dimethylamino)ethyl)-1H-indol-4-yl hydrogen phosphate | −7.84 | −3.4 | −5.68 | −9.58 | −10.17 | −8.71 |
| 7 | 2-bromo-3-(2-(dimethylamino)ethyl)-1H-indol-4-ol | −8.76 | −7.46 | −6.73 | −8.05 | −9.19 | −8.53 |
| 8 | 2-chloro-3-(2-(dimethylamino)ethyl)-1H-indol-4-ol | −8.74 | −6.49 | −6.81 | −7.68 | −8.98 | −8.44 |
| 9 | 1-(2-chloro-3-(2-(dimethylamino)ethyl)-1H-indol-4-yl)-N-methylmethanesulfonamide | −6.72 | −6.64 | −4.43 | −7.69 | −10.55 | −5.96 |
| 10 | 1-(2-bromo-3-(2-(dimethylamino)ethyl)-1H-indol-4-yl)-N-methylmethanesulfonamide | −3.85 | −6.37 | −5.87 | −10.83 | −10.46 | −8.54 |
| 11 | 1-(3-(2-(dimethylamino)ethyl)-1H-indol-4-yl)-N-methylmethanesulfonamide | −7.53 | −7.47 | −6.92 | −11.54 | −10.41 | −8.07 |
| 12 | 2-(2-chloro-4-methoxy-1H-indol-3-yl)-N,N-dimethylethan-1-amine | −8.86 | −5.81 | −6.26 | −9.26 | −10.95 | −8.37 |
| 13 | 2-(2-bromo-4-methoxy-1H-indol-3-yl)-N,N-dimethylethan-1-amine | −8.77 | −6.43 | −6.24 | −8.51 | −9.03 | −8.49 |
| 14 | (R)-1-(2-chloro-1H-indol-3-yl)propan-2-amine | −7.71 | −6.36 | −6.46 | −8.31 | −7.89 | −8.63 |
| 15 | (R)-1-(2-chloro-1H-indol-3-yl)-N-methylpropan-2-amine | −8.76 | −6.77 | −6.31 | −8.04 | −8.78 | −9 |
| 16 | (R)-1-(2-chloro-1H-indol-3-yl)-N,N-dimethylpropan-2-amine | −9.55 | −6.15 | −6.9 | −9.04 | −8.23 | −8.91 |
| 17 | (S)-1-(2-chloro-1H-indol-3-yl)-N,N-dimethylpropan-2-amine | −9.07 | −7.06 | −7.48 | −9.05 | −7.52 | −8.69 |
| 18 | (S)-1-(2-chloro-1H-indol-3-yl)propan-2-amine | −7.98 | −6.52 | −7.19 | −7.49 | −7.69 | −8.96 |
| 19 | (S)-1-(2-chloro-1H-indol-3-yl)-N-methylpropan-2-amine | −8.74 | −6.74 | −7.2 | −9.76 | −7.62 | −9.28 |
| 20 | (R)-1-(2-bromo-1H-indol-3-yl)propan-2-amine | −7.93 | −6.58 | −6.66 | −8.25 | −8.06 | −8.64 |
| 21 | (R)-1-(2-bromo-1H-indol-3-yl)-N-methylpropan-2-amine | −10.36 | −6.7 | −7.31 | −8.2 | −8.81 | −8.99 |
| 22 | (R)-1-(2-bromo-1H-indol-3-yl)-N,N-dimethylpropan-2-amine | −8.75 | −6.29 | −7.1 | −9.02 | −7.89 | −8.82 |
| 23 | (S)-1-(2-bromo-1H-indol-3-yl)-N,N-dimethylpropan-2-amine | −9.23 | −7.13 | −7.44 | −9.31 | −6.66 | −8.8 |
| 24 | (S)-1-(2-bromo-1H-indol-3-yl)propan-2-amine | −9.27 | −6.85 | −7.2 | −8.27 | −8.3 | −8.14 |
| 25 | (S)-1-(2-bromo-1H-indol-3-yl)-N-methylpropan-2-amine | −9.06 | −7.01 | −7.48 | −8.12 | −7.7 | −9.09 |
| 26 | 2-(2-chloro-1H-indol-3-yl)-N,N-diethylethan-1-amine | −10.49 | −7.5 | −7.53 | −9.91 | −8.49 | −8.93 |
| 27 | N-(2-(2-chloro-1H-indol-3-yl)ethyl)-N-isopropylpropan-2-amine | −9.68 | −7.61 | −6.39 | −8.91 | −9.5 | −9.44 |
| 28 | N-(2-(2-chloro-1H-indol-3-yl)ethyl)-N-vinylethenamine | −9.46 | −6.84 | −7.1 | −9.33 | −8.52 | −8.76 |
| 29 | 2-(2-bromo-1H-indol-3-yl)-N,N-diethylethan-1-amine | −9.59 | −7.57 | −7.63 | −8.88 | −9.63 | −9.5 |
| 30 | N-(2-(2-bromo-1H-indol-3-yl)ethyl)-N-isopropylpropan-2-amine | −7.42 | −7.92 | −6.01 | −9.25 | −9.75 | −9.4 |
| 31 | N-(2-(2-bromo-1H-indol-3-yl)ethyl)-N-vinylethenamine | −9.22 | −7.27 | −7.75 | −9.34 | −8.5 | −8.98 |

The present disclosure has been described in connection with certain embodiments and examples; however, unless otherwise indicated, the claimed invention should not be unduly limited to such specific embodiments and examples.

The invention claimed is:

1. A method of treating treatment resistant depression in a subject in need thereof, the method comprising mucosally administering to the subject:

a therapeutically effective amount of 5-methoxy-N,N-dimethyltryptamine (5-MeO-DMT) or a pharmaceutically acceptable salt thereof, wherein the mucosal administration provides absorption of the 5-MeO-DMT into the blood of the subject after administration and the subject is on concurrent antidepressant therapy.

2. The method of claim 1, wherein the subject's concurrent antidepressant therapy is a monoamine oxidase inhibitor (MAOI), a selective serotonin reuptake inhibitor (SSRI), a serotonin and norepinephrine reuptake inhibitor (SNRI), a tricyclic antidepressant (TCA), an atypical antidepressant, or a combination thereof.

3. The method of claim 1, wherein the subject's concurrent antidepressant therapy is an SSRI or SNRI.

4. The method of claim 1, where the subject's concurrent antidepressant therapy is administered for 4 weeks prior to administration of 5-MeO-DMT or a pharmaceutically acceptable salt thereof.

5. The method of claim 1, where the subject's concurrent antidepressant therapy is administered for 4 weeks after administration of 5-MeO-DMT or a pharmaceutically acceptable salt thereof.

6. The method of claim 1, where the subject's concurrent antidepressant therapy is administered for 3 weeks prior to administration of 5-MeO-DMT or a pharmaceutically acceptable salt thereof.

7. The method of claim 1, where the subject's concurrent antidepressant therapy is administered for 3 weeks after administration of 5-MeO-DMT or a pharmaceutically acceptable salt thereof.

8. The method of claim 1, where the subject's concurrent antidepressant therapy is administered for 2 weeks prior to administration of 5-MeO-DMT or a pharmaceutically acceptable salt thereof.

9. The method of claim 1, where the subject's concurrent antidepressant therapy is administered for 2 weeks after administration of 5-MeO-DMT or a pharmaceutically acceptable salt thereof.

10. The method of claim 1, where the subject's concurrent antidepressant therapy is administered for 1 week prior to administration of 5-MeO-DMT or a pharmaceutically acceptable salt thereof.

11. The method of claim 1, where the subject's concurrent antidepressant therapy is administered for 1 week after administration of 5-MeO-DMT or a pharmaceutically acceptable salt thereof.

12. The method of claim 1, wherein the mucosal administration is sublingual, buccal, nasal, inhalation, or oral.

13. The method of claim 1, wherein the 5-MeO-DMT is administered in the form of a strip, a solution, a suspension, a gel, a liquid, an emulsion, liposomes, microparticles, a film, a powder, or a patch.

14. The method of claim 1, wherein the 5-MeO-DMT is administered in the form of a spray.

15. The method of claim 1, wherein the 5-MeO-DMT is administered in the form of a film.

16. The method of claim 1, wherein the 5-MeO-DMT is administered in the form of a strip.

17. The method of claim 1, wherein the 5-MeO-DMT is administered in the form of a solution.

18. The method of claim 1, wherein the 5-MeO-DMT is administered in the form of a suspension.

19. The method of claim 1, wherein the 5-MeO-DMT is administered in the form of a liquid.

20. The method of claim 1, wherein the 5-MeO-DMT is administered in the form of a pharmaceutical composition comprising 5-MeO-DMT and a pharmaceutically acceptable carrier.

21. The method of claim 1, wherein the mucosal administration comprises administration to the nasal mucosa, lung mucosa, gastric mucosa, esophageal mucosa, or intestinal mucosa.

22. The method of claim 21, wherein about 5 mg to about 25 mg of 5-MeO-DMT or a pharmaceutically acceptable salt thereof is administered to the subject.

23. The method of claim 22, wherein about 6 mg of 5-MeO-DMT or a pharmaceutically acceptable salt thereof is administered to the subject.

24. The method of claim 22, wherein about 8 mg of 5-MeO-DMT or a pharmaceutically acceptable salt thereof is administered to the subject.

25. The method of claim 22, wherein about 12 mg of 5-MeO-DMT or a pharmaceutically acceptable salt thereof is administered to the subject.

26. The method of claim 22, wherein about 18 mg of 5-MeO-DMT or a pharmaceutically acceptable salt thereof is administered to the subject.

27. The method of claim 23, wherein the method further comprises subsequently administering about 12 mg of 5-MeO-DMT or a pharmaceutically acceptable salt thereof to the subject.

28. The method of claim 25, wherein the method further comprises subsequently administering about 18 mg of 5-MeO-DMT or a pharmaceutically acceptable salt thereof to the subject.

29. The method of claim 27, wherein the method further comprises subsequently administering about 18 mg of 5-MeO-DMT or a pharmaceutically acceptable salt thereof to the subject.

* * * * *